United States Patent
Ryu et al.

(10) Patent No.: US 10,522,761 B2
(45) Date of Patent: Dec. 31, 2019

(54) COMPOUND FOR ORGANIC OPTOELECTRONIC DEVICE, ORGANIC LIGHT EMITTING DIODE INCLUDING THE SAME AND DISPLAY INCLUDING THE ORGANIC LIGHT EMITTING DIODE

(71) Applicant: SAMSUNG SDI CO., LTD., Yongin-si, Gyeonggi-do (KR)

(72) Inventors: Dong-Wan Ryu, Suwon-si (KR); Eui-Su Kang, Suwon-si (KR); Han-Ill Lee, Suwon-si (KR); Sung-Hyun Jung, Suwon-si (KR); Young-Kyoung Jo, Suwon-si (KR); Mi-Young Chae, Suwon-si (KR); Dal-Ho Huh, Suwon-si (KR); Jin-Seok Hong, Suwon-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 454 days.

(21) Appl. No.: 14/626,410

(22) Filed: Feb. 19, 2015

(65) Prior Publication Data
US 2015/0162542 A1    Jun. 11, 2015

Related U.S. Application Data

(63) Continuation-in-part of application No. PCT/KR2013/003865, filed on May 13, 2013.

(30) Foreign Application Priority Data

Aug. 21, 2012  (KR) .................. 10-2012-0091342

(51) Int. Cl.
*H01L 51/00* (2006.01)
*C07F 7/08* (2006.01)
(Continued)

(52) U.S. Cl.
CPC ........ *H01L 51/0061* (2013.01); *C07D 311/82* (2013.01); *C07D 327/08* (2013.01);
(Continued)

(58) Field of Classification Search
CPC ............. H01L 51/0059; H01L 51/0073; H01L 51/0074; H01L 51/0094; H01L 51/0071;
(Continued)

(56) References Cited

U.S. PATENT DOCUMENTS

2007/0129555 A1* 6/2007 Kai ...................... C07D 319/24
549/359
2017/0062720 A1* 3/2017 Kim ...................... C09K 11/07

FOREIGN PATENT DOCUMENTS

JP     2008239797    * 10/2005    ............. C09K 11/06
JP     2009-046685 A    3/2009
(Continued)

OTHER PUBLICATIONS

English language translation of WO 2010/151084, pp. 1-30, Mar. 21, 2018.*
(Continued)

*Primary Examiner* — Alexander C Kollias
(74) *Attorney, Agent, or Firm* — Lee & Morse, P.C.

(57) ABSTRACT

Provided are a compound for an organic optoelectronic device represented by Chemical Formula 1, an organic light emitting diode including the same, and a display device including the organic light emitting diode. The structure of Chemical Formula 1 is shown in the specification.

The compound for an organic optoelectronic device provides an organic light emitting diode having life-span characteristics due to excellent electrochemical and thermal stability, and having high luminous efficiency at a low driving voltage.

12 Claims, 3 Drawing Sheets

(51) Int. Cl.
  *C07D 407/12* (2006.01)
  *C07D 409/12* (2006.01)
  *C09K 11/06* (2006.01)
  *C07D 311/82* (2006.01)
  *C07D 327/08* (2006.01)
  *C07D 335/12* (2006.01)
  *C07D 339/08* (2006.01)
  *C07D 409/14* (2006.01)
  *H05B 33/10* (2006.01)
  *H01L 51/50* (2006.01)

(52) U.S. Cl.
  CPC ......... *C07D 335/12* (2013.01); *C07D 339/08* (2013.01); *C07D 407/12* (2013.01); *C07D 409/12* (2013.01); *C07D 409/14* (2013.01); *C07F 7/081* (2013.01); *C07F 7/0816* (2013.01); *C09K 11/06* (2013.01); *H01L 51/006* (2013.01); *H01L 51/0059* (2013.01); *H01L 51/0071* (2013.01); *H01L 51/0073* (2013.01); *H01L 51/0074* (2013.01); *H01L 51/0094* (2013.01); *H05B 33/10* (2013.01); *C09K 2211/1007* (2013.01); *C09K 2211/1011* (2013.01); *C09K 2211/1014* (2013.01); *C09K 2211/1088* (2013.01); *C09K 2211/1092* (2013.01); *C09K 2211/1096* (2013.01); *H01L 51/5012* (2013.01); *H01L 51/5016* (2013.01); *H01L 51/5056* (2013.01); *H01L 51/5088* (2013.01); *Y02E 10/549* (2013.01)

(58) Field of Classification Search
  CPC . H01L 51/0061; C07D 407/12; C07D 409/12; C07D 311/82; C07D 327/08; C07D 335/12; C07D 339/08; C07D 409/14; C09K 11/06; H05B 33/10
  See application file for complete search history.

(56) References Cited

FOREIGN PATENT DOCUMENTS

| | | | |
|---|---|---|---|
| JP | 2009-260276 A | 11/2009 | |
| JP | 4384536 B2 | 12/2009 | |
| KR | 10-2003-0077437 A | 10/2003 | |
| KR | 10-2006-0032930 A | 4/2006 | |
| KR | 10-2006-0127181 A | 12/2006 | |
| KR | 10-2008-0037699 A | 4/2008 | |
| KR | 10-2010-0048210 A | 5/2010 | |
| KR | 10-2010-0138631 A | 12/2010 | |
| WO | WO 2005/075451 A1 | 8/2005 | |
| WO | WO 2006/041263 A1 | 4/2006 | |
| WO | WO 2007/015412 A1 | 2/2007 | |
| WO | WO-2010151084 | * 12/2010 | ............. H05B 33/10 |

OTHER PUBLICATIONS

English language translation of JP 2009040957, pp. 1-37, Aug. 14, 2018.*

English langauge translation of WO 2010/0151084, pp. 1-22, Aug. 14, 2018.*

English language translation of JP-2008-239797, pp. 1-29, Apr. 18, 2019.*

* cited by examiner

COMPOUND FOR ORGANIC OPTOELECTRONIC DEVICE, ORGANIC LIGHT EMITTING DIODE INCLUDING THE SAME AND DISPLAY INCLUDING THE ORGANIC LIGHT EMITTING DIODE

CROSS-REFERENCE TO RELATED APPLICATIONS

This application is a continuation of pending International Application No. PCT/KR2013/003865, entitled "Compound for Organic Optoelectronic Device, Organic Light Emitting Diode Including the Same and Display Including the Organic Light Emitting Diode," which was filed on May 3, 2013, the entire contents of which are hereby incorporated by reference.

Korean Patent Application No. 10-2012-0091342, filed on Aug. 21, 2012, in the Korean Intellectual Property Office, and entitled: "Compound for Organic Optoelectronic Device, Organic Light Emitting Diode Including the Same and Display Including the Organic Light Emitting Diode," is incorporated by reference herein in its entirety.

BACKGROUND

1. Field

A compound for an organic optoelectronic device being capable of providing an organic optoelectronic device having excellent life-span, efficiency, electrochemical stability, and thermal stability, an organic light emitting diode including the compound, and a display device including the organic light emitting diode are disclosed.

2. Description of the Related Art

An organic optoelectronic device is a device requiring a charge exchange between an electrode and an organic material by using holes or electrons.

An organic optoelectronic device may be classified as follows in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of an organic optoelectronic device include an organic photoelectric device, an organic light emitting diode, an organic solar cell, an organic photo conductor drum, an organic transistor, and the like, which require a hole injecting or transport material, an electron injecting or transport material, or a light emitting material.

Particularly, an organic light emitting diode (OLED) has recently drawn attention due to an increase in demand for flat panel displays. In general, organic light emission refers to conversion of electrical energy into photo-energy.

Such an organic light emitting diode converts electrical energy into light by applying current to an organic light emitting material. It has a structure in which a functional organic material layer is interposed between an anode and a cathode. The organic material layer includes a multi-layer including different materials, for example a hole injection layer, a hole transport layer, an emission layer, an electron transport layer, and an electron injection layer, in order to improve efficiency and stability of an organic light emitting diode.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

Recently, it has become known that a phosphorescent light emitting material may be used for a light emitting material of an organic light emitting diode in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect. Therefore, a host/dopant system is included as a light emitting material in order to improve color purity and increase luminous efficiency and stability through energy transfer.

In order to implement excellent performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting diode has thus far not been satisfactory and thus there is a need for a novel material. This material development is also required for other organic optoelectronic devices.

The low molecular organic light emitting diode is manufactured as a thin film in a vacuum deposition method and can have good efficiency and life-span performance. A polymer organic light emitting diode is manufactured in an inkjet or spin coating method has an advantage of low initial cost and being large-sized.

Both low molecular organic light emitting and polymer organic light emitting diodes have an advantage of self-light emitting, high speed response, wide viewing angle, ultra-thin, high image quality, durability, large driving temperature range, and the like. In particular, they have good visibility due to self-light emitting characteristics compared with a conventional LCD (liquid crystal display) and have an advantage of decreasing thickness and weight of LCD up to a third, because they do not need a backlight.

In addition, since they have a response speed 1000 time faster microsecond unit than LCD, they can realize a perfect motion picture without after-image. Based on these advantages, they have been remarkably developed to have 80 times efficiency and more than 100 times life-span since they come out for the first time in the late 1980s. Recently, they keep being rapidly larger such as a 40-inch organic light emitting diode panel.

They are simultaneously required to have improved luminous efficiency and life-span in order to be larger. Herein, their luminous efficiency need smooth combination between holes and electrons in an emission layer. However, since an organic material in general has slower electron mobility than hole mobility, it has a drawback of inefficient combination between holes and electrons. Accordingly, while increasing electron injection and mobility from a cathode and simultaneously preventing movement of holes is required.

In order to improve life-span, a material crystallization caused by Joule heats generated during device operating is required to be prevented. Accordingly, there has been a strong need for an organic compound having excellent electron injection and mobility, and high electrochemical stability.

SUMMARY

Technical Problem

A compound for an organic optoelectronic device that may act as a hole injection and transport material or an electron injection and transport material, and also act as a light emitting host along with an appropriate dopant is provided.

Technical Solution

An organic light emitting diode having excellent life-span, efficiency, driving voltage, electrochemical stability, and thermal stability and a display device including the same are provided.

In one embodiment of the present invention, a compound represented by the following Chemical Formula 1 for an organic optoelectronic device is provided.

[Chemical Formula 1]

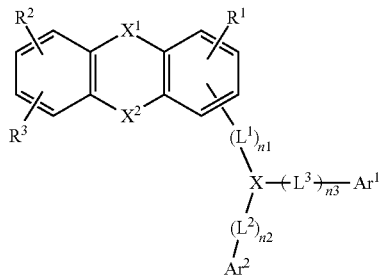

In the Chemical Formula 1, X is boron (B), nitrogen (N) or phosphorus (P), $X^1$ and $X^2$ are independently, —O—, —S—, —S(O$_2$)—, —CR'R"—, —SiR'R"— or —GeR'R"—, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, $L^1$ to $L^3$ are independently, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, $Ar^1$ and $Ar^2$ are independently substituted or unsubstituted C6 to C30 aryl group or a substituted or unsubstituted C2 to C30 heteroaryl group, $R^1$ to $R^3$ are independently, hydrogen, deuterium, a substituted or unsubstituted C1 to C10 alkyl group, a substituted or unsubstituted C6 to C30 aryl group or a substituted or unsubstituted C2 to C30 heteroaryl group, and n1 to n3 are independently integers of 0 to 3.

In the Chemical Formula 1, X may be nitrogen (N), $X^1$ may be —O—, —S—, —CR'R" or —SiR'R"—, wherein the R' and R" are independently hydrogen, deuterium, a substituted or unsubstituted C1 to C10 alkyl group, a substituted or unsubstituted C6 to C18 aryl group, $X^2$ may be —O— or —S—, $L^1$ to $L^3$ may be independently a phenyl group, and n1 to n3 may be independently 0 or 1.

In addition, X may be nitrogen (N), $X^1$ may be —O—, —S—, —CR'R" or —SiR'R"—, wherein the R' and R" are independently hydrogen, deuterium, a substituted or unsubstituted C1 to C 10 alkyl group, a substituted or unsubstituted C6 to C18 aryl group, $X^2$ may be —O— or —S—, $L^1$ to $L^3$ may be independently a phenyl group, n1 to n3 may be independently 0 or 1, and $Ar^1$ and $Ar^2$ may be independently substituted or unsubstituted C6 to C30 aryl group.

The $Ar^1$ and $Ar^2$ may be independently one of a substituted or unsubstituted phenyl group, a substituted or unsubstituted biphenyl group, a substituted or unsubstituted triphenyl group, a substituted or unsubstituted phenanthryl group, a substituted or unsubstituted naphthyl group, a substituted or unsubstituted anthracenyl group, and a substituted or unsubstituted fluorenyl group.

In another embodiment of the present invention, a compound for an organic optoelectronic device represented by the following Chemical Formula 2 is provided.

[Chemical Formula 2]

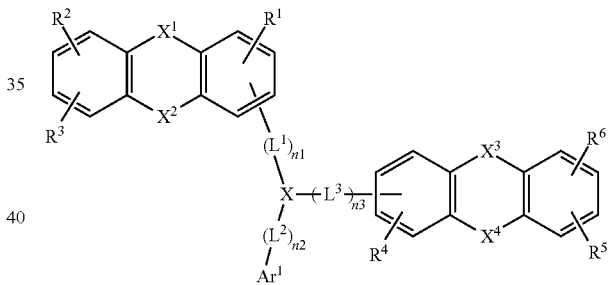

In the Chemical Formula 2, X is boron (B), nitrogen (N), or phosphorus (P), $X^1$ to $X^4$ are independently, —O—, —S—, —S(O$_2$)—, —CR'R"—, —SiR'R" or —GeR'R"—, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, at least one of $X^1$ or $X^3$ is —CR'R"—, —SiR'R"— or —GeR'R"—, $L^1$ to $L^3$ are independently, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, $Ar^1$ is a substituted or unsubstituted C6 to C30 aryl group or a substituted or unsubstituted C2 to C30 heteroaryl group, $R^1$ to $R^6$ are independently, hydrogen, deuterium, a substituted or unsubstituted C1 to C10 alkyl group, a substituted or unsubstituted C6 to C30 aryl group or a substituted or unsubstituted C2 to C30 heteroaryl group, and n1 to n3 are independently integers of 0 to 3.

$Ar^1$ may be a substituted or unsubstituted C6 to C30 aryl group.

$Ar^1$ may be a substituted or unsubstituted C2 to C30 heteroaryl group.

In another embodiment of the present invention, a compound for an organic optoelectronic device represented by the following Chemical Formula 3 is provided.

[Chemical Formula 3]

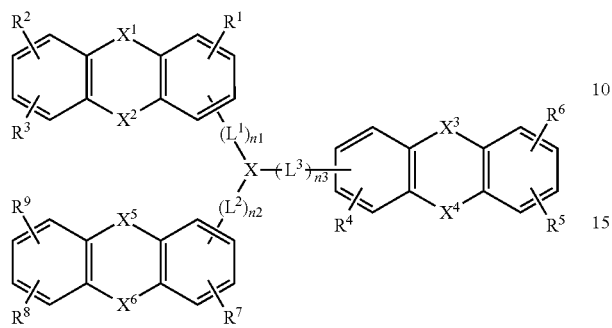

In the Chemical Formula 3, X is boron (B), nitrogen (N), or phosphorus (P), $X^1$ to $X^6$ are independently, —O—, —S—, —S(O$_2$)—, —CR'R"—, —SiR'R"— or —GeR'R"—, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, at least one of $X^1$, $X^3$ or $X^5$ is —CR'R"—, —SiR'R"— or —GeR'R"—, $X^6$ is a single bond, $L^1$ to $L^3$ are independently, a substituted or unsubstituted C2 to C 10 alkenylene group, a substituted or unsubstituted C2 to C 10 alkynylene group, a substituted or unsubstituted C6 to C30 arylene group or a substituted or unsubstituted C2 to C30 heteroarylene group, $R^1$ to $R^9$ are independently, hydrogen, deuterium, a substituted or unsubstituted C1 to C10 alkyl group, a substituted or unsubstituted C6 to C30 aryl group or a substituted or unsubstituted C2 to C30 heteroaryl group, and n1 to n3 are independently integers of 0 to 3.

The compound for an organic optoelectronic device may be represented by one of the following Chemical Formulae A-132, B-56, Chemical Formulae C-113, C-127, C-143, C-144, C-160, C-206, C-236 or C-243.

[A-132]

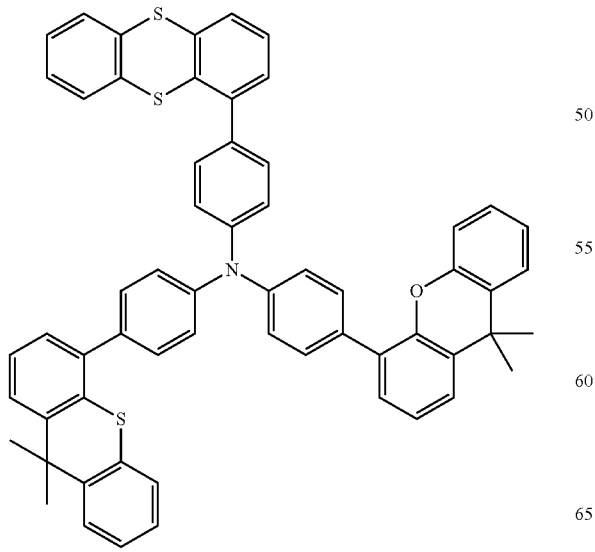

[B-56]

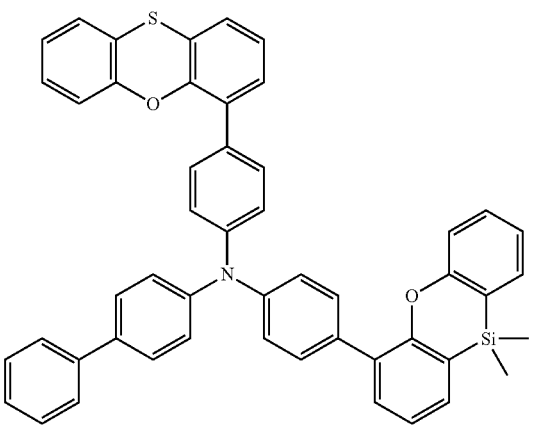

[C-113]

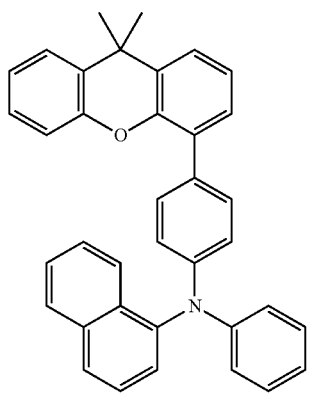

[C-127]

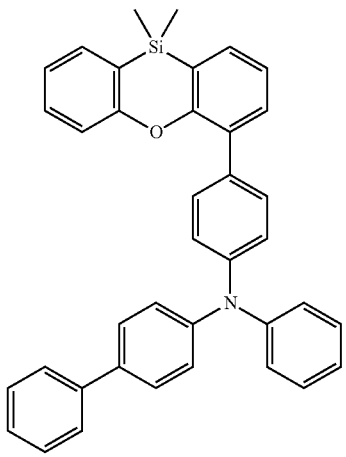

[C-143]
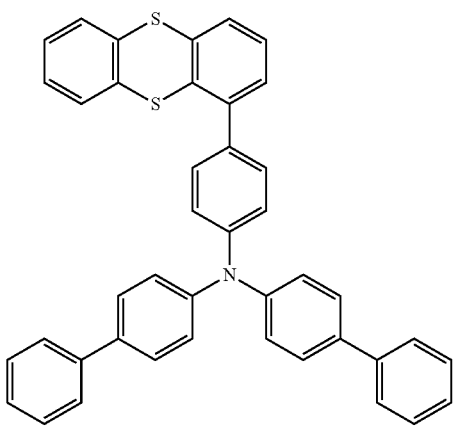

[C-144]
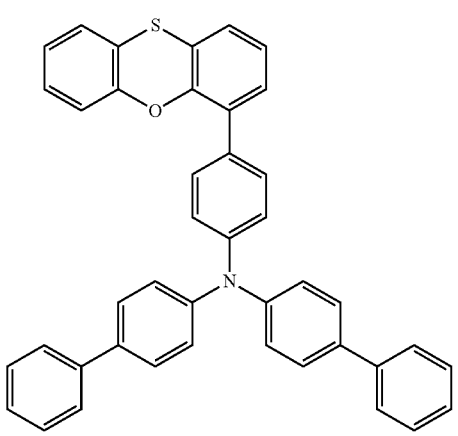

[C-160]
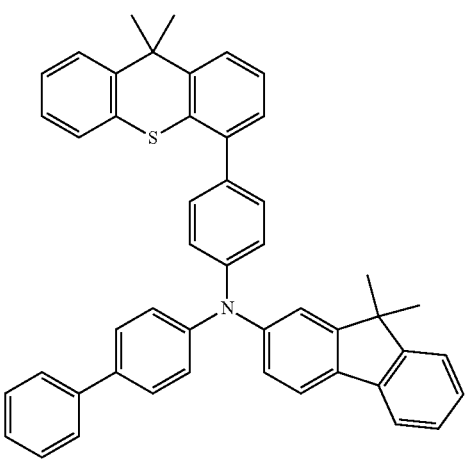

[C-206]
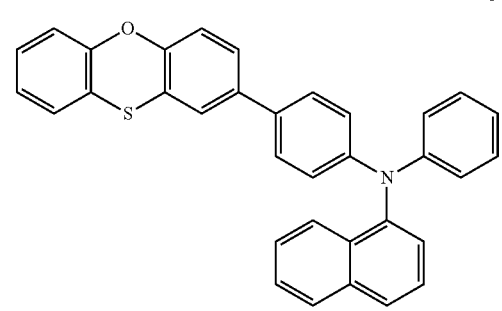

[C-236]
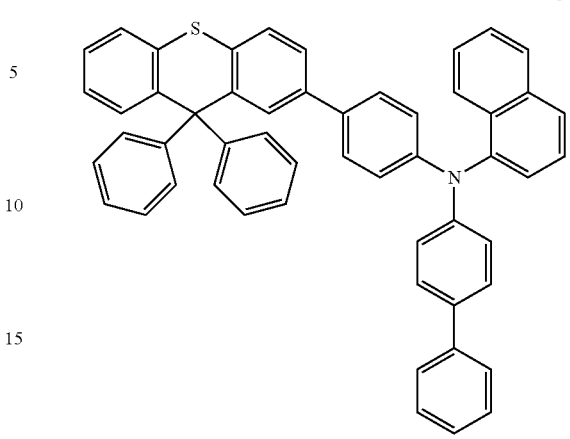

[C-243]
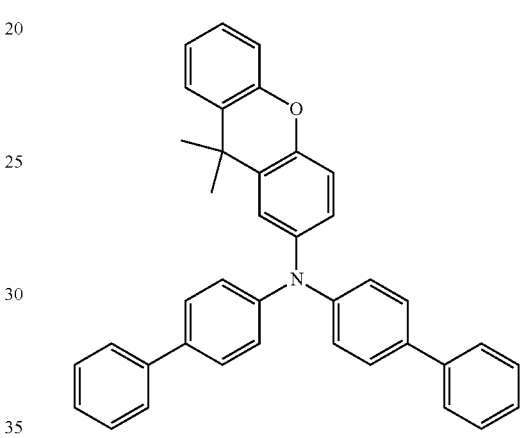

The compound for an organic optoelectronic device may have triplet exciton energy (T1) of greater than or equal to 2.0 eV.

The organic optoelectronic device may be selected from an organic photoelectric device, an organic light emitting diode, an organic solar cell, an organic transistor, an organic photo-conductor drum, and an organic memory device.

In another embodiment of the present invention, provided is an organic light emitting diode including an anode, a cathode, and at least one organic thin layer interposed between the anode and cathode, wherein at least one of the organic thin layers includes the compound for an organic optoelectronic device.

The organic thin layer may be selected from an emission layer, a hole transport layer, a hole injection layer, an electron transport layer, an electron injection layer, a hole blocking layer, and a combination thereof.

The compound for an organic optoelectronic device may be included in a hole transport layer (HTL) or a hole injection layer (HIL).

The compound for an organic optoelectronic device may be included in an emission layer.

The compound for an organic optoelectronic device may be used as a phosphorescent or fluorescent host material in an emission layer.

In yet another embodiment of the present invention, a display device including the above organic light emitting diode is provided.

Advantageous Effects

A compound having high hole or electron transport properties, film stability, thermal stability, and high triplet exciton energy may be provided.

Such a compound may be used as a hole injection/transport material, host material, or electron injection/transport material of an emission layer. An organic optoelectronic device using the same has improved life-span characteristics, and high luminous efficiency at a low driving voltage due to excellent electrochemical and thermal stability.

BRIEF DESCRIPTION OF THE DRAWINGS

Features will be apparent to those of skill in the art by describing in detail exemplary embodiments with reference to the attached drawings in which.

DESCRIPTION OF REFERENCE NUMERALS INDICATING PRIMARY ELEMENTS IN THE DRAWINGS

Figure 1:
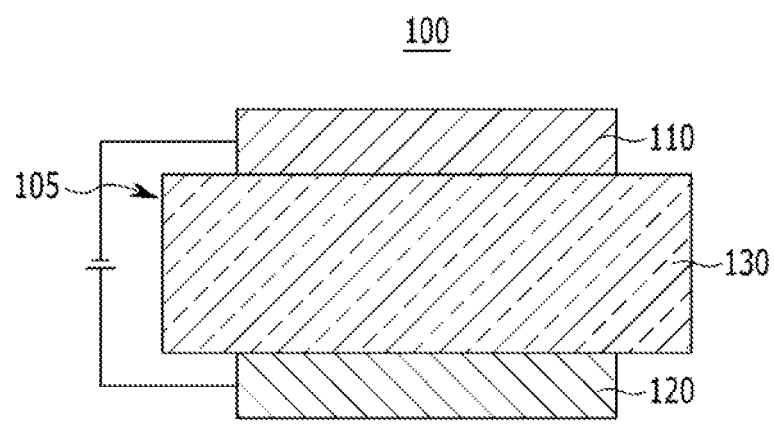
FIGS. 1 to 5 illustrate cross-sectional views showing organic light emitting diodes according to various embodiments including the compound for an organic optoelectronic device according to one embodiment.

100: organic light emitting diode 110: cathode
120: positive electrode 105: organic thin layer
130: emission layer 140: hole transport layer (HTL)
150: electron transport layer (ETL) 160: electron injection layer (EIL)
170: hole injection layer (HIL) 230: emission layer+ electron transport layer (ETL)

DETAILED DESCRIPTION

Hereinafter, embodiments of the present invention are described in detail. However, these embodiments are exemplary, and the present invention is not limited thereto and is limited by the claims.

In the present specification, when a definition is not otherwise provided, "substituted" refers to one substituted with deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C 10 trifluoroalkyl group such as a trifluoromethyl group and the like, or a cyano group, instead of at least one hydrogen of a substituent or a compound.

The two adjacent substituents selected from the substituted halogen, hydroxy group, an amino group, a substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group and the like, or cyano group may be fused to form a ring. For example, the substituted C6 to C30 aryl group may be fused to another adjacent substituted C6 to C30 aryl group to provide a substituted or unsubstituted fluorene ring.

In the present specification, when specific definition is not otherwise provided, "hetero" refers to one including 1 to 3 hetero atoms selected from the group consisting of N, O, S, and P, and remaining carbons in one functional group.

In the present specification, when a definition is not otherwise provided, "combination thereof" refers to at least two substituents bound to each other by a linker, or at least two substituents condensed to each other.

In the present specification, when a definition is not otherwise provided, "alkyl group" refers to an aliphatic hydrocarbon group. The alkyl group may be "a saturated alkyl group" without any double bond or triple bond. The alkyl group may be a branched, linear, or cyclic alkyl group.

The alkyl group may be a C1 to C20 alkyl group. More specifically, the alkyl group may be a C1 to C10 alkyl group or a C1 to C6 alkyl group. For example, a C1 to C4 alkyl group may have 1 to 4 carbon atoms in an alkyl chain which may be selected from the group consisting of methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

The "alkenylene group" refers to a functional group of at least one carbon-carbon double bond of at least two carbons, and the "alkynylene group" refers to a functional group of at least one carbon-carbon triple bond of at least two carbons.

"Aromatic group" refers to a cyclic functional group where all elements have p-orbitals, and these p-orbitals forms conjugation. Specific examples are aryl group and a heteroaryl group.

"Aryl group" refers to a substituent where all elements have p-orbitals, and these p-orbitals forms conjugation, and includes monocyclic or fused ring polycyclic (i.e., rings sharing adjacent pairs of carbon atoms) groups.

"Heteroaryl group" refers to aryl group including 1 to 3 hetero atoms selected from the group consisting of N, O, S, and P, and remaining carbons. When the heteroaryl group is a fused ring, each ring may include 1 to 3 hetero atoms.

In the present specification, the carbazole-based derivative may refer to a substituted structure where a nitrogen atom of a substituted or unsubstituted carbazolyl group is substituted with a hetero atom except nitrogen, or carbon. Specific examples may be dibenzofuran (dibenzofuranyl group), dibenzothiophene (dibenzothiophenyl group), fluorene (fluorenyl group), and the like.

In the present specification, hole characteristics refer to characteristics that holes formed in the anode is easily injected into the emission layer and transported in the emission layer due to conductive characteristics according to HOMO level. More specifically, it is similar to electron-repelling characteristics.

Electron characteristics refer to characteristics that electron formed in the cathode is easily injected into the emission layer and transported in the emission layer due to conductive characteristics according to LUMO level.

More specifically, it is similar to electron-withdrawing characteristics.

According to one embodiment of the present invention, the compound for an organic optoelectronic device may be a compound represented by the following Chemical Formula 1 for an organic optoelectronic device.

[Chemical Formula 1]

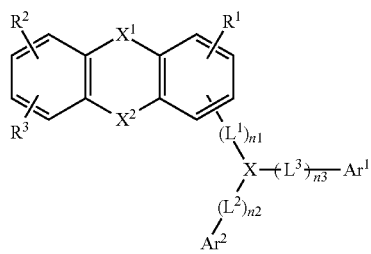

In the Chemical Formula 1, X is boron (B), nitrogen (N), or phosphorus (P), $X^1$ and $X^2$ are independently, —O—, —S—, —S(O$_2$)—, —CR'R"—, —SiR'R"— or —GeR'R"—, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, $L^1$ to $L^3$ are independently, a substituted or unsubstituted C2 to C10 alkenylene group, a substituted or unsubstituted C2 to C 10 alkynylene group, a substituted or unsubstituted C6 to C30 arylene group or a substituted or unsubstituted C2 to C30 heteroarylene group, $Ar^1$ and $Ar^2$ are independently substituted or unsubstituted C6 to C30 aryl group or a substituted or unsubstituted C2 to C30 heteroaryl group, $R^1$ to $R^3$ are independently, hydrogen, deuterium, a substituted or unsubstituted C1 to C10 alkyl group, a substituted or unsubstituted C6 to C30 aryl group or a substituted or unsubstituted C2 to C30 heteroaryl group, and n1 to n3 are independently integers of 0 to 3.

Specific examples of the $Ar^1$ and $Ar^2$ may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthryl group, a substituted or unsubstituted pyrenyl group, a substituted or unsubstituted fluorenyl group, a substituted or unsubstituted naphthacenyl group, a substituted or unsubstituted chrysenyl group, a substituted or unsubstituted triphenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group. substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group and a substituted or unsubstituted phenoxazinyl group.

In one embodiment of the present invention, provided is a compound for an organic optoelectronic device where in the Chemical Formula 1, X is nitrogen(N), $X^1$ is —O—, —S—, —CR'R" or —SiR'R"—, wherein the R' and R" are independently hydrogen, deuterium, a substituted or unsubstituted C1 to C10 alkyl group, a substituted or unsubstituted C6 to C18 aryl group, $X^2$ is —O— or —S—, $L^1$ to $L^3$ are independently a phenyl group, n1 to n3 are 0 or 1, and $R^1$ to $R^3$, $Ar^1$ and $Ar^2$ are the same as defined above.

In one embodiment of the present invention, provided is a compound for an organic optoelectronic device where in the Chemical Formula 1, X is nitrogen (N), $X^1$ is —O—, —S—, —CR'R" or —SiR'R"—, wherein the R' and R" are independently hydrogen, deuterium, a substituted or unsubstituted C1 to C10 alkyl group, a substituted or unsubstituted C6 to C18 aryl group, $X^2$ is —O— or —S—, $L^1$ to $L^3$ are independently a phenyl group, n1 to n3 are 0 or 1, $Ar^1$ and $Ar^2$ are independently a substituted or unsubstituted C6 to C30 aryl group, and $R^1$ to $R^3$ are the same as defined above. Herein, $Ar^1$ and $Ar^2$ are independently one of a substituted or unsubstituted phenyl group, a substituted or unsubstituted biphenyl group, a substituted or unsubstituted triphenyl group, a substituted or unsubstituted phenanthryl group, a substituted or unsubstituted naphthyl group, a substituted or unsubstituted anthracenyl group, and a substituted or unsubstituted fluorenyl group, but is not limited thereto.

The structure represented by the Chemical Formula 1 may be used as a light emitting material, a hole injection material or a hole transport material of an organic optoelectronic device. Particularly, it may be appropriate for a hole injection material or hole transport material.

The compound for an organic optoelectronic device includes a core part and various substituents for a substituent for substituting the core part and thus may have various energy bandgaps.

When the compound having an appropriate energy level depending on a substituent is used to manufacture an organic optoelectronic device, the compound reinforces hole transport capability or electron transport capability and thus, brings about excellent effects in terms of efficiency and a driving voltage, and also, has excellent electrochemical and thermal stability and thus, may improve life-span characteristics of the organic optoelectronic device.

The X may be boron (B), nitrogen (N) or phosphorus (P). The nitrogen (N), boron (B) or phosphorus (P) has polarity, and thus makes charge injection easy due to interaction with an electrode.

The X is bonded with the substituent while linking groups $L^1$ to $L^3$ are positioned therebetween, and thus charge mobility increases, and a driving voltage of a device may be lowered.

A total pi conjugation length (π-conjugation length) is determined by controlling a length of the $L^1$ to $L^3$, and thereby bandgap and triplet energy level may be controlled appropriately.

Specific examples of the $L^1$ to $L^3$ may be a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylenyl group, a substituted or unsubstituted pyrenylene group, a substituted or unsubstituted fluorenylene group, a substituted or unsubstituted naphthacenyl group, a substituted or unsubstituted chrysenyl group, a substituted or unsubstituted triphenylenyl group, or a substituted or unsubstituted perylenyl group.

More specifically, $L^1$ to $L^3$ is a substituted or unsubstituted phenylene group and may be the following Chemical Formulae S-1, S-2 and S-3.

[Chemical Formula S-1]

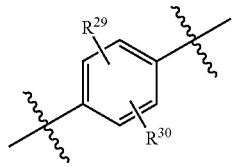

[Chemical Formula S-2]

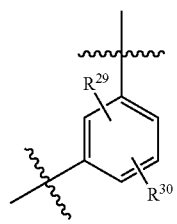

[Chemical Formula S-3]

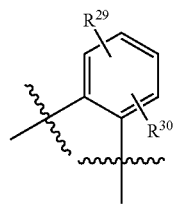

More specifically, the substituted or unsubstituted biphenylene group may be the following Chemical Formulae S-4, S-5 and S-6.

[Chemical Formula S-4]

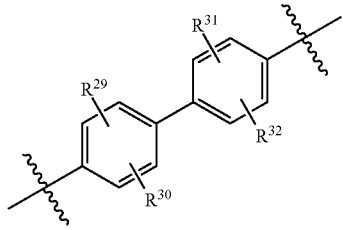

[Chemical Formula S-5]

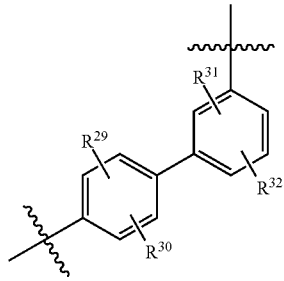

[Chemical Formula S-6]

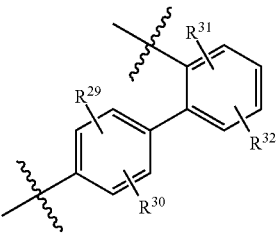

More specifically, the substituted or unsubstituted p-terphenylene group may be the following Chemical Formulae S-7, S-8 and S-9.

[Chemical Formula S-7]

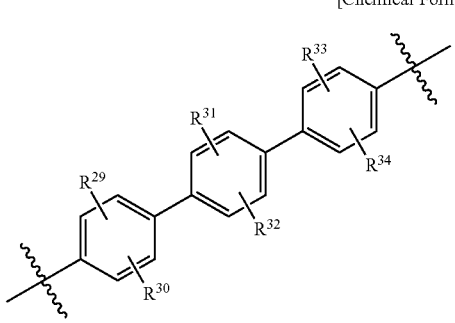

[Chemical Formula S-8]

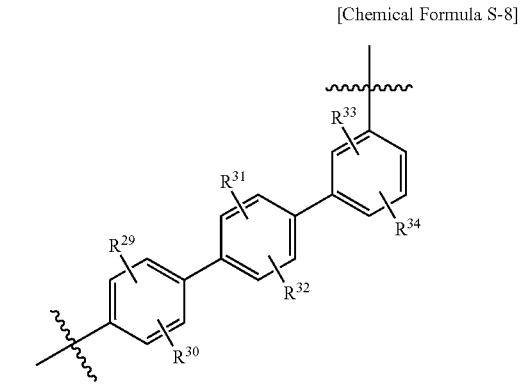

[Chemical Formula S-9]

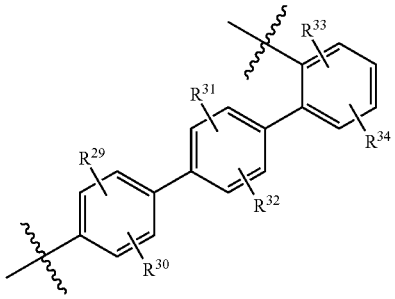

More specifically, the substituted or unsubstituted m-terphenylene group may be the following Chemical Formulae S-10, S-11 and S-12.

[Chemical Formula S-10]

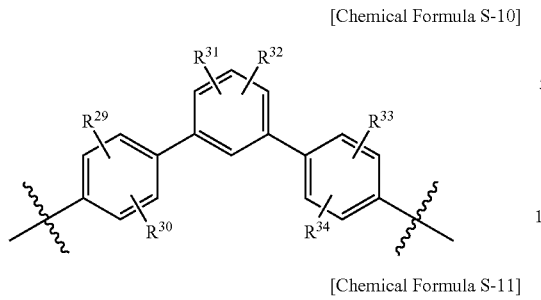

[Chemical Formula S-11]

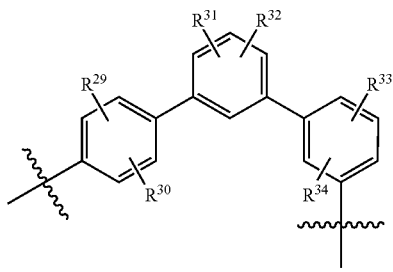

[Chemical Formula S-12]

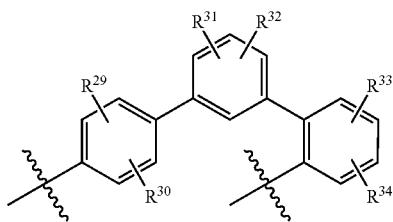

More specifically, the substituted or unsubstituted o-terphenylene group may be the following Chemical Formulae S-13, S-14 and S-15.

[Chemical Formula S-13]

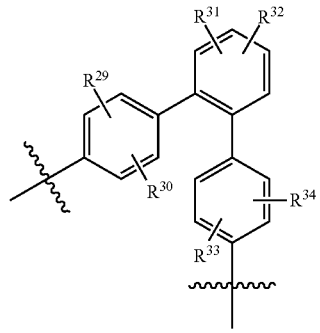

[Chemical Formula S-14]

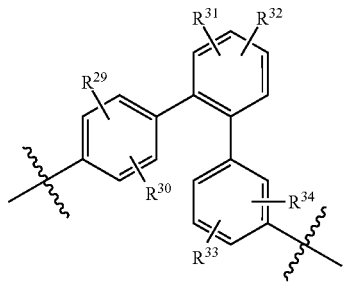

[Chemical Formula S-15]

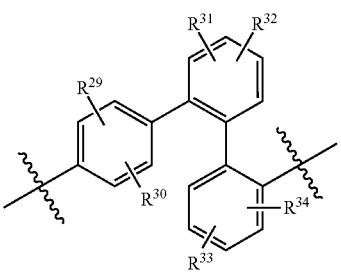

More specifically, a substituted or unsubstituted naphthylene group may be the following Chemical Formulae S-16, S-17, S-18, S-19, S-20, S-21 and S-22.

[Chemical Formula S-16]

[Chemical Formula S-17]

[Chemical Formula S-18]

[Chemical Formula S-19]

[Chemical Formula S-20]

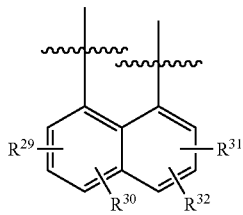

[Chemical Formula S-21]

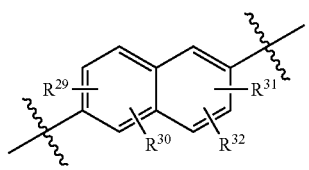

[Chemical Formula S-22]

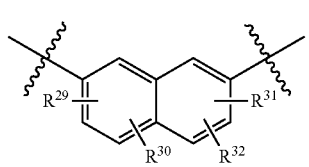

More specifically, the substituted or unsubstituted anthracenylene group may be the following Chemical Formulae S-23, S-24, S-25, S-26, S-27, S-28 and S-29.

[Chemical Formula S-23]

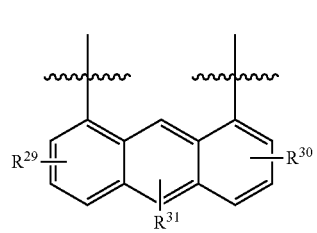

[Chemical Formula S-24]

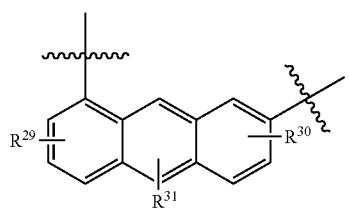

[Chemical Formula S-25]

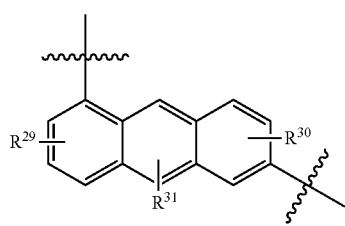

[Chemical Formula S-26]

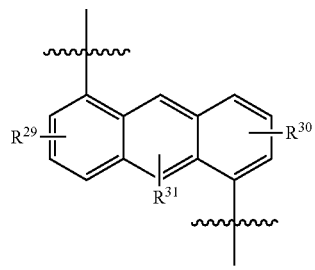

[Chemical Formula S-27]

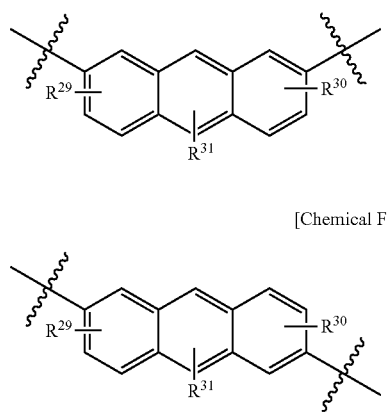

[Chemical Formula S-28]

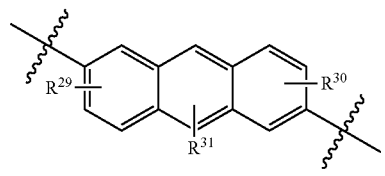

[Chemical Formula S-29]

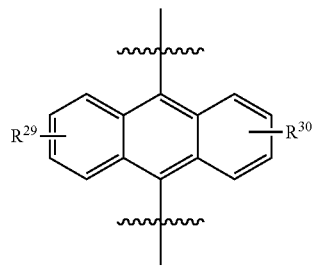

More specifically, the substituted or unsubstituted phenanthrylenyl group may be the following Chemical Formulae S-30, S-31, S-32, S-33, S-34, S-35, S-36, S-37, S-38, S-39 and S-40.

[Chemical Formula S-30]

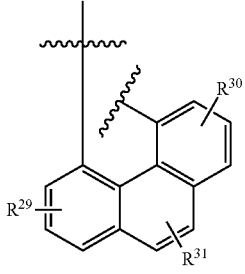

[Chemical Formula S-31]

[Chemical Formula S-32]

[Chemical Formula S-33]

[Chemical Formula S-34]

[Chemical Formula S-35]

[Chemical Formula S-36]

[Chemical Formula S-37]

[Chemical Formula S-38]

[Chemical Formula S-39]

[Chemical Formula S-40]

More specifically, the substituted or unsubstituted pyrenylene group may be the following Chemical Formulae S-41, S-42, S-43, S-44, S-45 and S-46.

[Chemical Formula S-41]

[Chemical Formula S-42]

[Chemical Formula S-43]

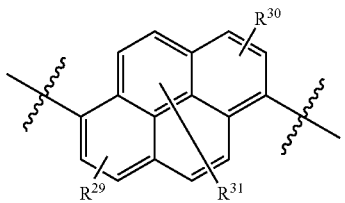

[Chemical Formula S-44]

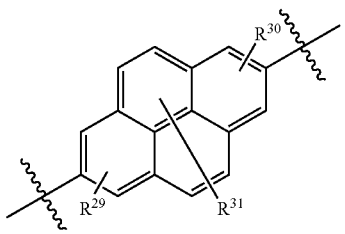

[Chemical Formula S-45]

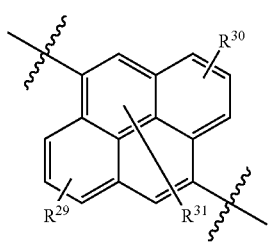

[Chemical Formula S-46]

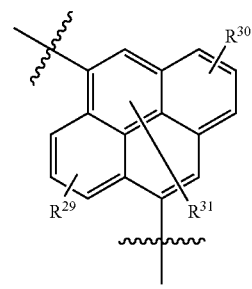

More specifically, the substituted or unsubstituted fluorenylene group may be the following Chemical Formulae S-47, S-48, S-49, S-50, S-51, S-52, S-53, S-54, S-55 and S-56.

[Chemical Formula S-47]

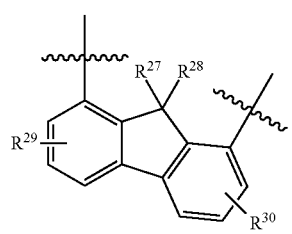

[Chemical Formula S-48]

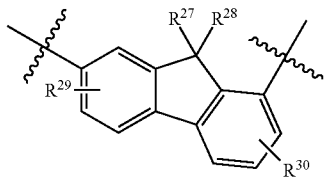

[Chemical Formula S-49]

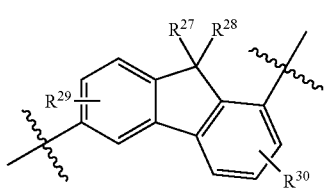

[Chemical Formula S-50]

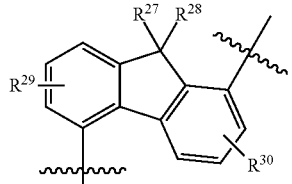

[Chemical Formula S-51]

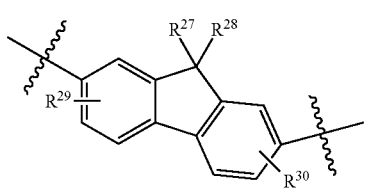

[Chemical Formula S-52]

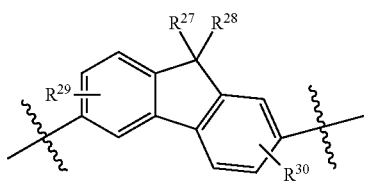

[Chemical Formula S-53]

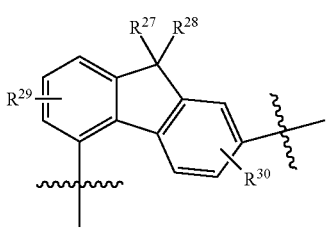

[Chemical Formula S-54]

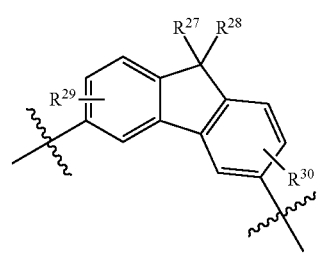

-continued

[Chemical Formula S-55]

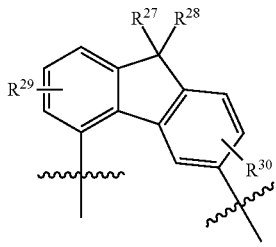

[Chemical Formula S-56]

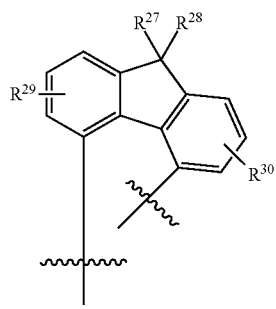

In specific examples of the $L^1$ to $L^3$, $R^{27}$ to $R^{34}$ are independently, hydrogen, deuterium, a halogen, hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like, or a cyano group.

More specifically, at least one of $X^1$ or $X^2$ may be —CR'R"—, —SiR'R" or —GeR'R"—, and more specifically —CR'R" or —SiR'R"—.

In addition, the compound may suppress has a small molecular interaction due to steric hindrance, and thus crystallization may be suppressed. Thereby, a manufacture yield of a device is improved. In addition, life-span characteristics of a device may be improved.

The compound has a relatively large molecular weight, and a compound decomposition may be suppressed during deposition.

More specifically, the compound for an organic optoelectronic device may be represented by the following Chemical Formula 2.

[Chemical Formula 2]

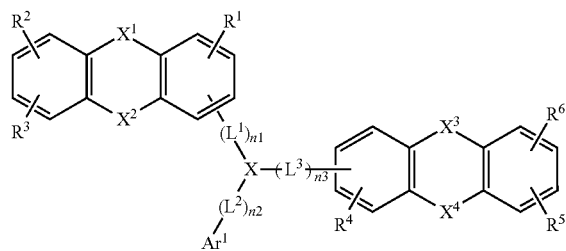

In the Chemical Formula 2, X is boron (B), nitrogen (N), or phosphorus (P), $X^1$ to $X^4$ are independently —O—, —S—, —S($O_2$)—, —CR'R"—, —SiR'R" or —GeR'R"—, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, at least one of $X^1$ or $X^3$ is —CR'R"—, —SiR'R" or —GeR'R"—, $L^1$ to $L^3$ are independently, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, $Ar^1$ is a substituted or unsubstituted C6 to C30 aryl group or a substituted or unsubstituted C2 to C30 heteroaryl group, $R^1$ to $R^6$ are independently, hydrogen, deuterium, a substituted or unsubstituted C1 to C10 alkyl group, a substituted or unsubstituted C6 to C30 aryl group or a substituted or unsubstituted C2 to C30 heteroaryl group, and n1 to n3 are independently integers of 0 to 3.

The $X^1$ or $X^3$ may be —CR'R"—, —SiR'R" or —GeR'R"—, and more specifically —CR'R" or —SiR'R"—. In this case, a molecule structure becomes to be rigid and thermal stability may be improved by increasing a glass transition temperature.

In addition, compared with a compound consisting of oxygen or sulfur having unshared electron pairs, bandgap energy and a tripletenergy level increases and thus high efficiency characteristics may be realized when being applied to a phosphorescent light emitting host material and a hole transport material.

$Ar^1$ is a substituted or unsubstituted C6 to C30 aryl group. The aryl group having an appropriate conjugation length increases hole mobility of the entire molecule and may realize a low driving voltage and high efficiency characteristics of an organic optoelectronic device when being applied as a hole transport layer (HTL) material.

$Ar^1$ is a substituted or unsubstituted C2 to C30 heteroaryl group. In this case, the entire molecule has a bipolar structure, it may be used as a phosphorescent host and hole barrier layer material. A compound having such a bipolar structure shows high efficiency characteristics.

In addition, the heteroaryl group may be an electron donor, and in this case, an ionization potential of the entire molecule increases and hole transport properties increases. When such a compound is used as a hole transport material, a low driving voltage, and high efficiency characteristics may be realized.

More specifically, the compound for an organic optoelectronic device may be represented by the following Chemical Formula 3.

[Chemical Formula 3]

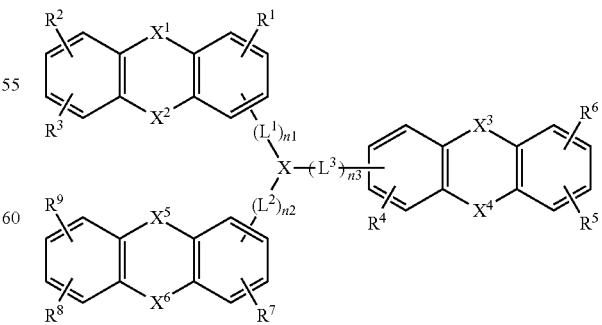

In the Chemical Formula 3, X is boron (B), nitrogen (N), or phosphorus (P), $X^1$ to $X^5$ are independently —O—, —S—, —S(O₂)—, —CR'R"—, —SiR'R" or —GeR'R"—, X⁶ is a single bond, —O—, —S—, —S(O₂)—, —CR'R"—, —SiR'R" or —GeR'R"—, wherein the R' and R" are independently hydrogen, deuterium, a substituted or unsubstituted C1 to C10 alkyl group, a substituted or unsubstituted C6 to C30 aryl group or a substituted or unsubstituted C2 to C30 heteroaryl group, at least one of X¹, X³ and X⁵ is —CR'R"—, —SiR'R" or —GeR'R"—, L¹ to L³ are independently, a substituted or unsubstituted C2 to C10 alkenylene group, a substituted or unsubstituted C2 to C10 alkynylene group, a substituted or unsubstituted C6 to C30 arylene group or a substituted or unsubstituted C2 to C30 heteroarylene group, R¹ to R⁹ are independently, hydrogen, deuterium, a substituted or unsubstituted C1 to C10 alkyl group, a substituted or unsubstituted C6 to C30 aryl group or a substituted or unsubstituted C2 to C30 heteroaryl group, and n1 to n3 are independently integers of 0 to 3.

At least one of the X¹, X³ or X⁵ may be —CR'R"—, —SiR'R" or —GeR'R"—, and more specifically —CR'R" or —SiR'R"—.

In this case, a molecule structure becomes to be rigid and thermal stability may be improved by increasing a glass transition temperature.

In addition, compared with a compound consisting of oxygen or sulfur having unshared electron pairs, bandgap energy and a tripletenergy level increases and thus high efficiency characteristics may be realized when being applied to a phosphorescent light emitting host material and a hole transport material.

The R¹ to R⁹ may be independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, or a combination thereof, but are not limited thereto.

In addition, R¹ to R⁹ of the Chemical Formula 3 may be the same as R¹ to R³ of the Chemical Formula 1 and R¹ to R⁶ of the Chemical Formula 2.

The compound for an organic optoelectronic device may have light emitting, hole or electron characteristics; film stability; thermal stability and improved triplet exciton energy (T1) due to the substituents.

More specifically, the compound for an organic optoelectronic device may be represented by one of the following Chemical Formulae A-1 to A-166, but is not limited thereto.

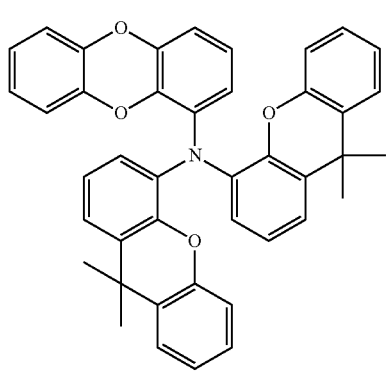

[A-1]

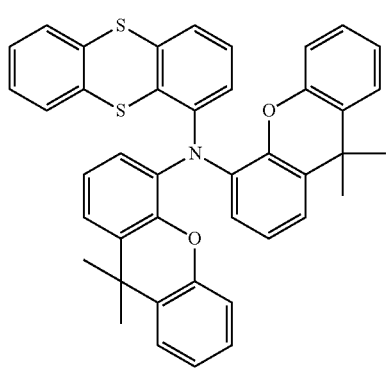

[A-2]

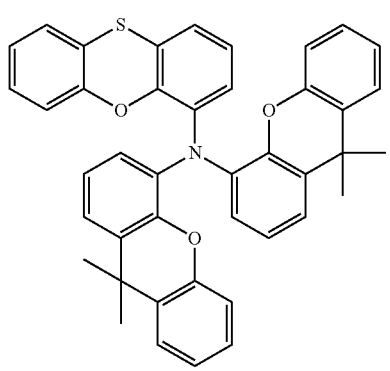

[A-3]

[A-4]
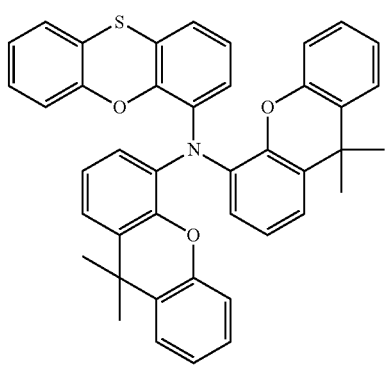
[A-8]
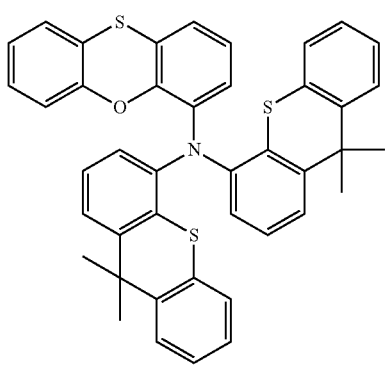
[A-5]
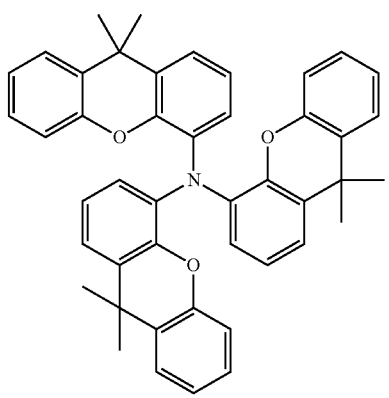
[A-9]
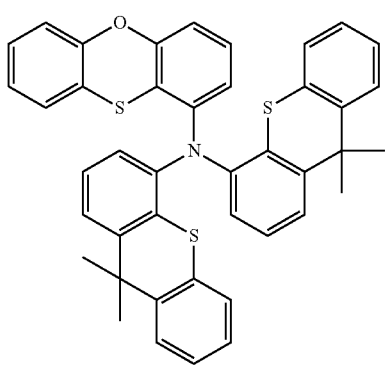
[A-6]
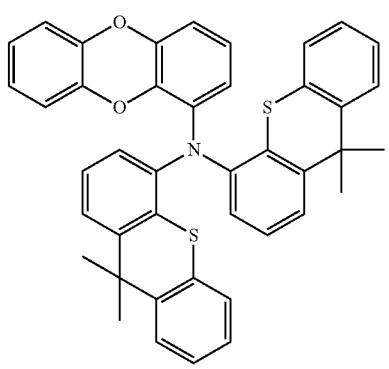
[A-10]
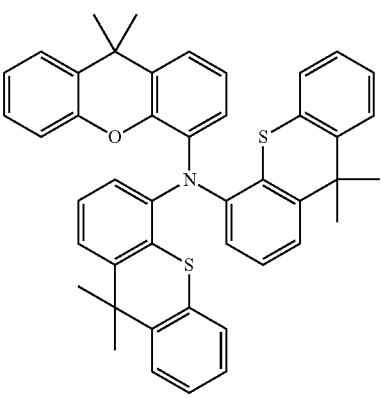
[A-7]
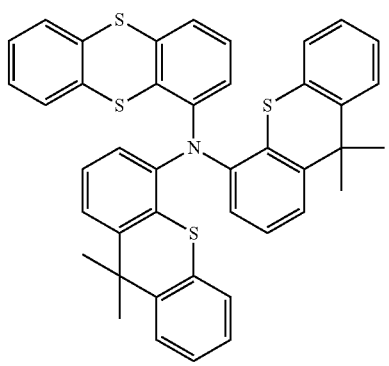
[A-11]
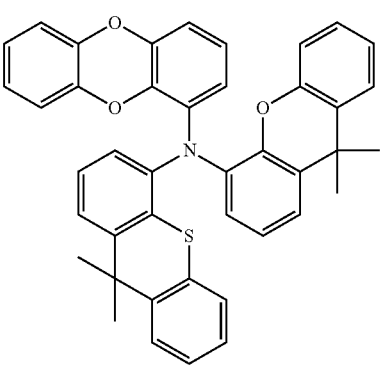

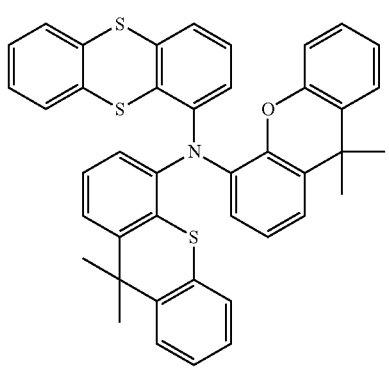
[A-12]
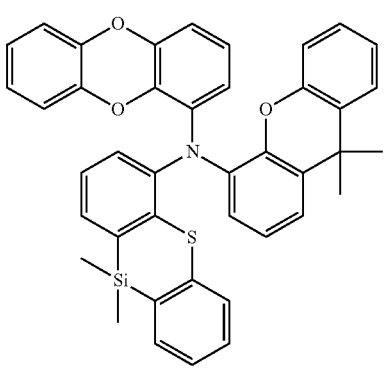
[A-16]
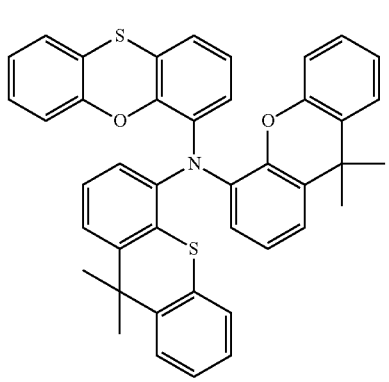
[A-13]
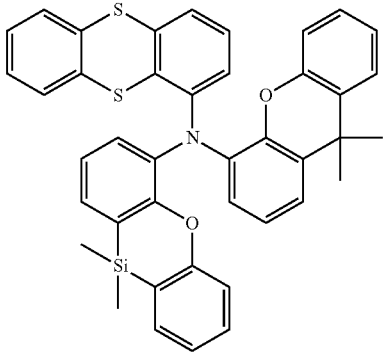
[A-17]
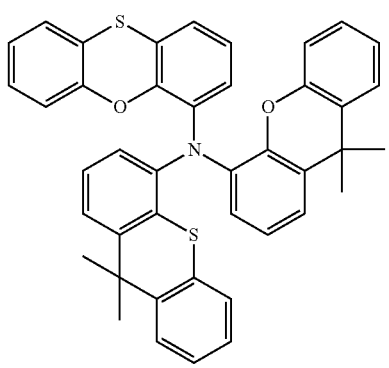
[A-14]
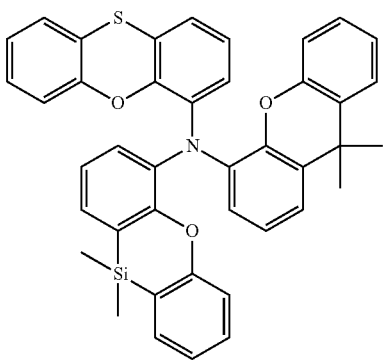
[A-18]
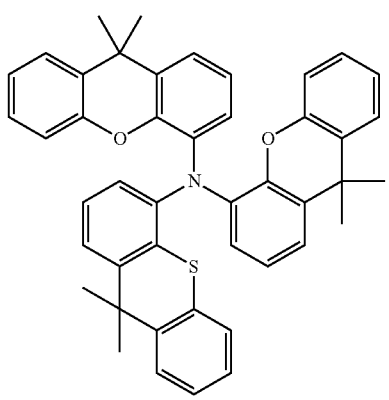
[A-15]
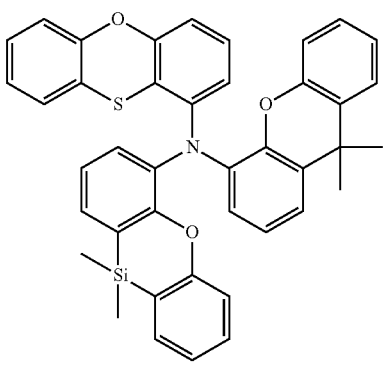
[A-19]

[A-20] 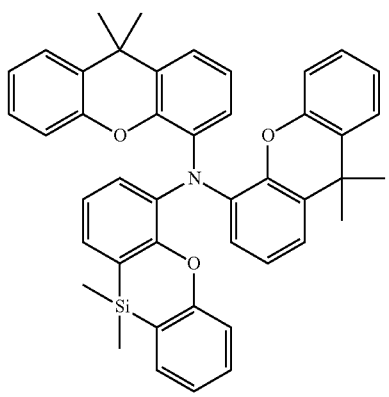
[A-24] 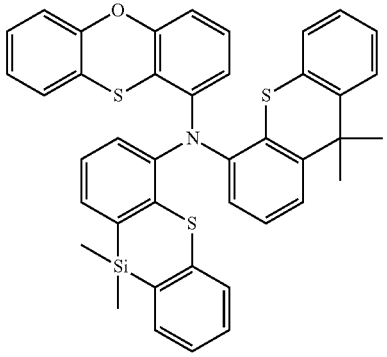
[A-21] 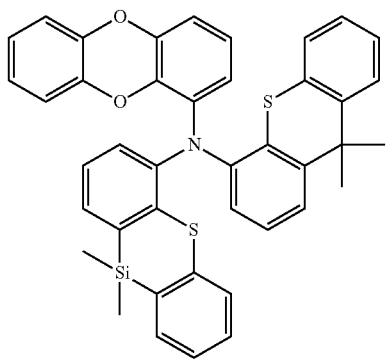
[A-25] 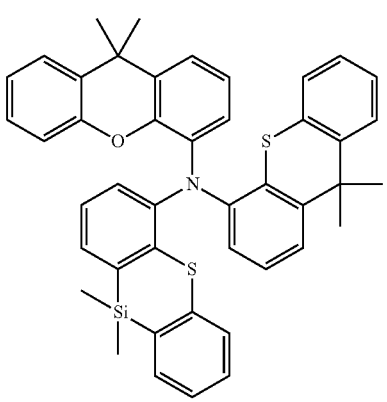
[A-22] 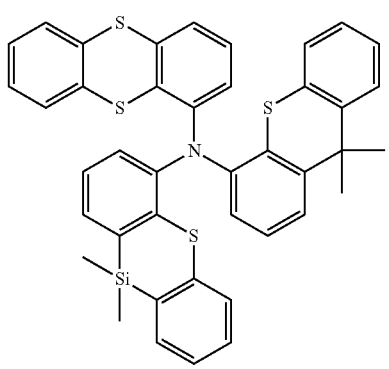
[A-26] 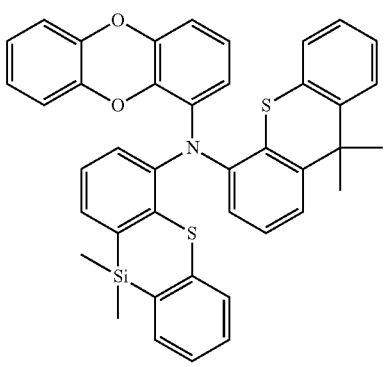
[A-23] 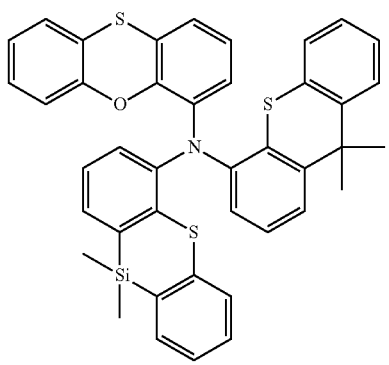
[A-27] 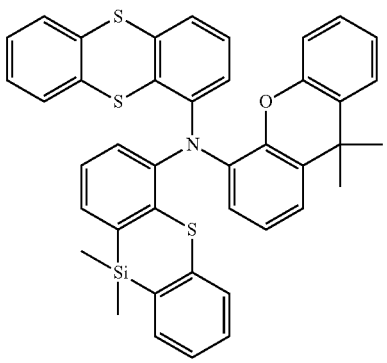

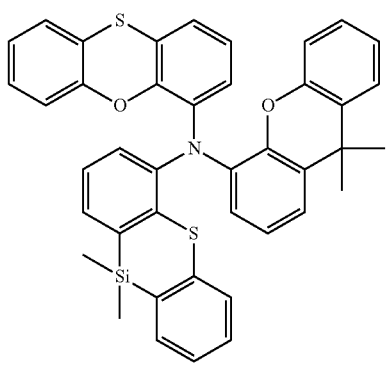
[A-28]
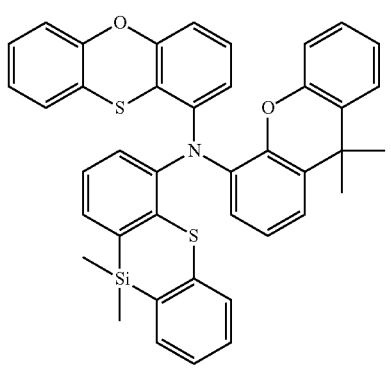
[A-29]
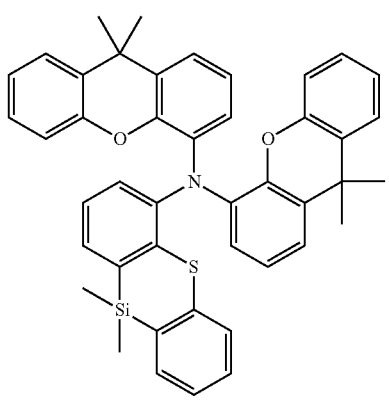
[A-30]
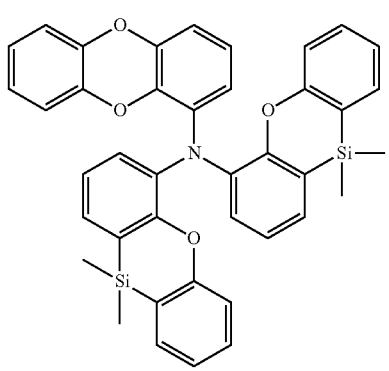
[A-31]
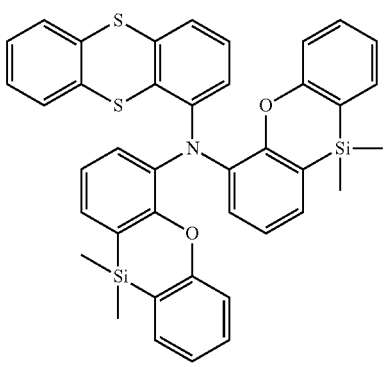
[A-32]
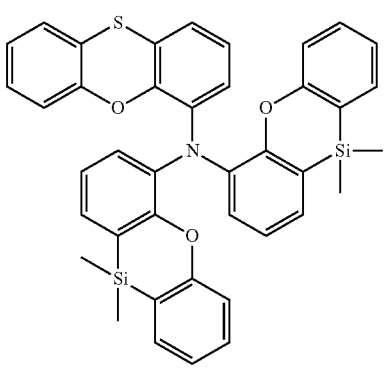
[A-33]
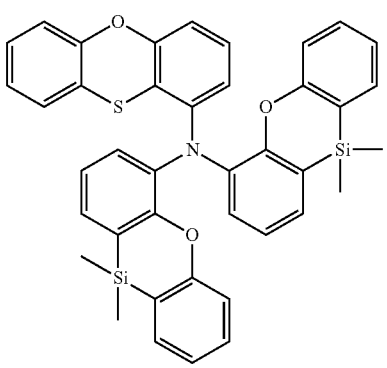
[A-34]
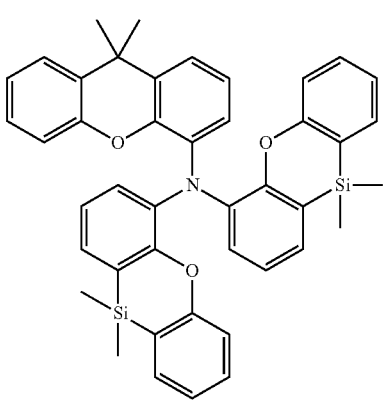
[A-35]

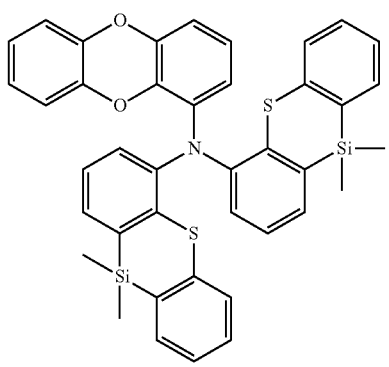
[A-36]
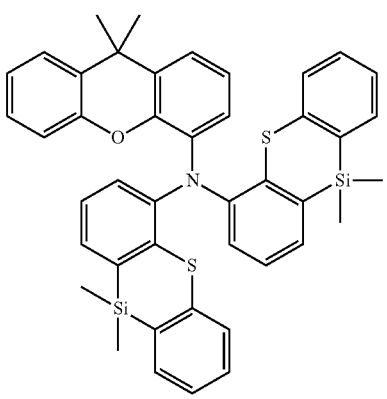
[A-40]
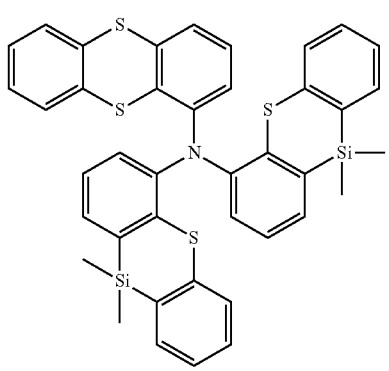
[A-37]
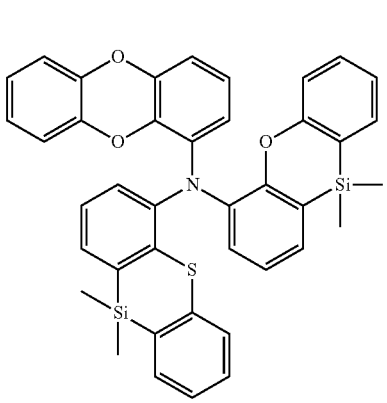
[A-41]
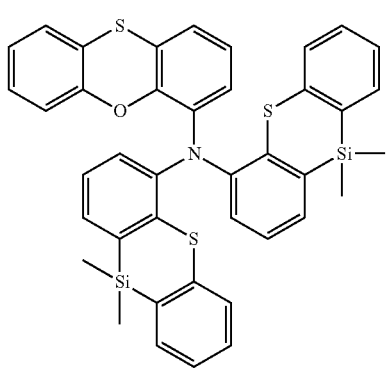
[A-38]
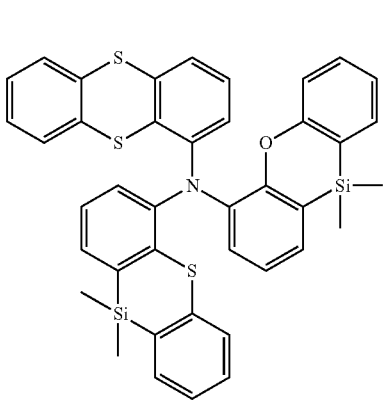
[A-42]
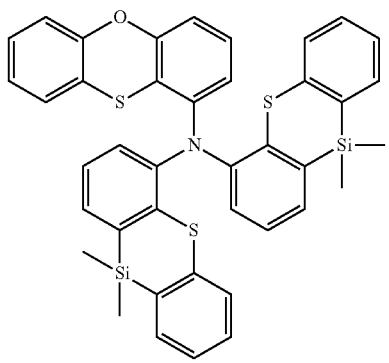
[A-39]
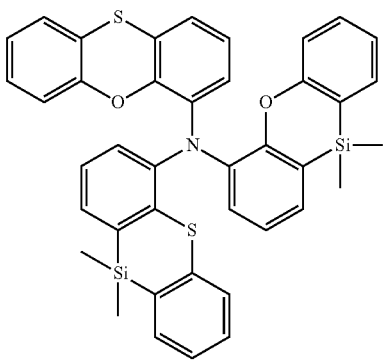
[A-43]

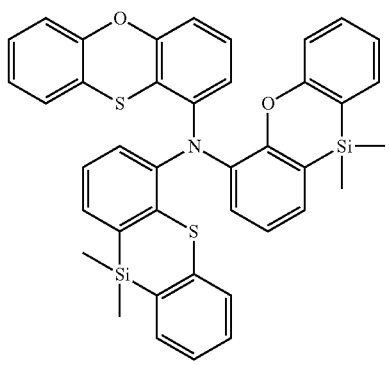
[A-44]
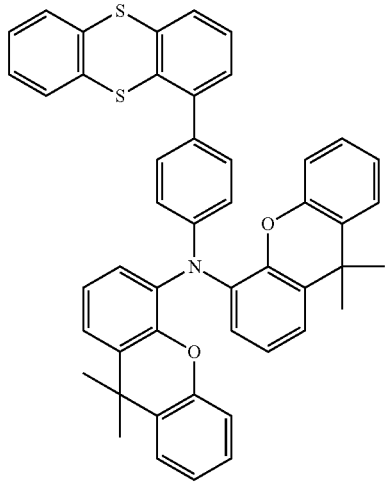
[A-47]
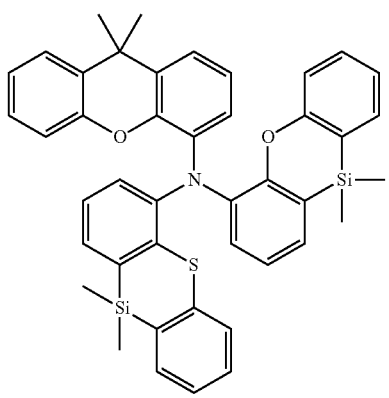
[A-45]
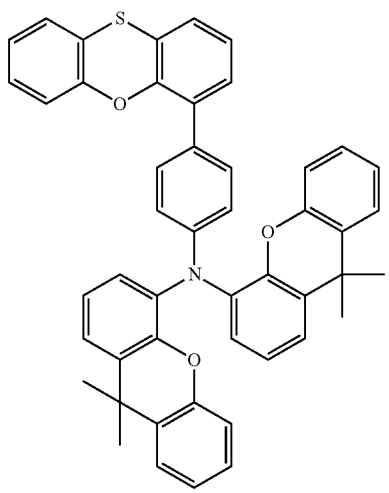
[A-48]
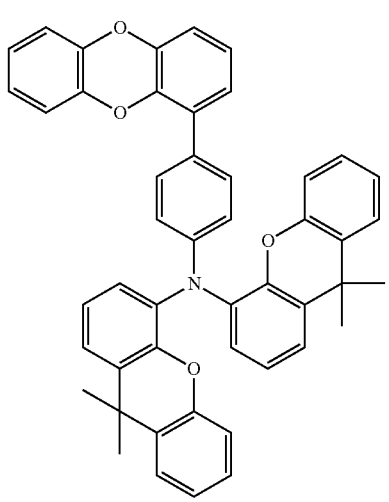
[A-46]
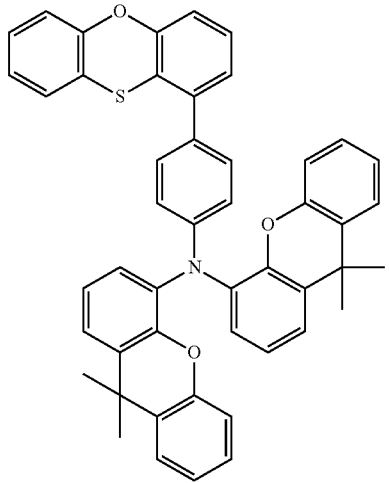
[A-49]

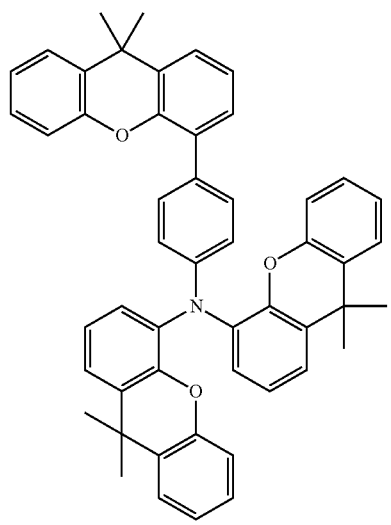
[A-50]
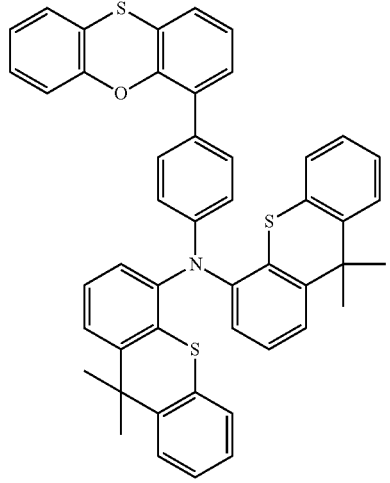
[A-53]
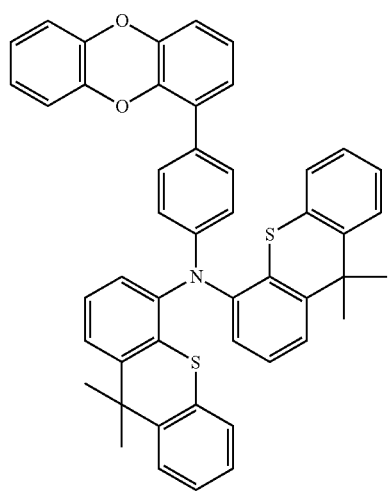
[A-51]
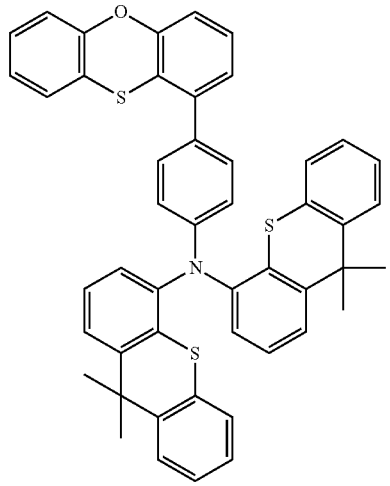
[A-54]
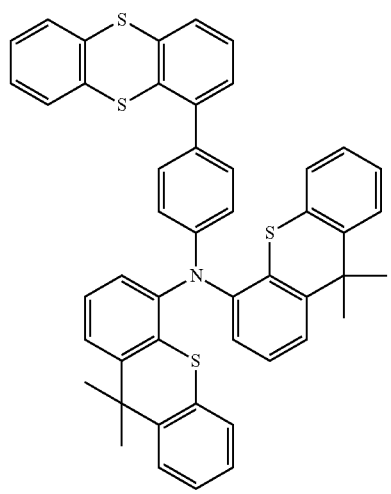
[A-52]
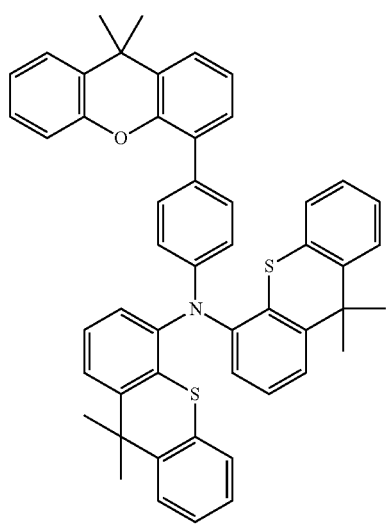
[A-55]

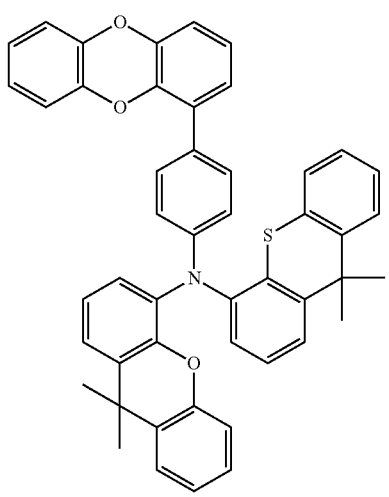
[A-56]
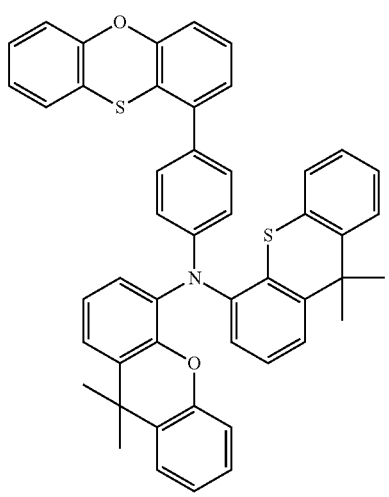
[A-59]
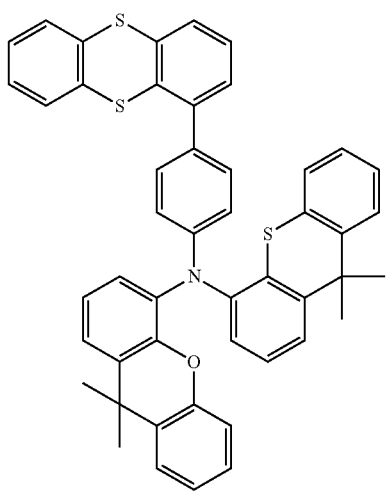
[A-57]
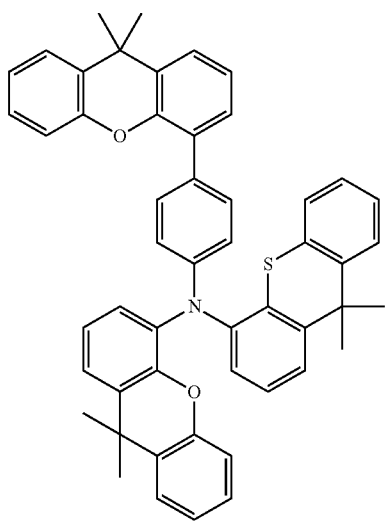
[A-60]
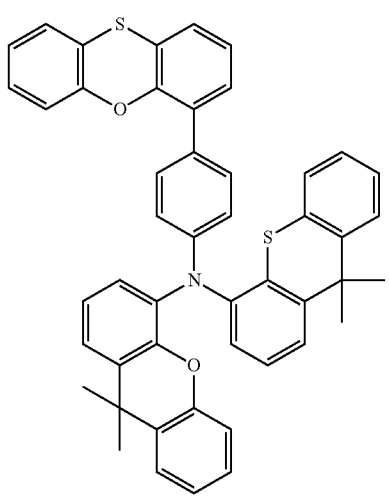
[A-58]
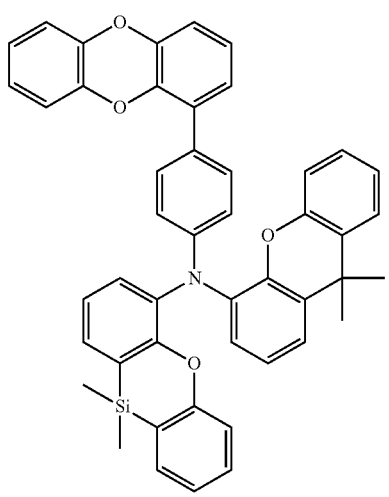
[A-61]

[A-62]
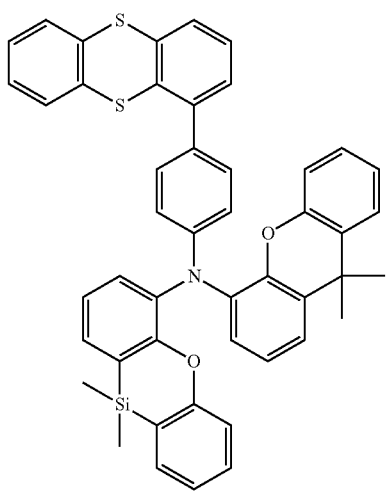
[A-65]
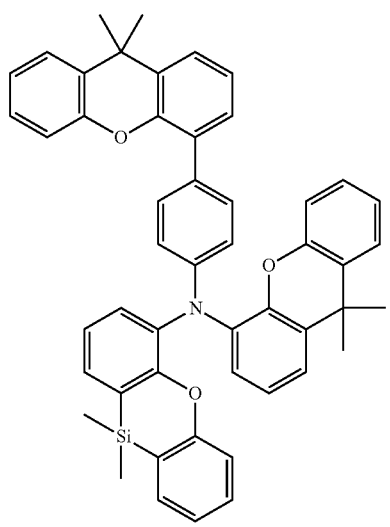
[A-63]
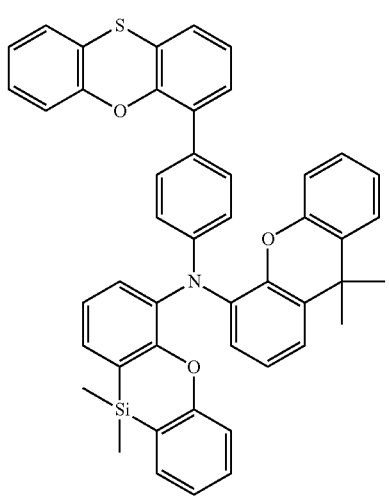
[A-66]
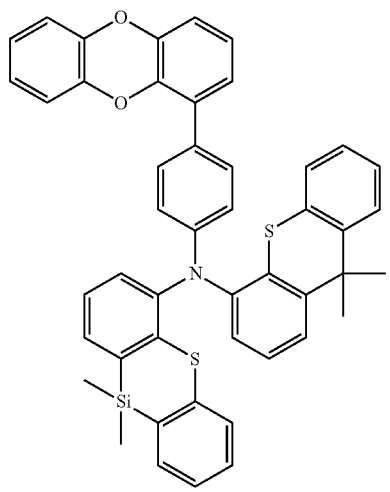
[A-64]
[A-67]
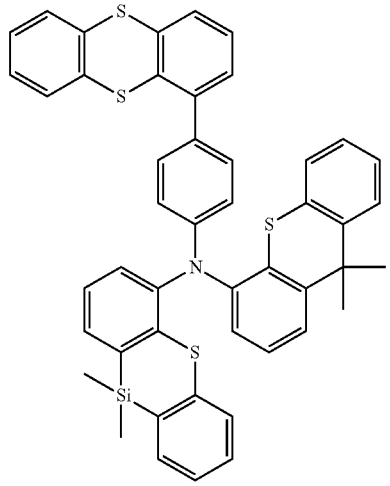

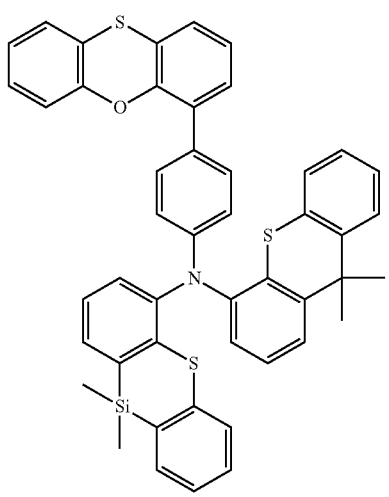
[A-68]
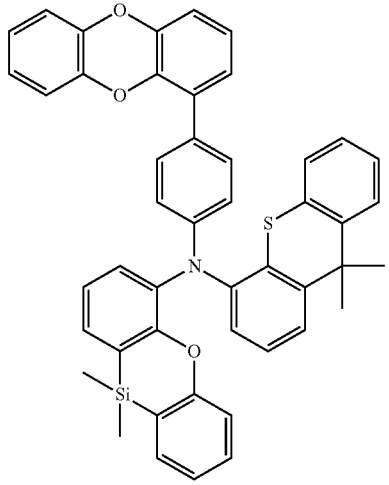
[A-71]
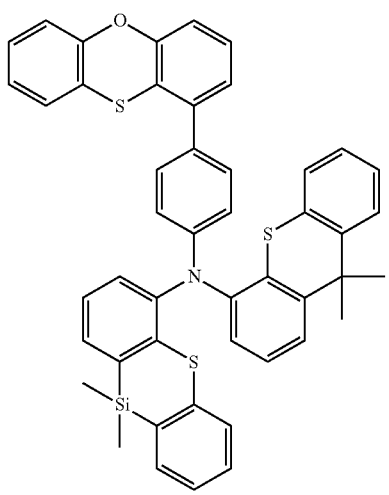
[A-69]
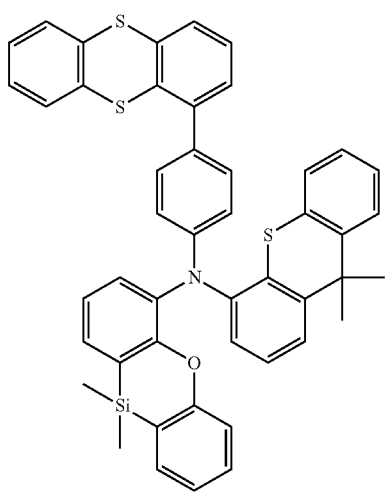
[A-72]
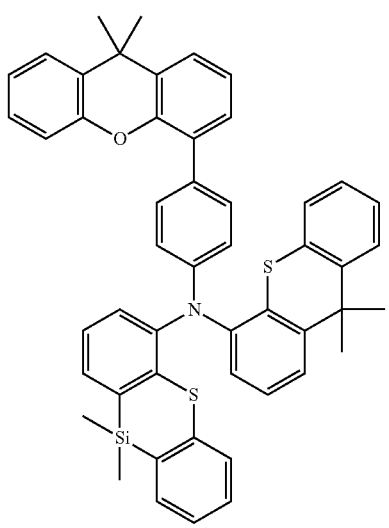
[A-70]
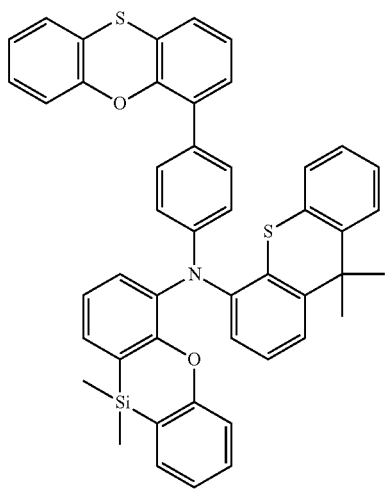
[A-73]

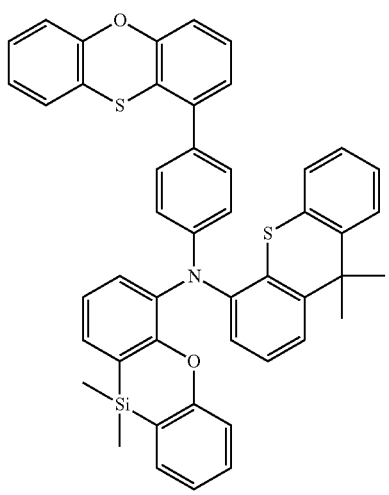
[A-74]
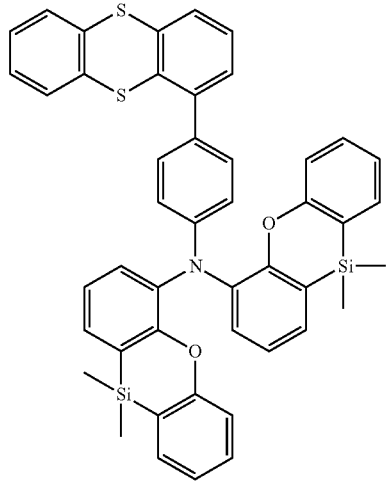
[A-77]
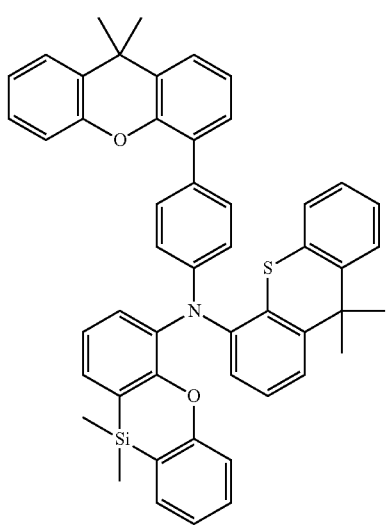
[A-75]
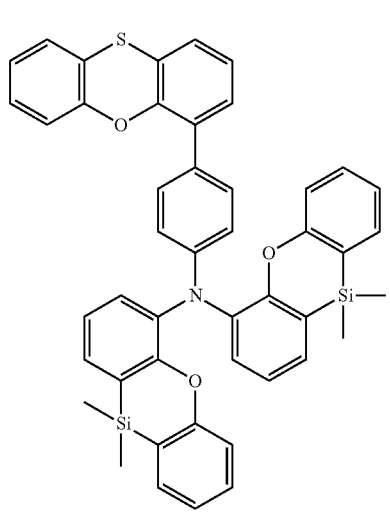
[A-78]
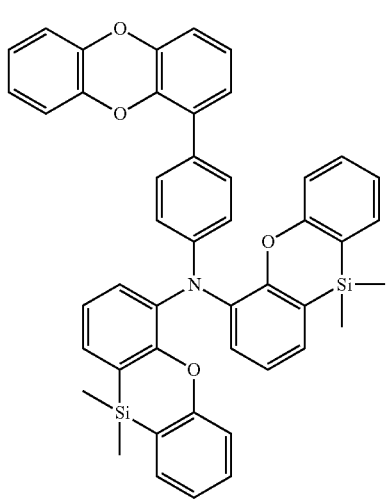
[A-76]
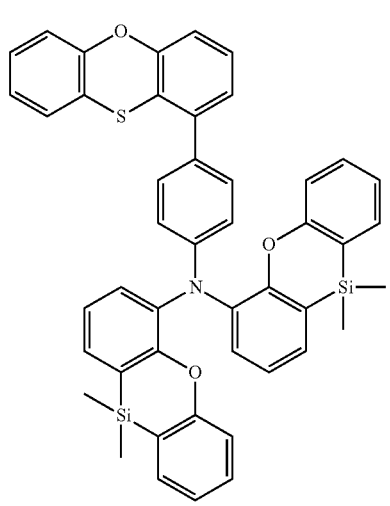
[A-79]

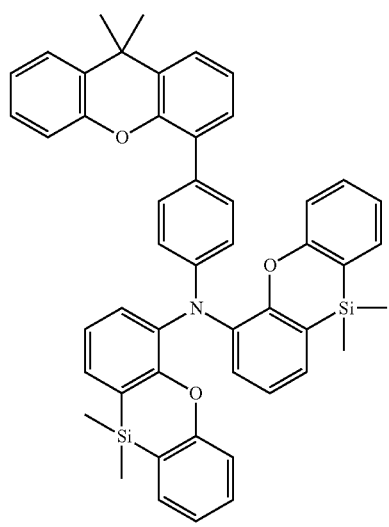
[A-80]
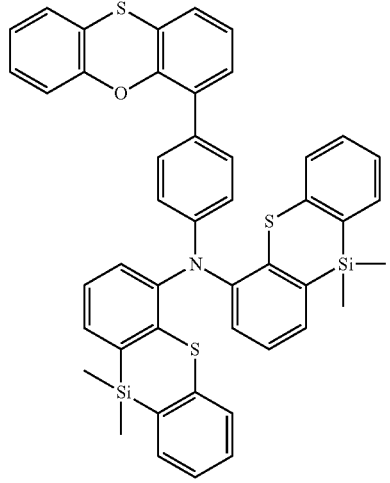
[A-83]
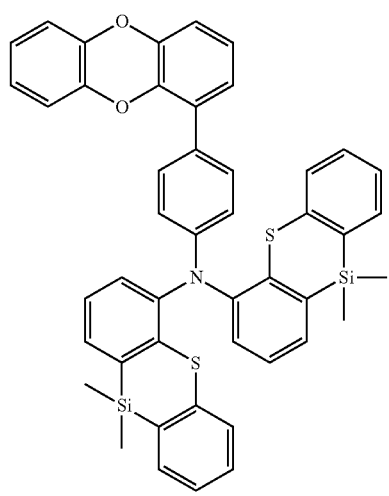
[A-81]
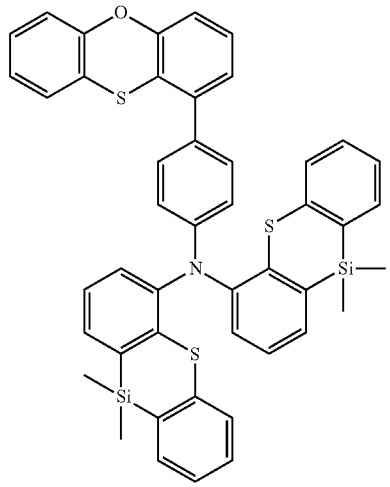
[A-84]
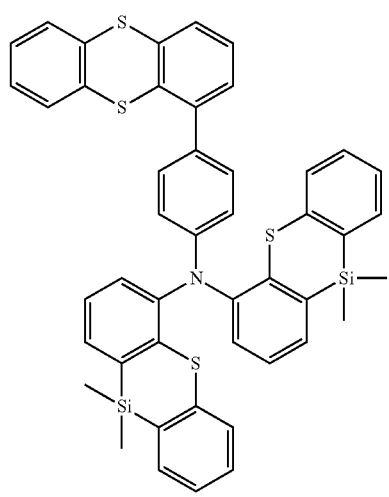
[A-82]
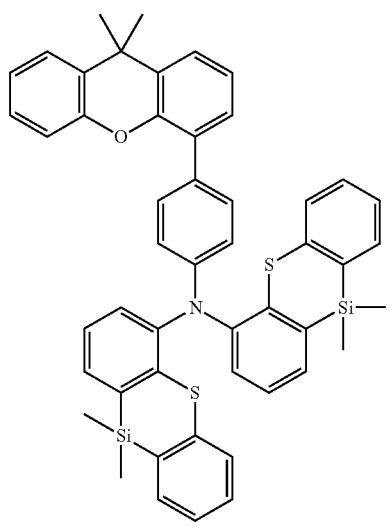
[A-85]

[A-86]
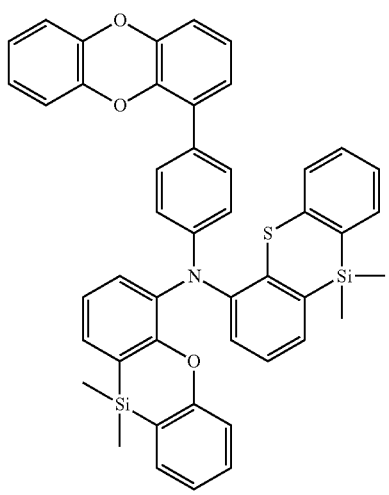
[A-89]
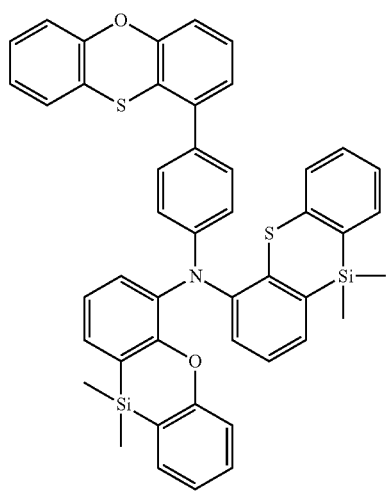
[A-87]
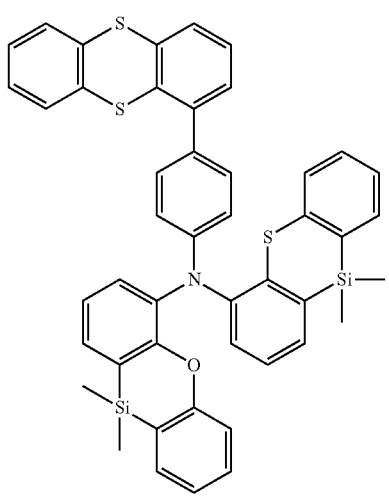
[A-90]
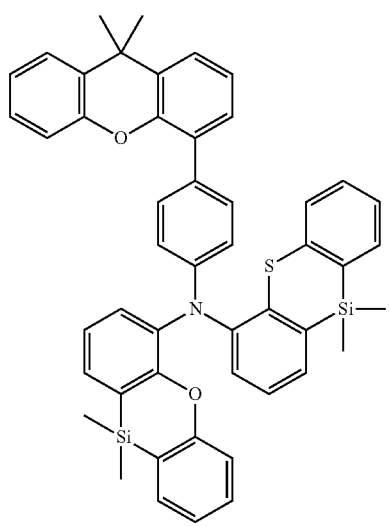
[A-88]
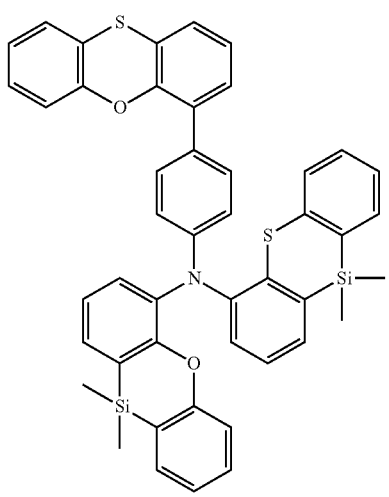
[A-91]
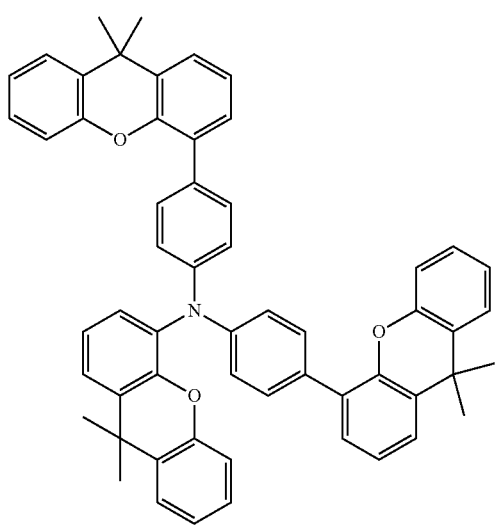

[A-92]
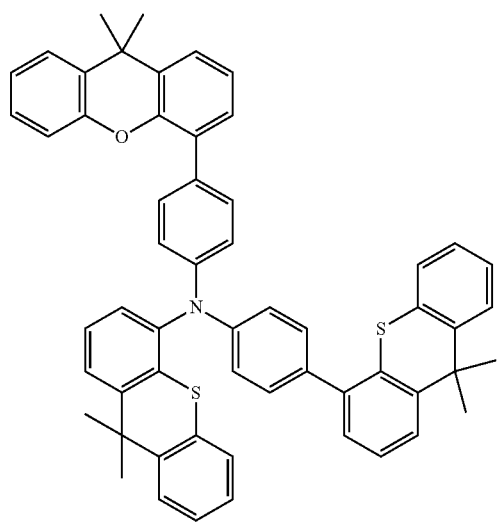
[A-95]
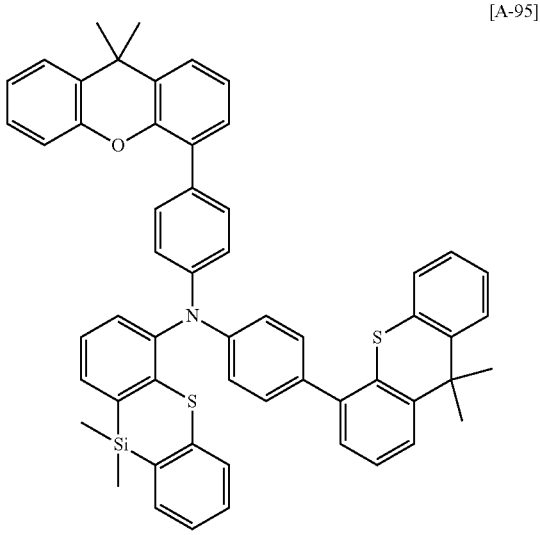
[A-93]
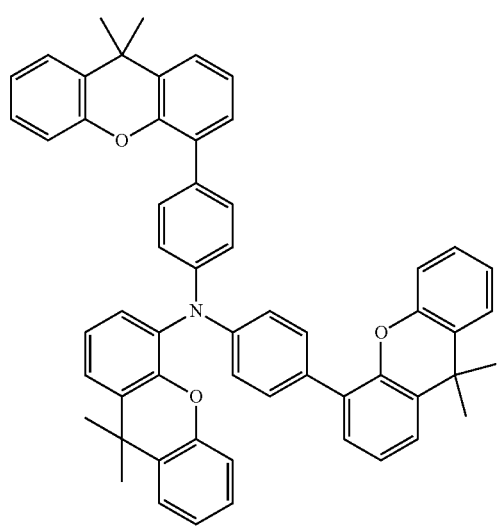
[A-96]
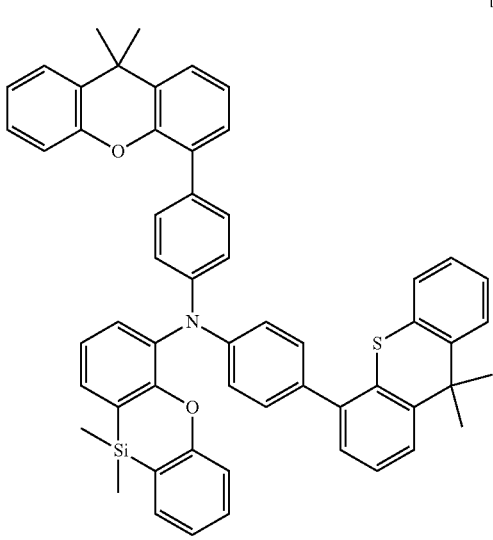
[A-94]
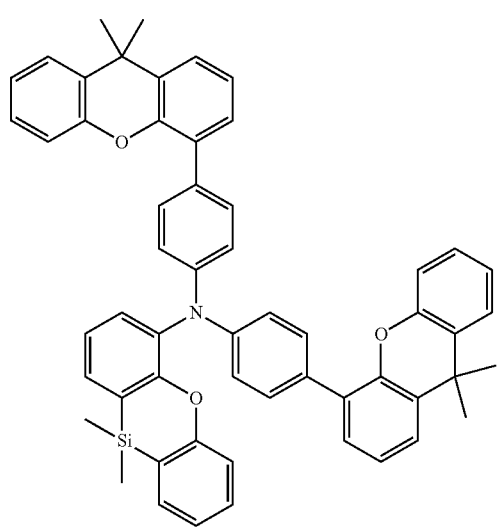
[A-97]
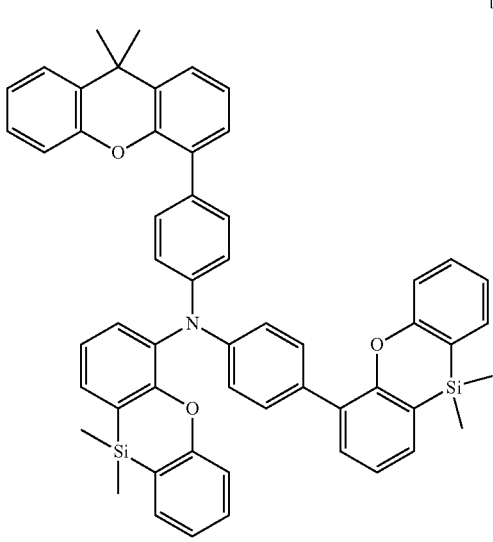

[A-98]
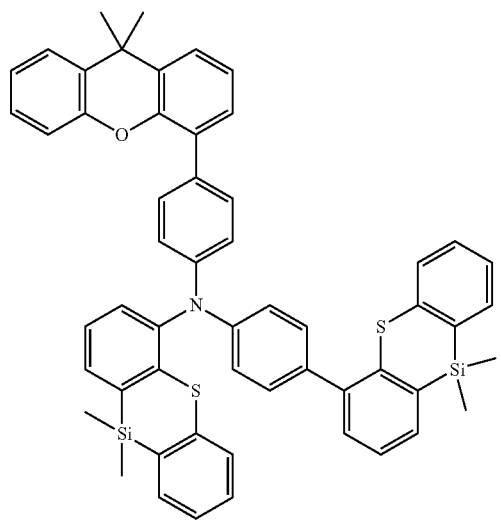
[A-99]
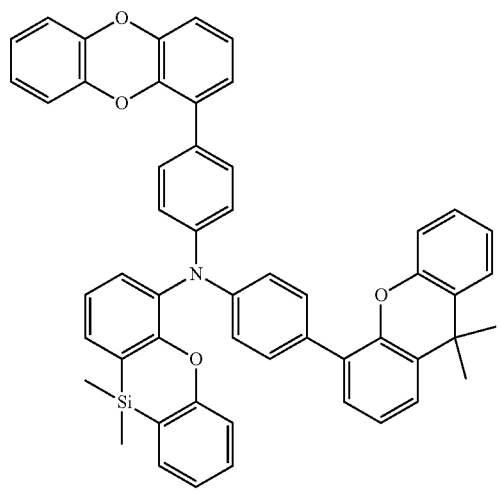
[A-100]
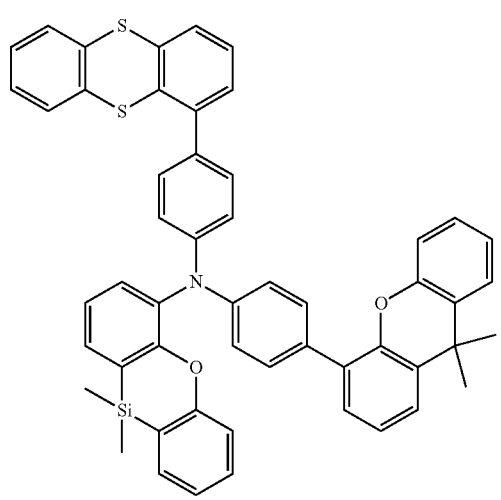
[A-101]
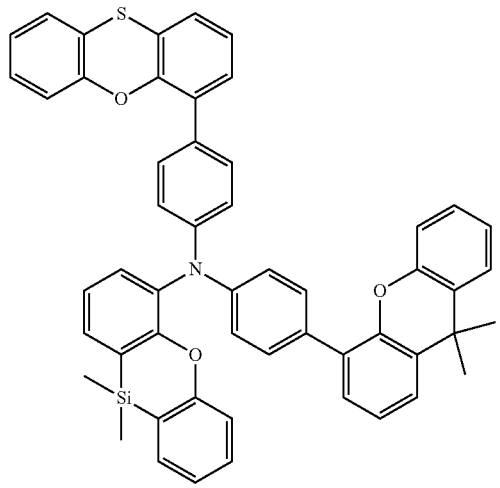
[A-102]
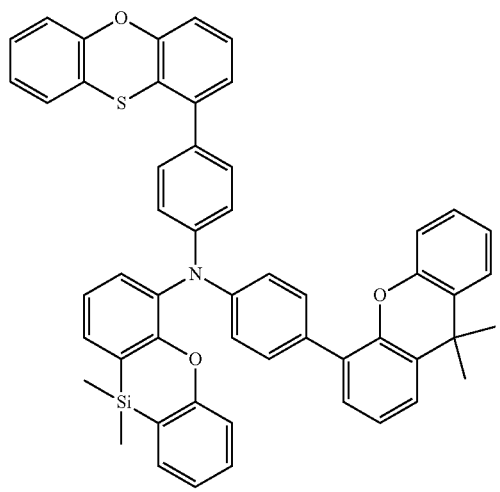
[A-103]
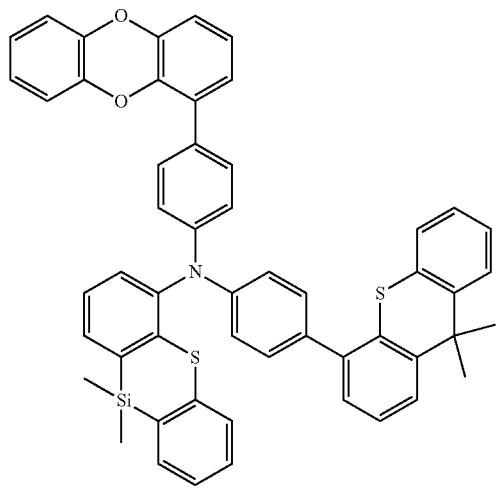

[A-104]
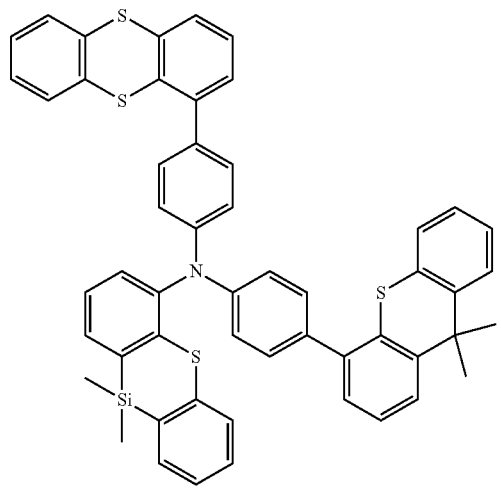
[A-107]
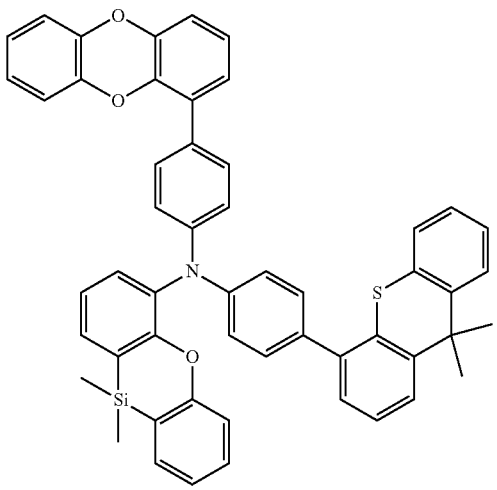
[A-105]
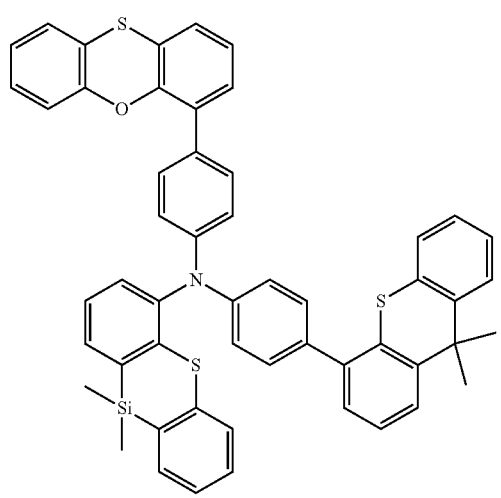
[A-108]
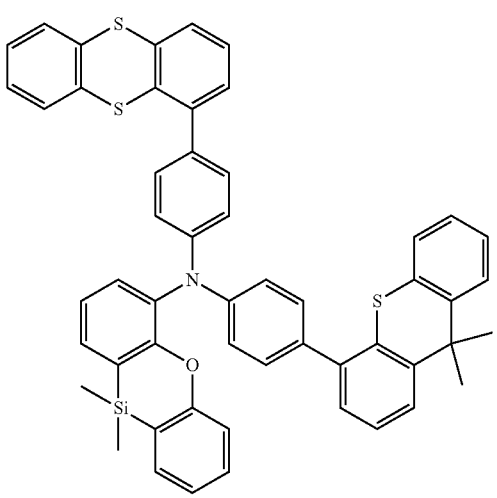
[A-106]
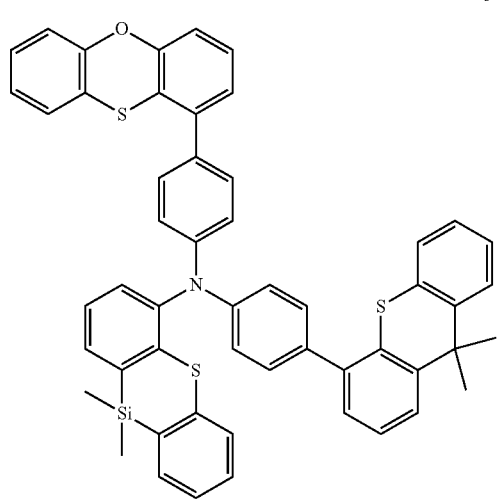
[A-109]
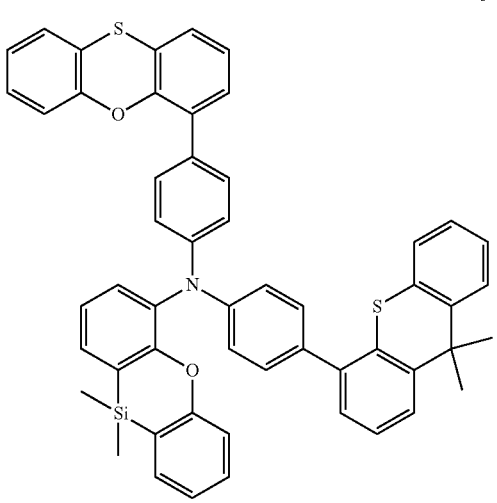

[A-110]
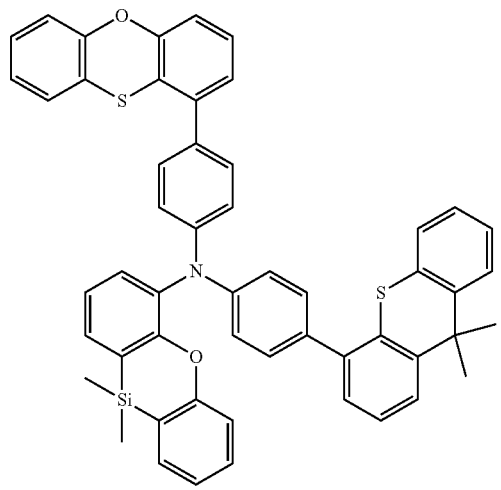
[A-113]
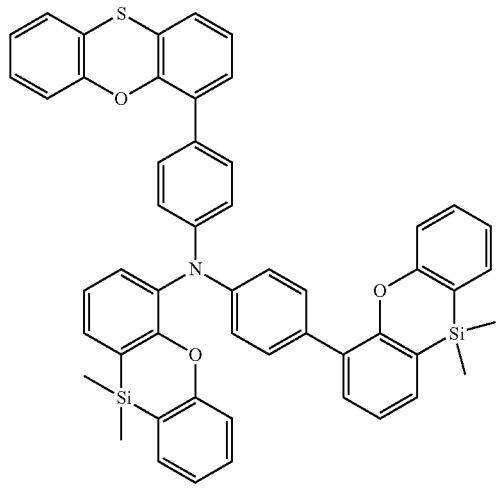
[A-111]
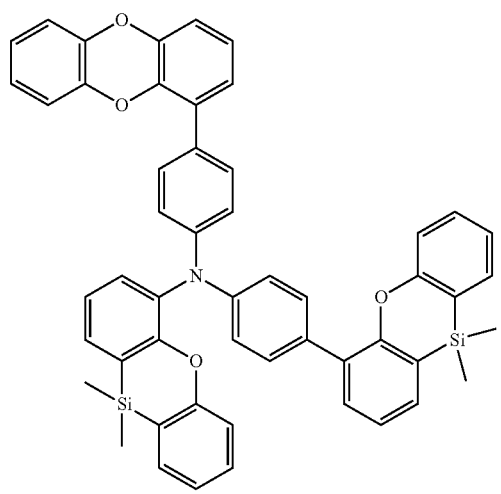
[A-114]
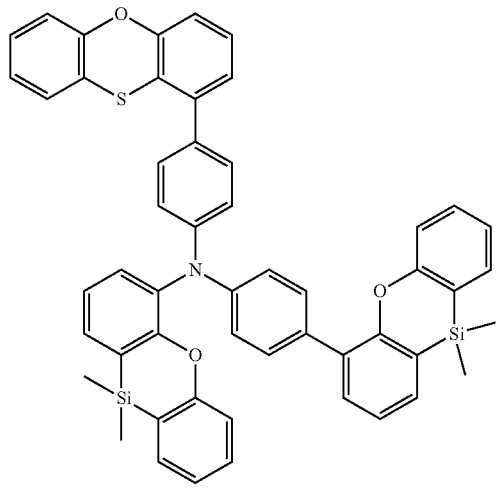
[A-112]
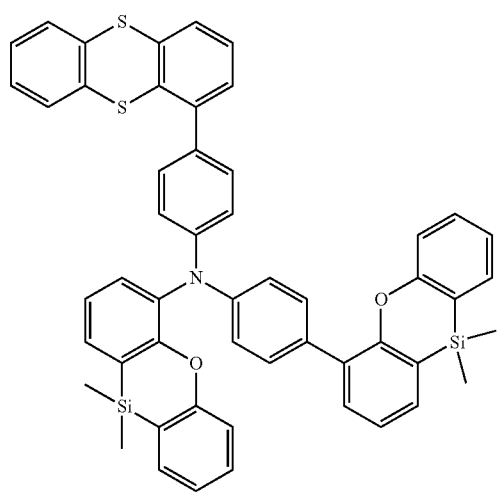
[A-115]
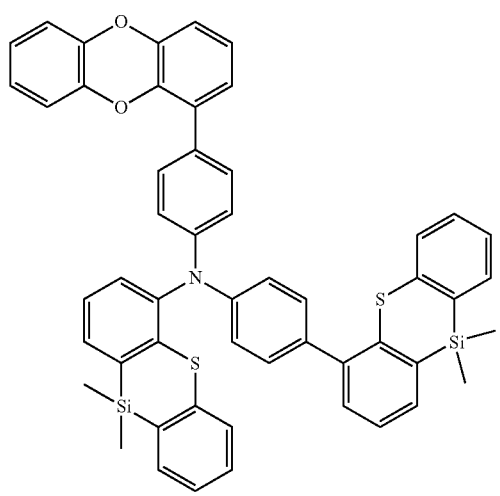

[A-116]
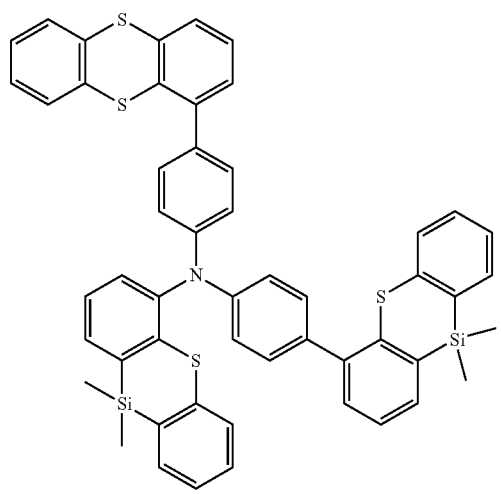
[A-117]
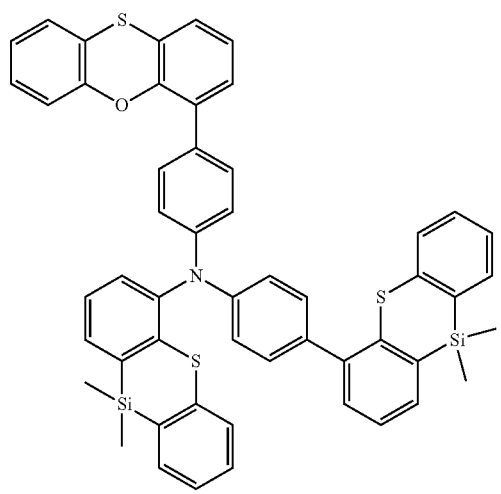
[A-118]
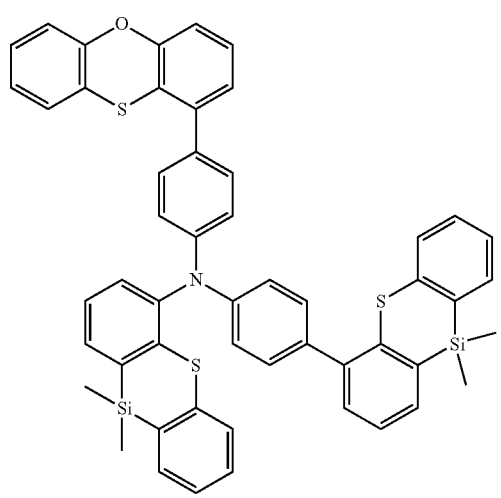
[A-119]
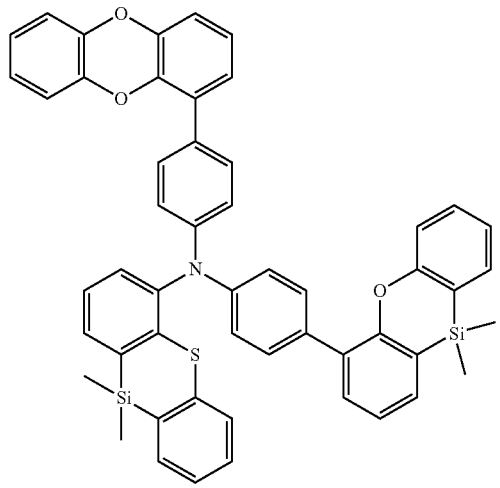
[A-120]
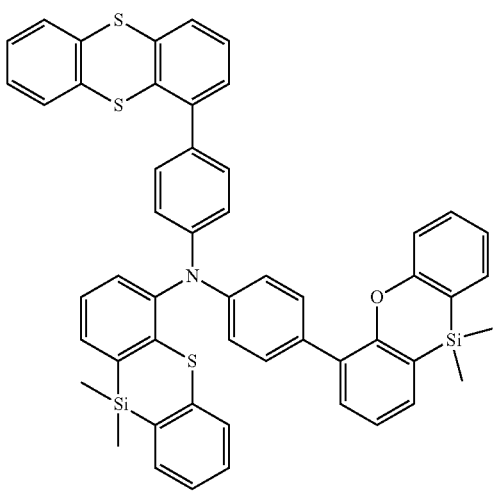
[A-121]
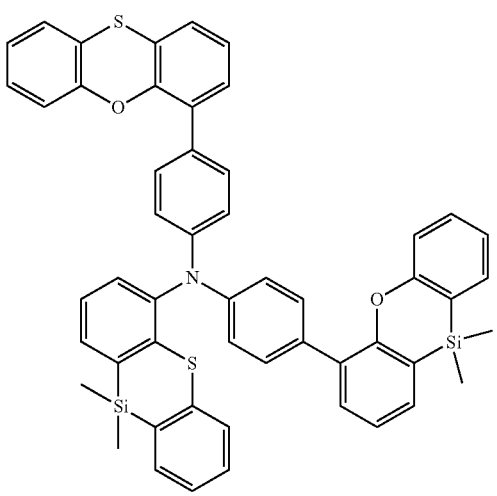

[A-122]
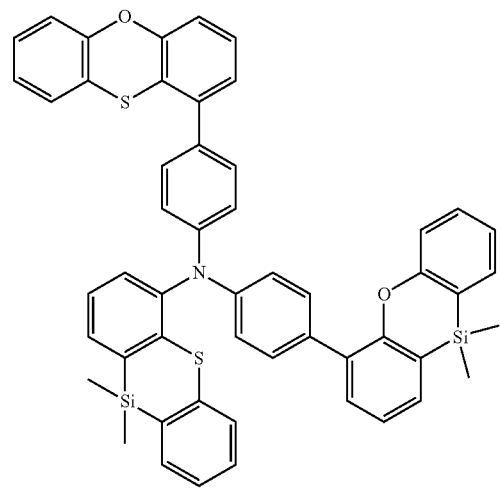
[A-123]
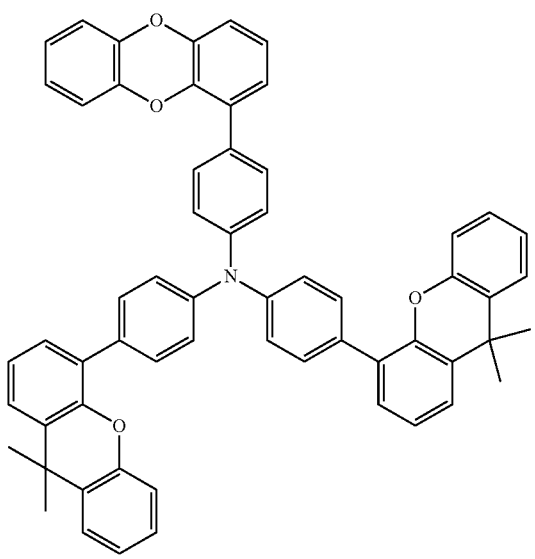
[A-124]
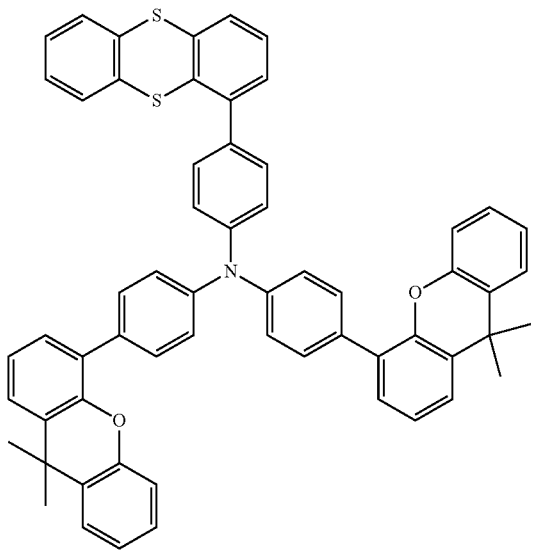
[A-125]
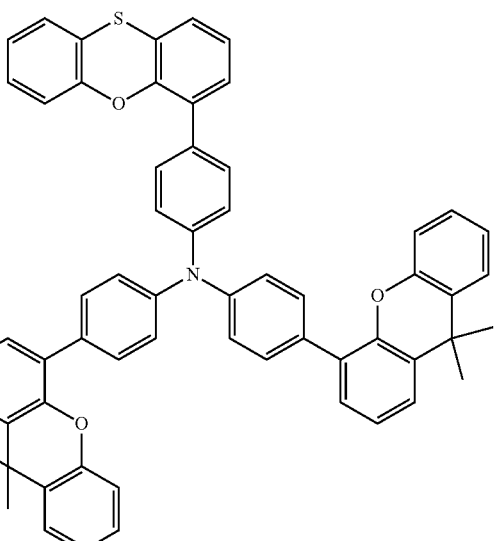
[A-126]
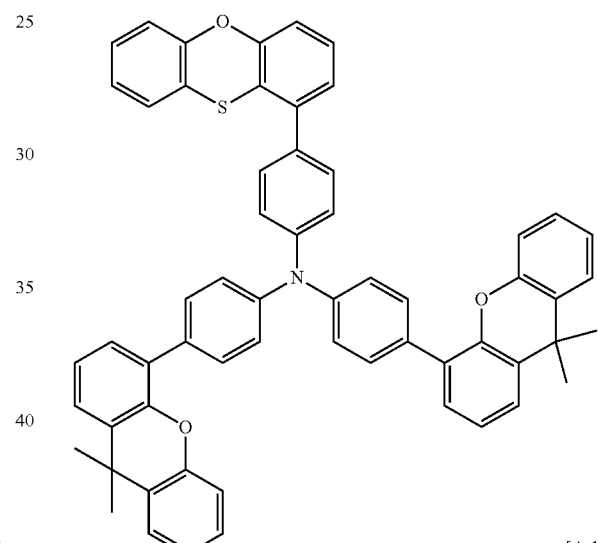
[A-127]
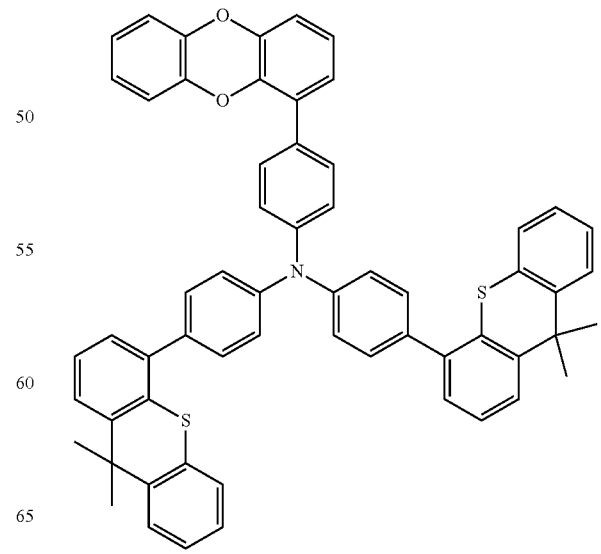

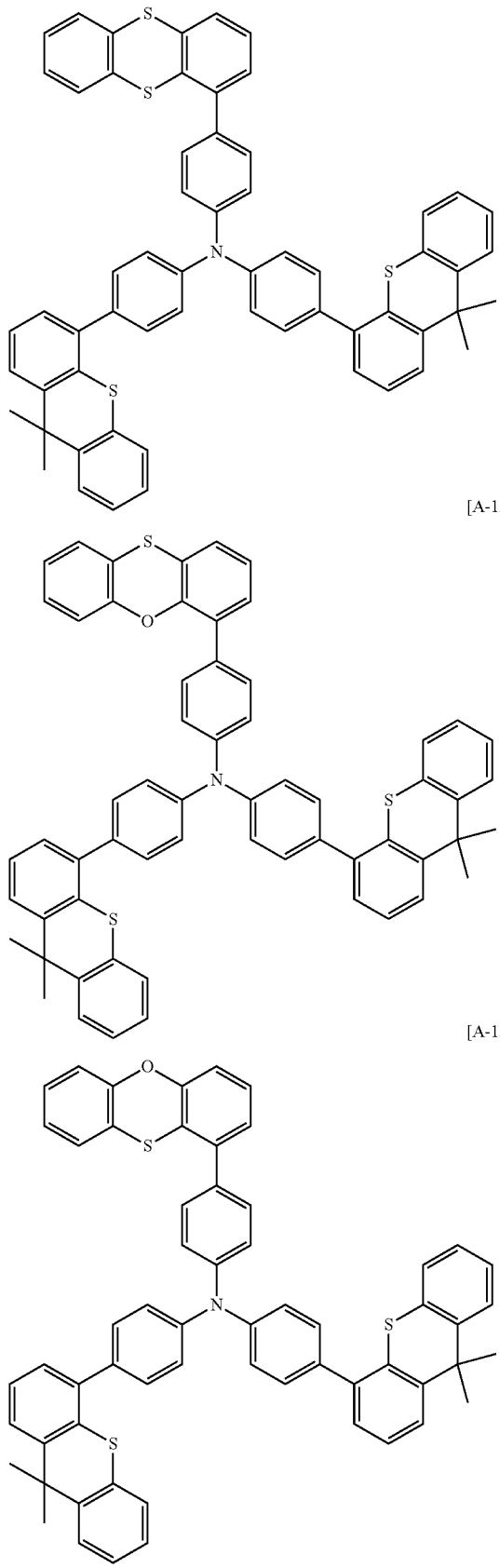
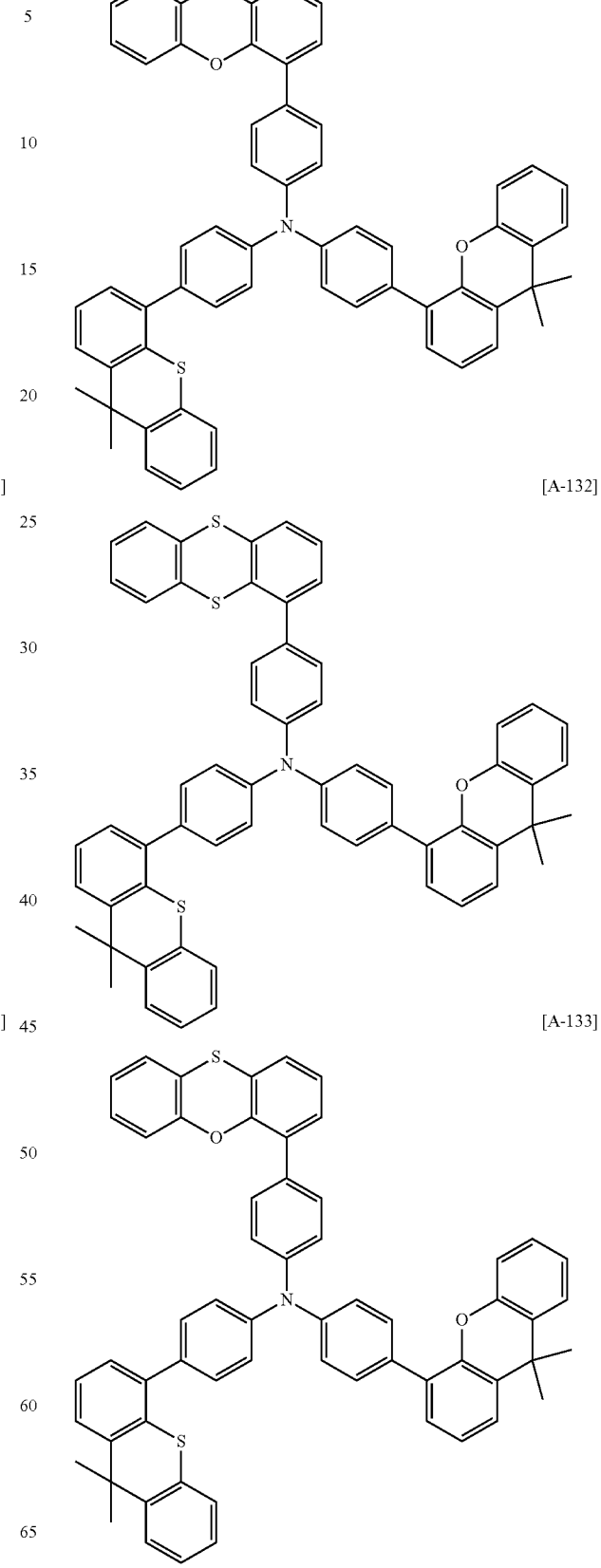

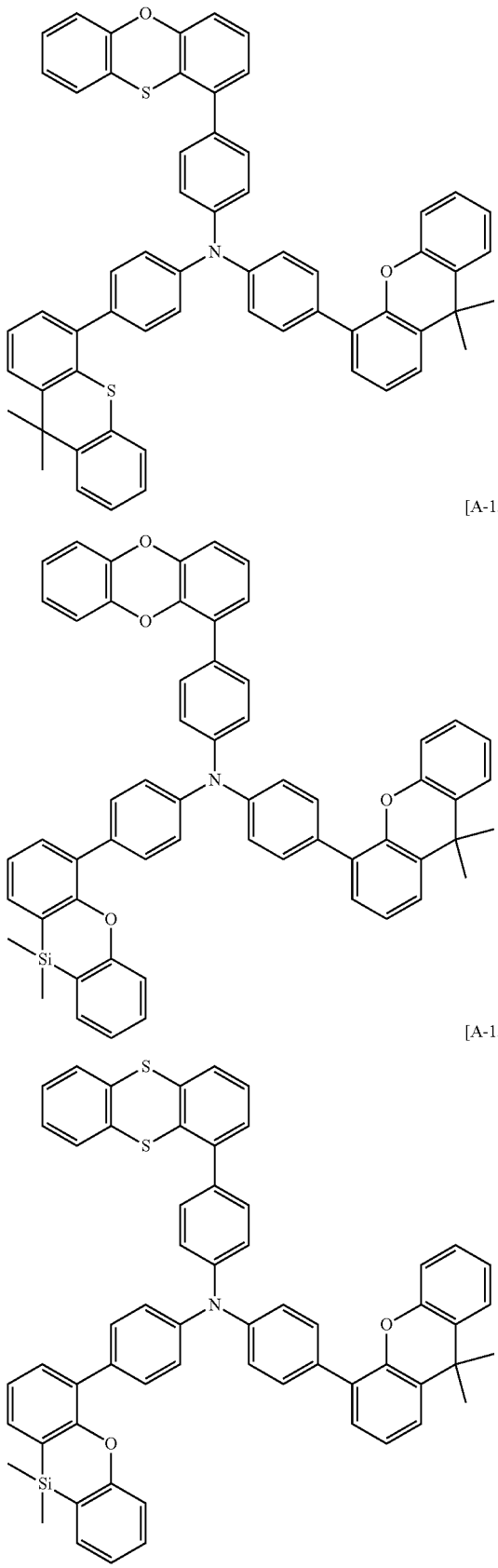
[A-134]
[A-135]
[A-136]
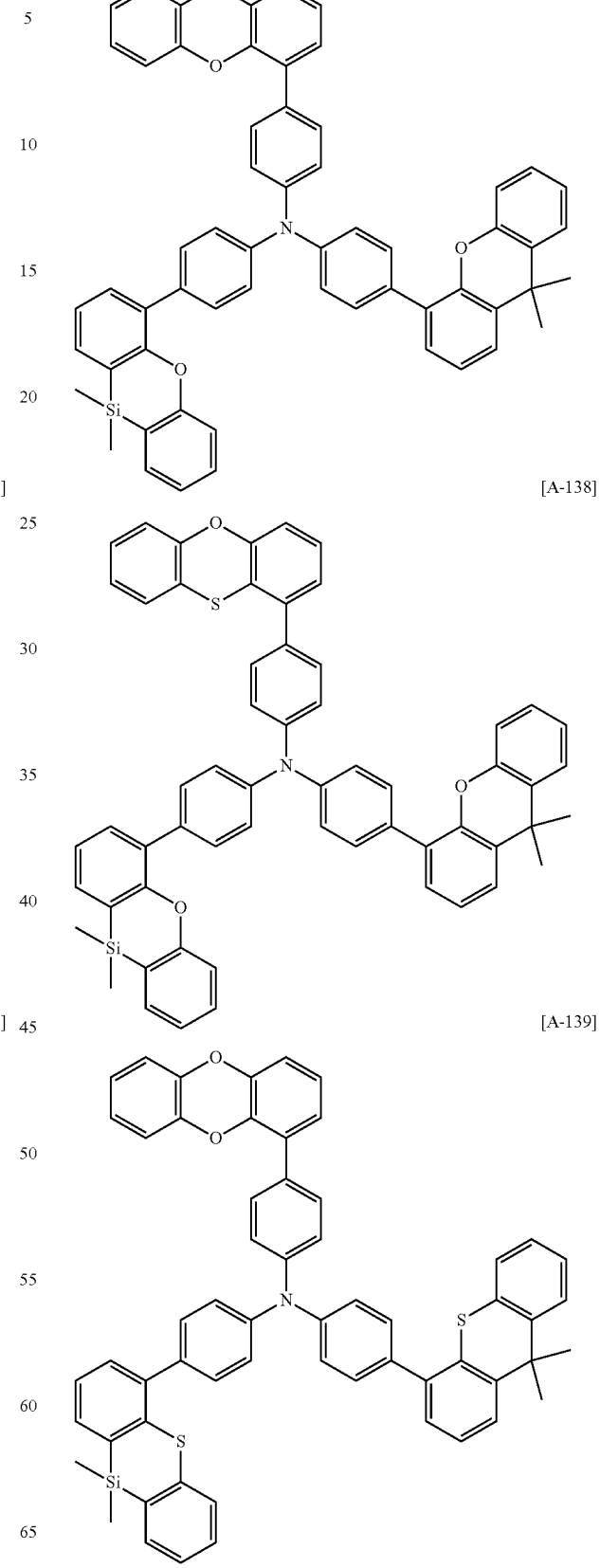
[A-137]
[A-138]
[A-139]

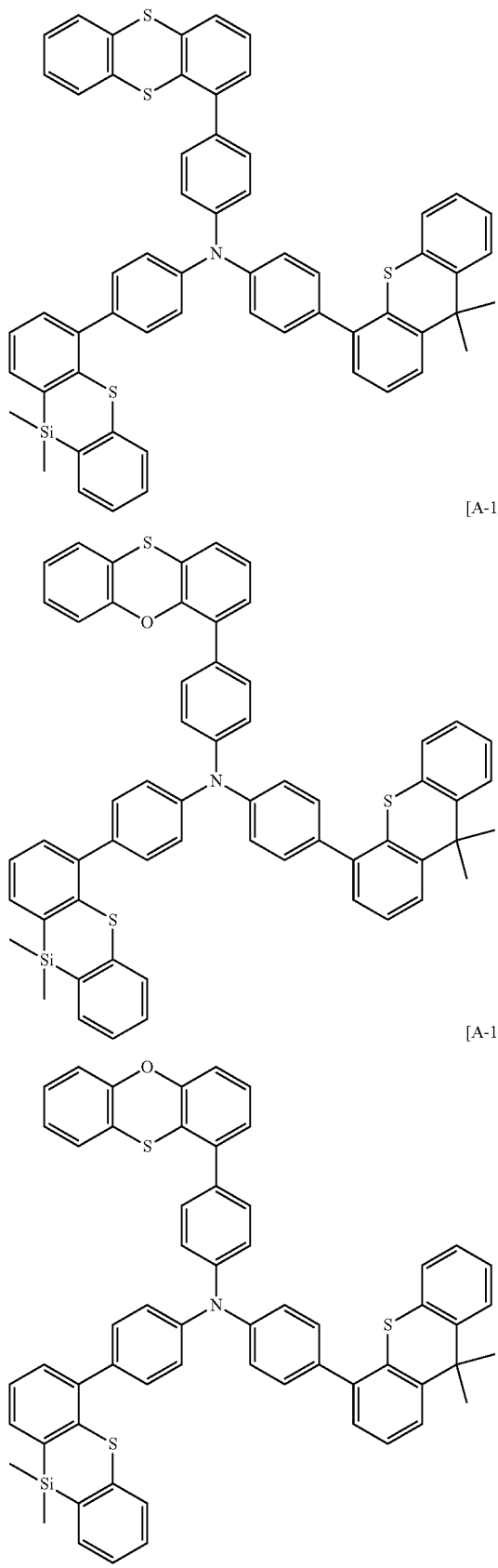
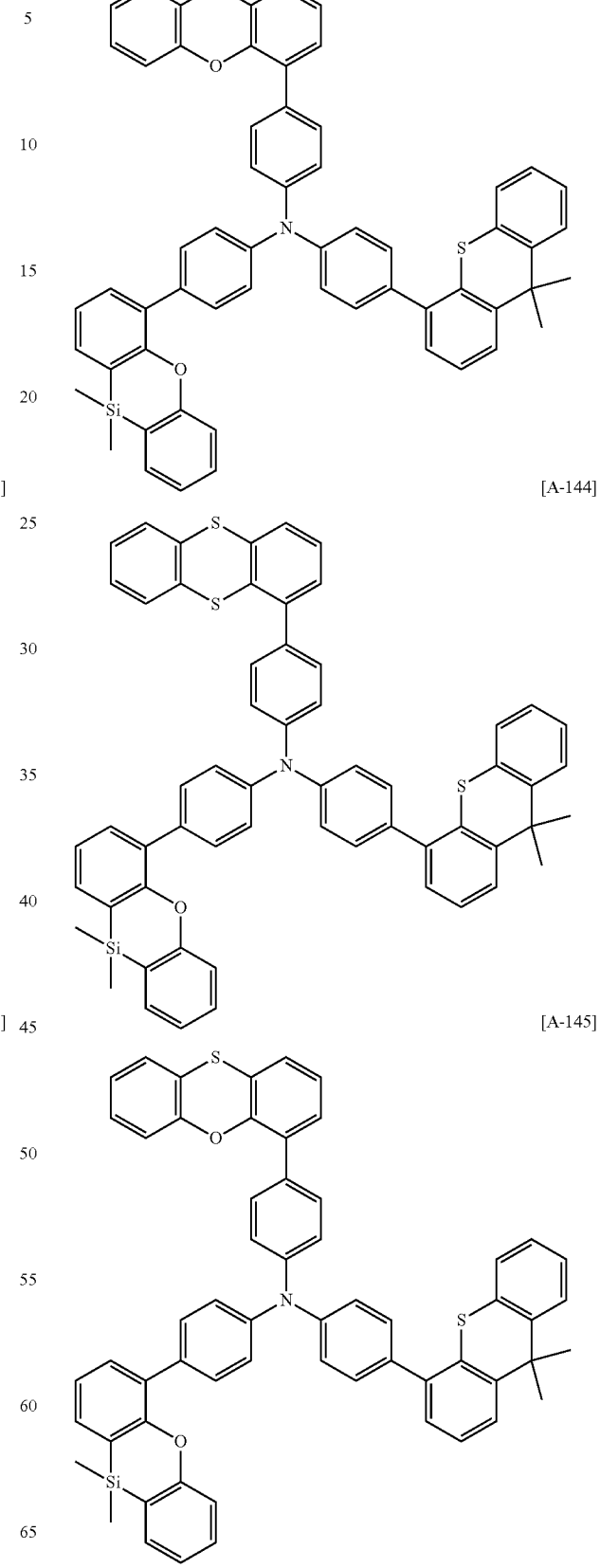

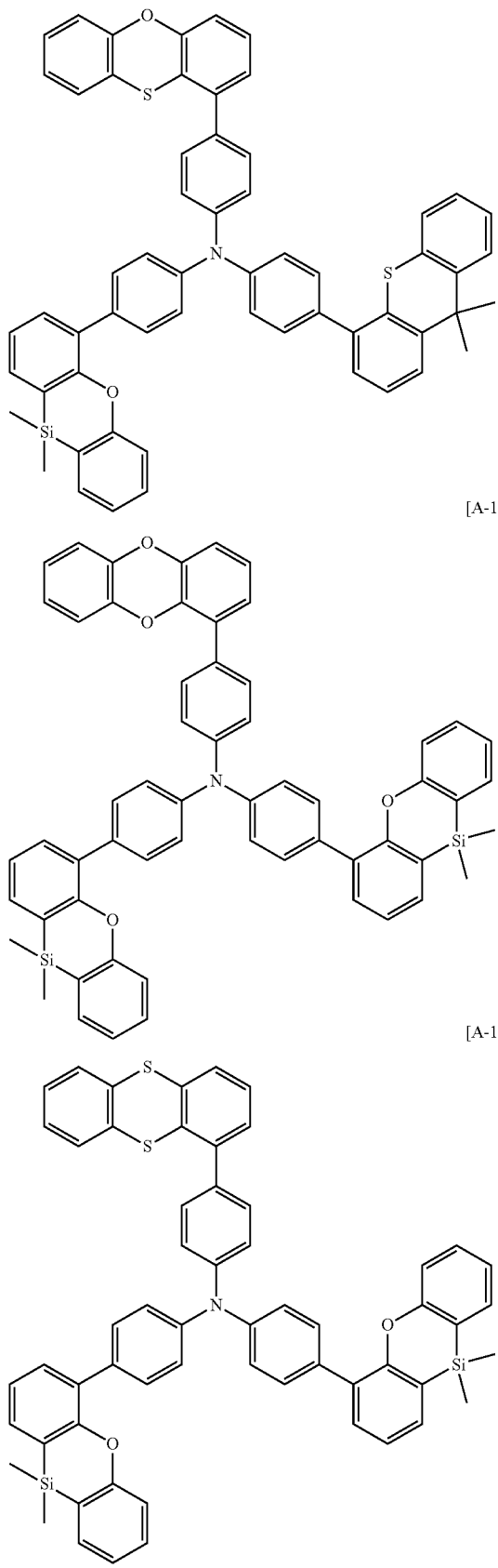
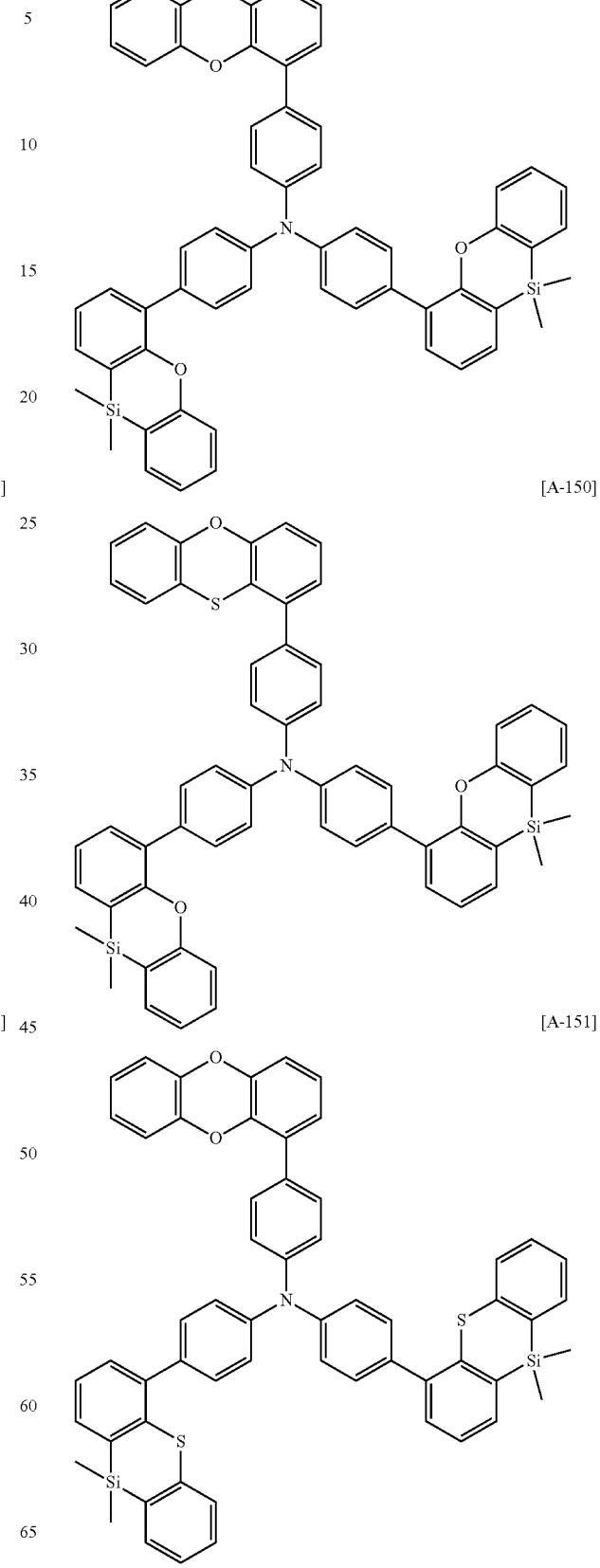

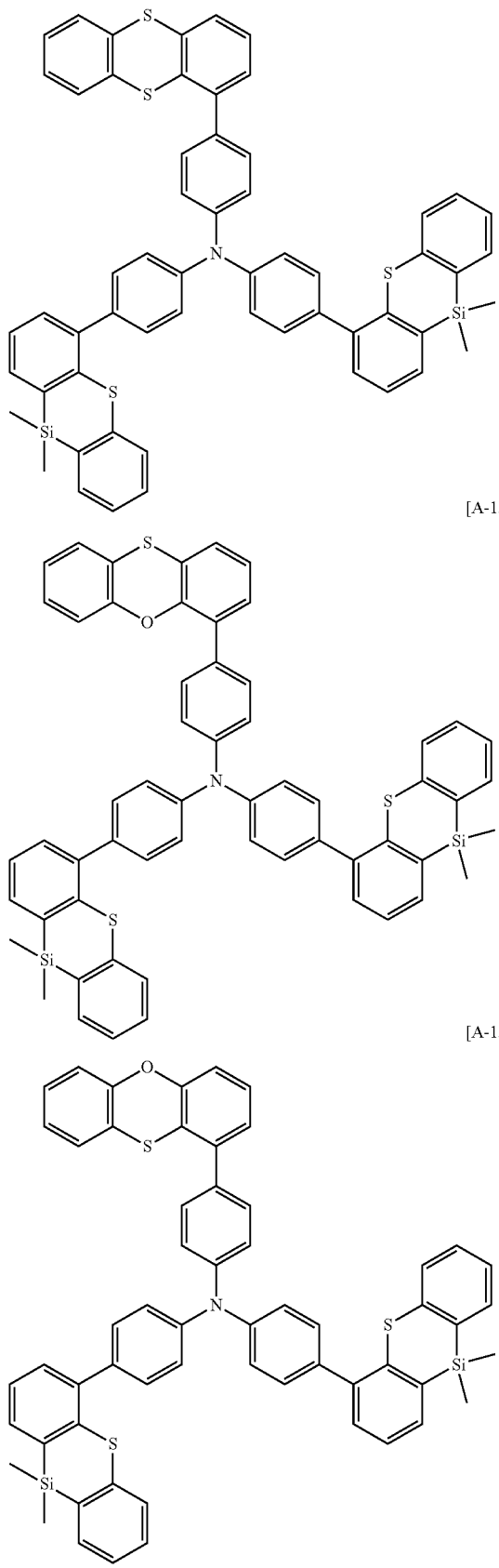
[A-152]
[A-153]
[A-154]
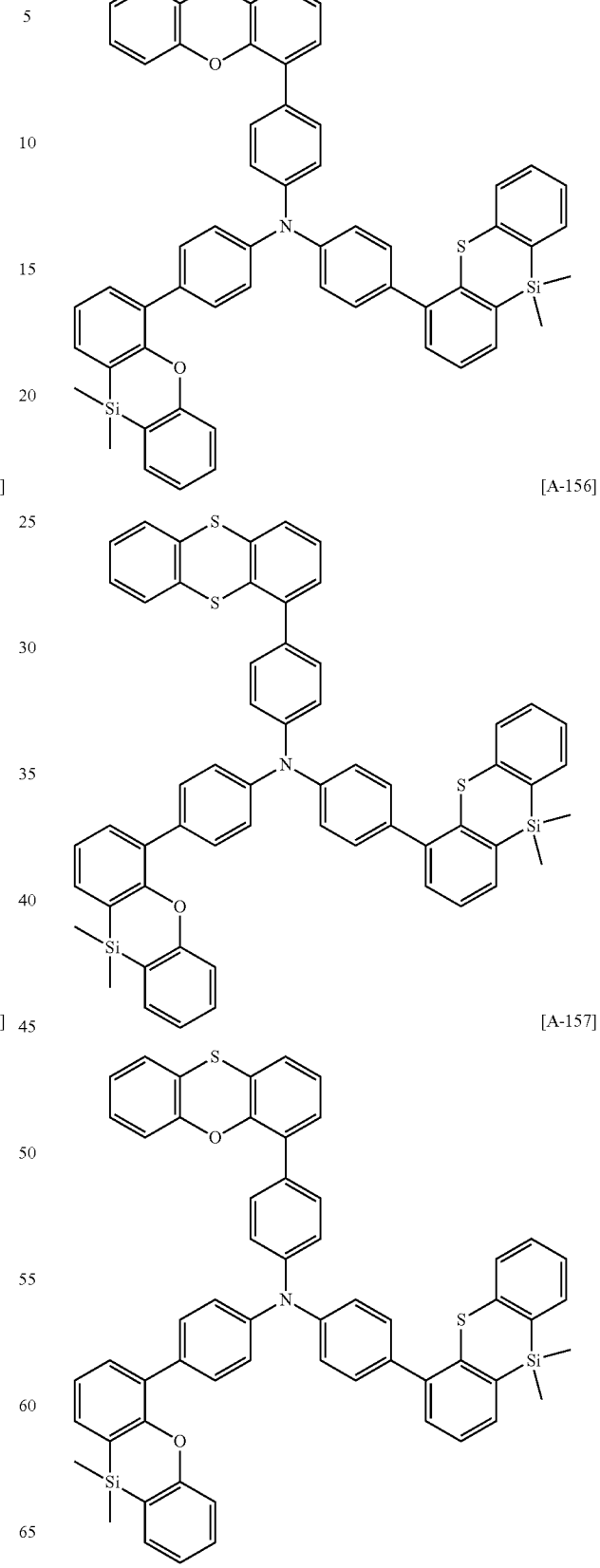
[A-155]
[A-156]
[A-157]

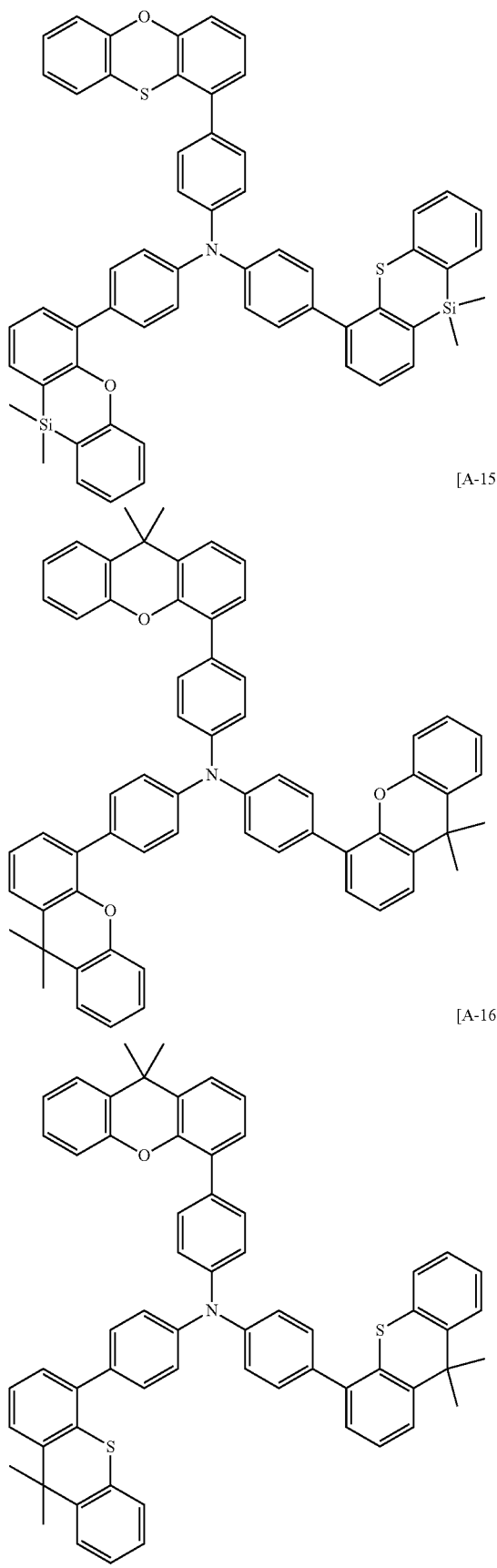
[A-158]
[A-159]
[A-160]
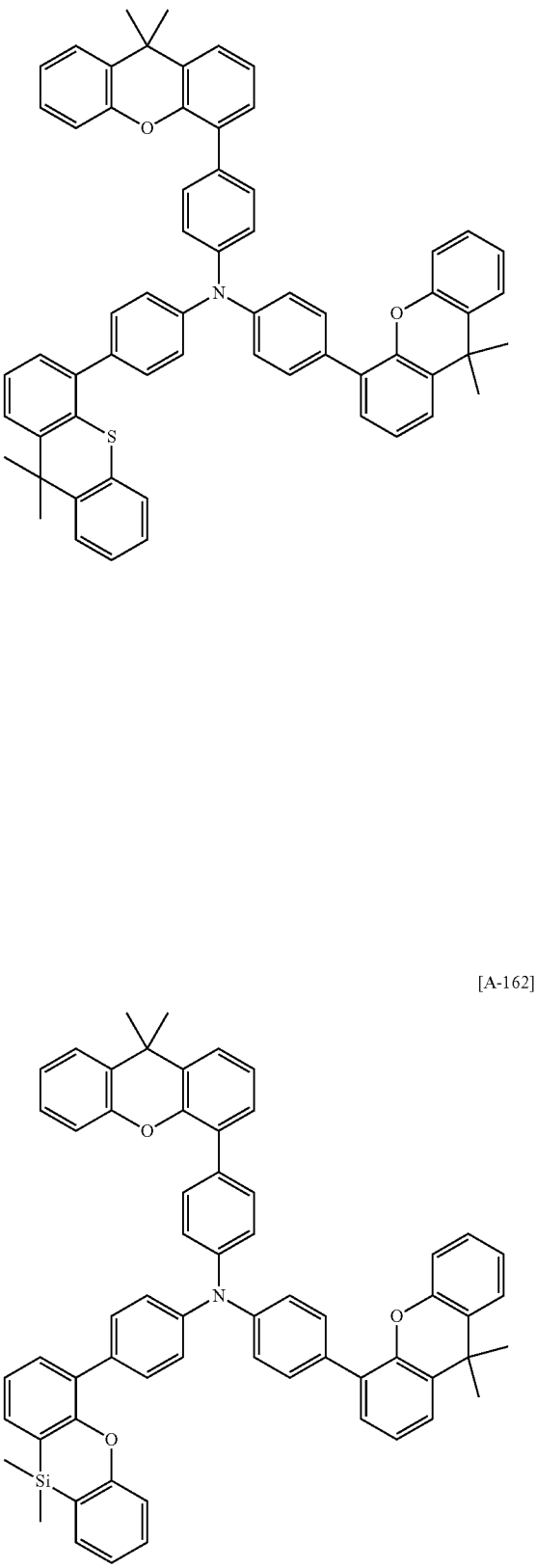
[A-161]
[A-162]

[A-163]
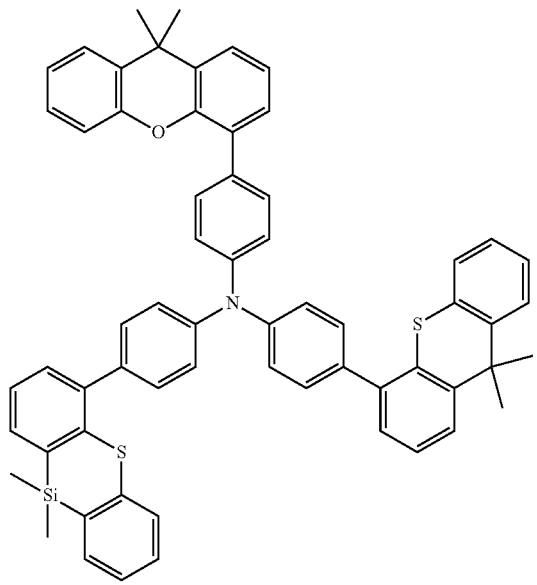
[A-164]
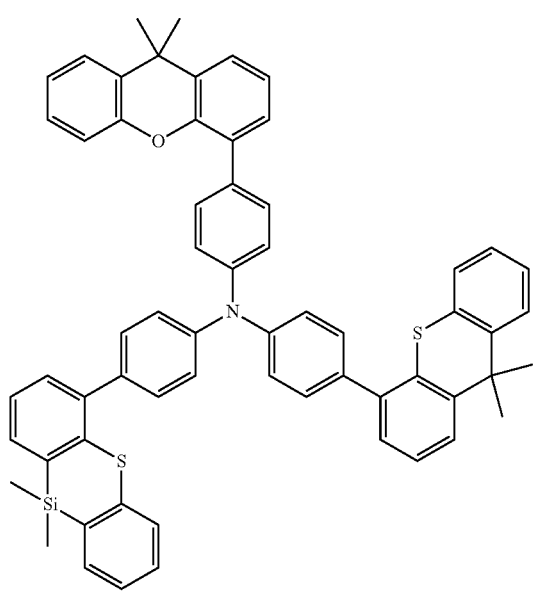
[A-165]
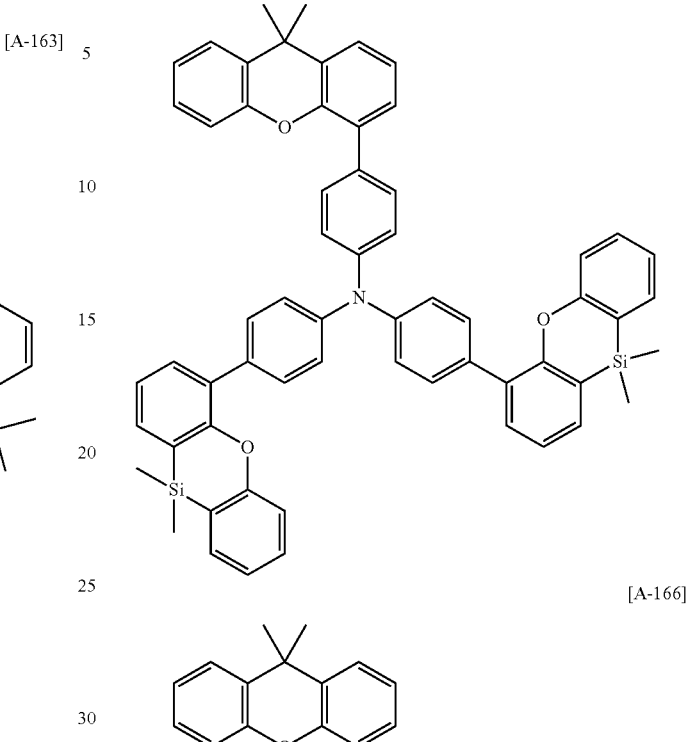
[A-166]
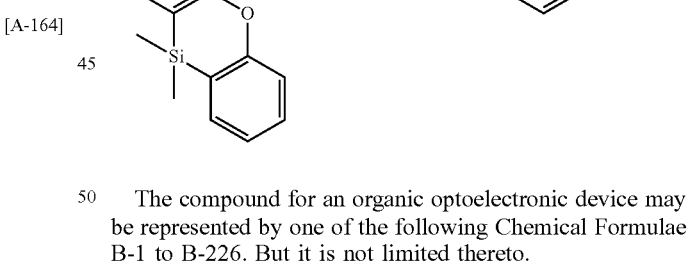
The compound for an organic optoelectronic device may be represented by one of the following Chemical Formulae B-1 to B-226. But it is not limited thereto.
[B-1]
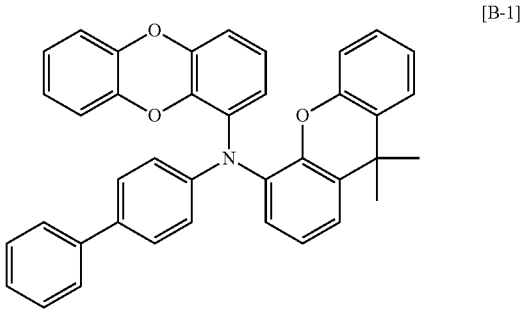

[B-2] 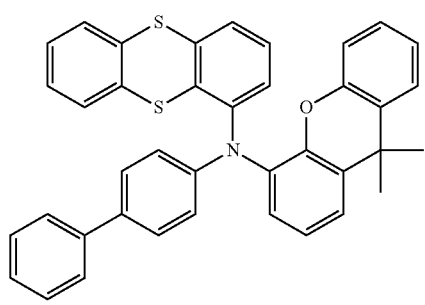
[B-3] 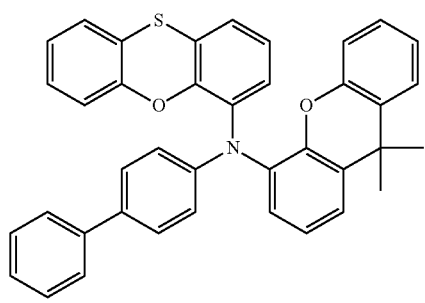
[B-4] 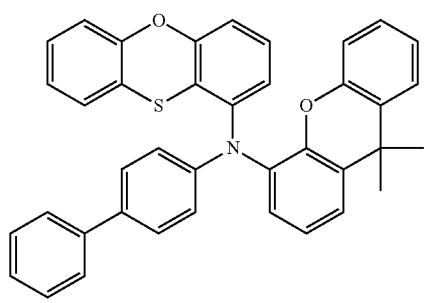
[B-5] 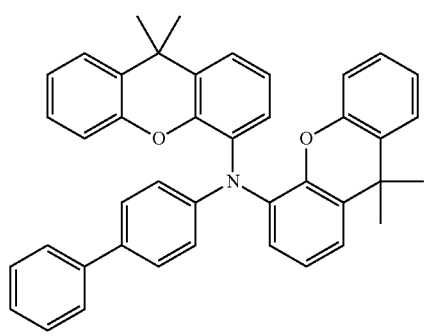
[B-6] 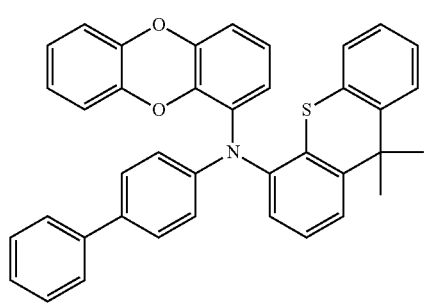
[B-7] 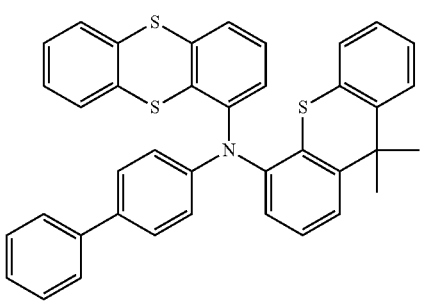
[B-8] 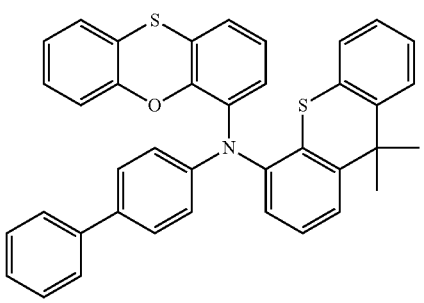
[B-9] 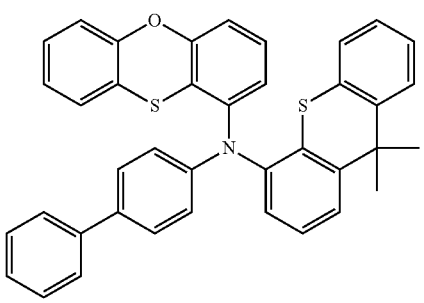
[B-10] 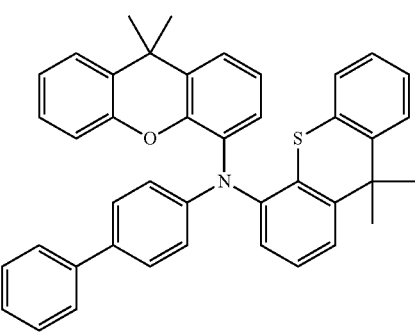
[B-11] 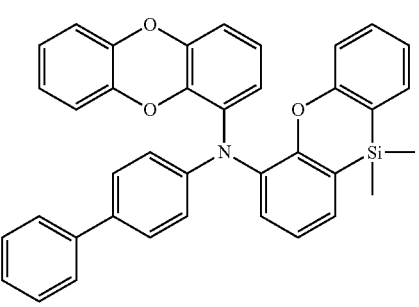

[B-12]
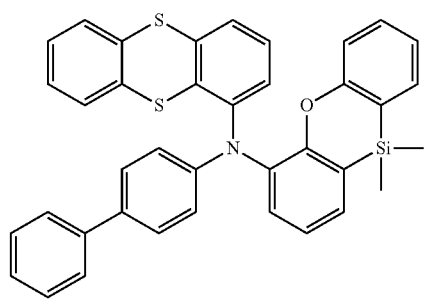
[B-17]
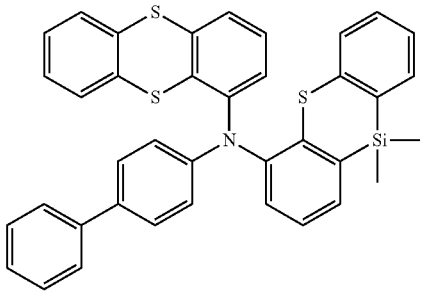
[B-13]
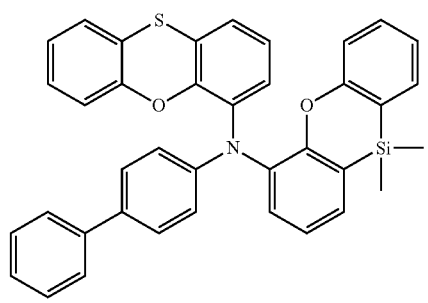
[B-18]
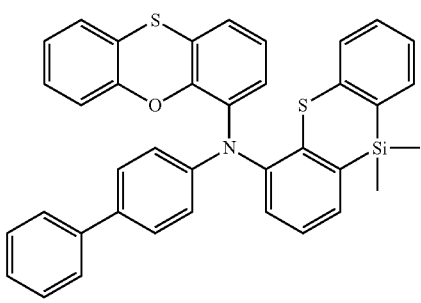
[B-14]
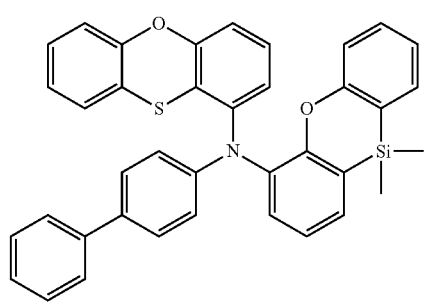
[B-19]
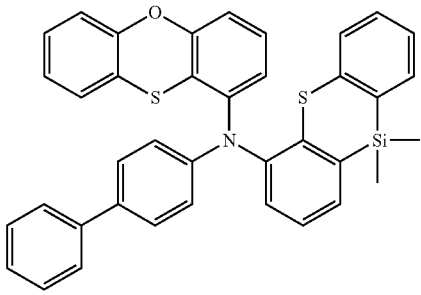
[B-15]
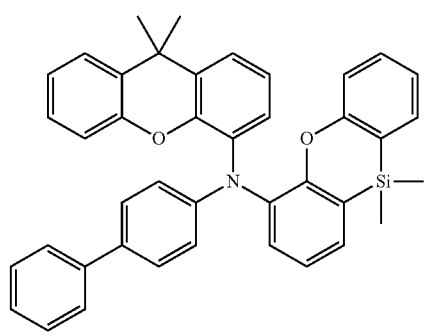
[B-20]
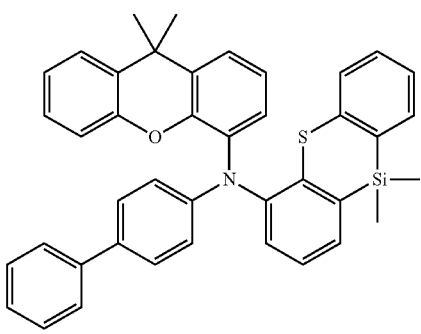
[B-16]
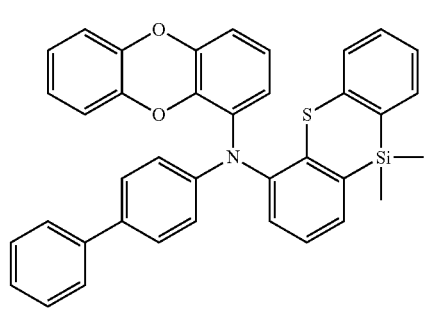
[B-21]
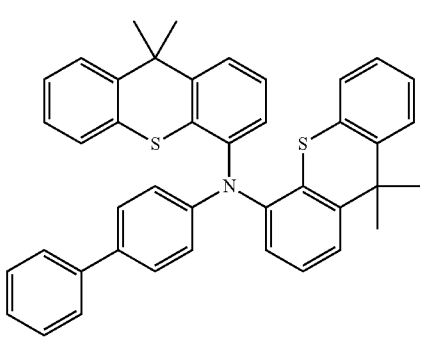

[B-22]
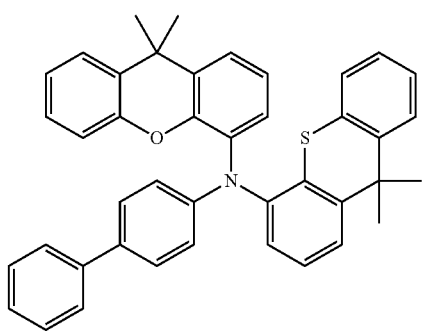
[B-23]
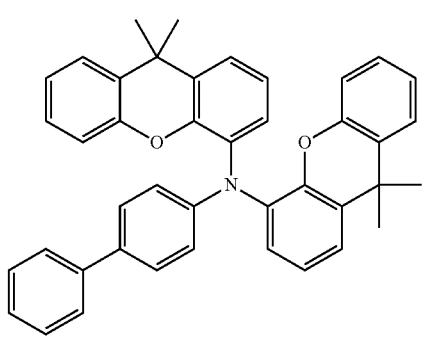
[B-24]
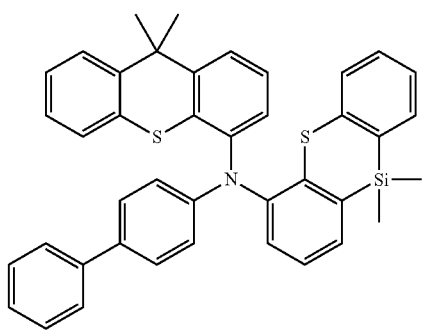
[B-25]
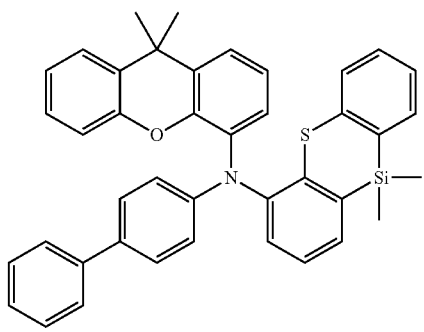
[B-26]
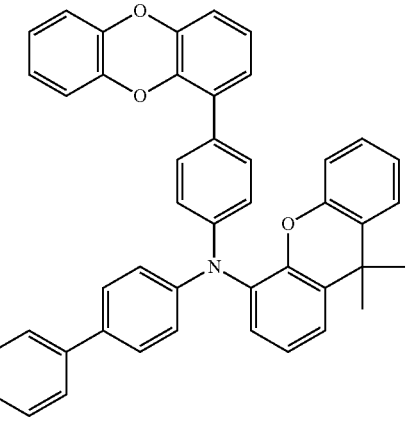
[B-27]
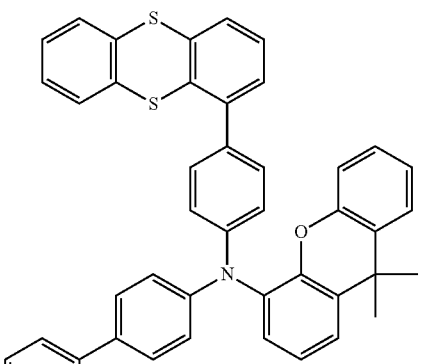
[B-28]
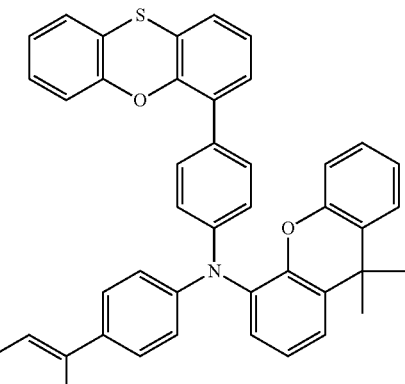

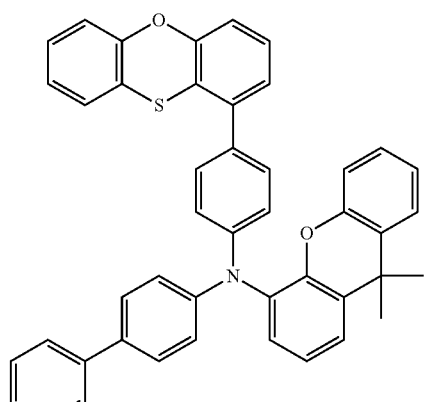
[B-29]
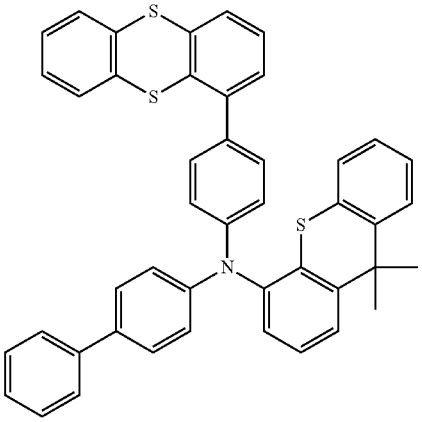
[B-32]
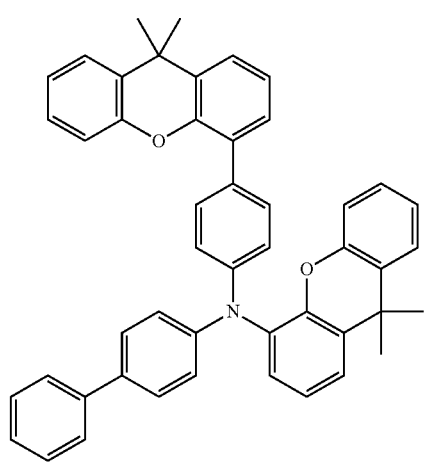
[B-30]
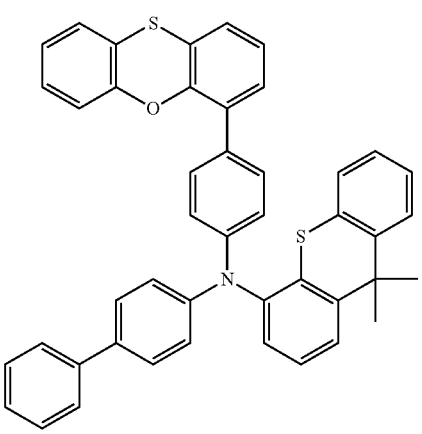
[B-33]
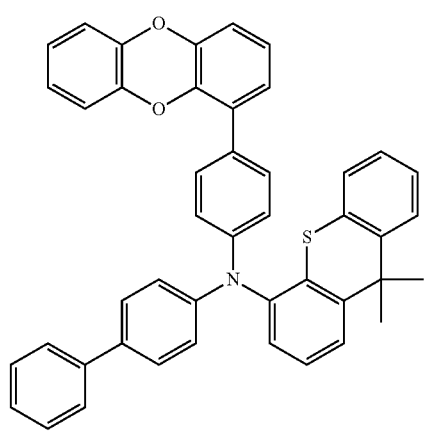
[B-31]
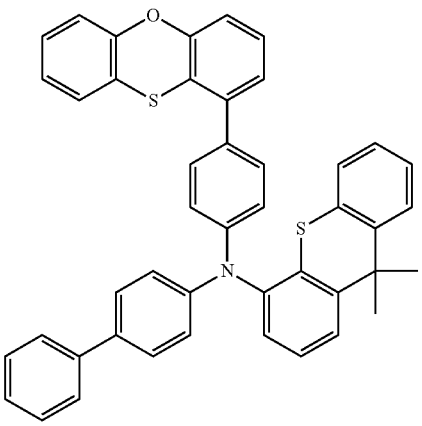
[B-34]

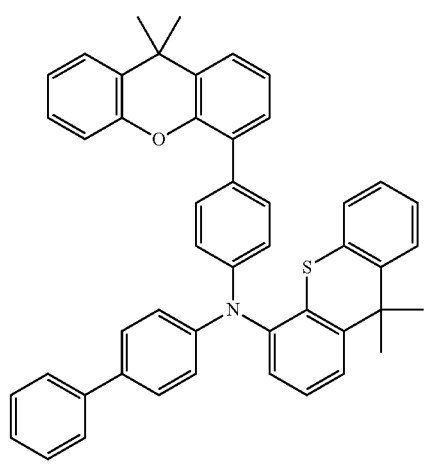
[B-35]
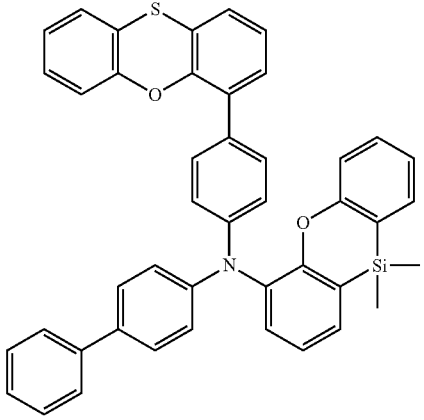
[B-38]
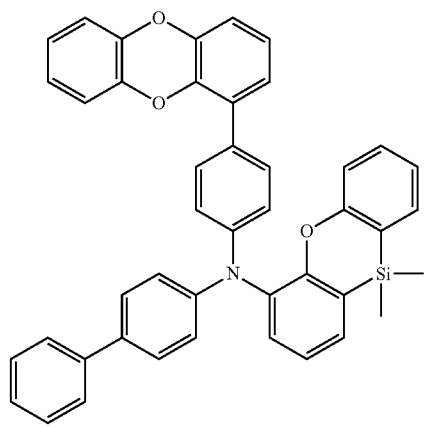
[B-36]
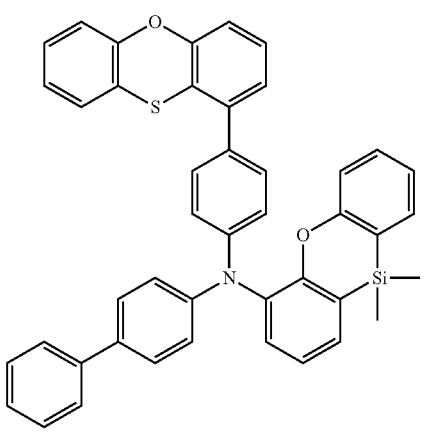
[B-39]
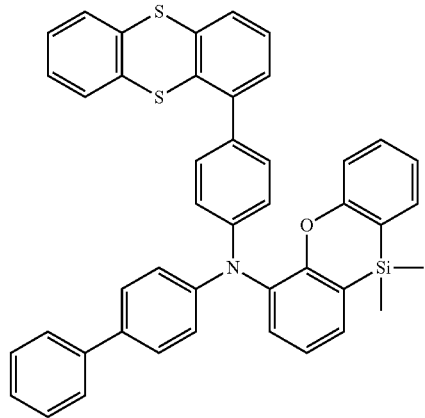
[B-37]
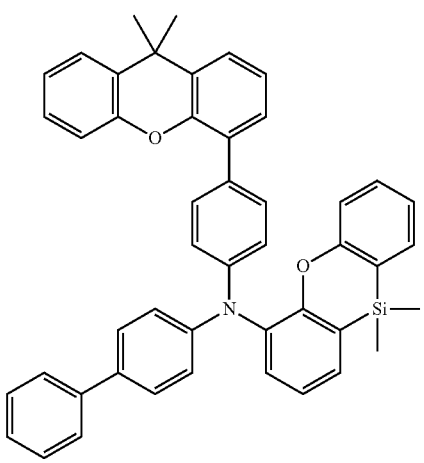
[B-40]

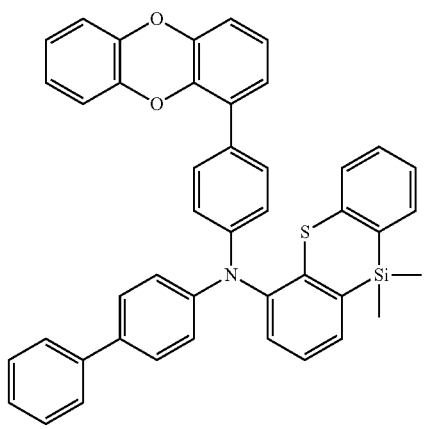
[B-41]
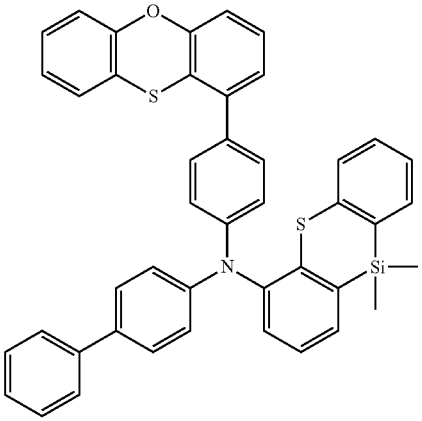
[B-44]
[B-42]
[B-45]
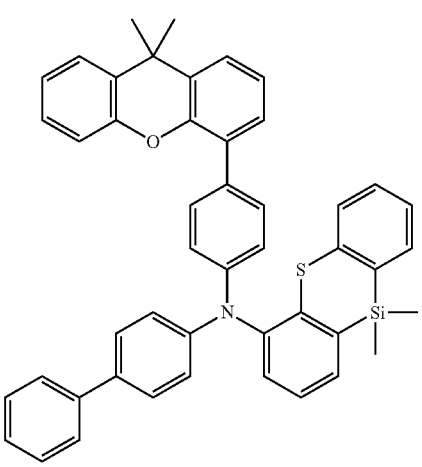
[B-43]
[B-46]
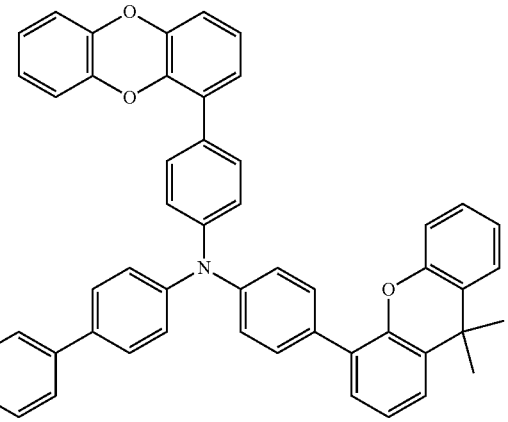

[B-47]
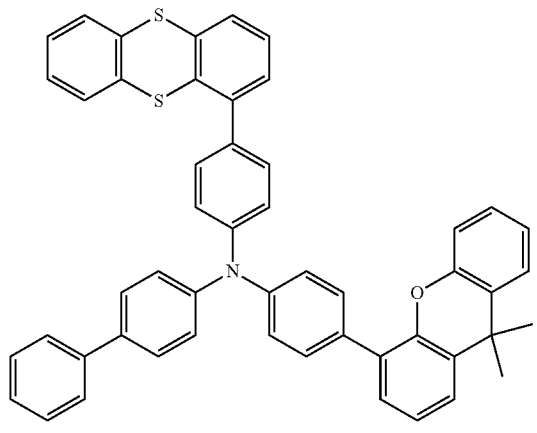
[B-50]
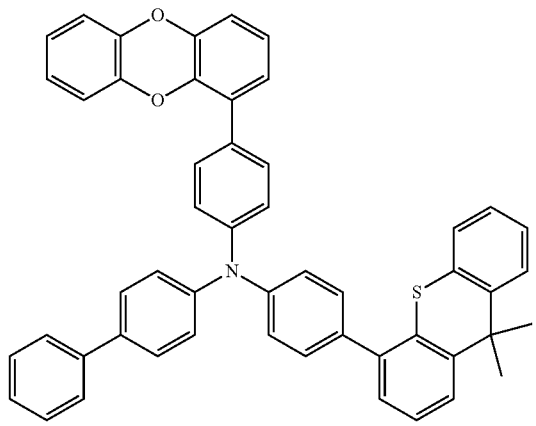
[B-48]
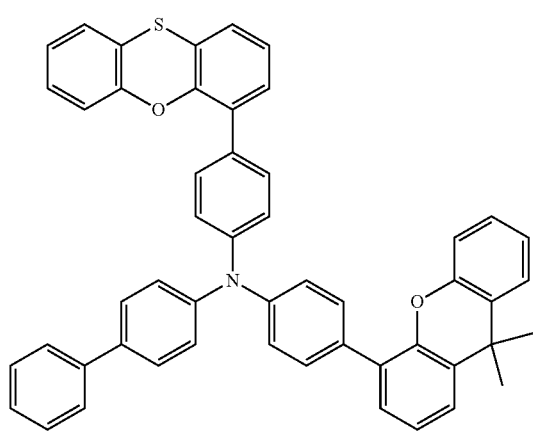
[B-51]
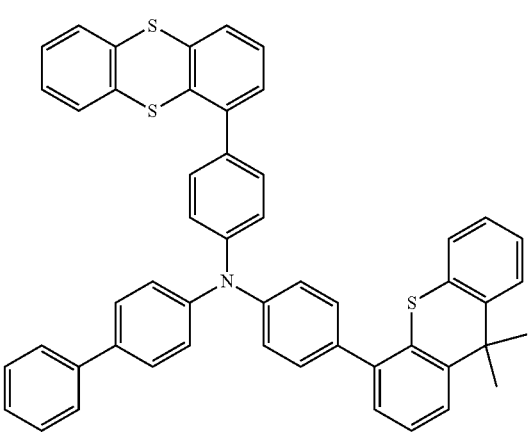
[B-49]
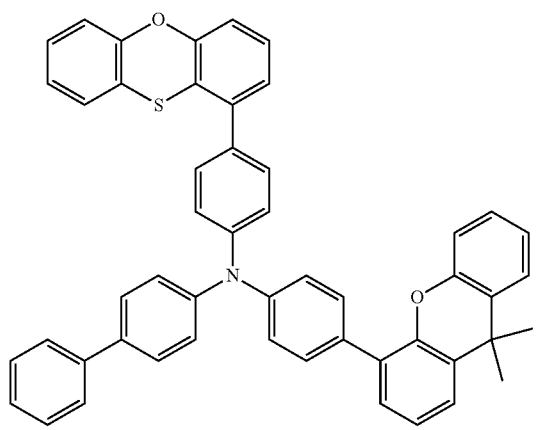
[B-52]
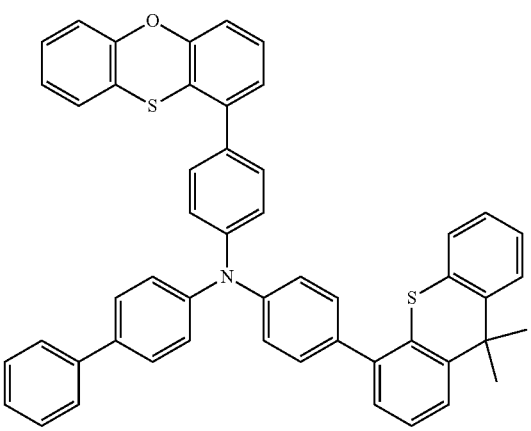

[B-53]
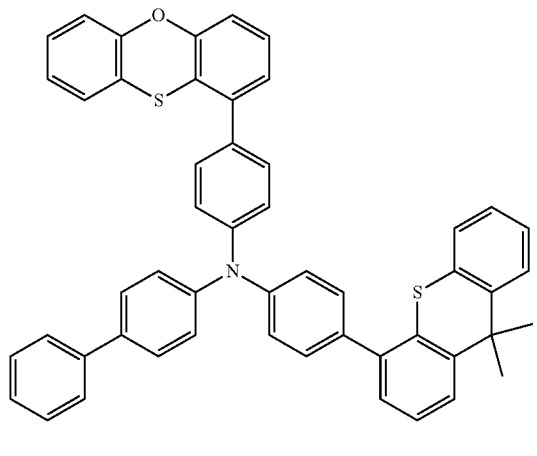
[B-56]
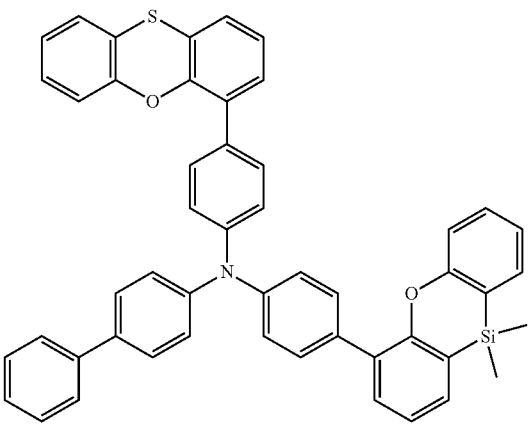
[B-54]
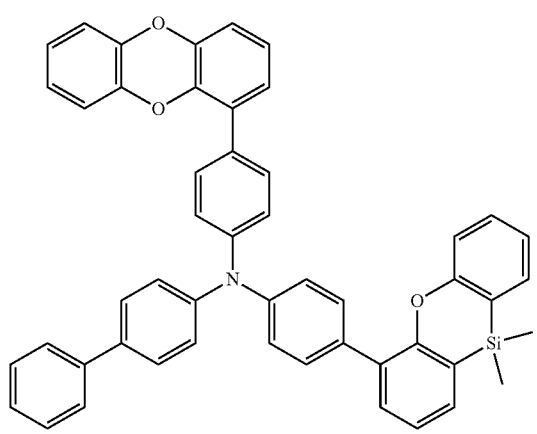
[B-57]
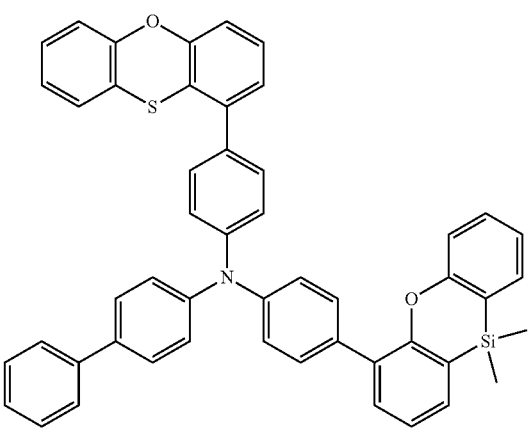
[B-55]
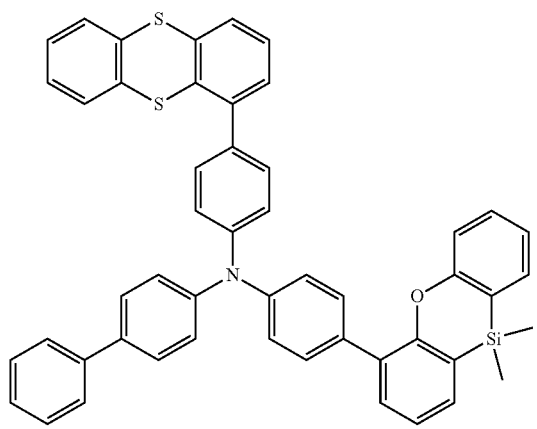
[B-58]
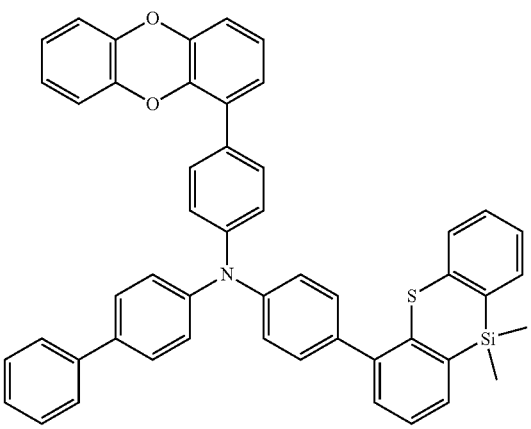

[B-59]
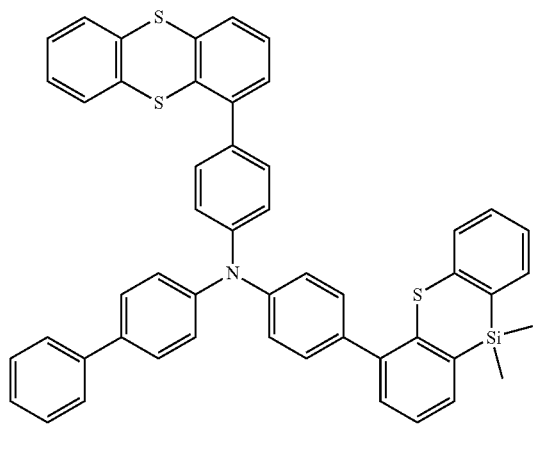
[B-62]
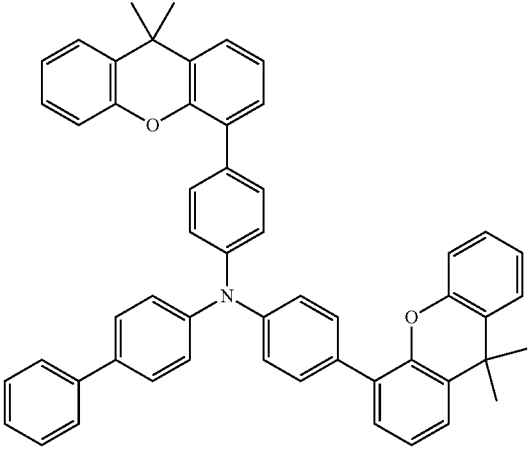
[B-60]
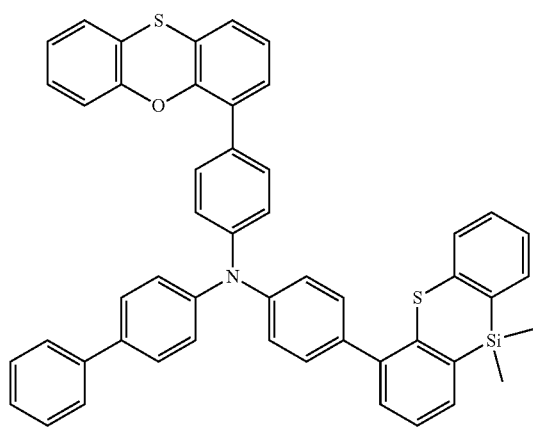
[B-63]
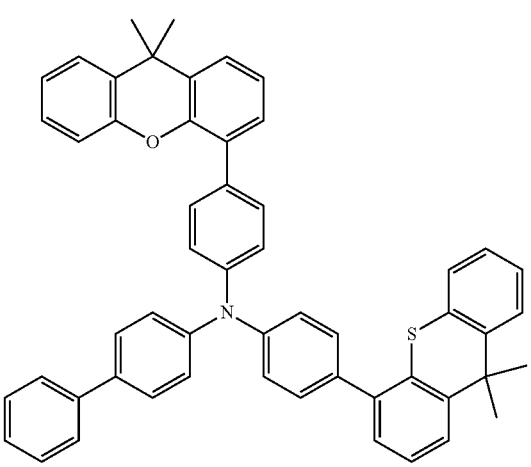
[B-61]
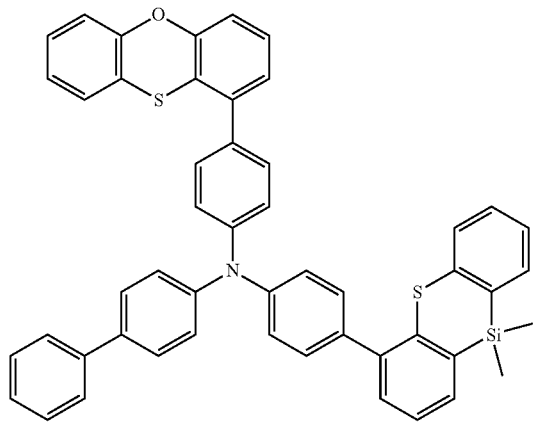
[B-64]
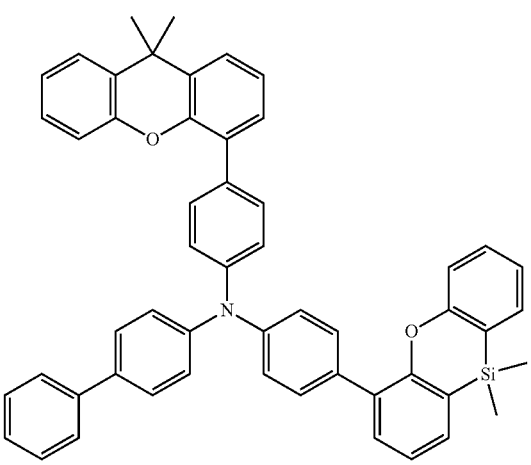

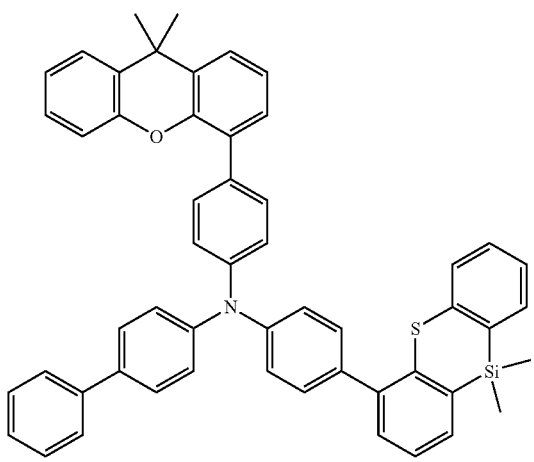
[B-65]
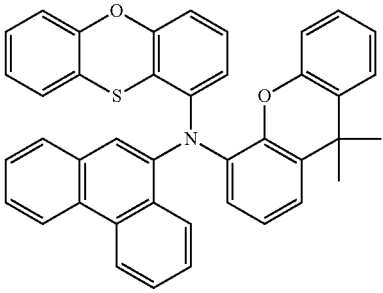
[B-69]
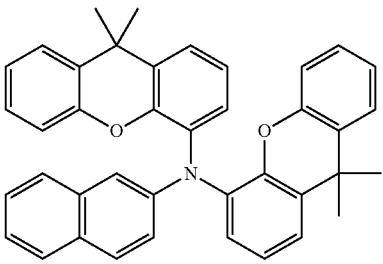
[B-70]
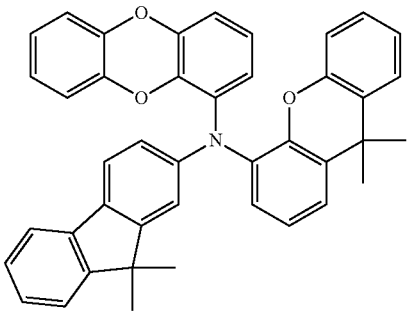
[B-71]
[B-66]
[B-67]
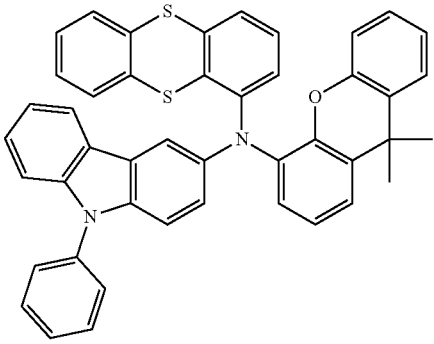
[B-72]
[B-68]
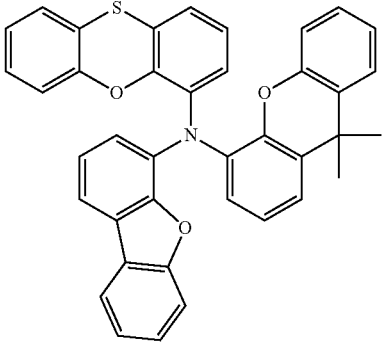
[B-73]

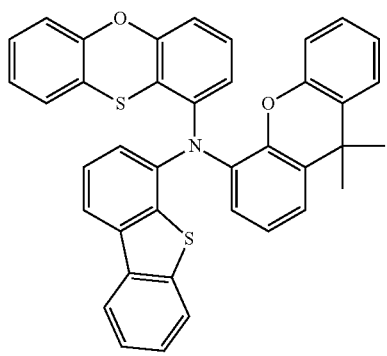
[B-74]
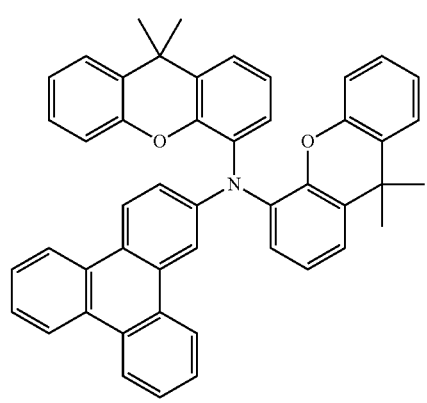
[B-75]
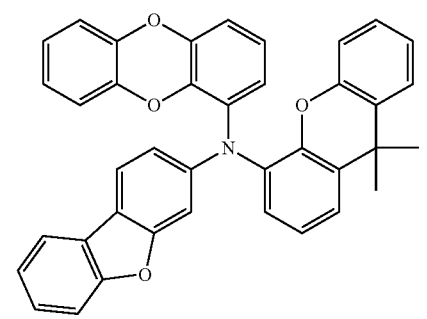
[B-76]
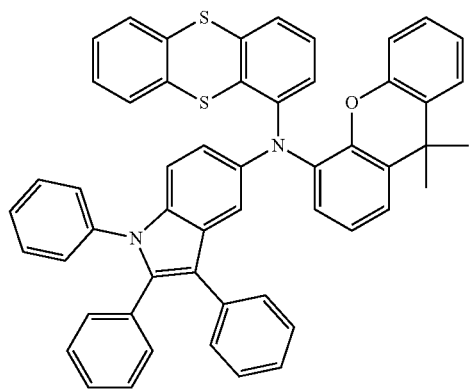
[B-77]
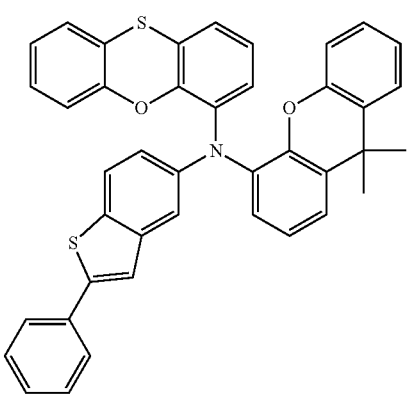
[B-78]
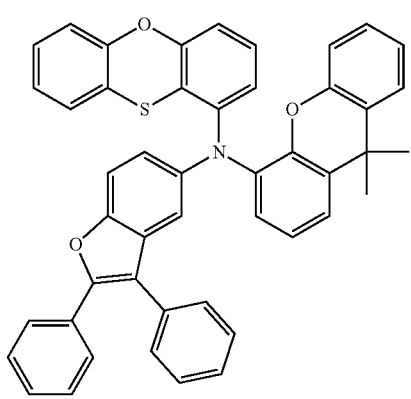
[B-79]
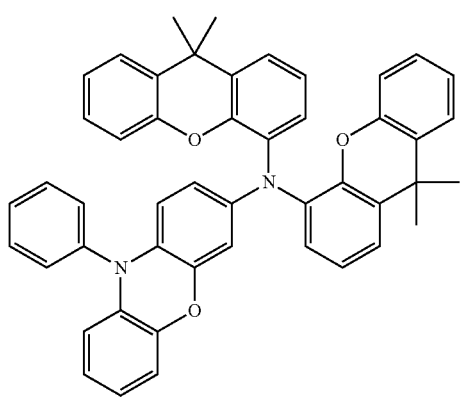
[B-80]
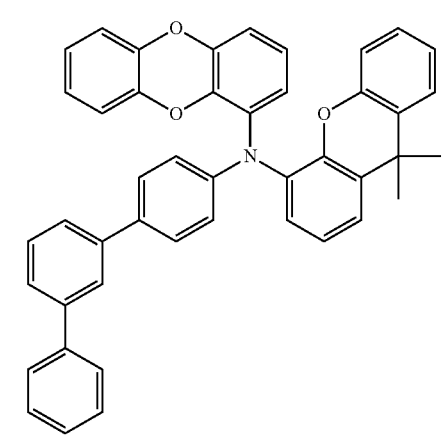
[B-81]

[B-82]
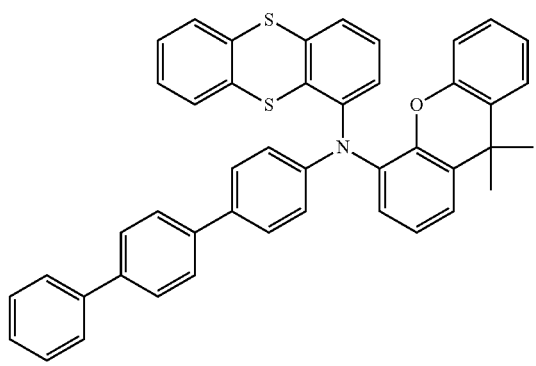
[B-83]
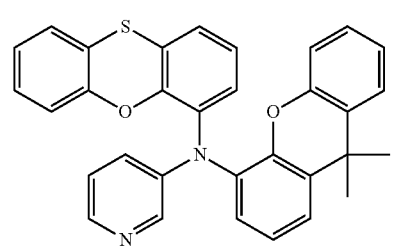
[B-84]
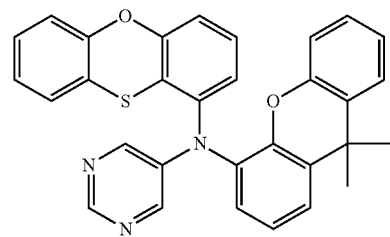
[B-85]
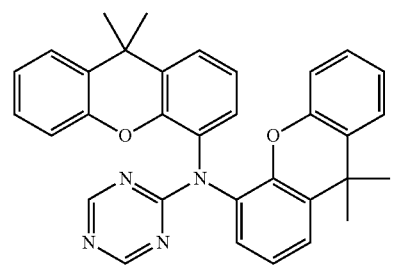
[B-86]
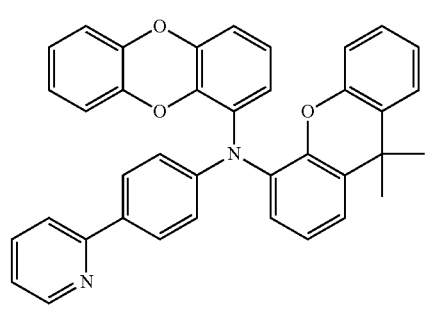
[B-87]
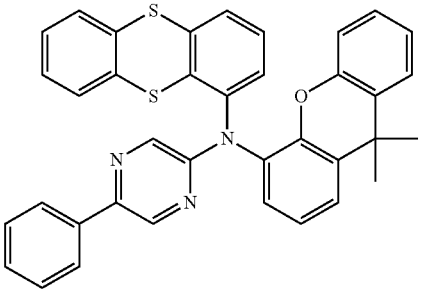
[B-88]
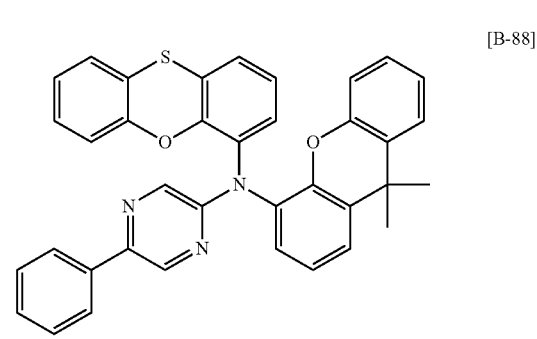
[B-89]
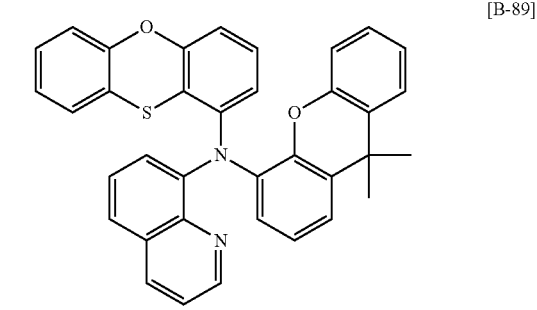
[B-90]
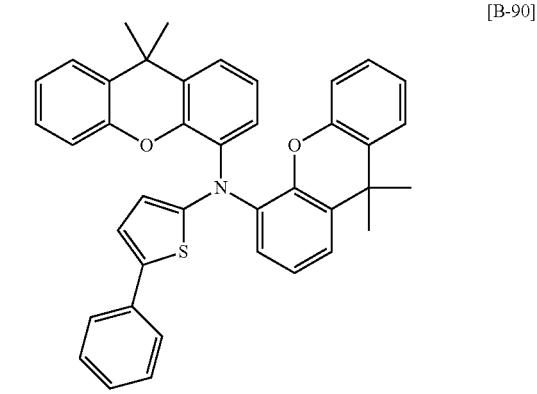
[B-91]
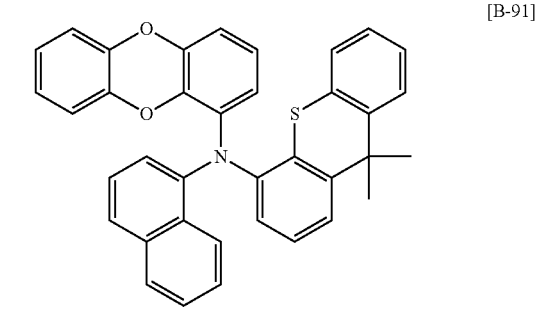

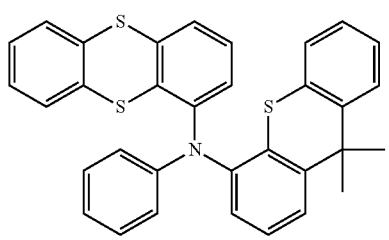 [B-92]
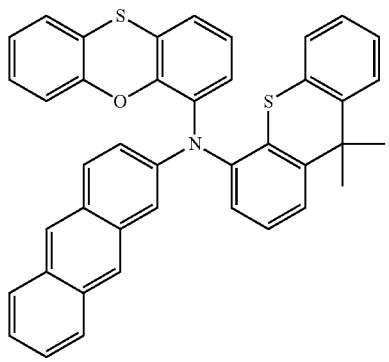 [B-93]
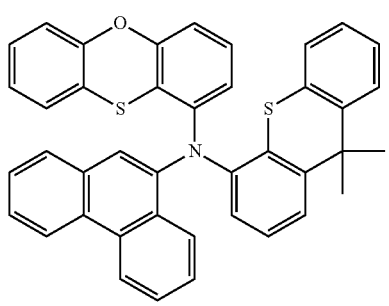 [B-94]
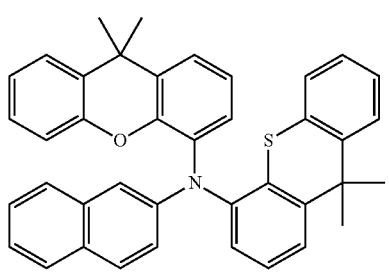 [B-95]
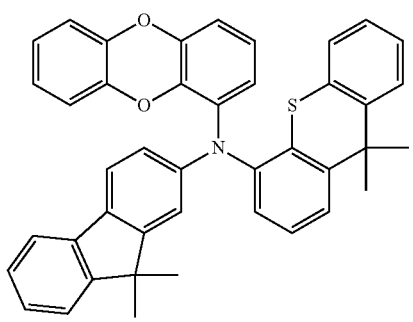 [B-96]
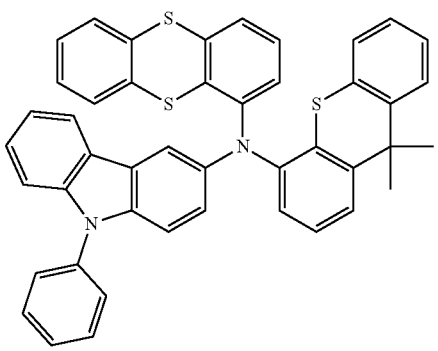 [B-97]
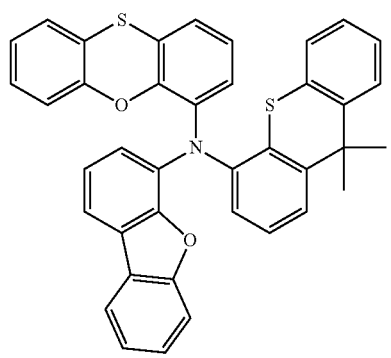 [B-98]
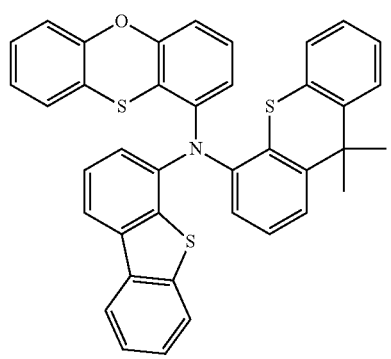 [B-99]
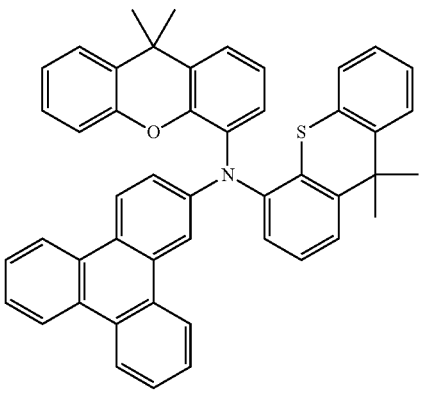 [B-100]

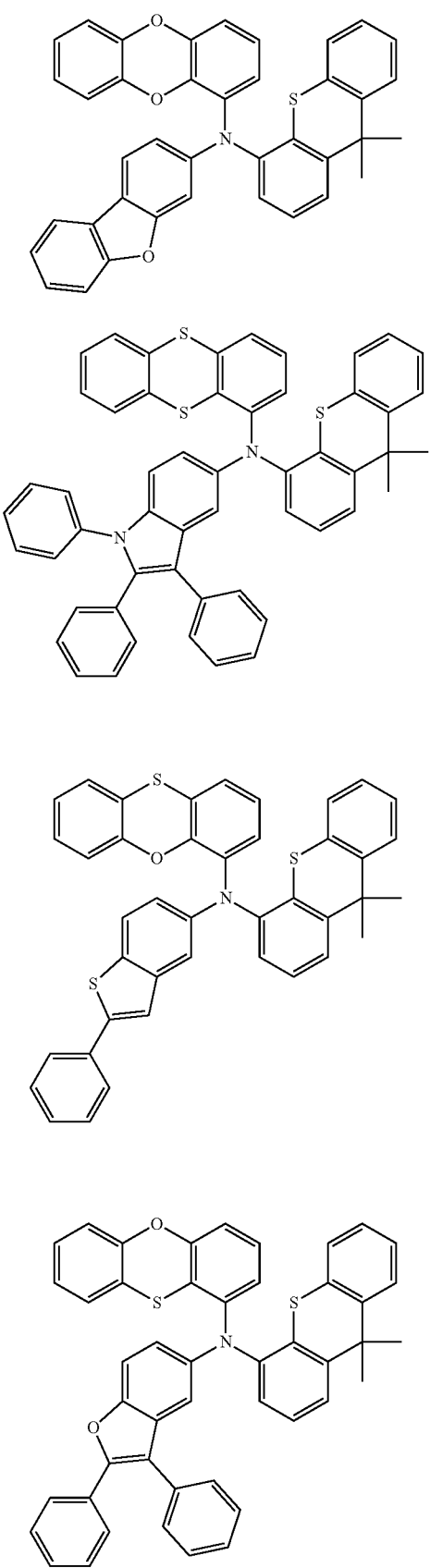
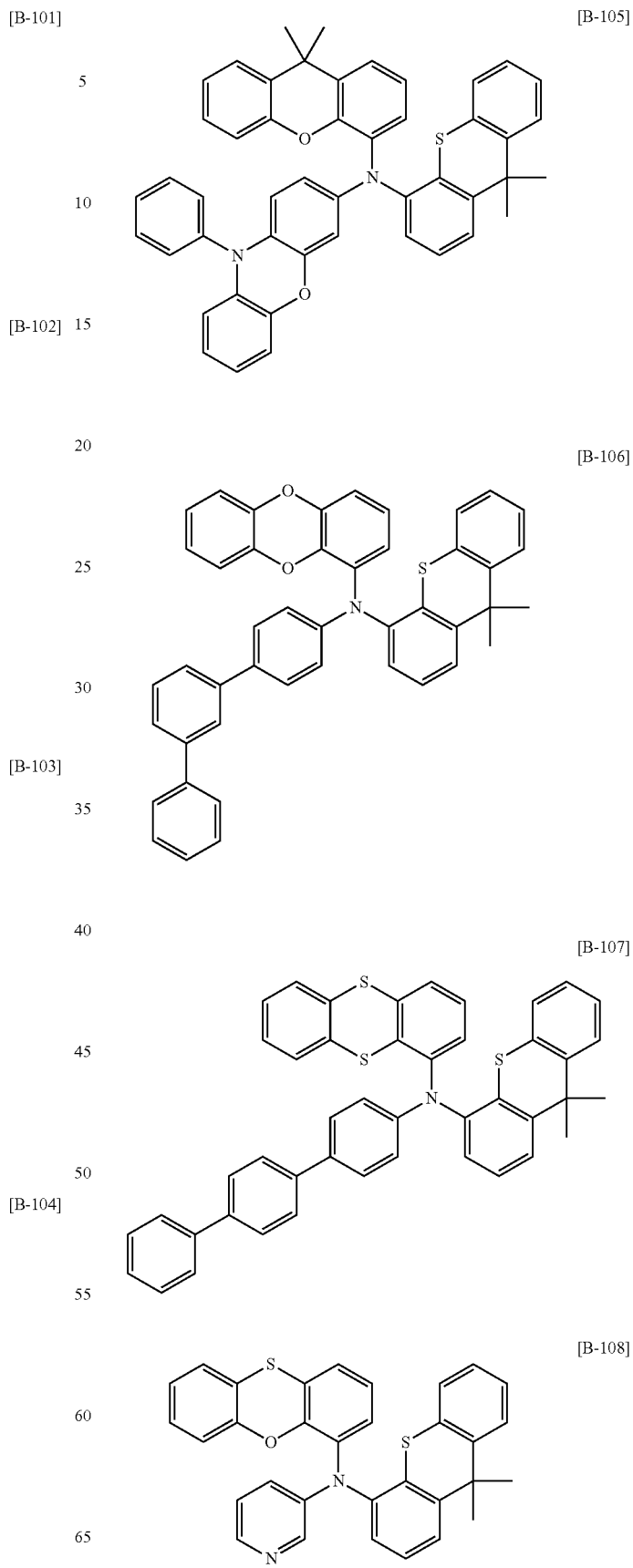

[B-109]
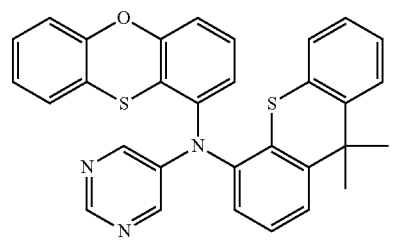
[B-110]
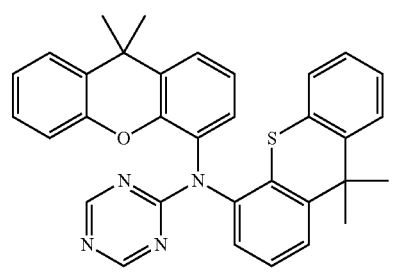
[B-111]
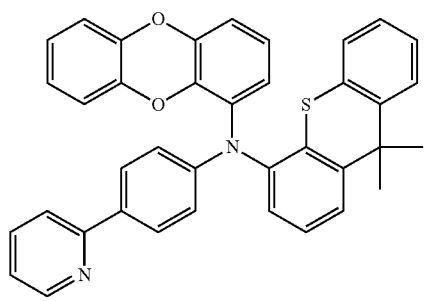
[B-112]
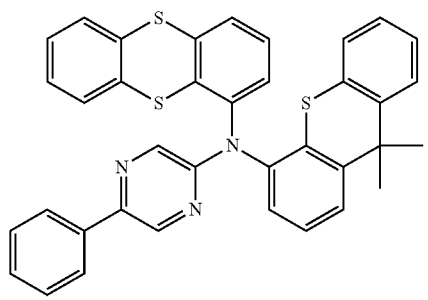
[B-113]
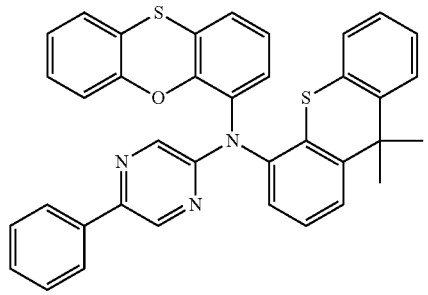
[B-114]
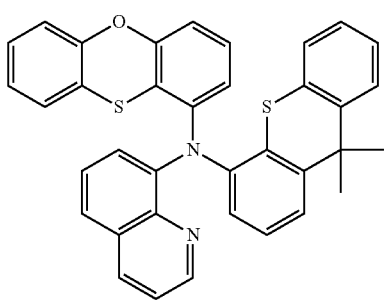
[B-115]
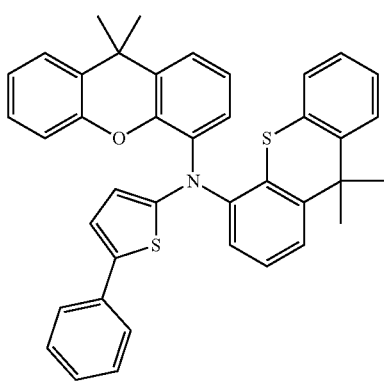
[B-116]
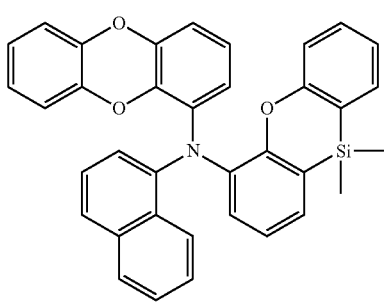
[B-117]
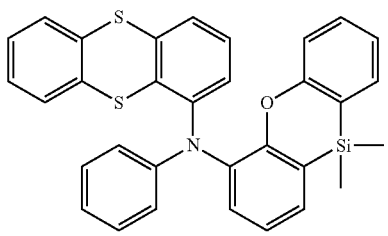
[B-118]
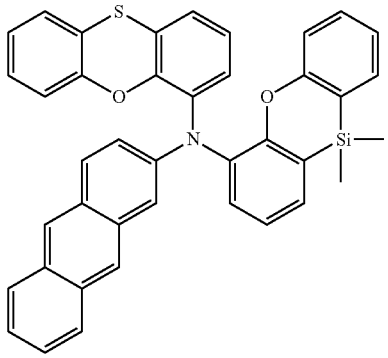

[B-119]
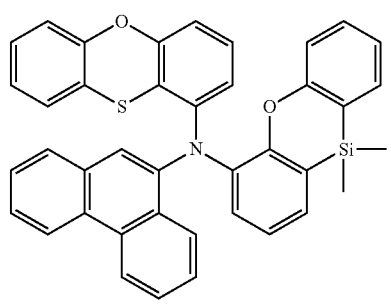
[B-124]
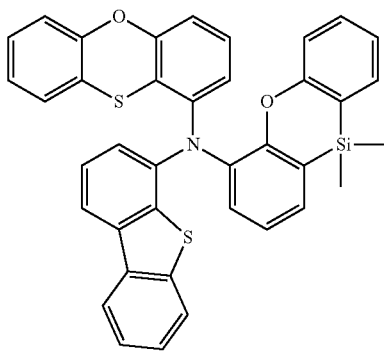
[B-120]
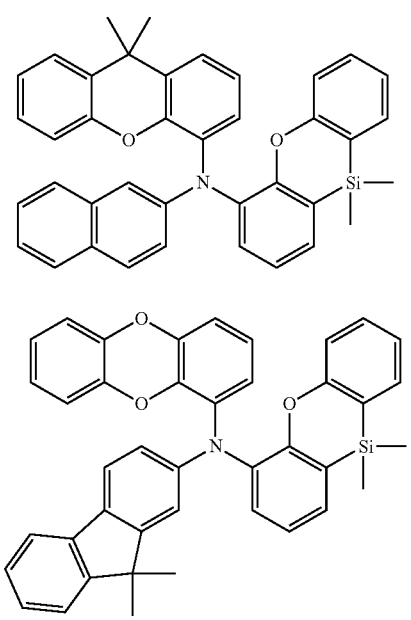
[B-125]
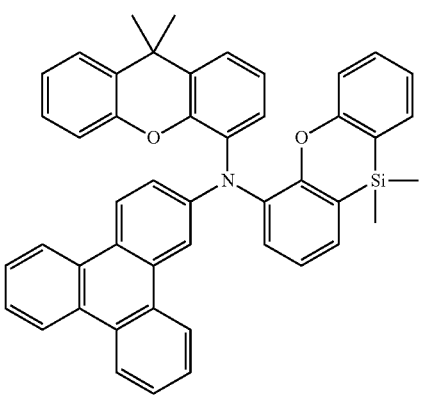
[B-121]
[B-126]
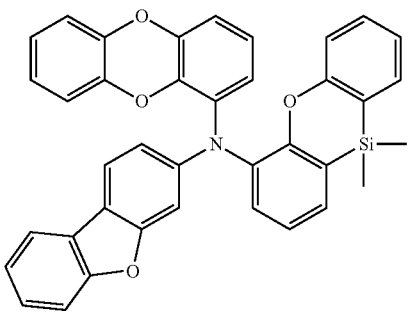
[B-122]
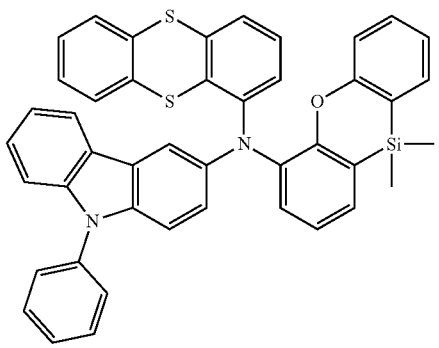
[B-123]
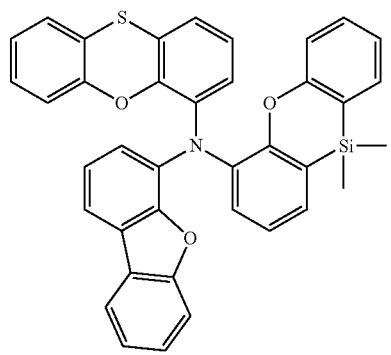
[B-127]
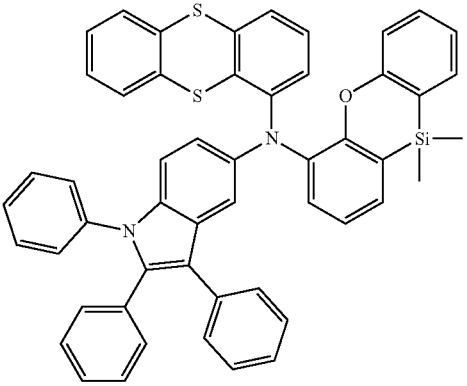

[B-128]
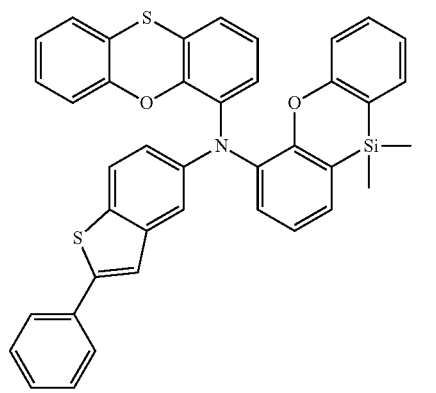
[B-129]
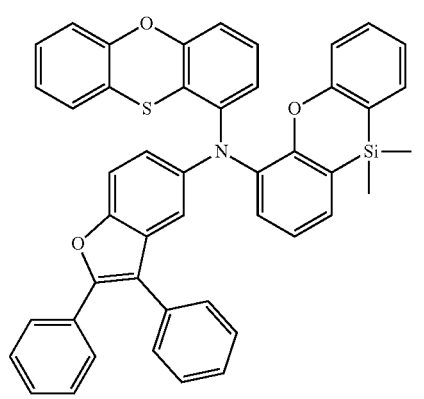
[B-130]
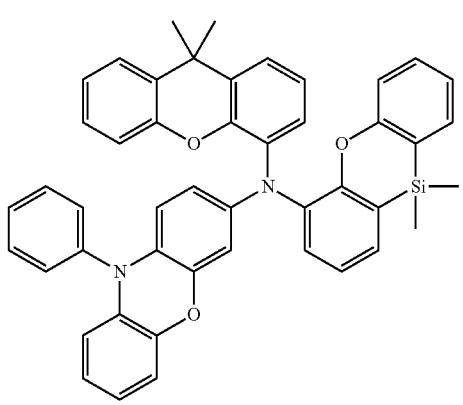
[B-131]
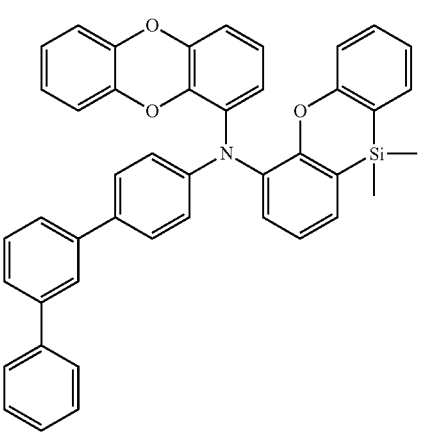
[B-132]
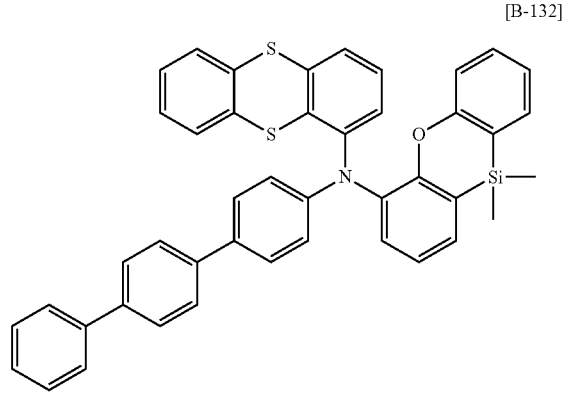
[B-133]
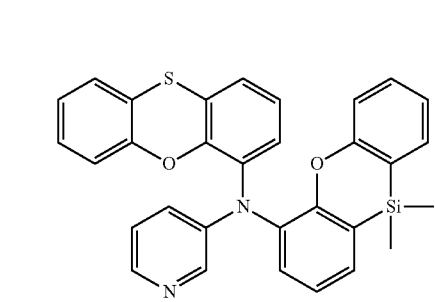
[B-134]
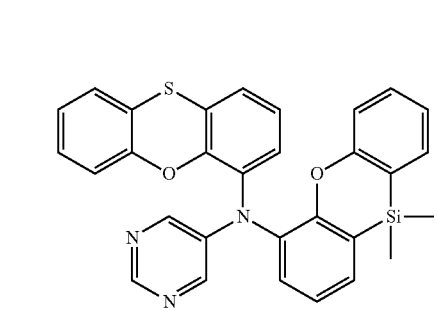
[B-135]
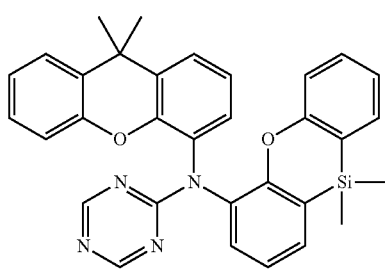
[B-136]
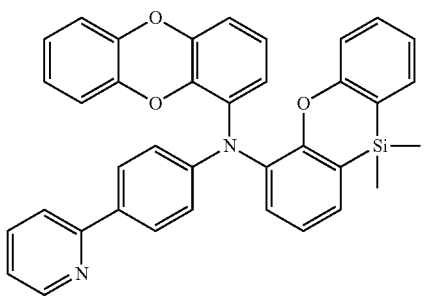

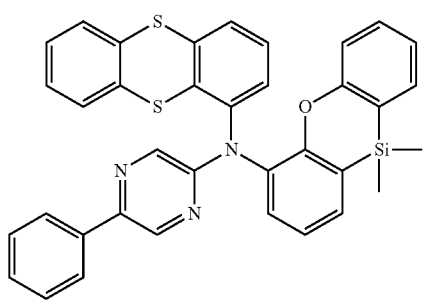 [B-137]
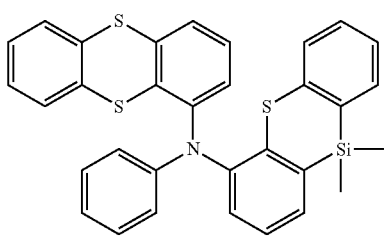 [B-143]
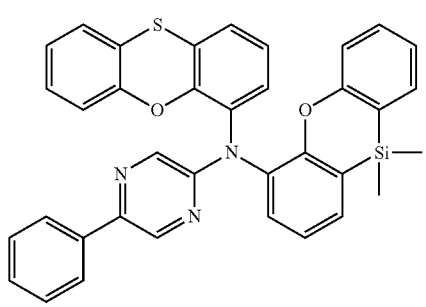 [B-138]
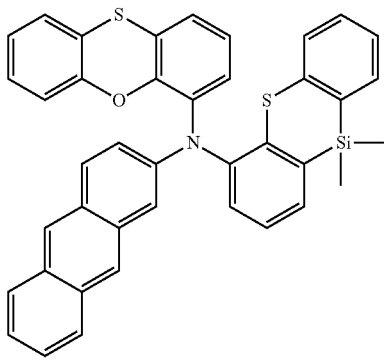 [B-144]
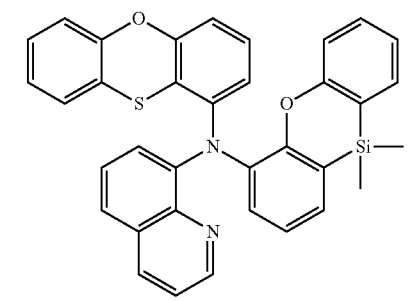 [B-140]
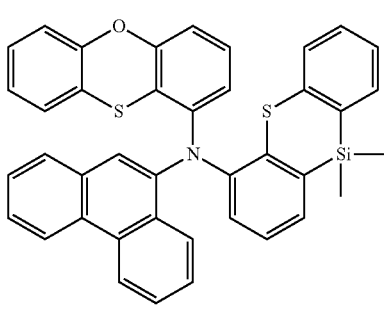 [B-145]
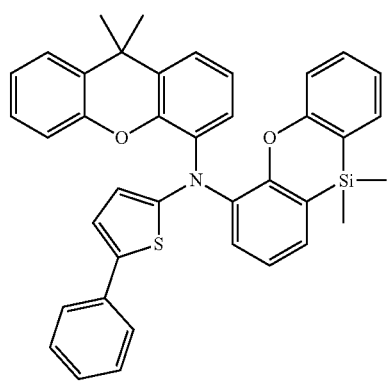 [B-141]
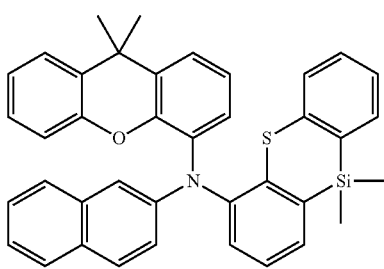 [B-146]
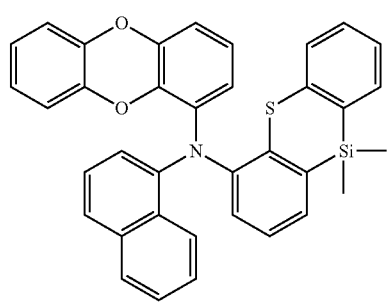 [B-142]
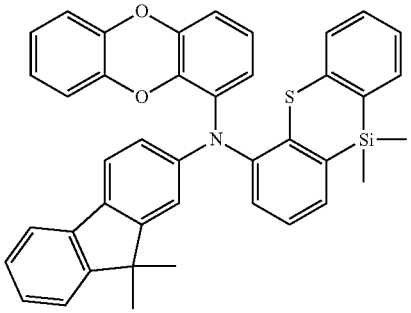 [B-147]

[B-148]
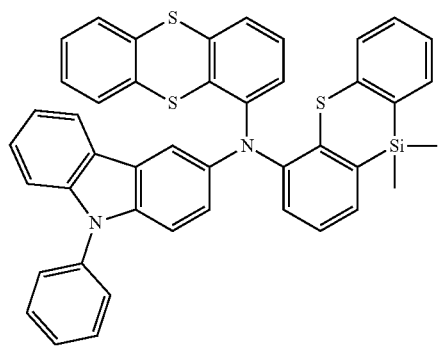
[B-152]
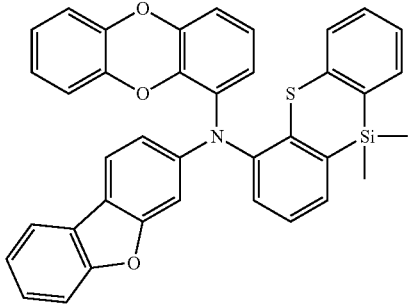
[B-149]
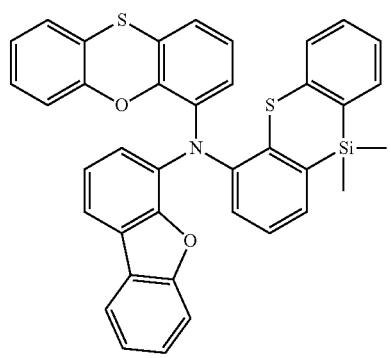
[B-153]
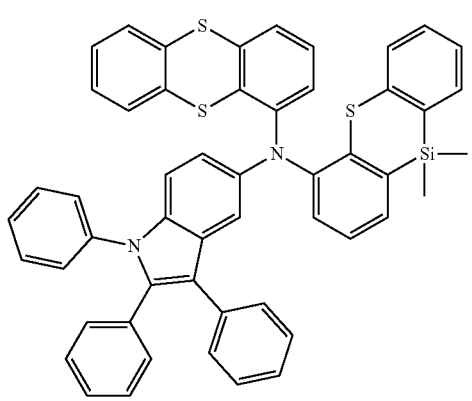
[B-150]
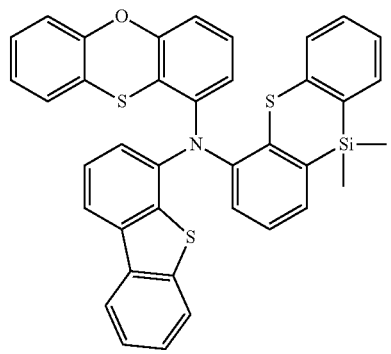
[B-154]
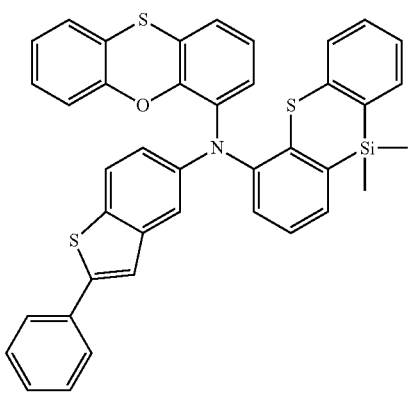
[B-151]
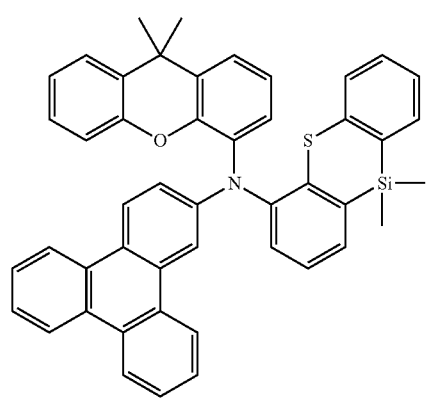
[B-155]
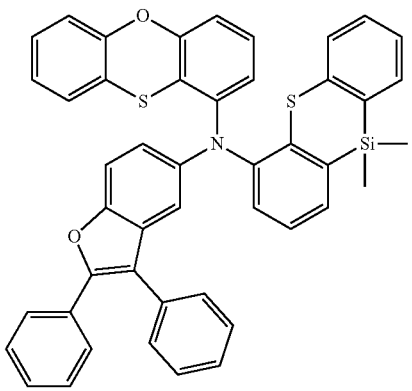

[B-156]
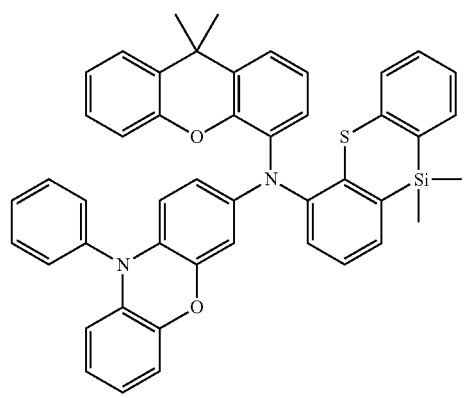
[B-157]
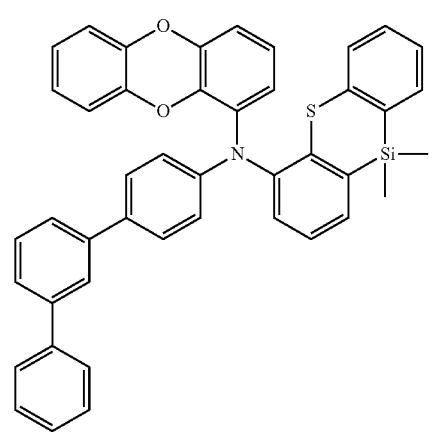
[B-158]
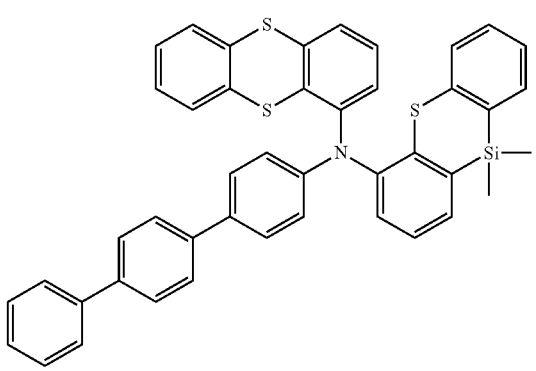
[B-159]
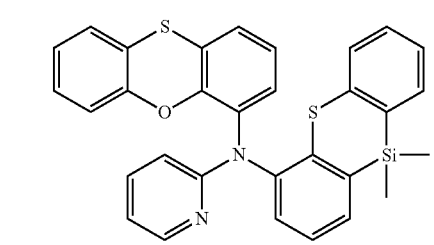
[B-160]
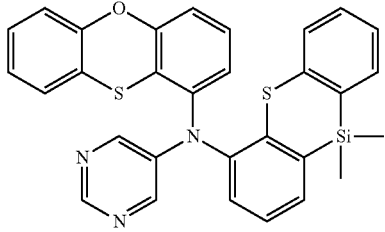
[B-161]
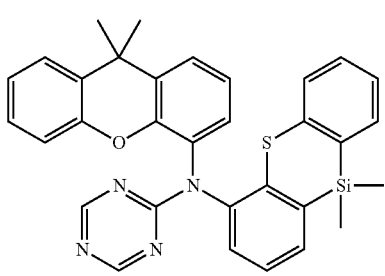
[B-162]
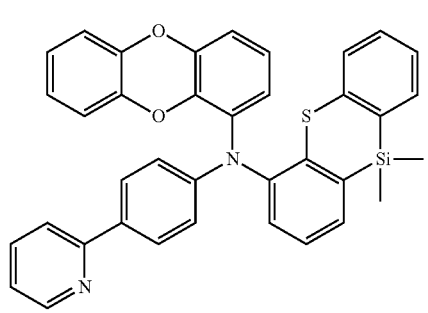
[B-163]
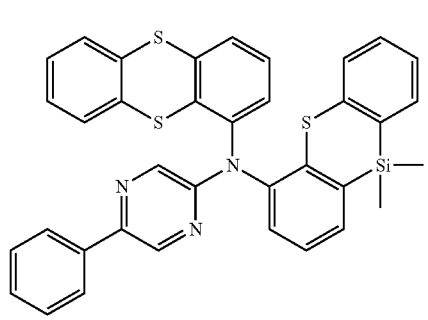
[B-164]
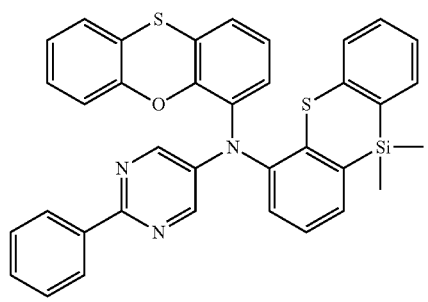

[B-165]
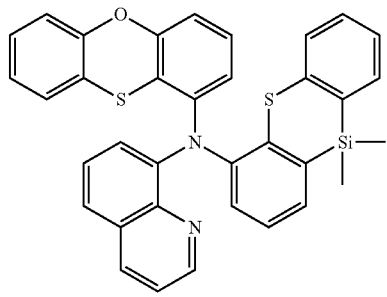
[B-166]
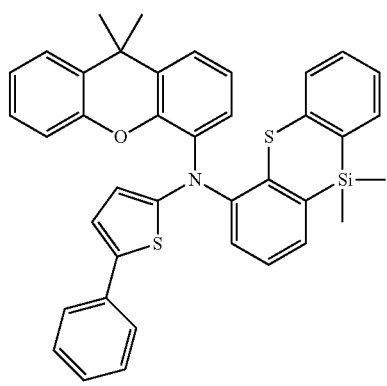
[B-167]
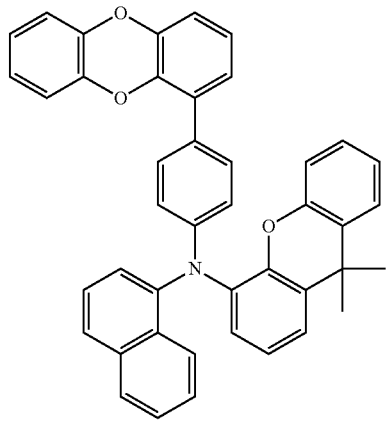
[B-168]
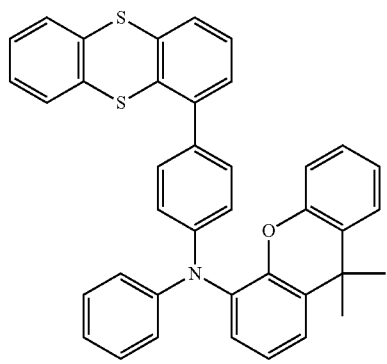
[B-169]
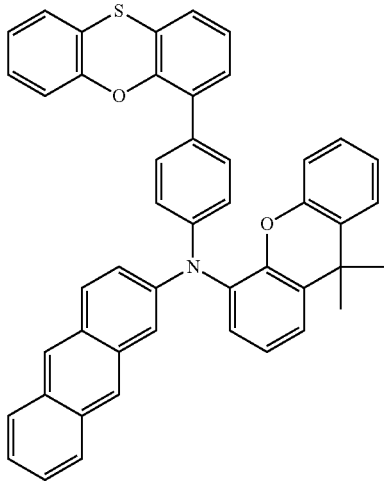
[B-170]
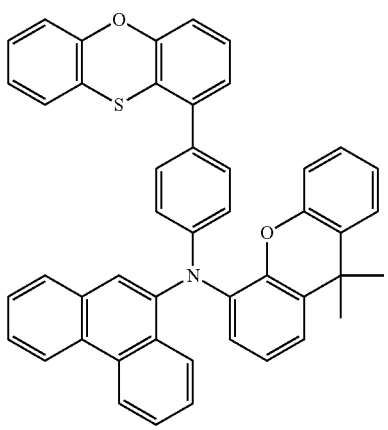
[B-171]
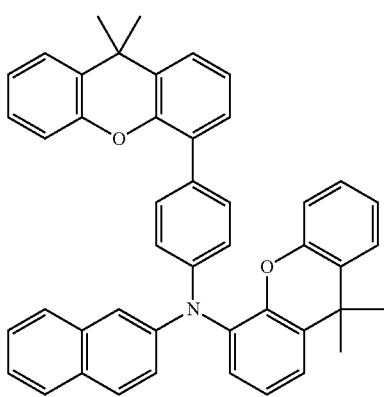

[B-172]
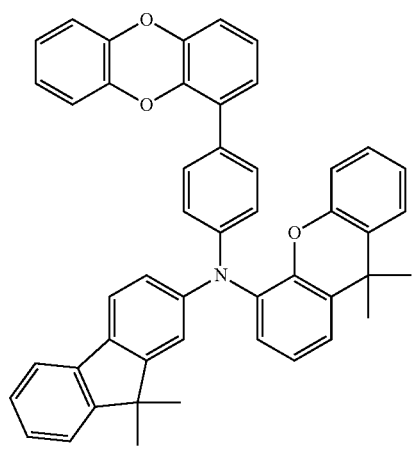
[B-173]
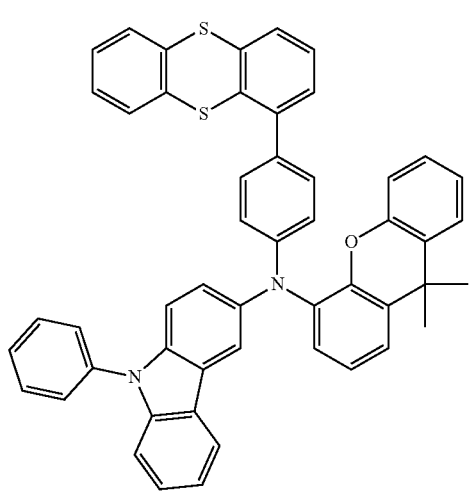
[B-174]
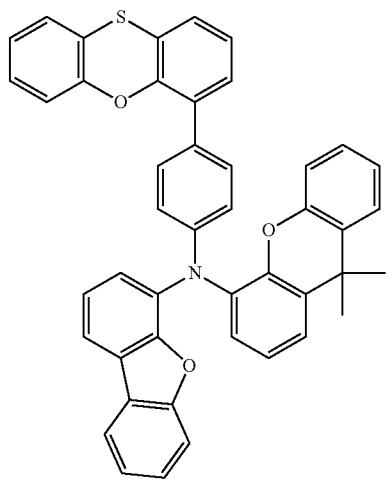
[B-175]
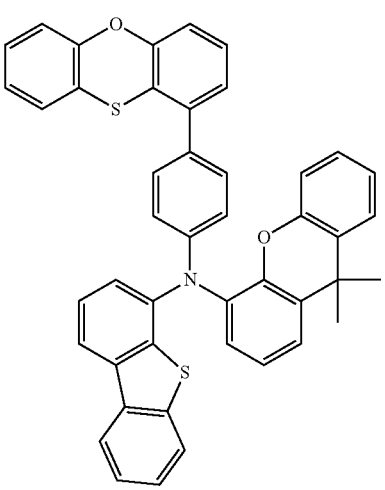
[B-176]
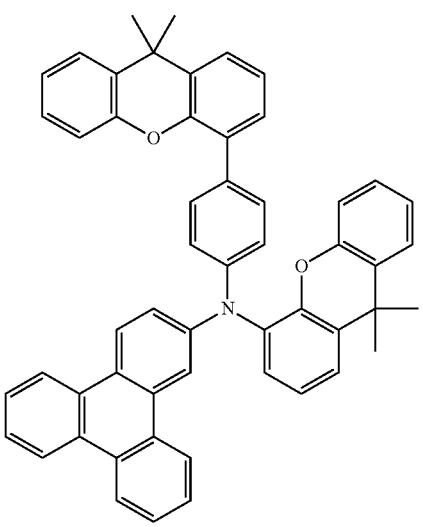
[B-177]
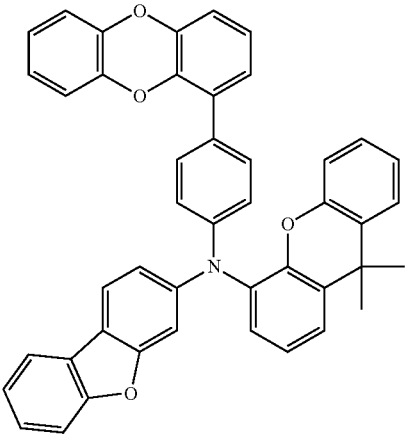

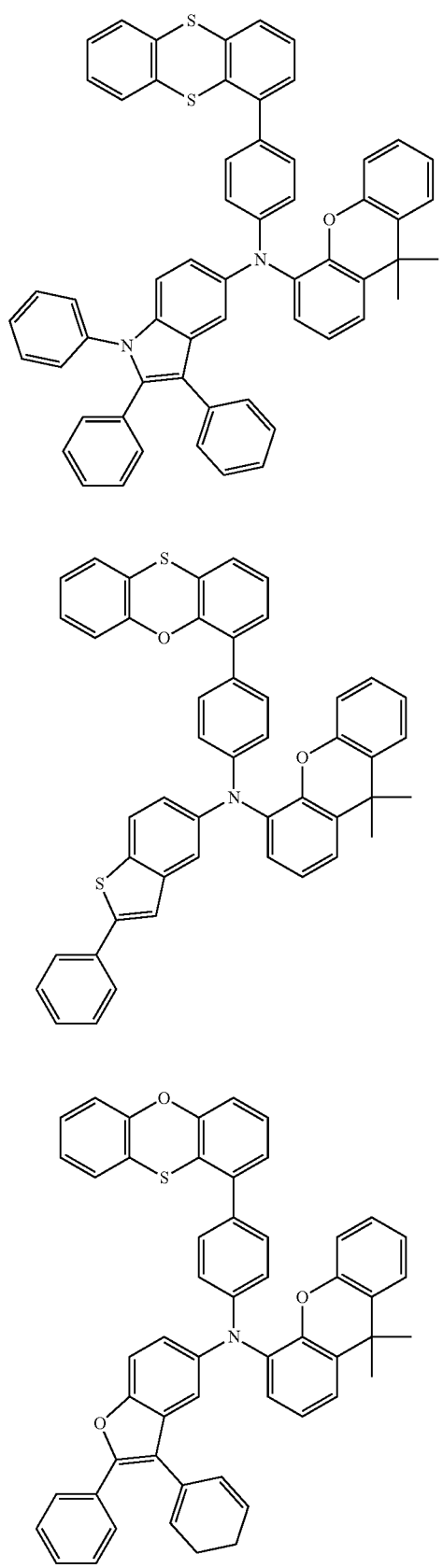
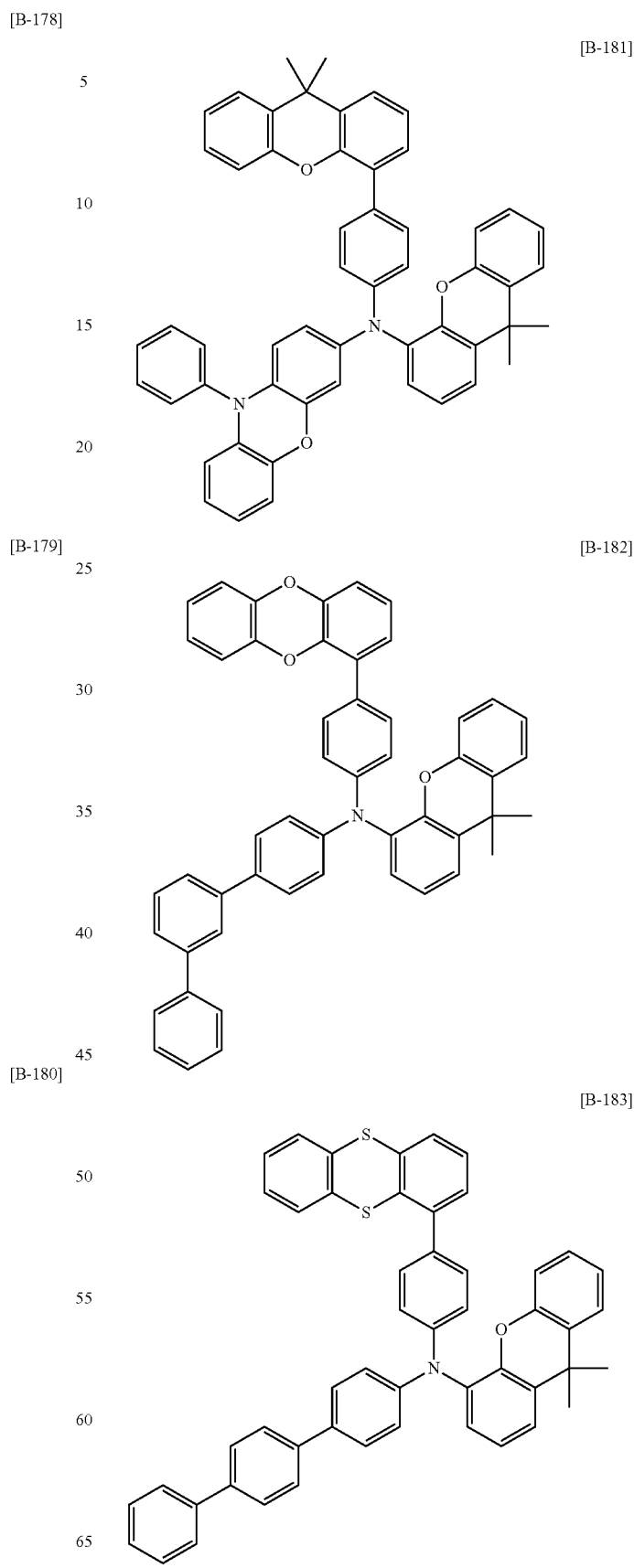

[B-184]
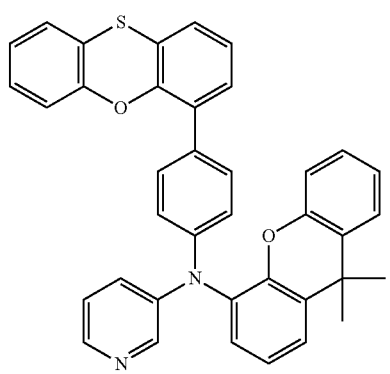
[B-185]
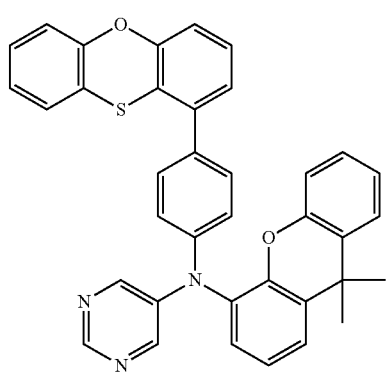
[B-186]
[B-187]
[B-188]
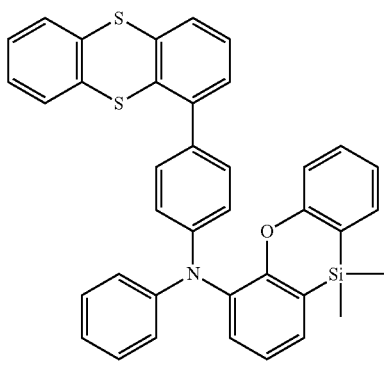
[B-189]
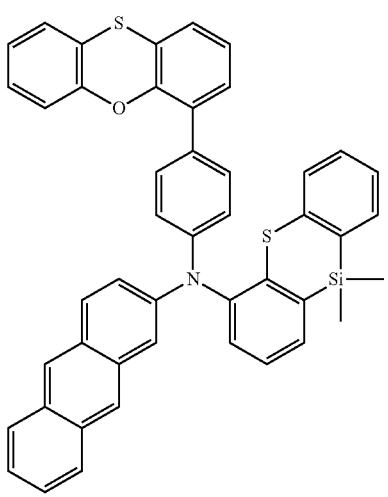
[B-190]
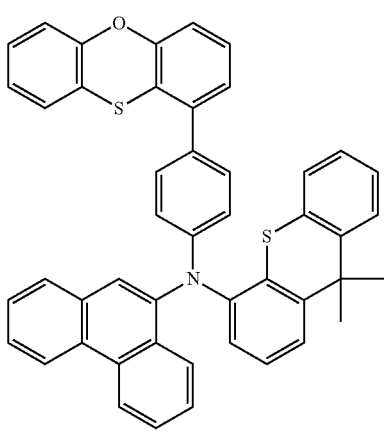

[B-191]
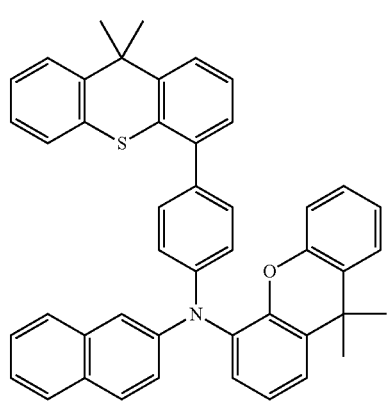
[B-194]
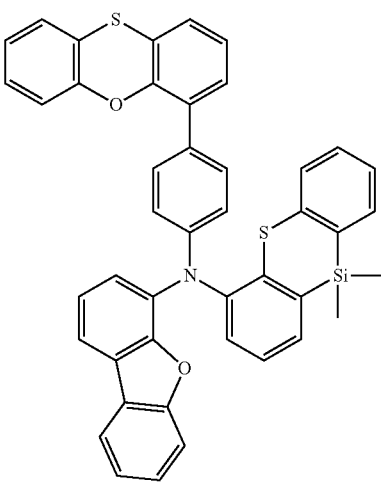
[B-192]
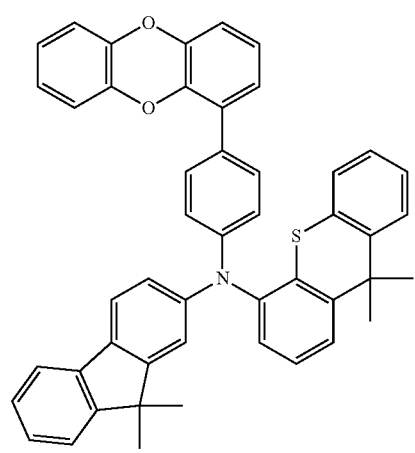
[B-195]
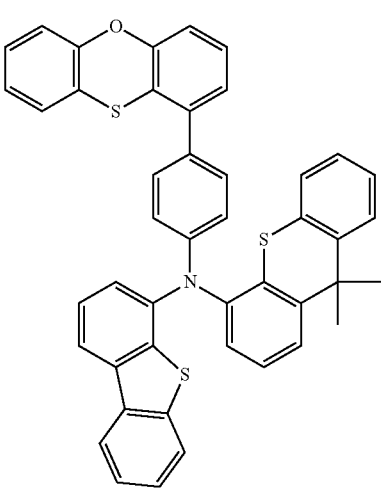
[B-193]
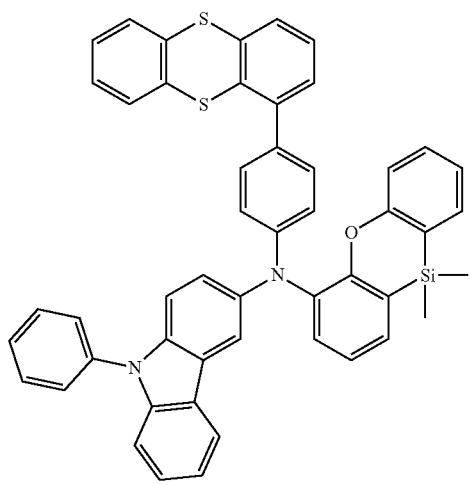
[B-196]
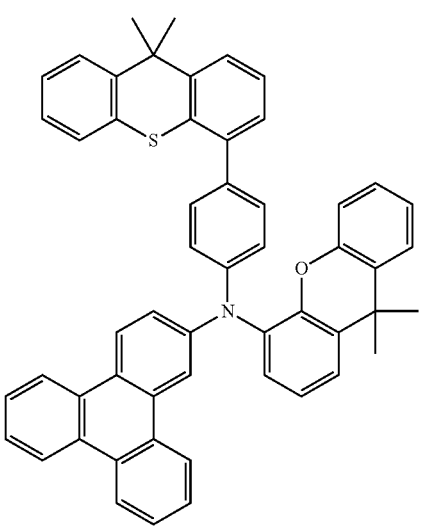

[B-197]
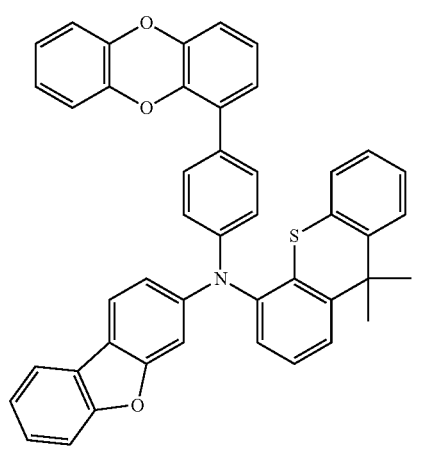
[B-198]
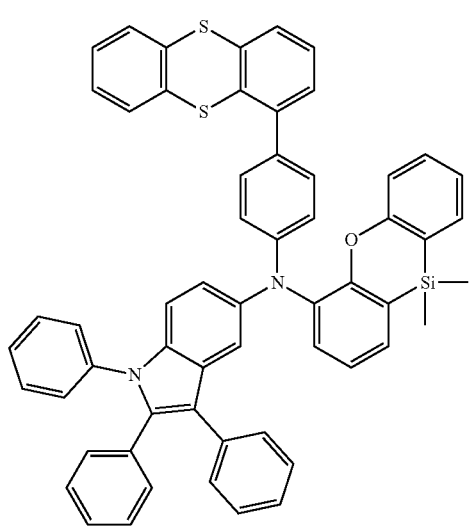
[B-199]
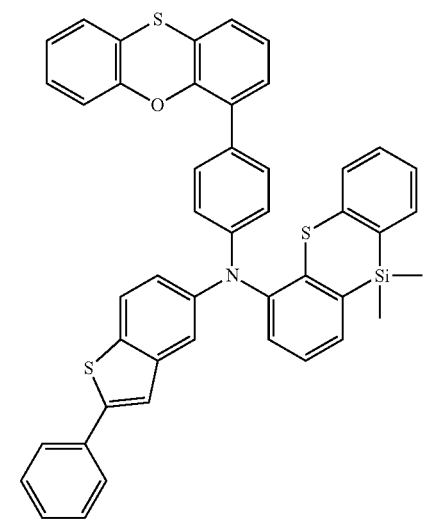
[B-200]
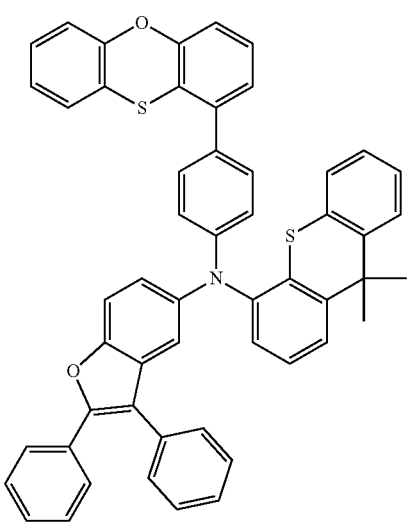
[B-201]
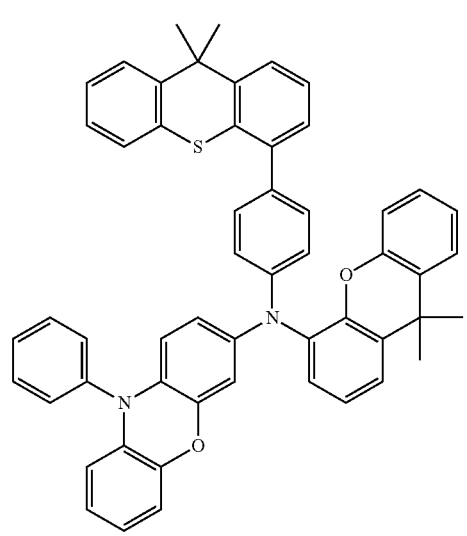
[B-202]
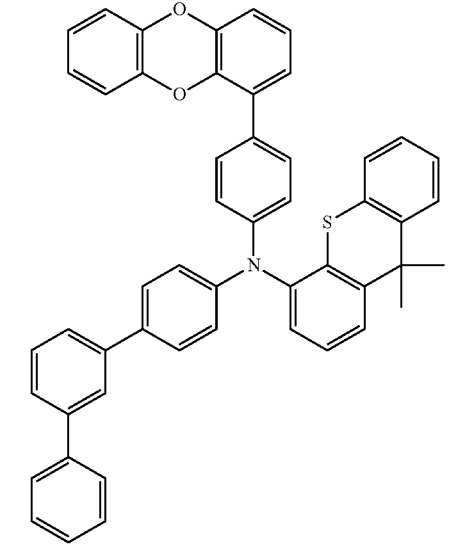

[B-203]
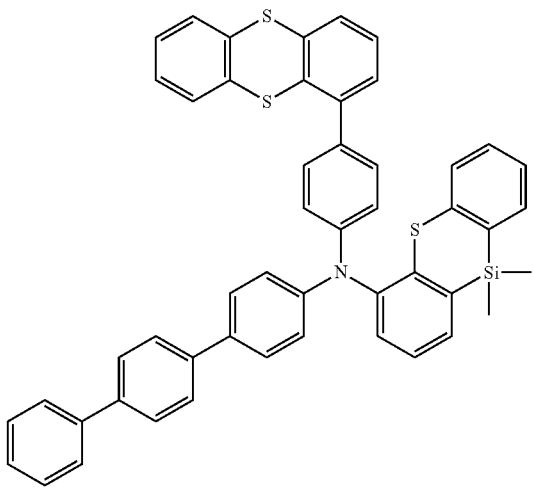
[B-207]
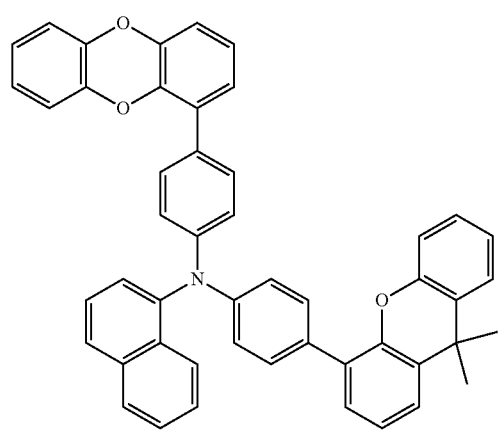
[B-204]
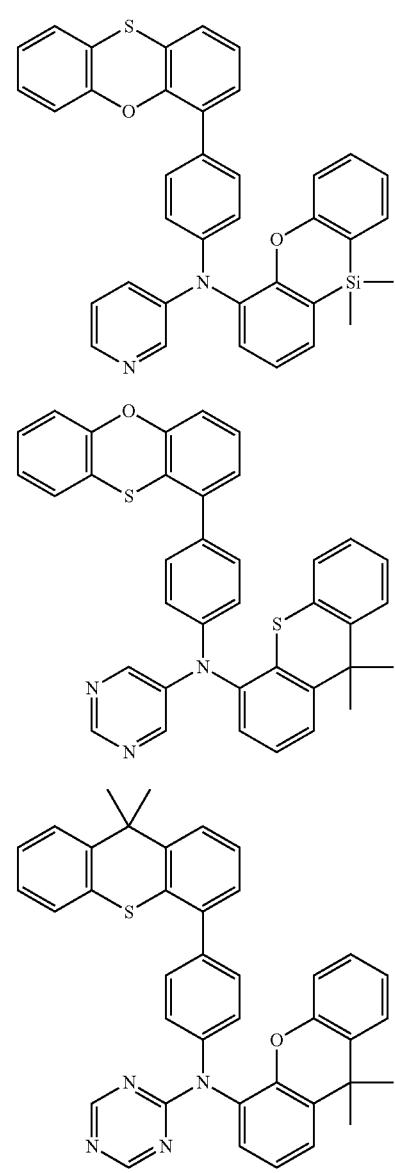
[B-208]
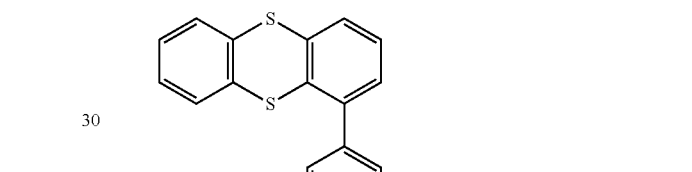
[B-205]
[B-206]
[B-209]
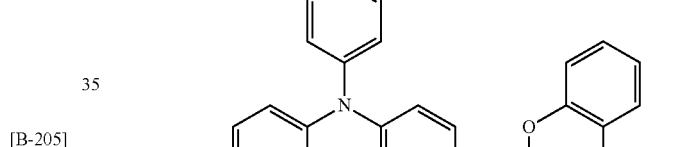
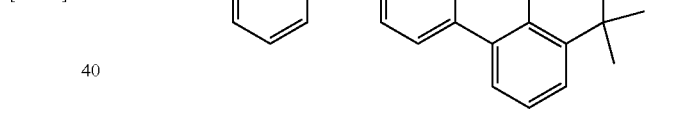

[B-210]
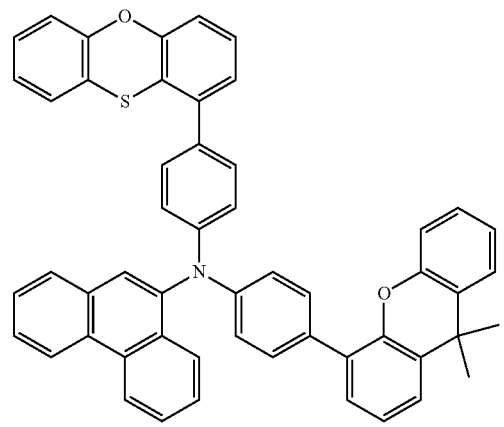
[B-213]
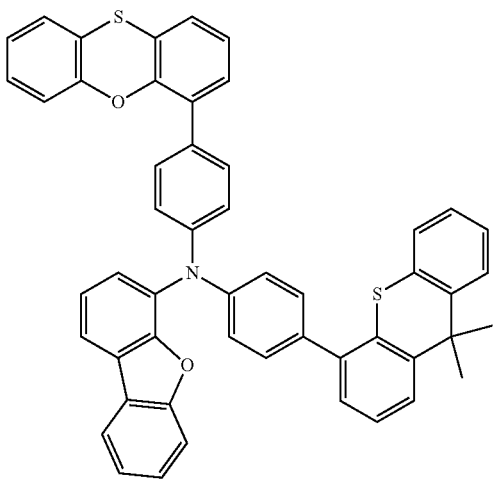
[B-211]
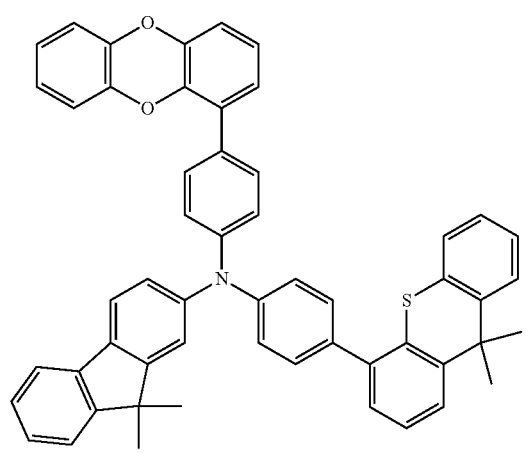
[B-214]
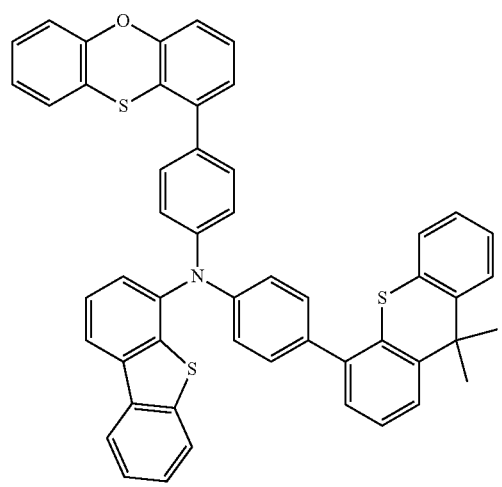
[B-212]
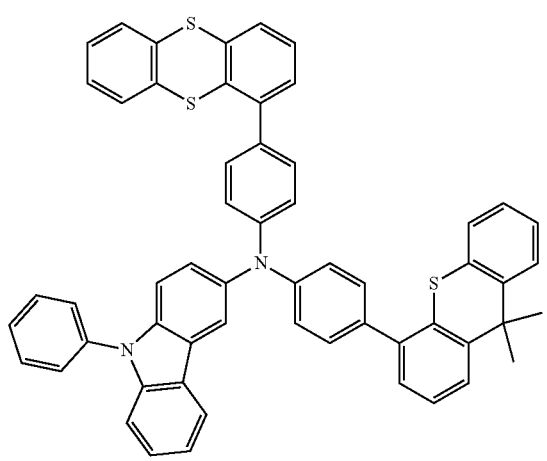
[B-215]
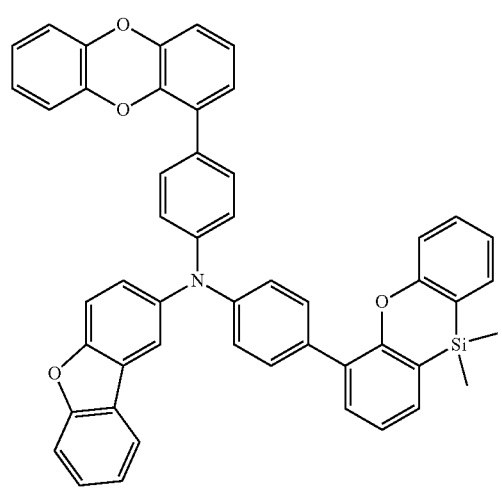

[B-216]
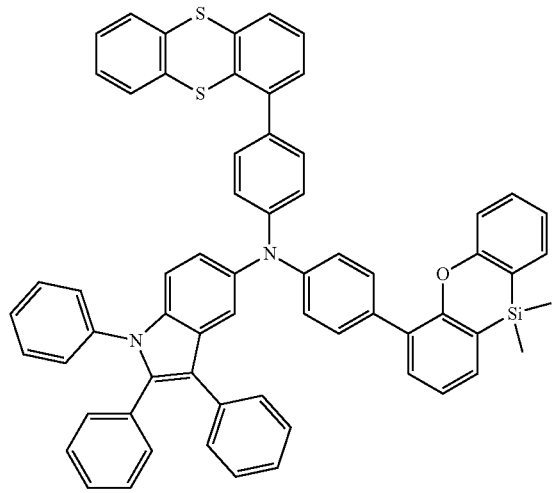
[B-217]
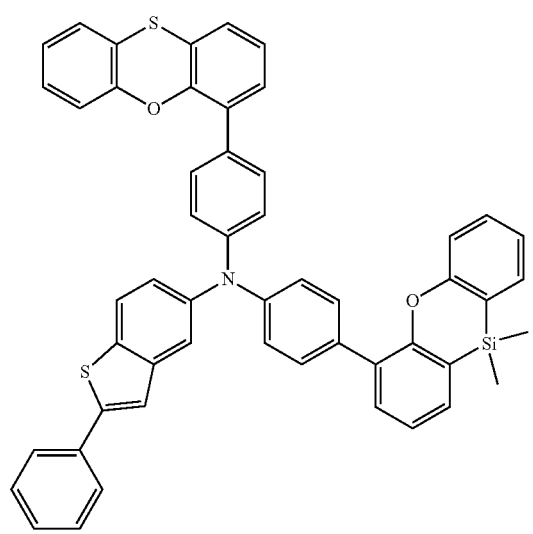
[B-218]
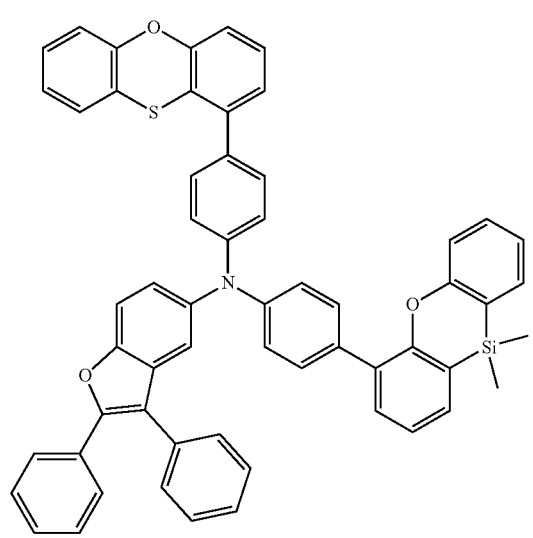
[B-219]
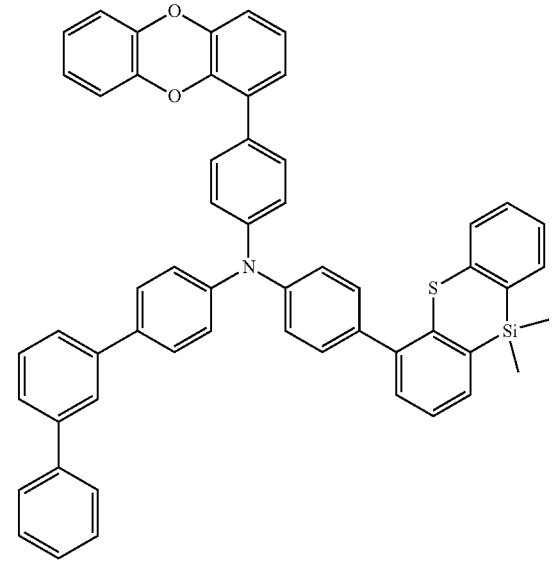
[B-220]
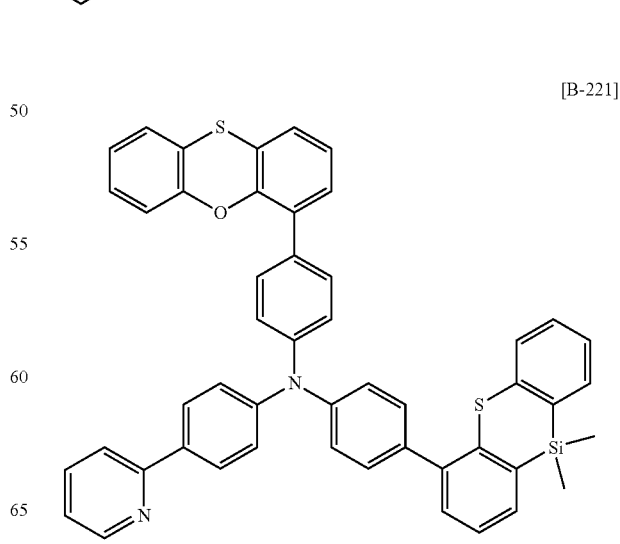
[B-221]

[B-222]
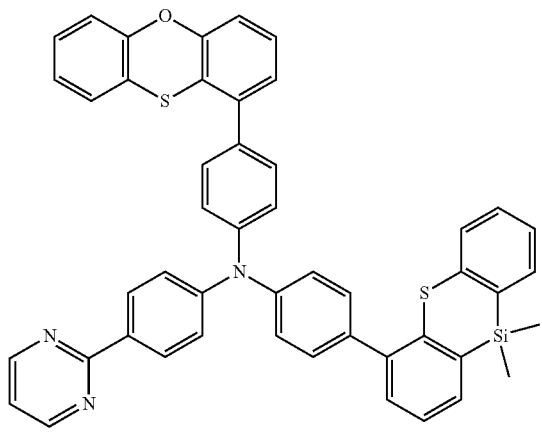
[B-223]
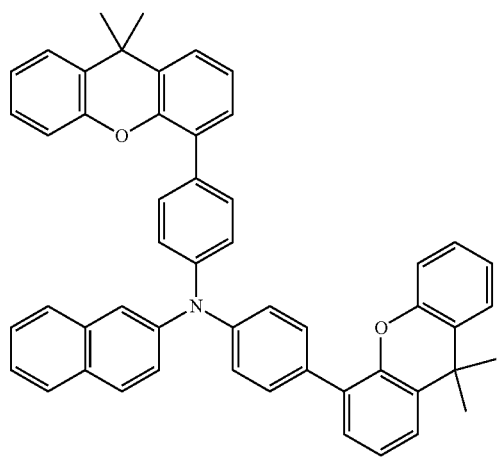
[B-224]
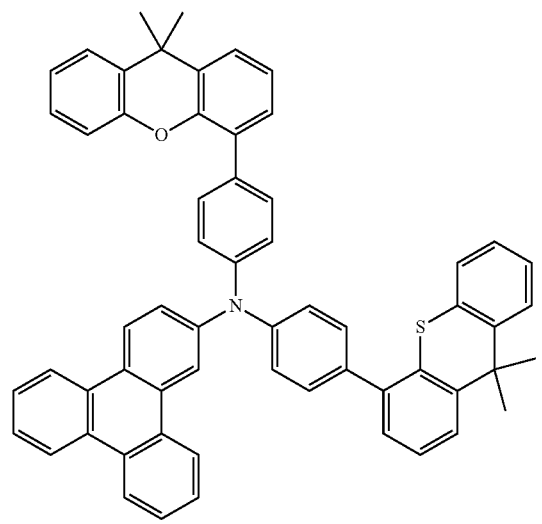
[B-225]
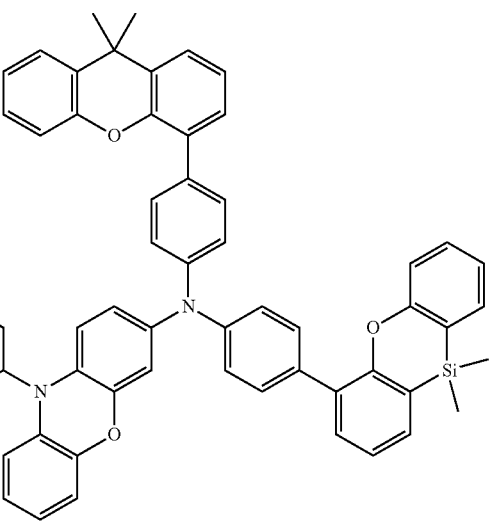
[B-226]
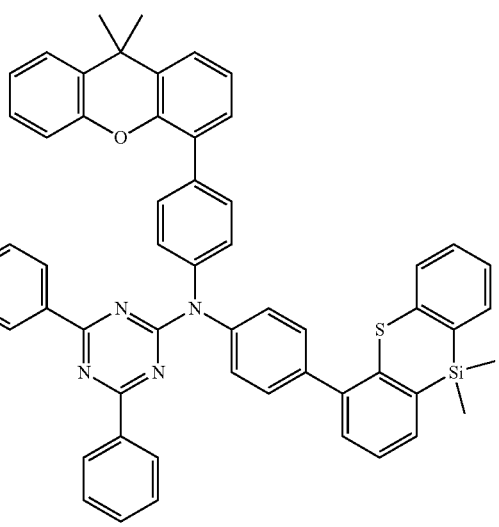
More specifically, the compound for an organic optoelectronic device may be represented by one of the following Chemical Formulae C-1 to C-286. But it is not limited thereto.
[C-1]
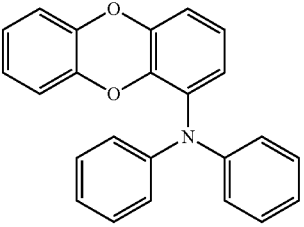

[C-2]
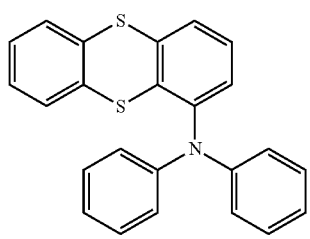
[C-3]
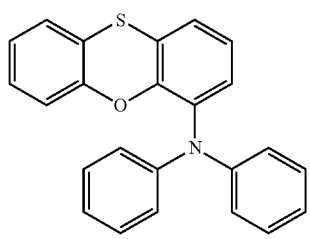
[C-4]
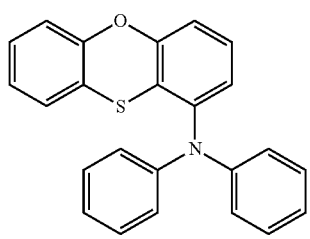
[C-5]
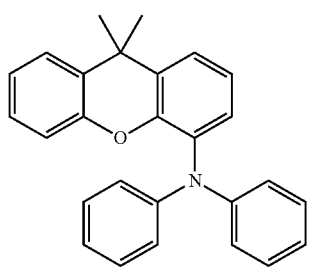
[C-6]
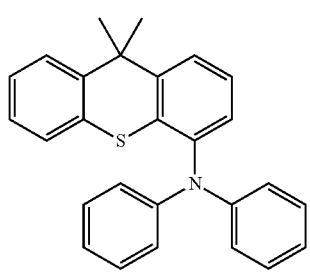
[C-7]
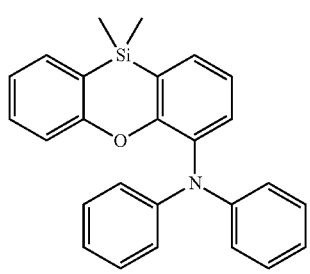
[C-8]
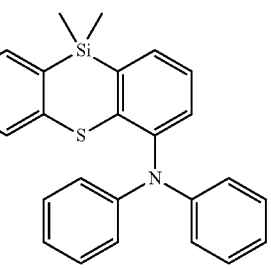
[C-9]
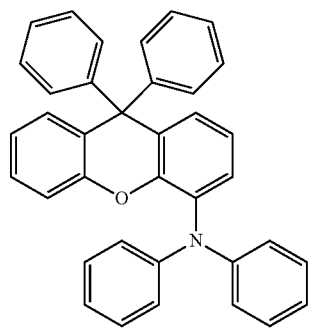
[C-10]
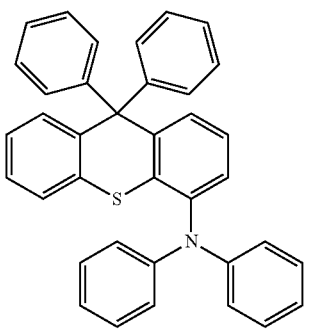
[C-11]
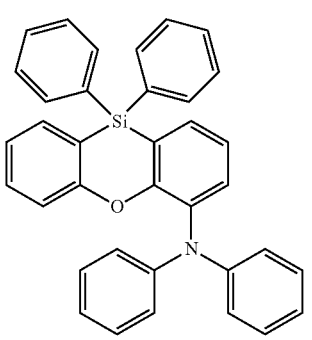
[C-12]
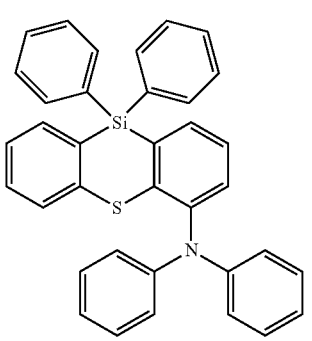

[C-13]
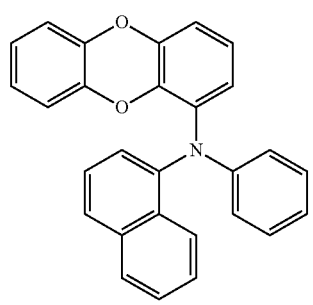
[C-14]
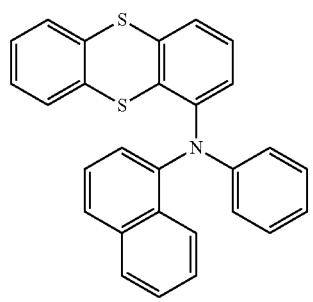
[C-15]
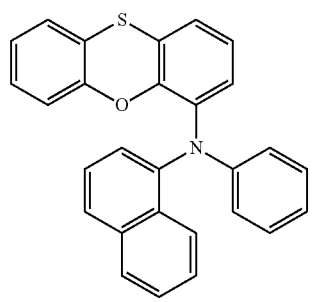
[C-16]
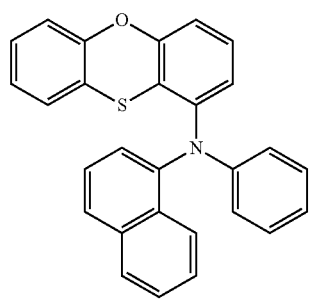
[C-17]
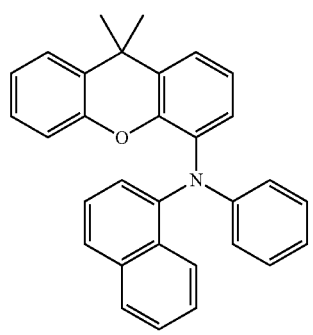
[C-18]
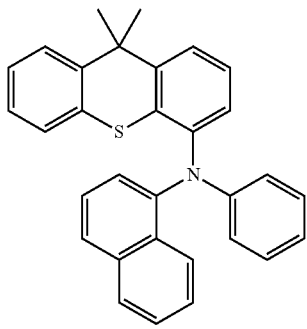
[C-19]
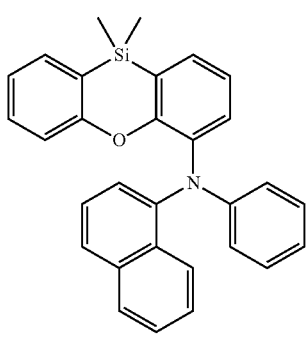
[C-20]
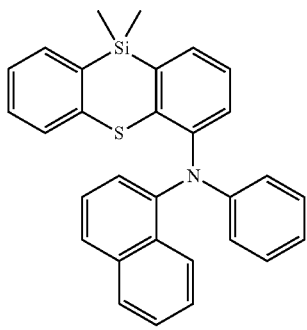
[C-21]
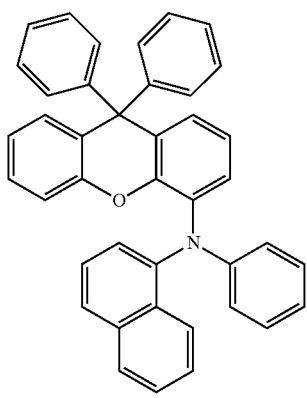

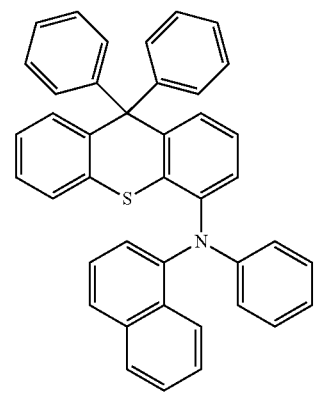
[C-22]
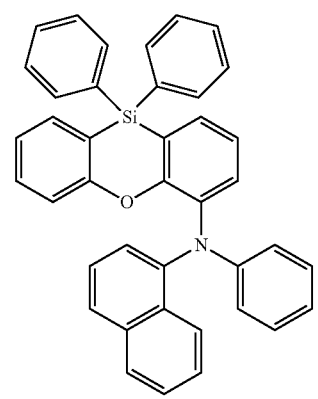
[C-23]
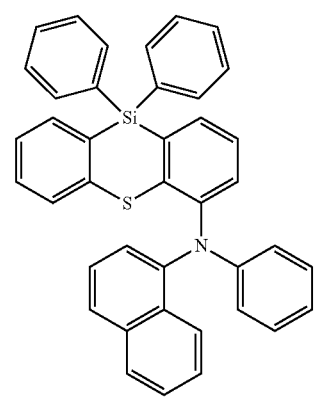
[C-24]
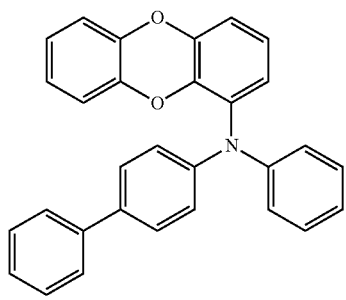
[C-25]
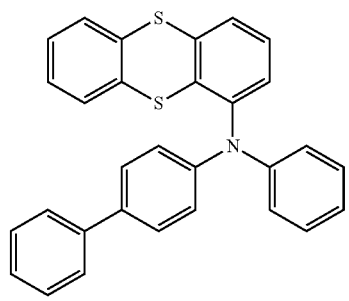
[C-26]
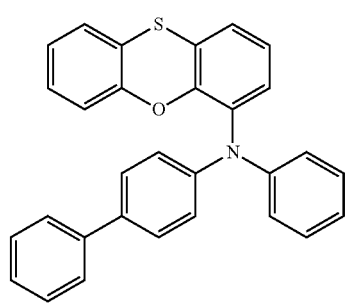
[C-27]
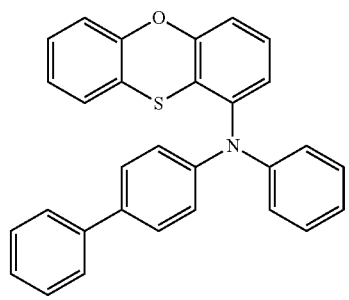
[C-28]
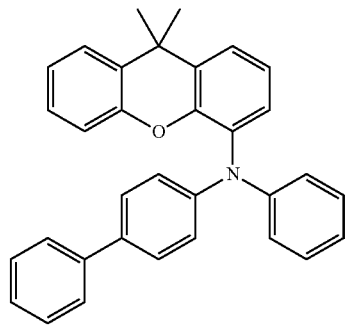
[C-29]
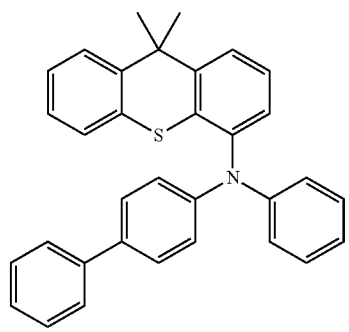
[C-30]

[C-31]
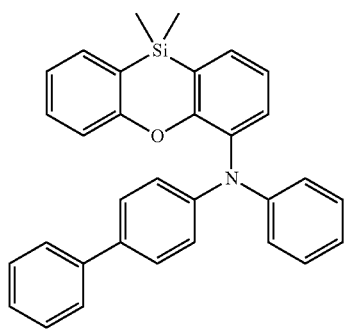
[C-32]
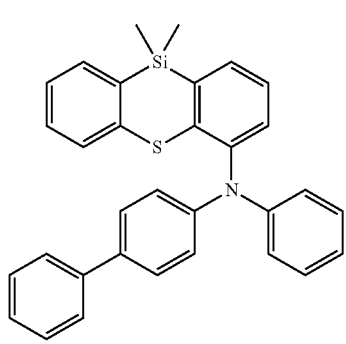
[C-33]
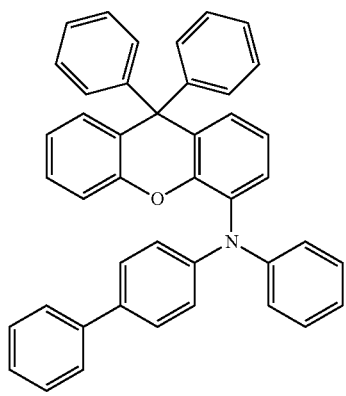
[C-34]
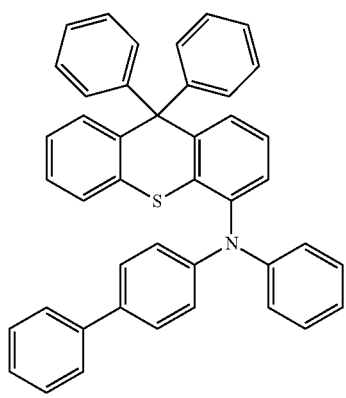
[C-35]
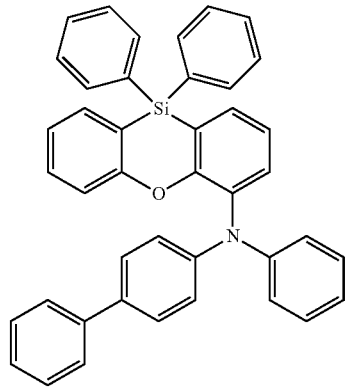
[C-36]
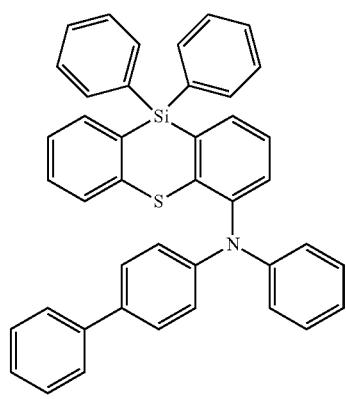
[C-37]
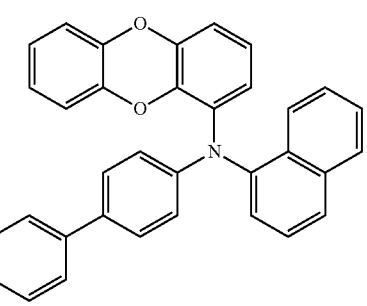
[C-38]
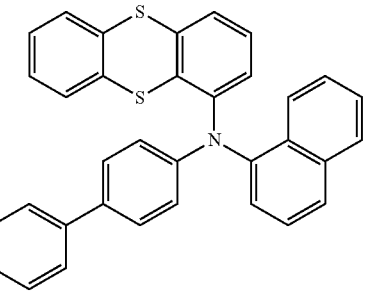

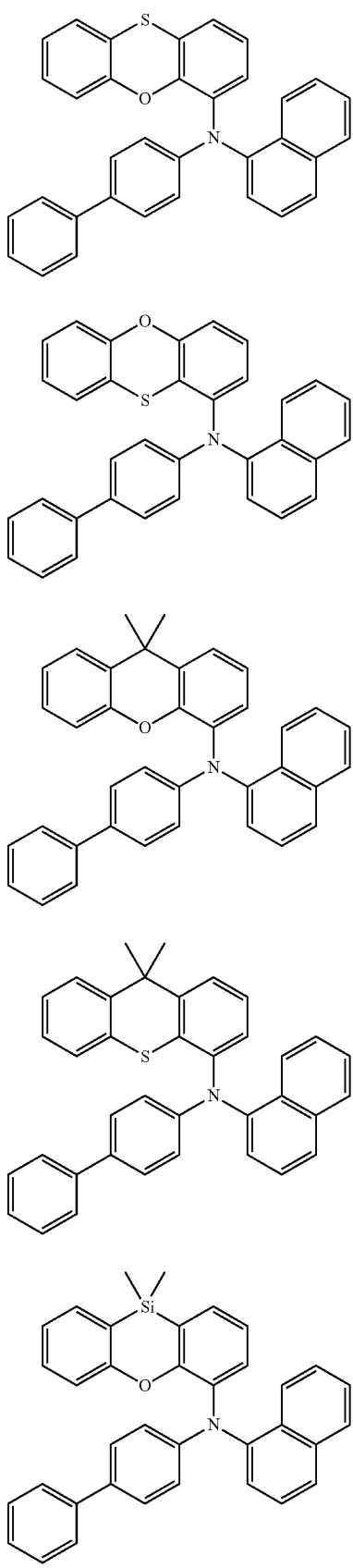
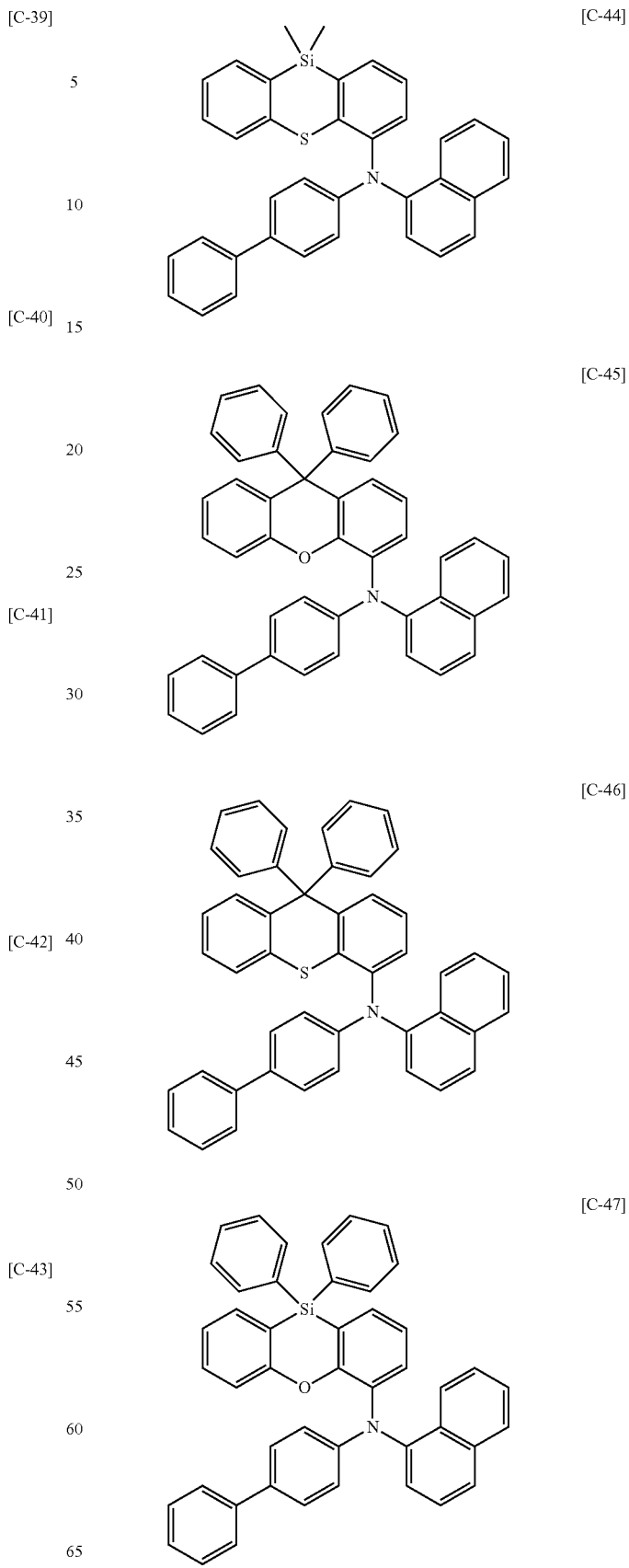

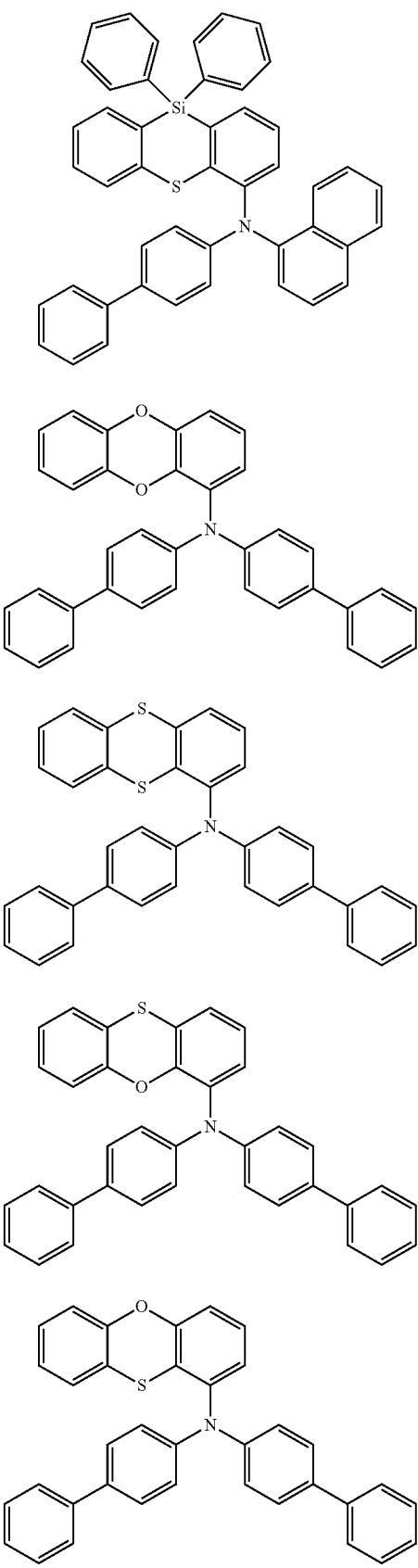
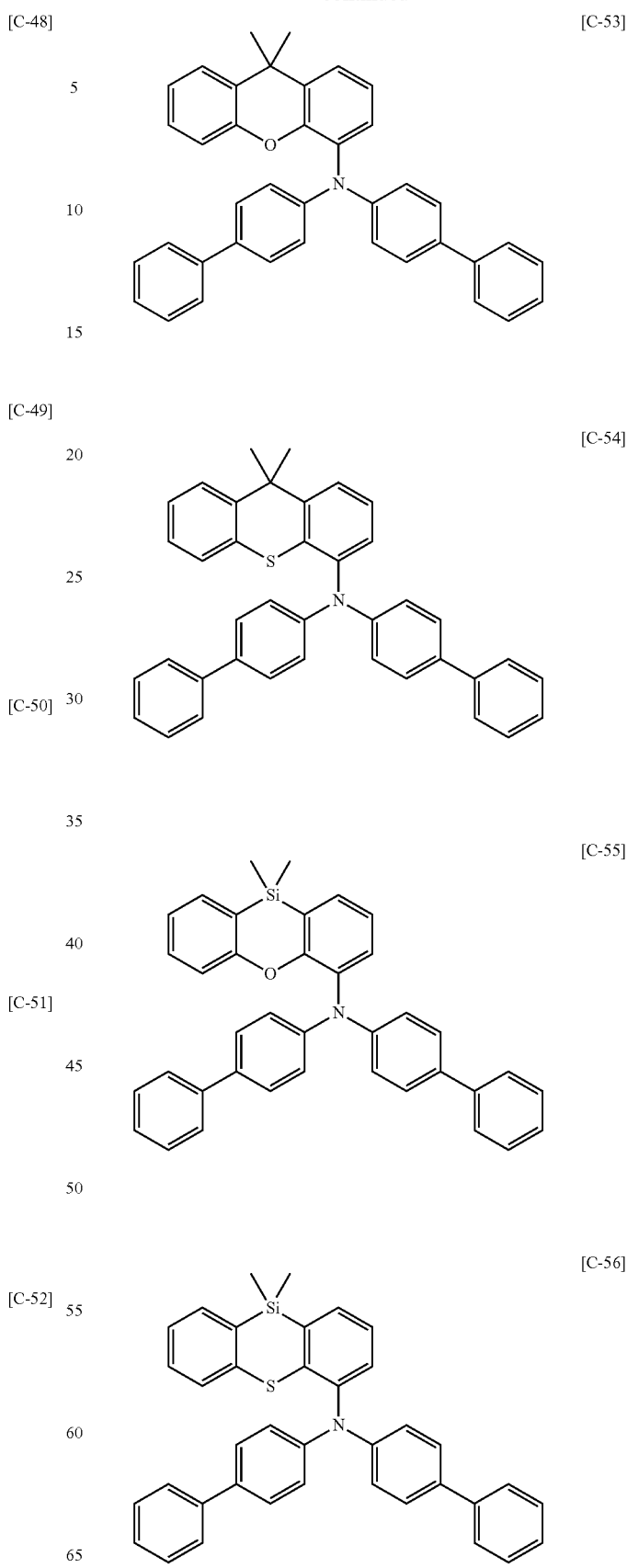

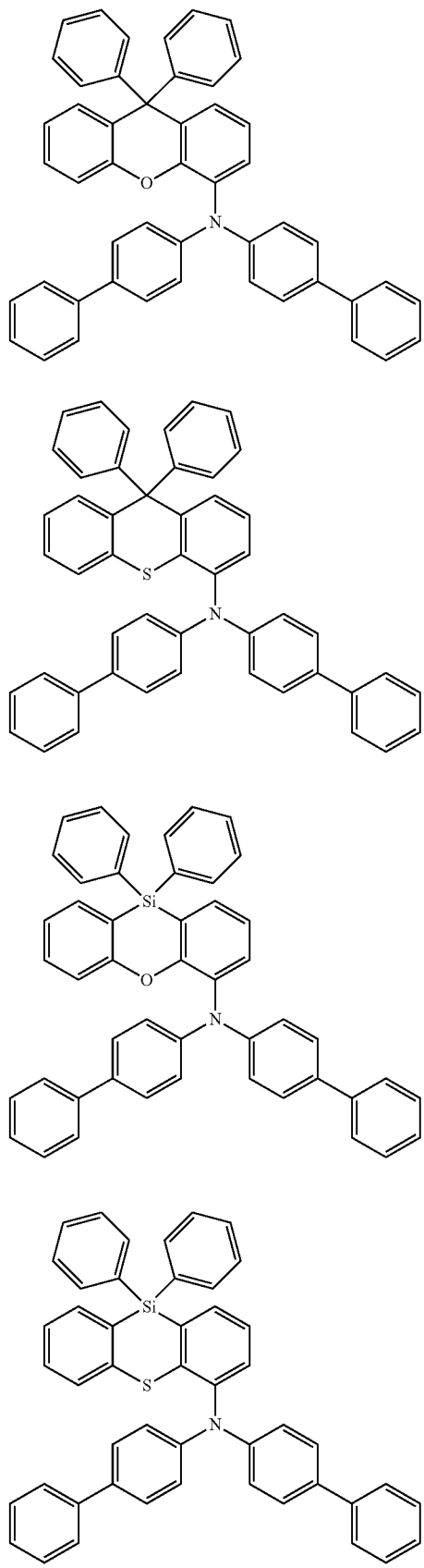
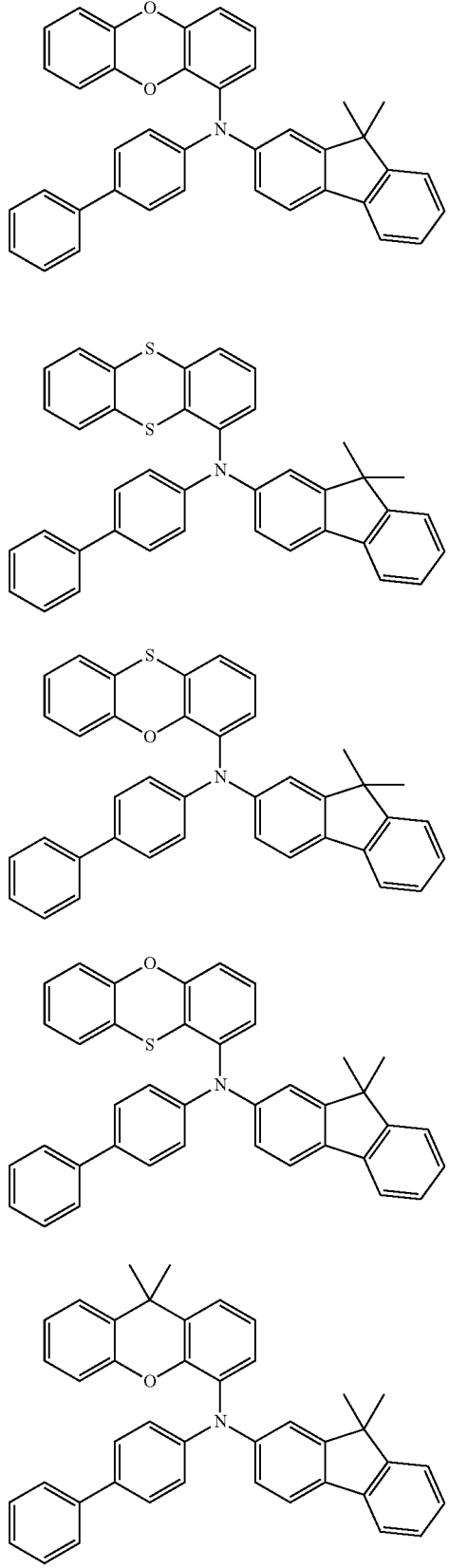

[C-66]
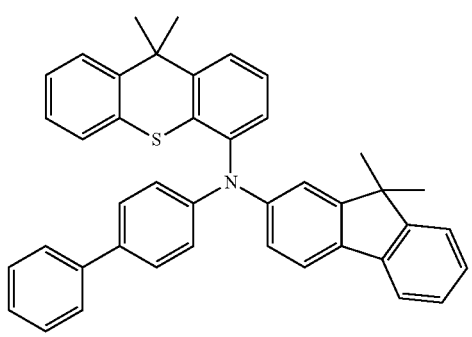
[C-70]
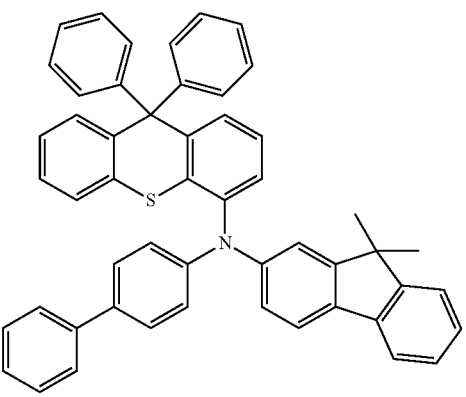
[C-67]
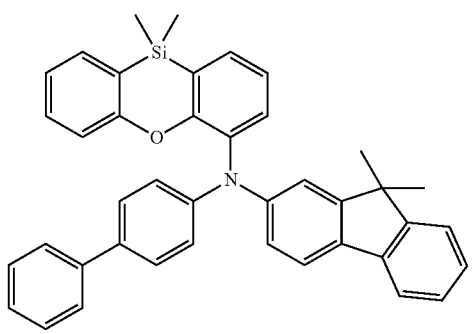
[C-71]
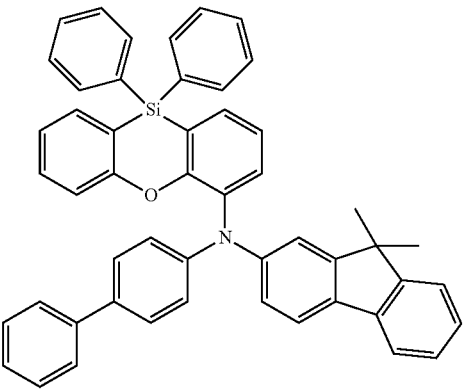
[C-68]
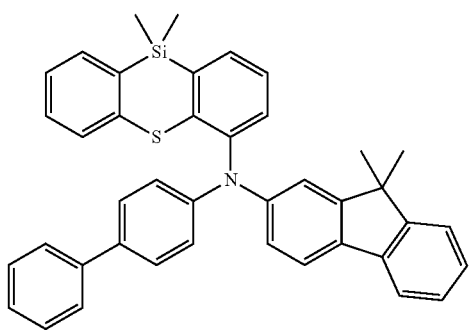
[C-72]
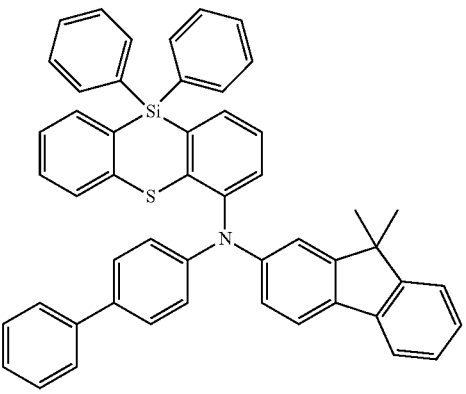
[C-69]
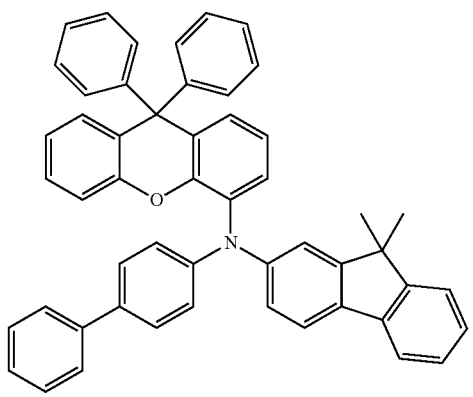
[C-73]
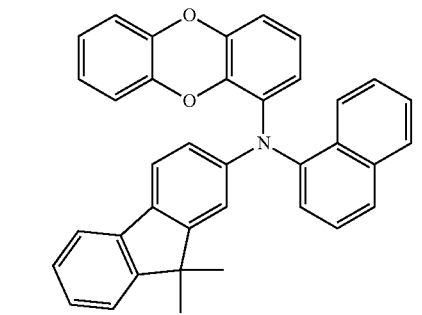

[C-74] 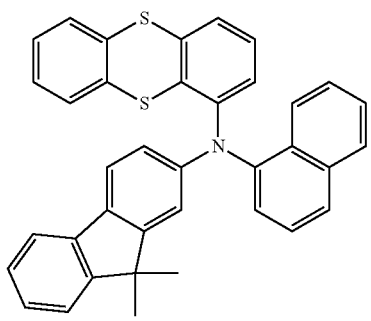
[C-75] 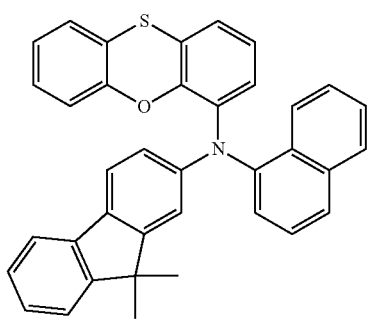
[C-76] 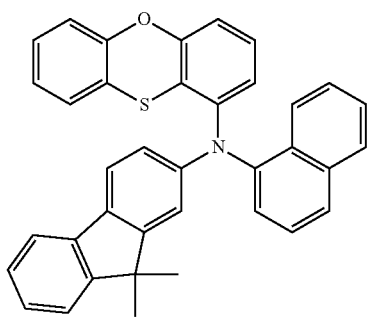
[C-77] 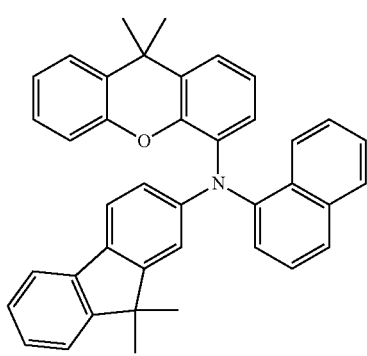
[C-78] 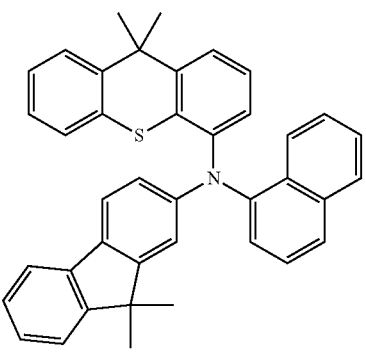
[C-79] 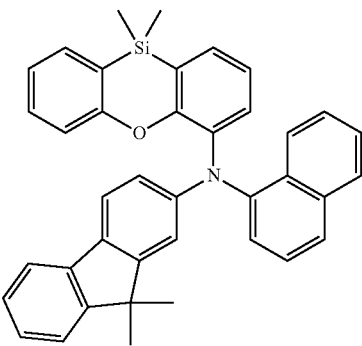
[C-80] 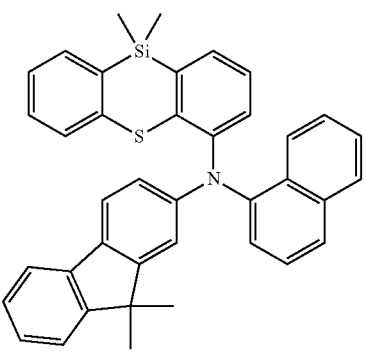
[C-81] 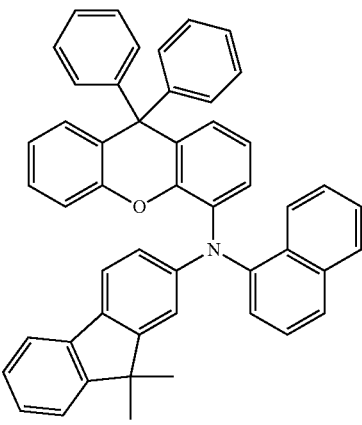

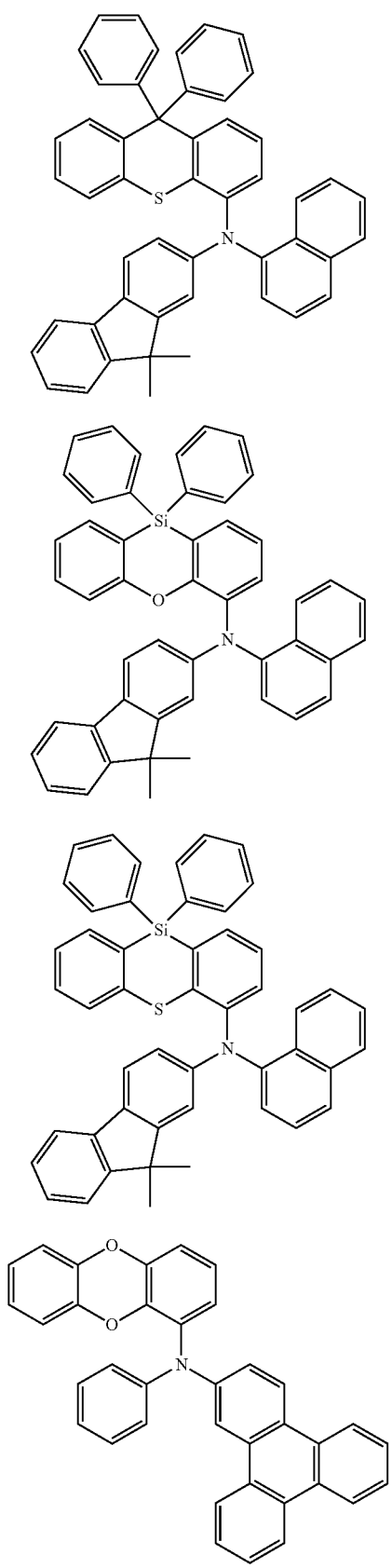
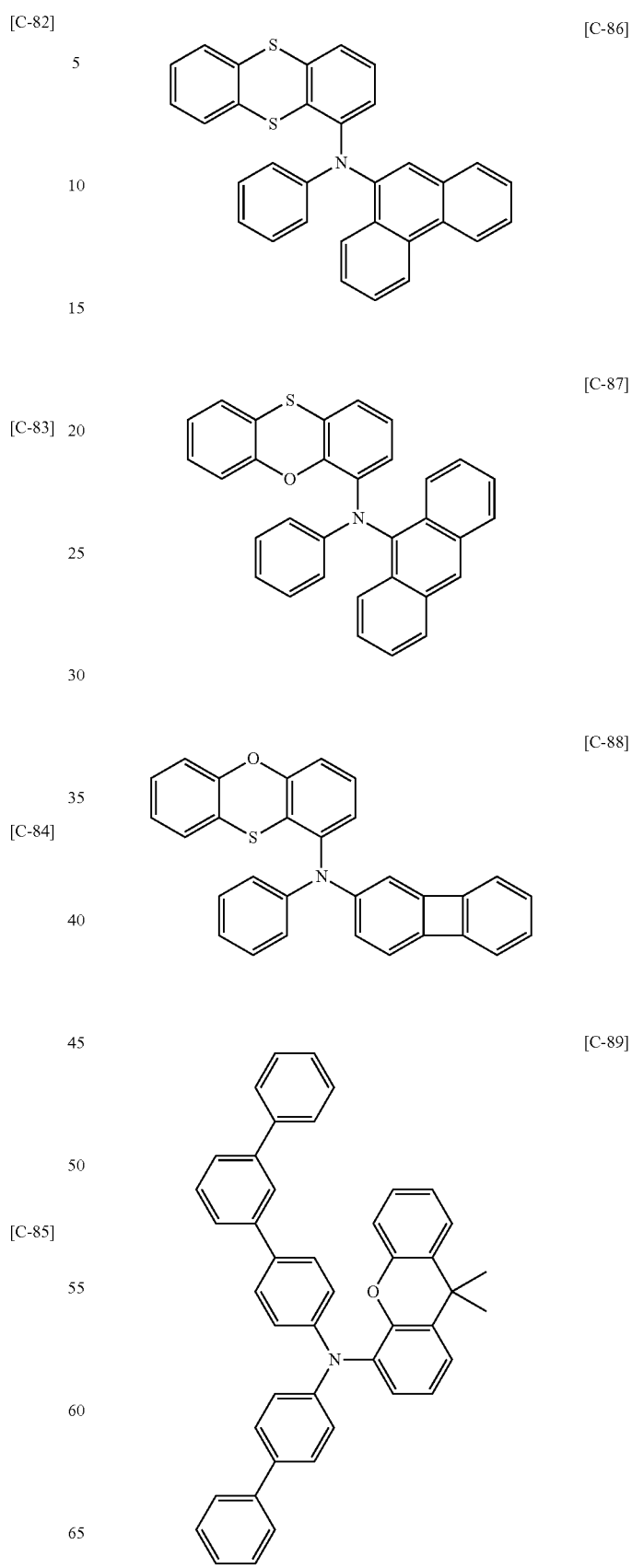

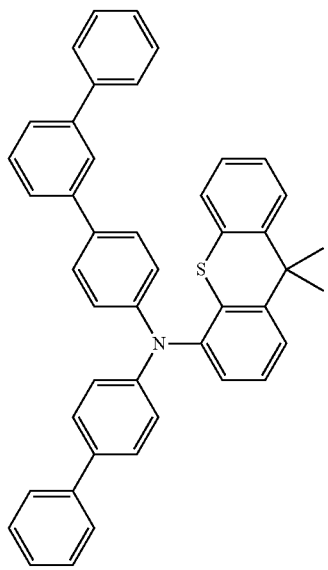
[C-90]
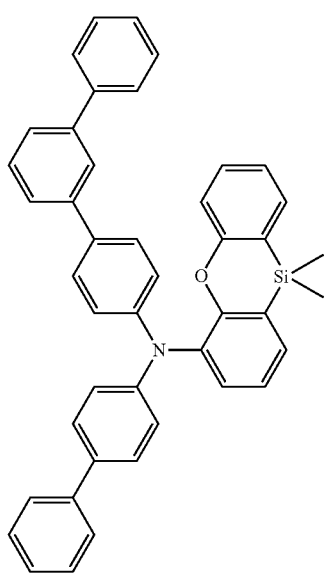
[C-91]
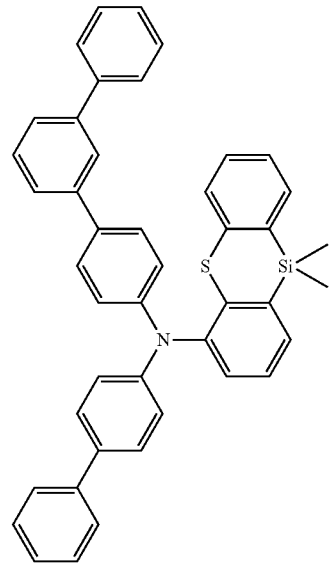
[C-92]
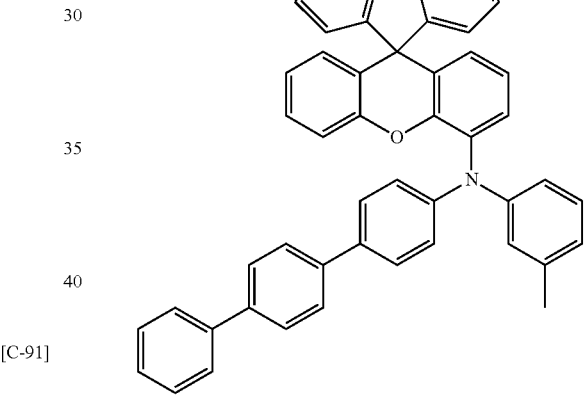
[C-93]
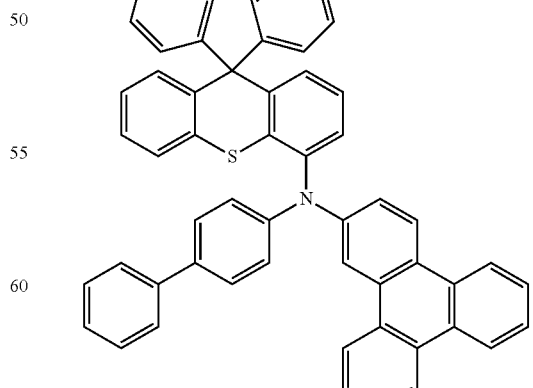
[C-94]

[C-95]
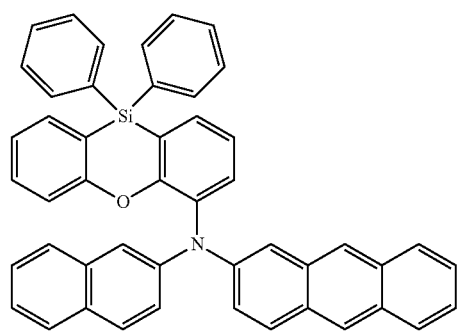
[C-96]
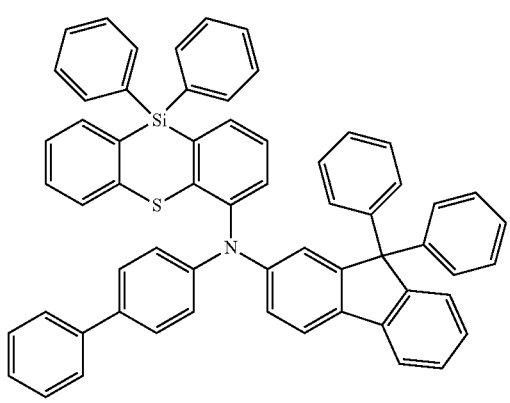
[C-97]
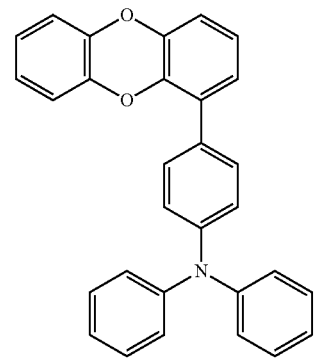
[C-98]
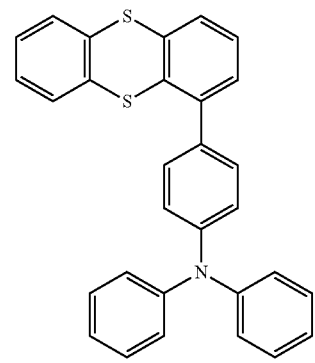
[C-99]
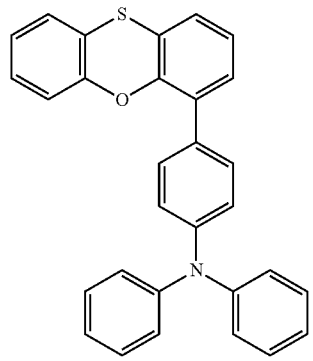
[C-100]
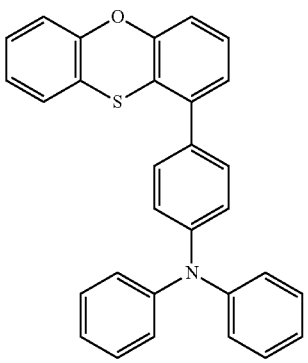
[C-101]
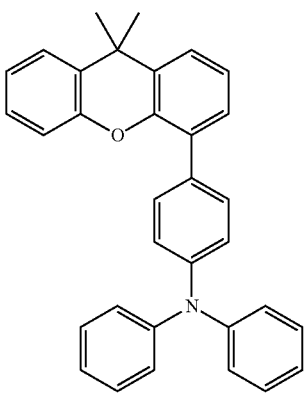
[C-102]
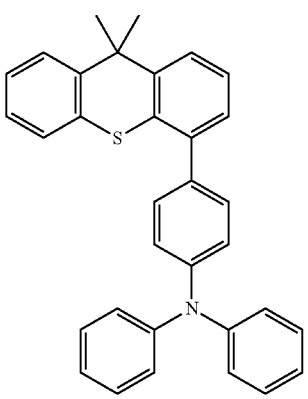

[C-103]
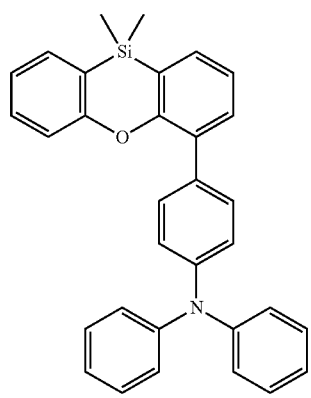
[C-104]
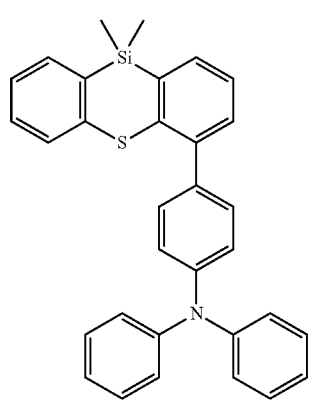
[C-105]
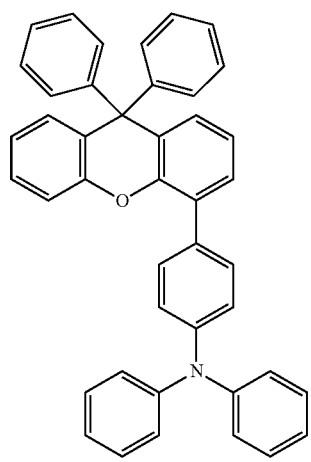
[C-106]
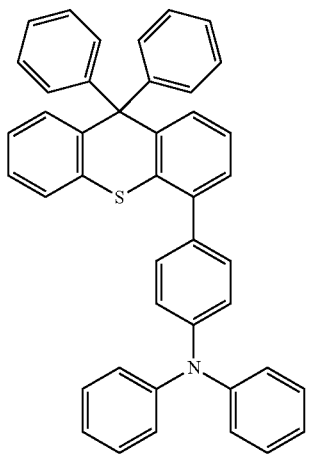
[C-107]
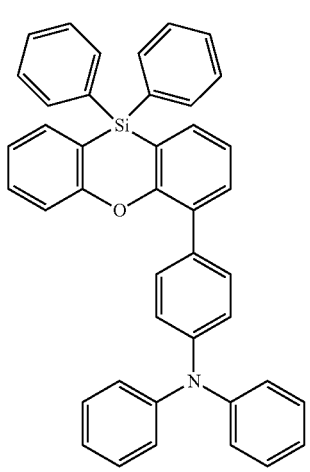
[C-108]

[C-109]
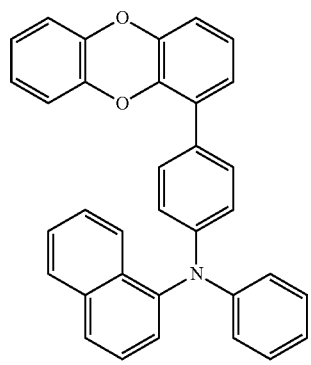
[C-110]
[C-111]
[C-112]
[C-113]
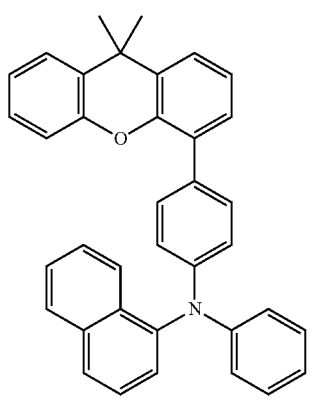
[C-114]
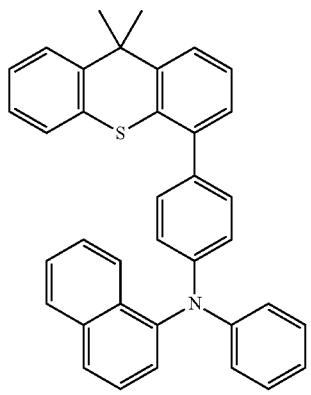
[C-115]
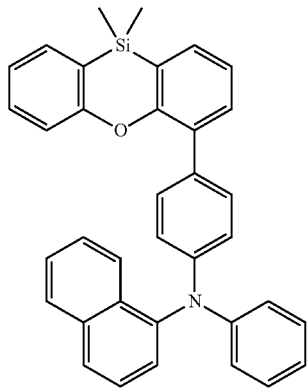
[C-116]
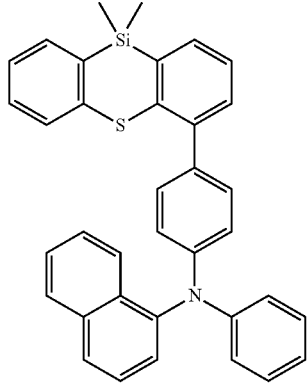

[C-117]
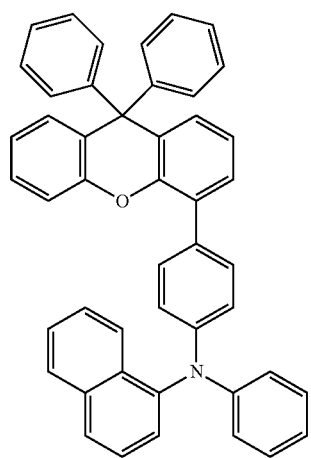
[C-118]
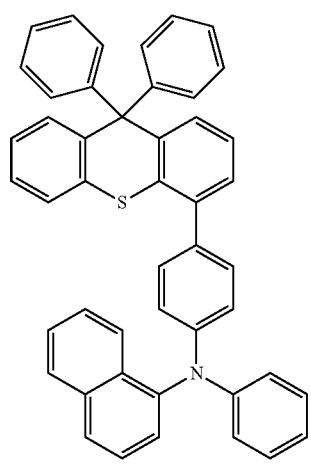
[C-119]
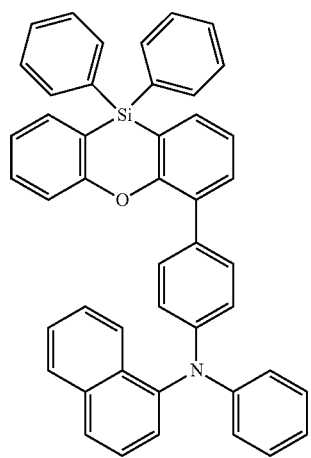
[C-120]
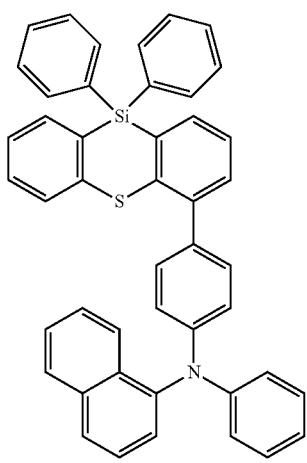
[C-121]
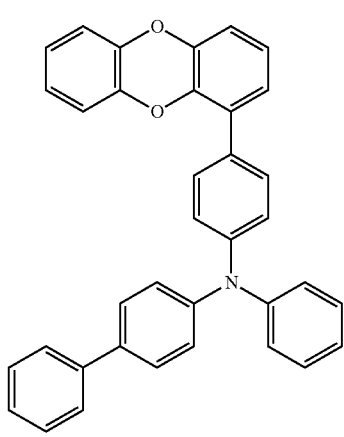
[C-122]
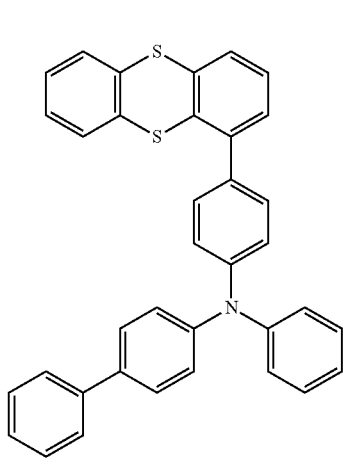

[C-123]
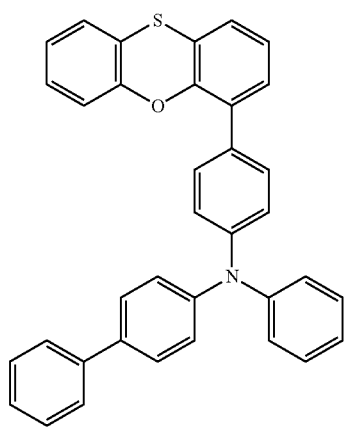
[C-124]
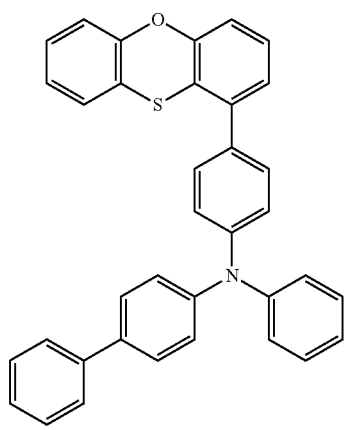
[C-125]
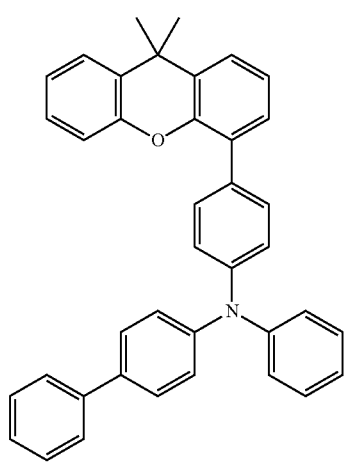
[C-126]
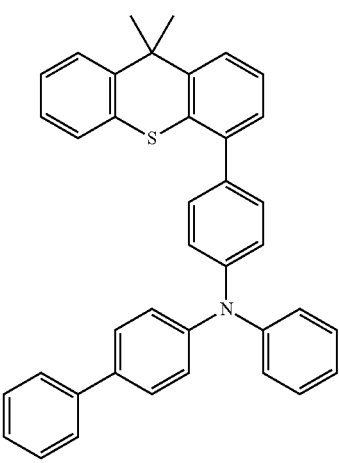
[C-127]
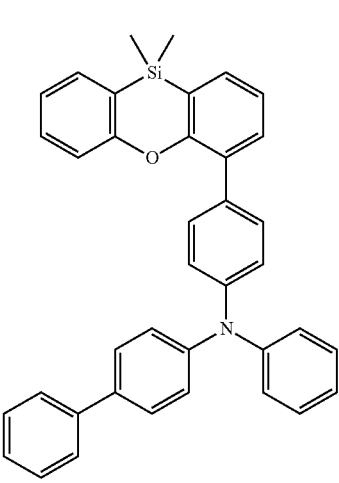
[C-128]
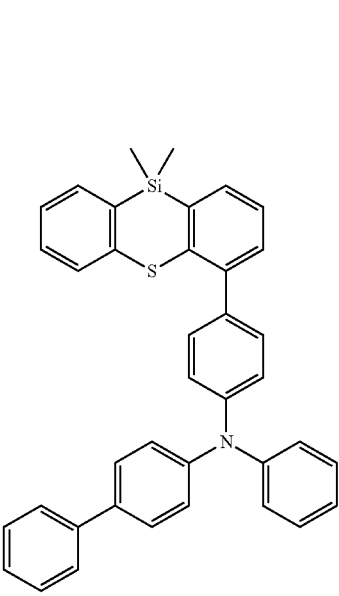

[C-129]
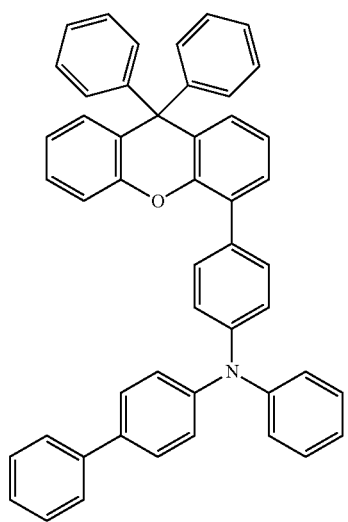
[C-130]
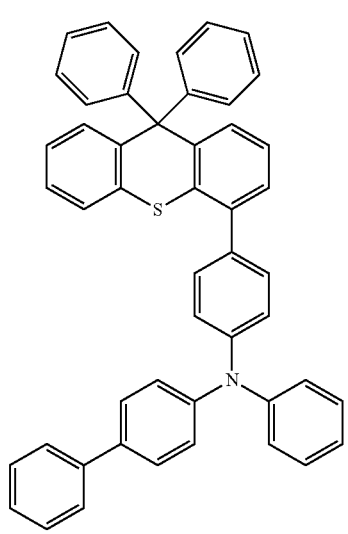
[C-131]
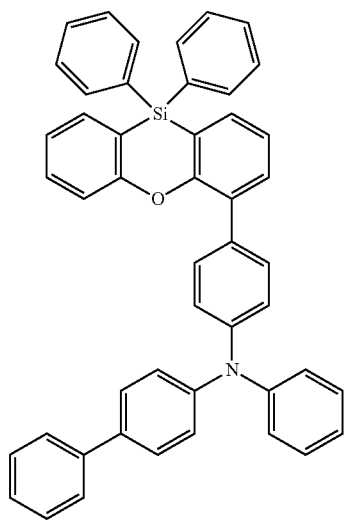
[C-132]
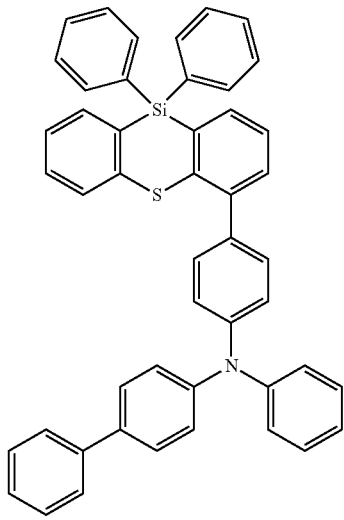
[C-130]
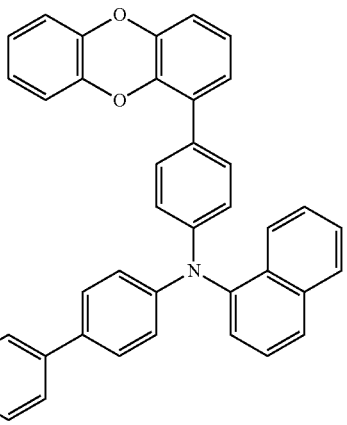
[C-131]
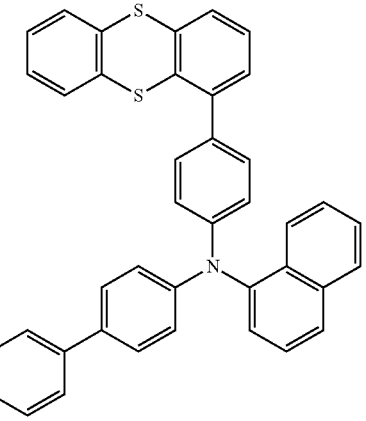

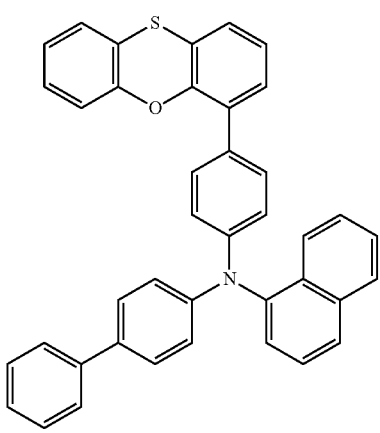
[C-132]
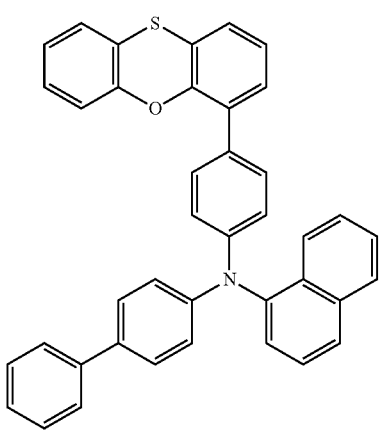
[C-133]
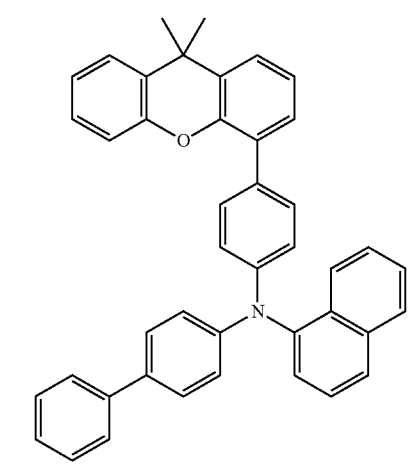
[C-134]
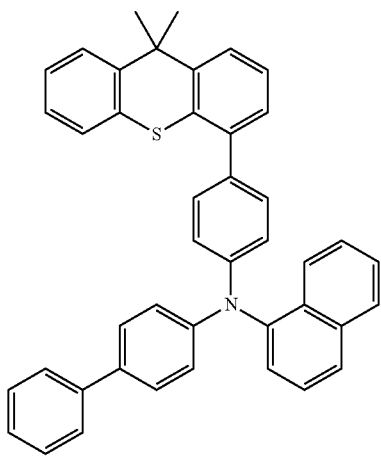
[C-135]
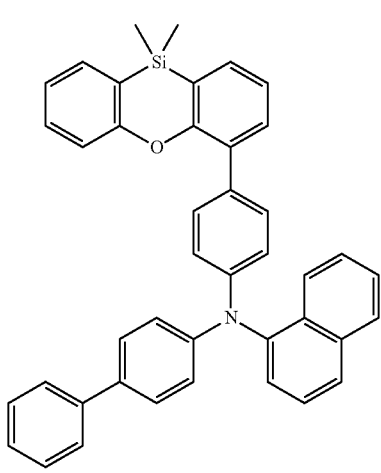
[C-136]
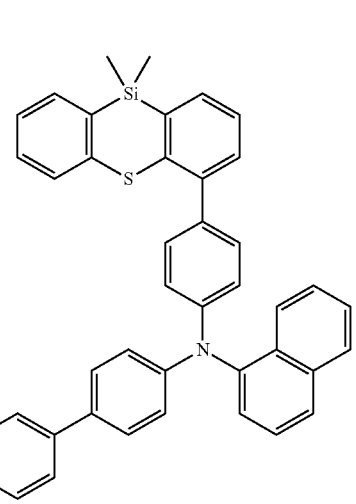
[C-137]

[C-138]
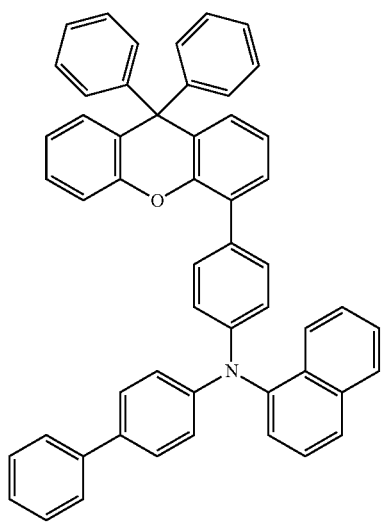
[C-141]
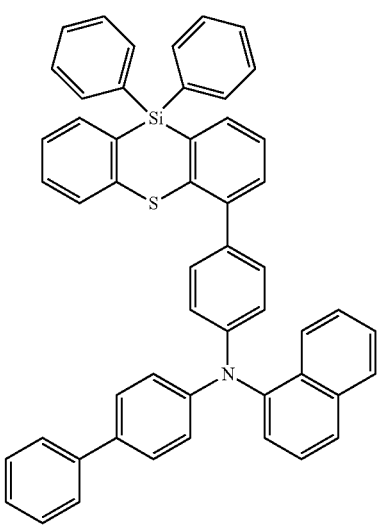
[C-139]
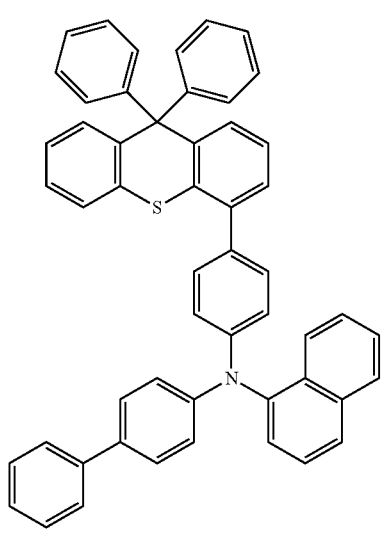
[C-142]
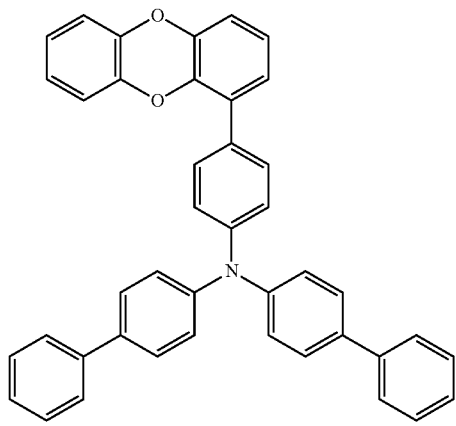
[C-140]
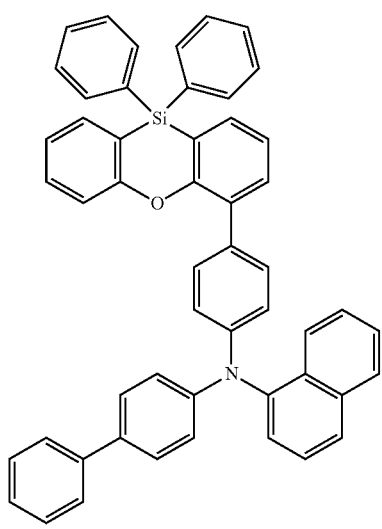
[C-143]
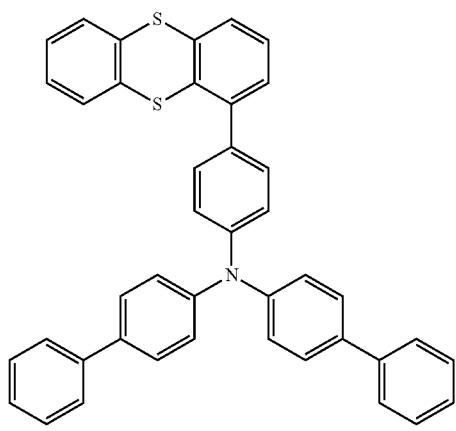

[C-144]
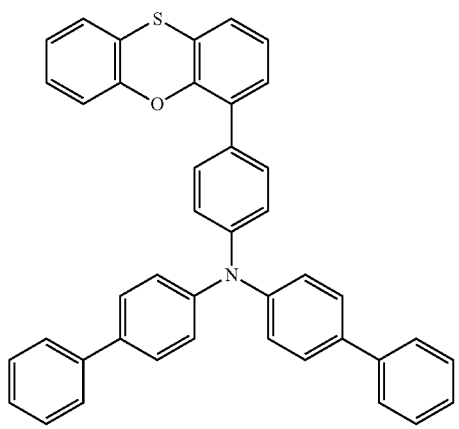
[C-145]
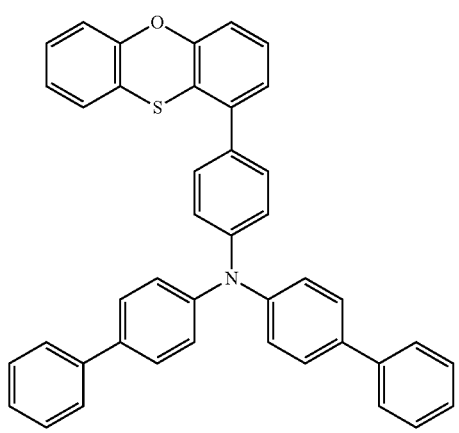
[C-146]
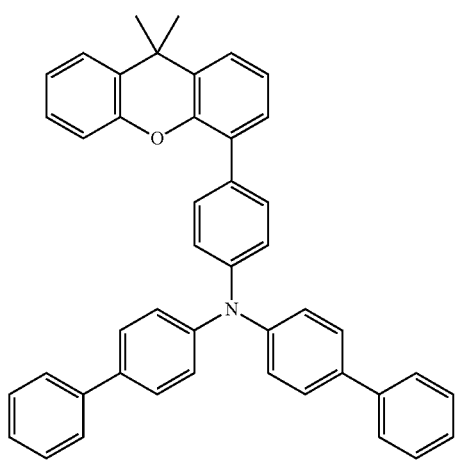
[C-147]
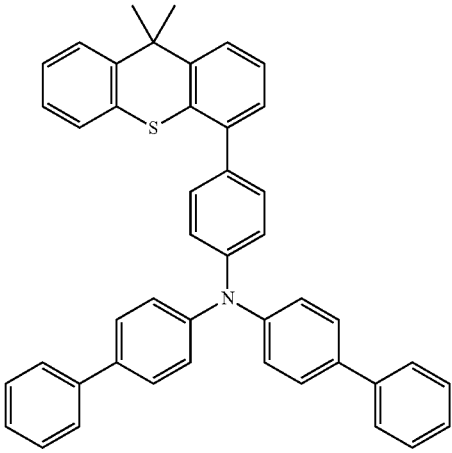
[C-148]
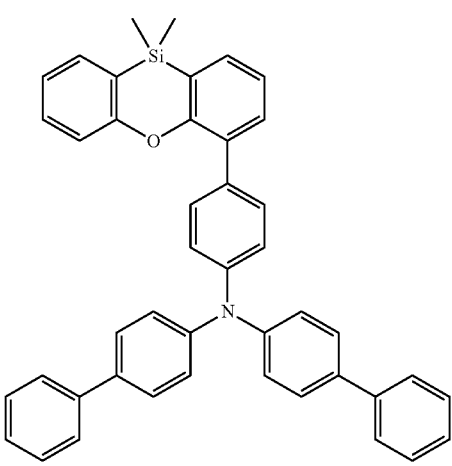
[C-149]
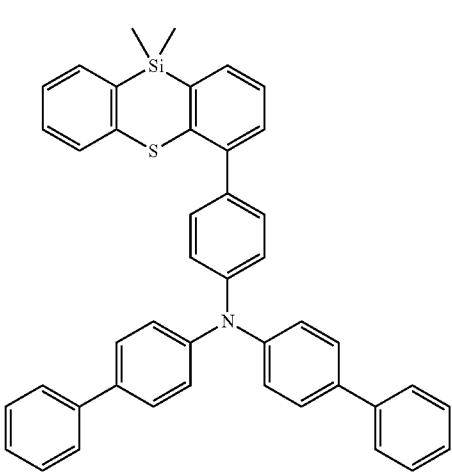

[C-150]
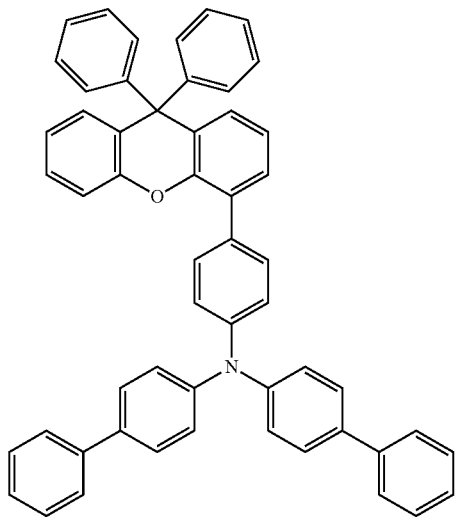
[C-152]
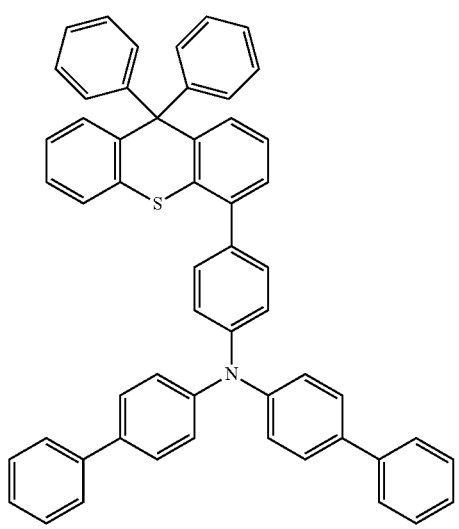
[C-153]
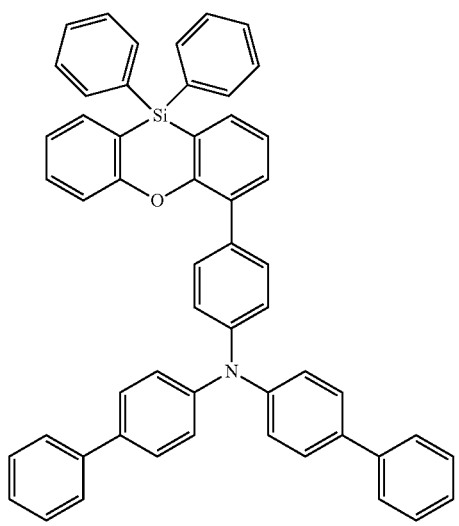
[C-154]
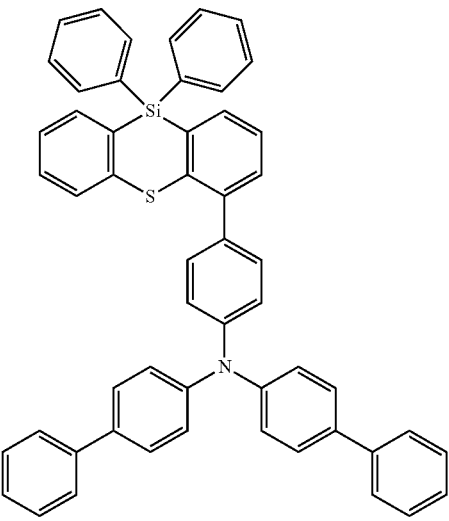
[C-155]
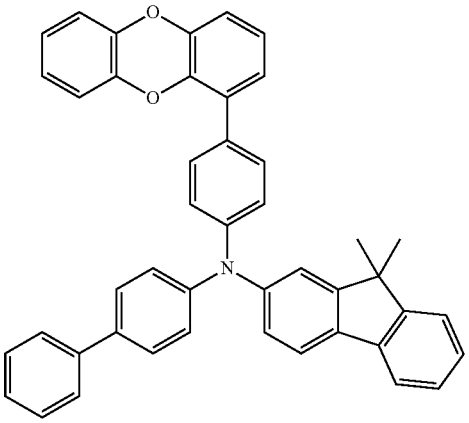
[C-156]
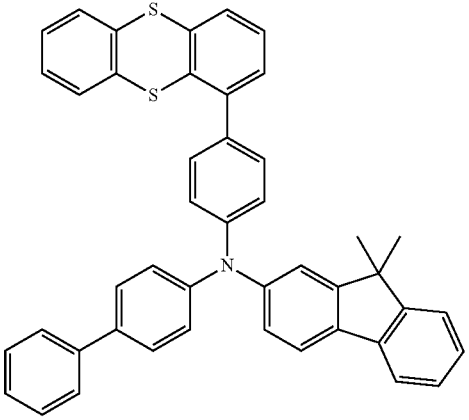

[C-157]
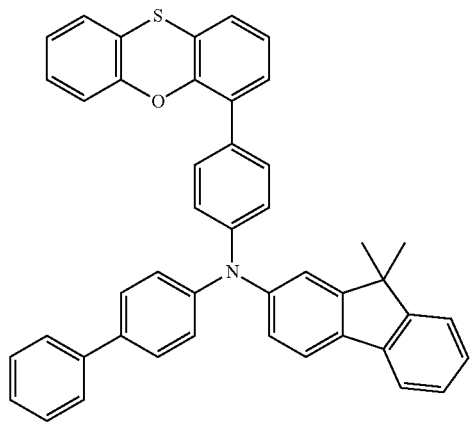
[C-158]
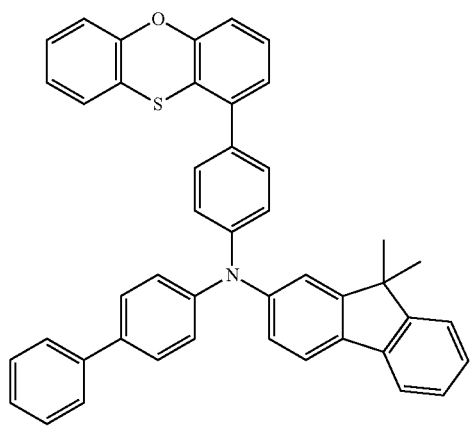
[C-159]
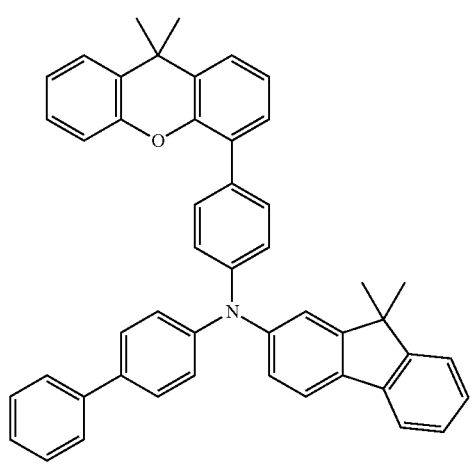
[C-160]
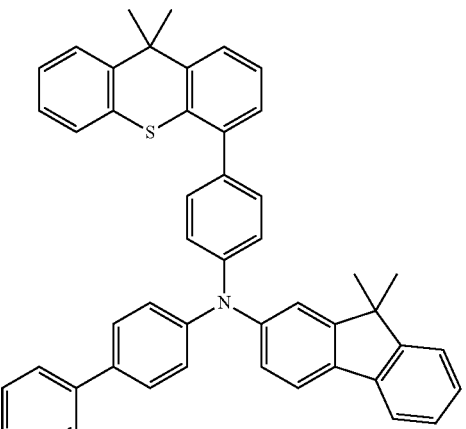
[C-161]
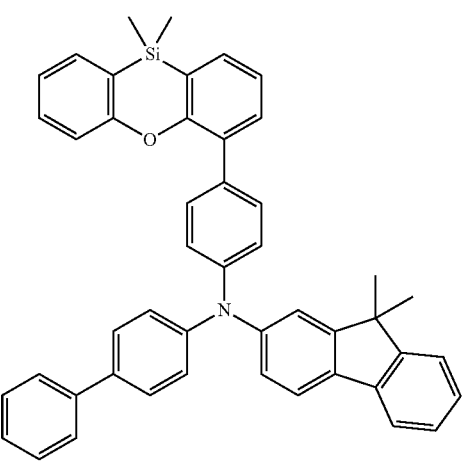
[C-162]
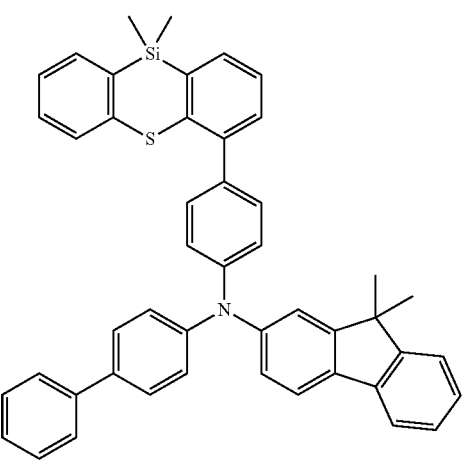

[C-163]
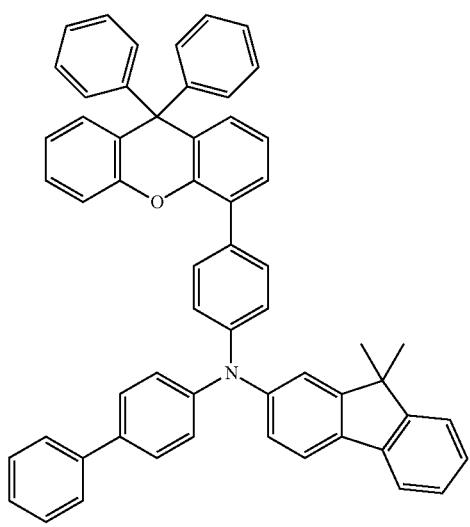
[C-164]
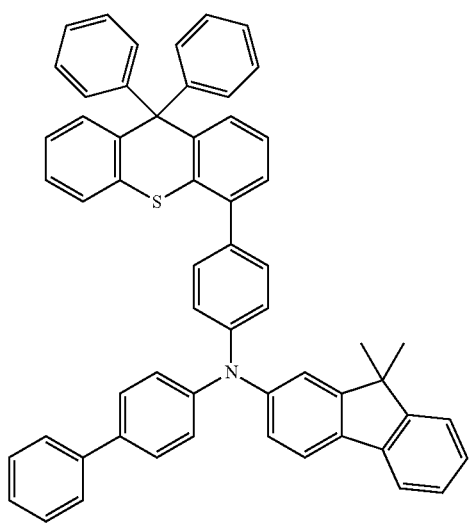
[C-165]
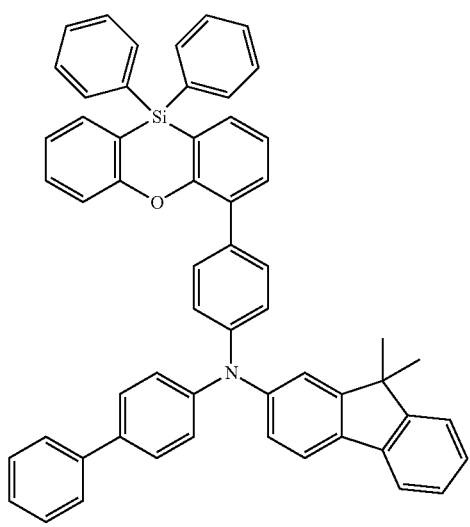
[C-166]
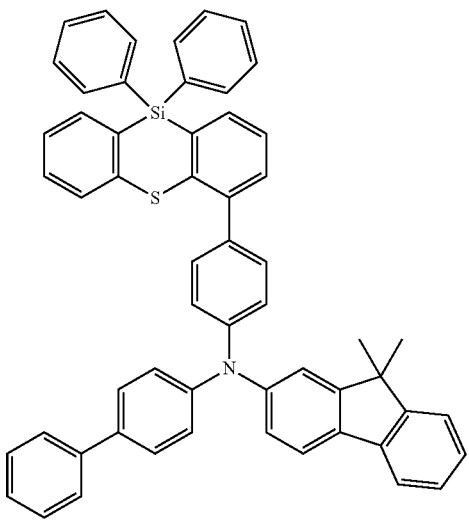
[C-167]
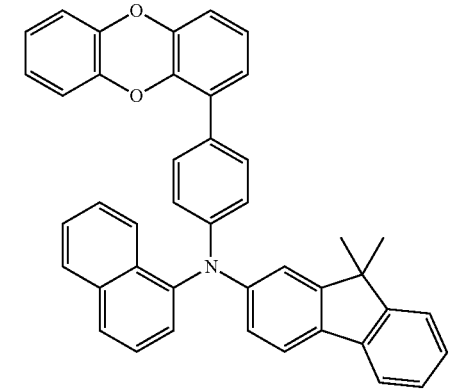
[C-168]
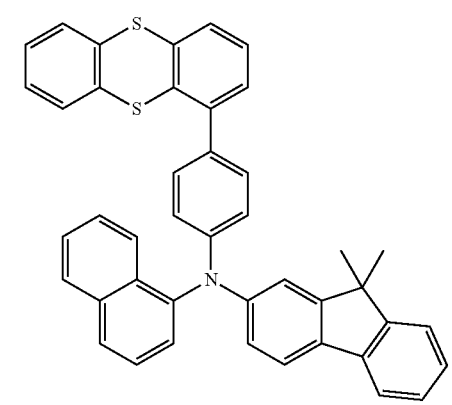

[C-169]
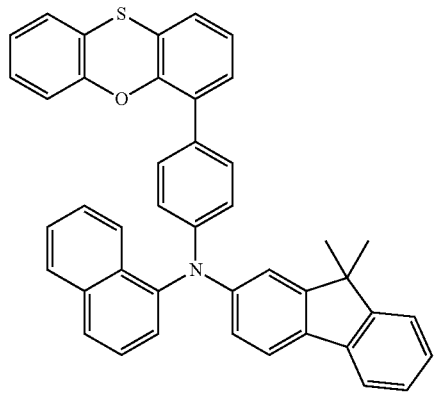
[C-170]
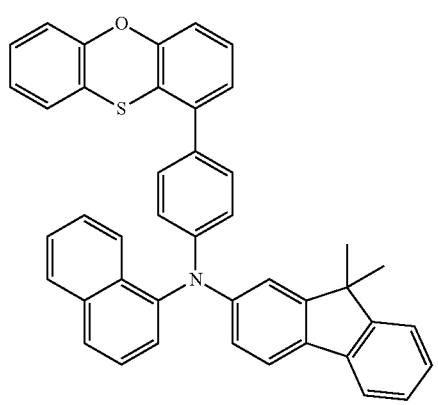
[C-171]
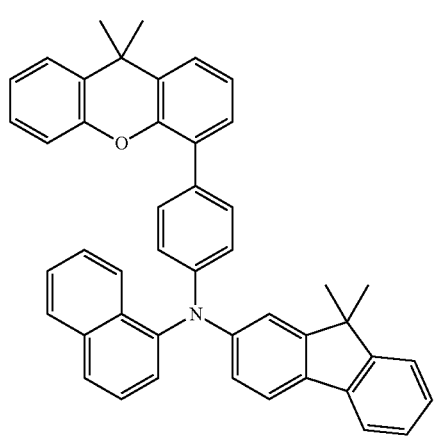
[C-172]
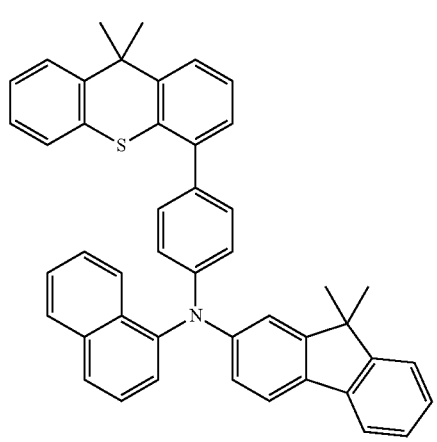
[C-173]
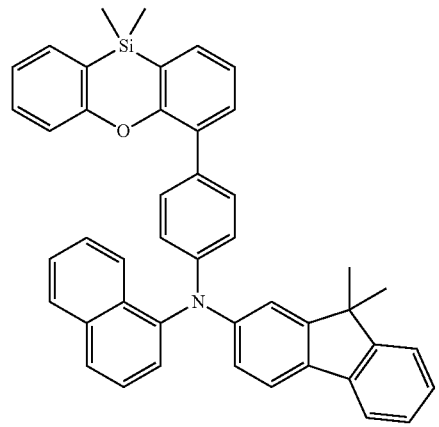
[C-174]
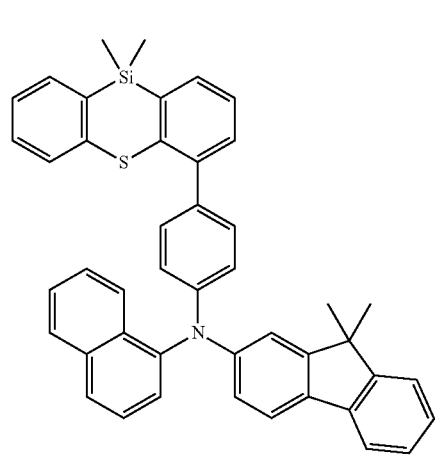
[C-175]
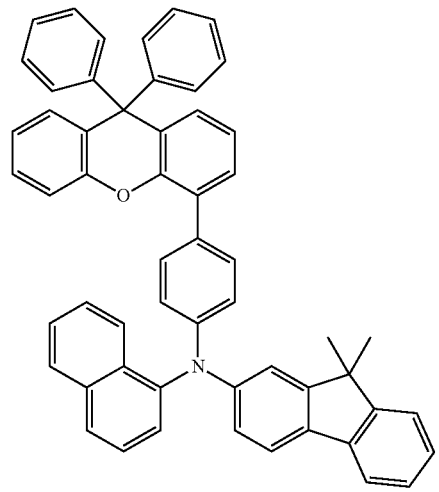

[C-176]
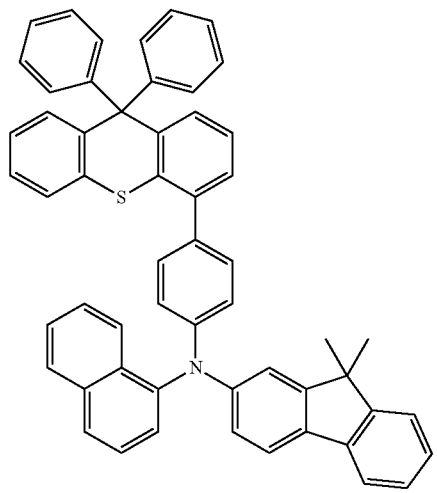
[C-177]
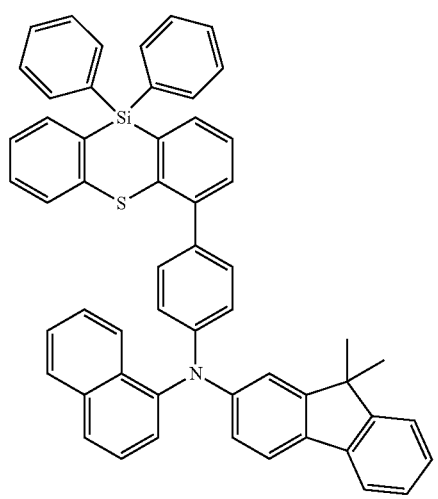
[C-178]
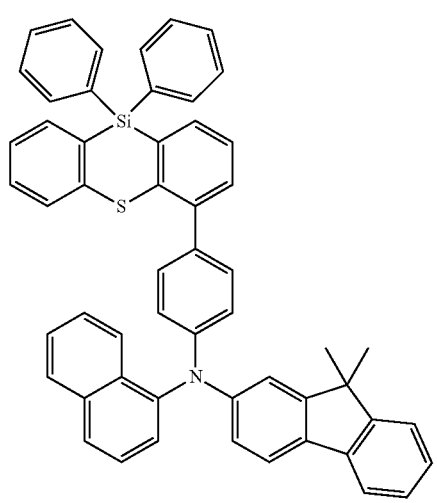
[C-179]
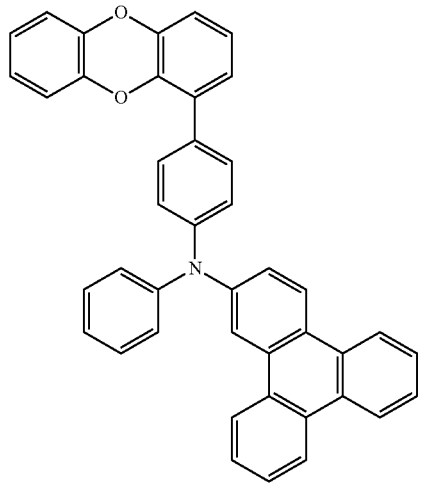
[C-180]
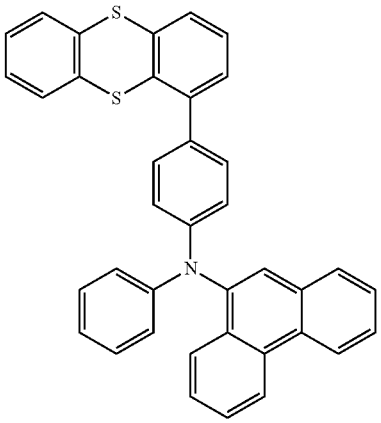
[C-181]
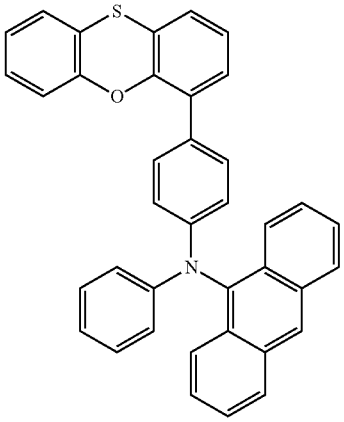

[C-182]
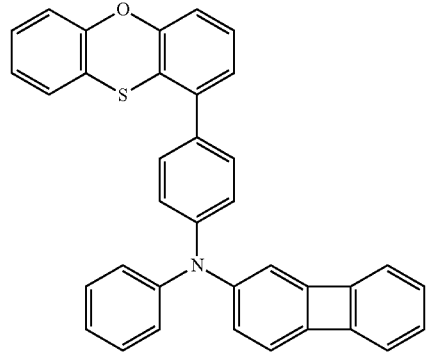
[C-183]
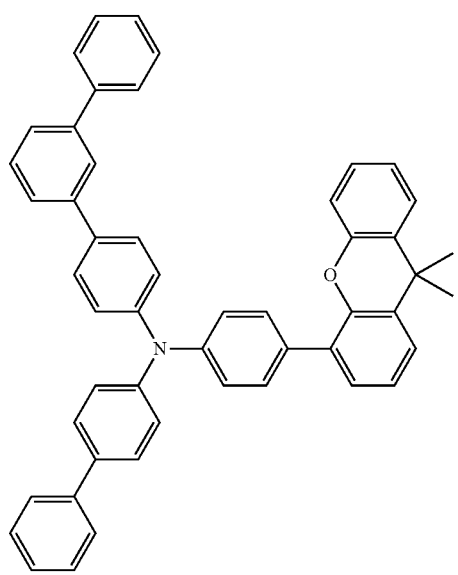
[C-184]
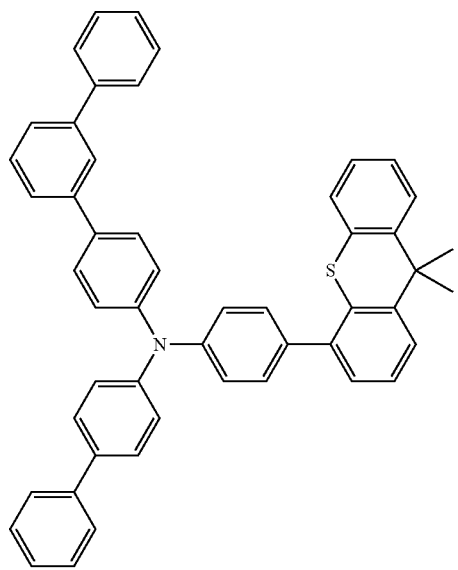
[C-185]
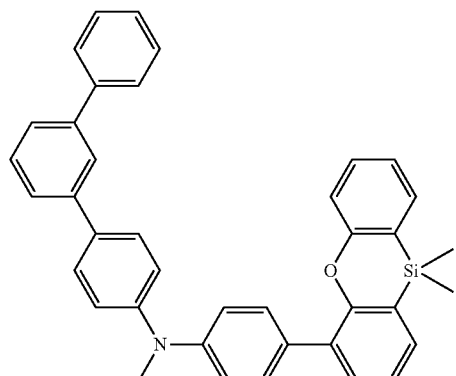
[C-186]
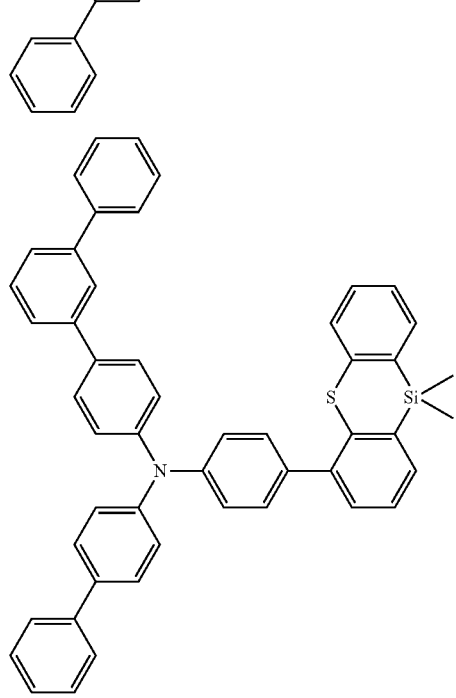
[C-187]
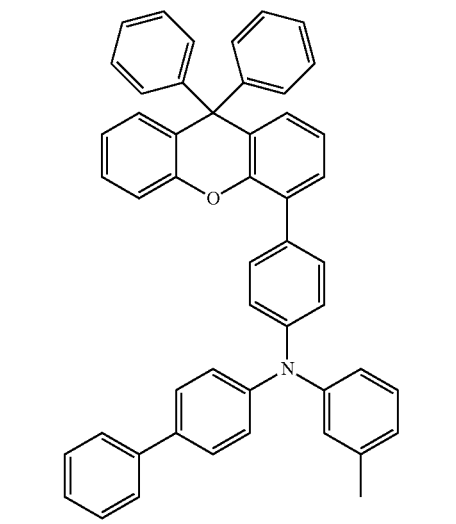

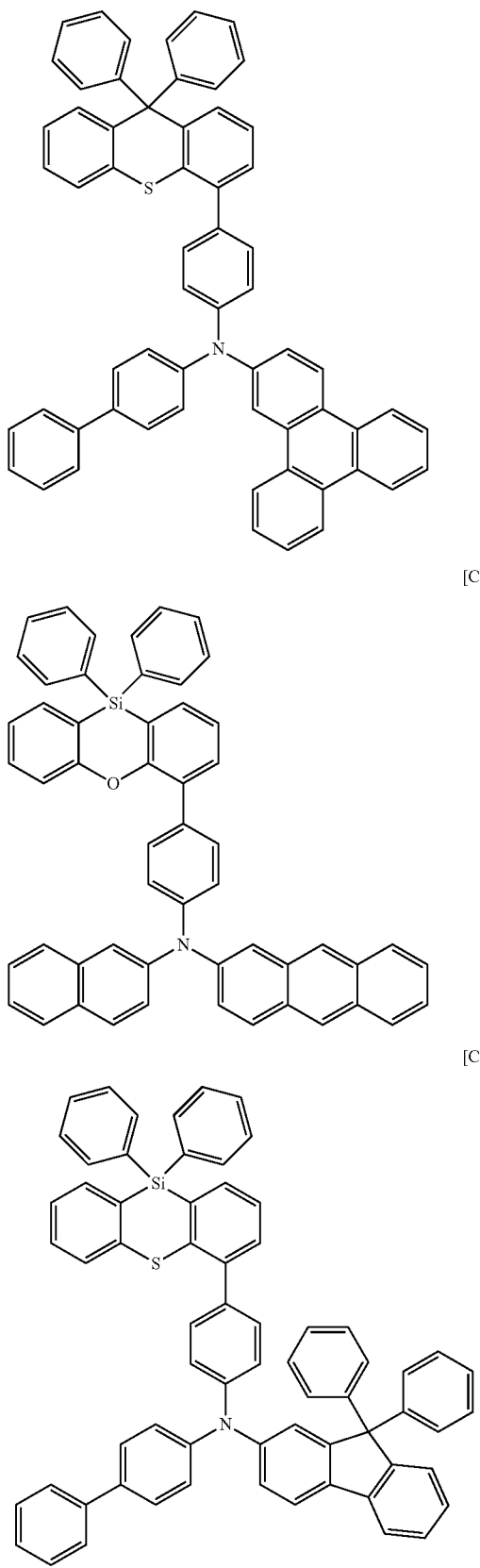
[C-188]
[C-189]
[C-190]
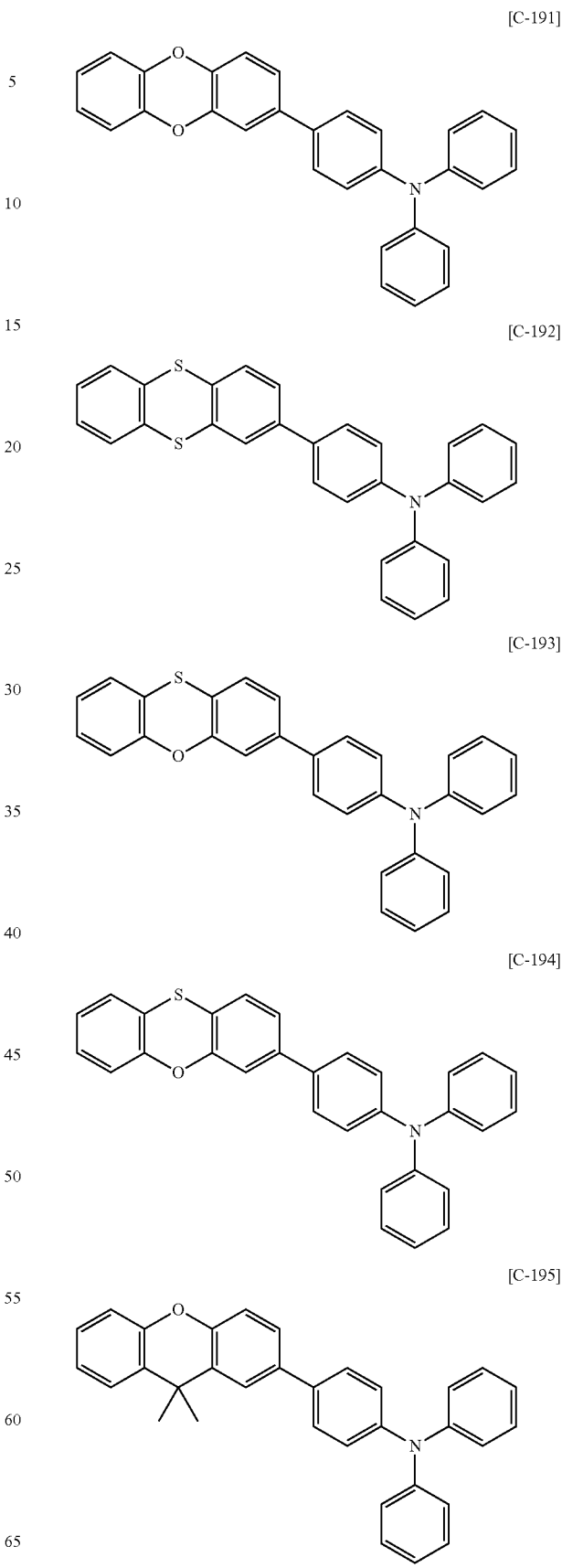
[C-191]
[C-192]
[C-193]
[C-194]
[C-195]

[C-196]
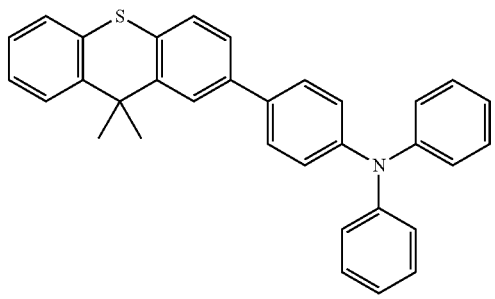
[C-197]
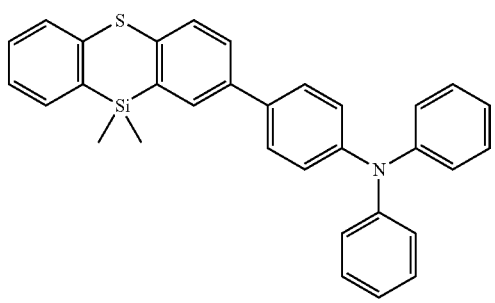
[C-198]
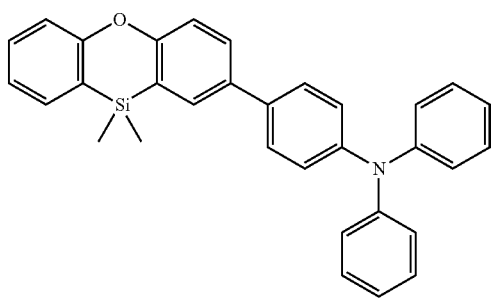
[C-199]
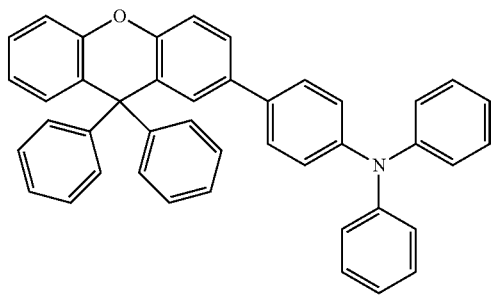
[C-200]
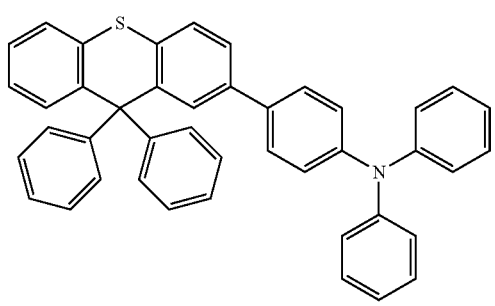
[C-201]
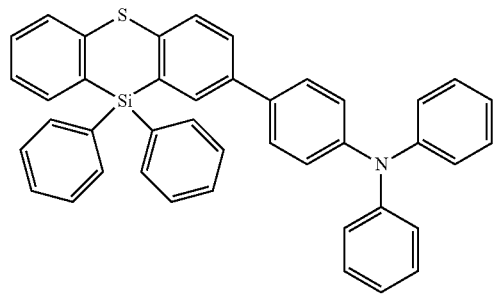
[C-202]
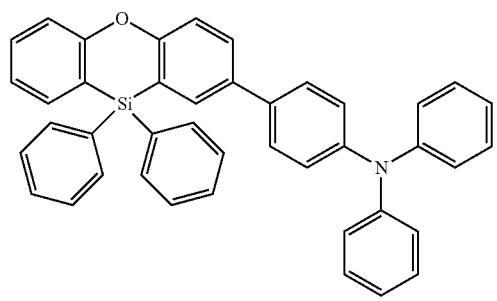
[C-203]
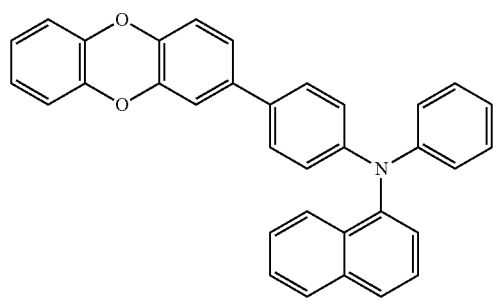
[C-204]
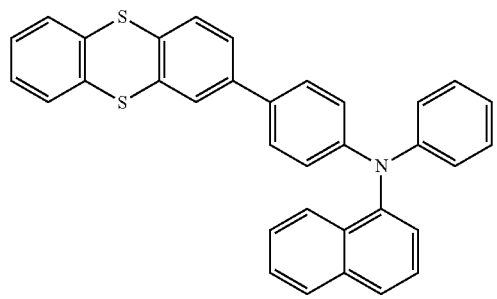
[C-205]
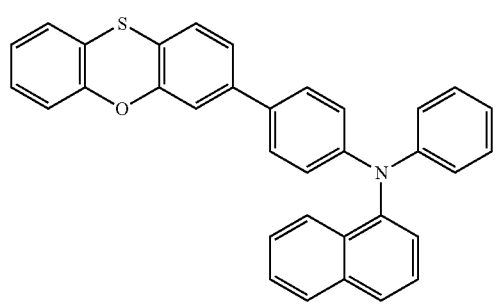

[C-206]
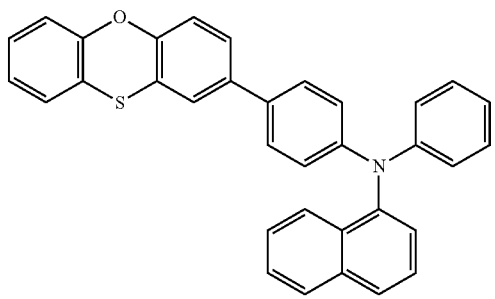
[C-207]
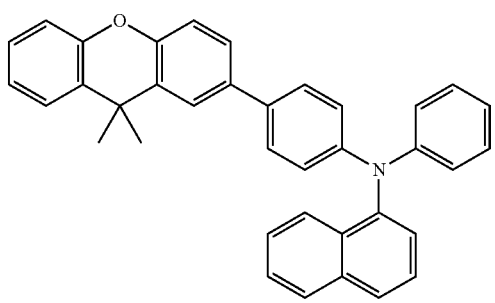
[C-208]
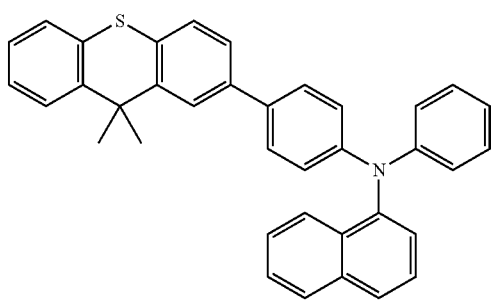
[C-209]
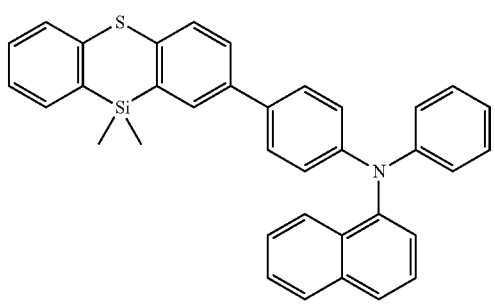
[C-210]
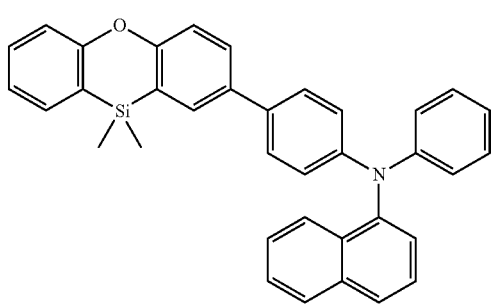
[C-211]
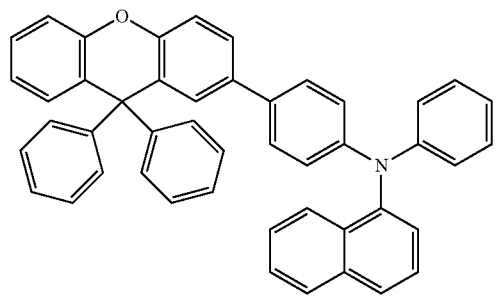
[C-212]
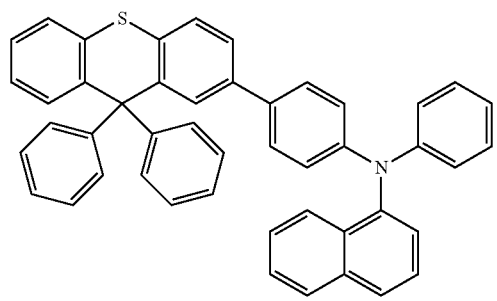
[C-213]
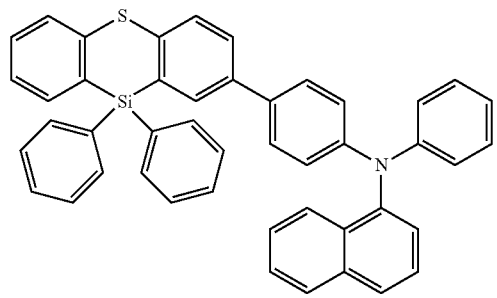
[C-214]
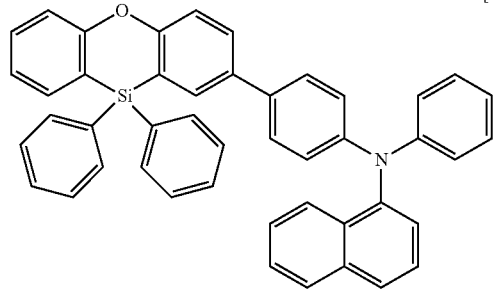

[C-215]
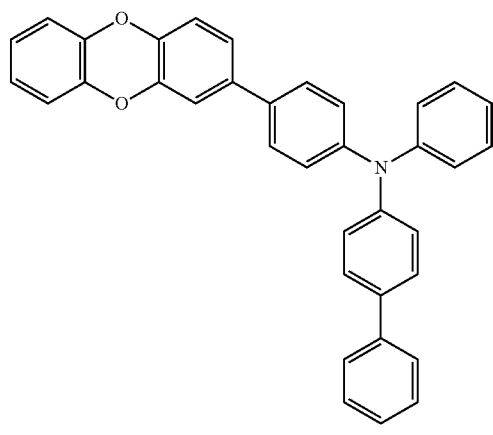
[C-216]
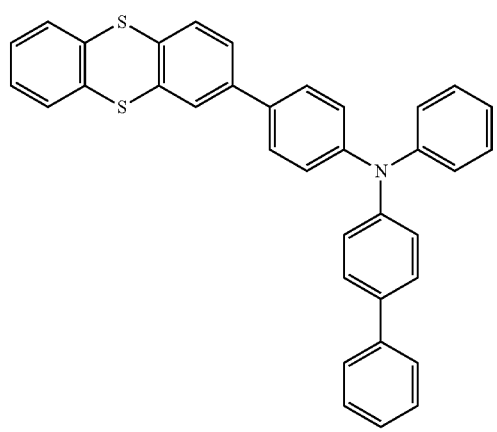
[C-217]
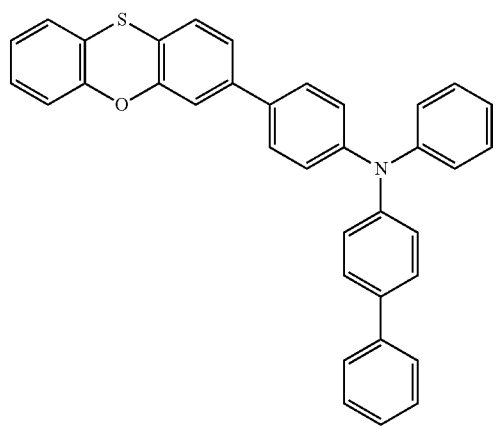
[C-218]
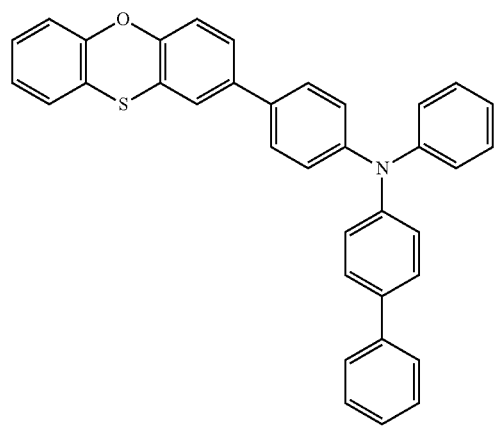
[C-219]
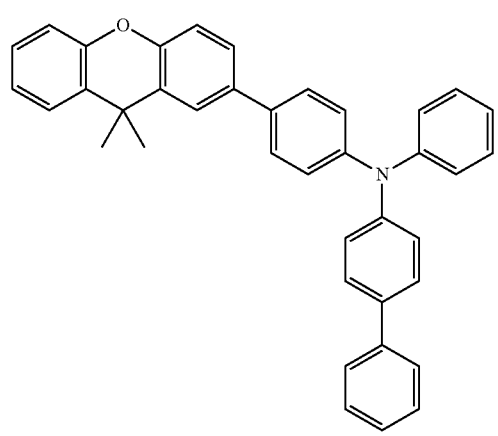
[C-220]
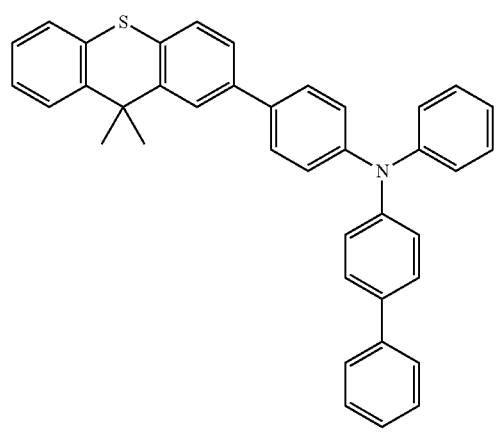

[C-221]
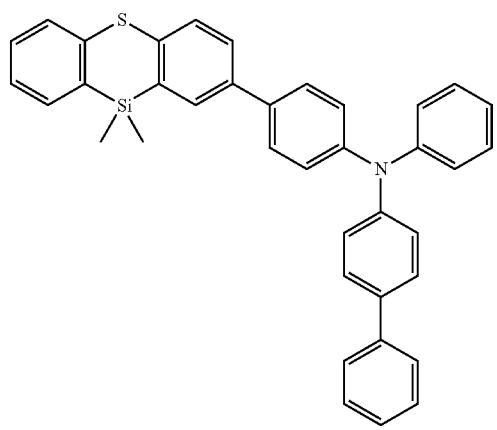
[C-224]
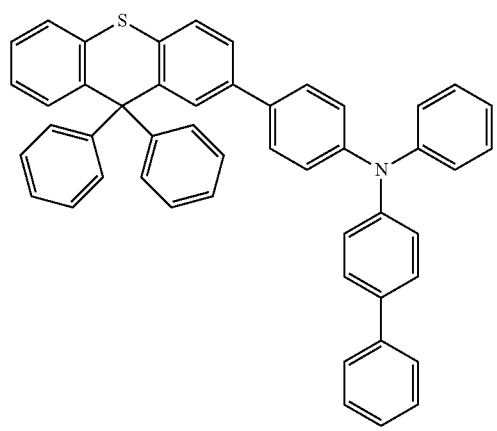
[C-222]
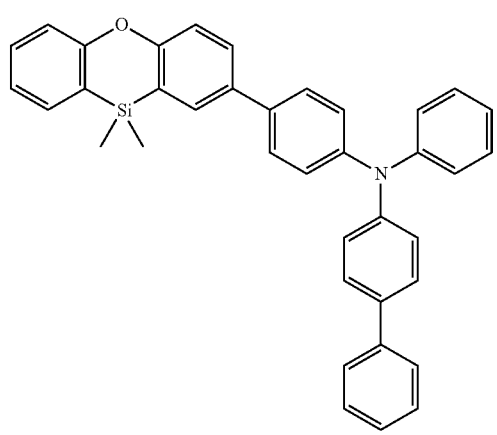
[C-225]
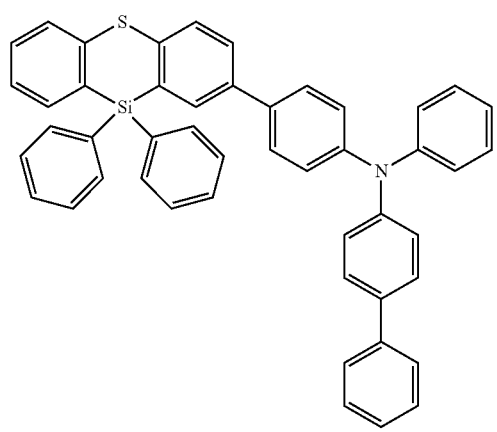
[C-223]
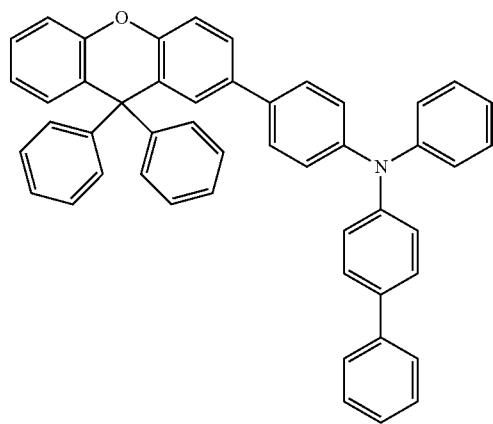
[C-226]
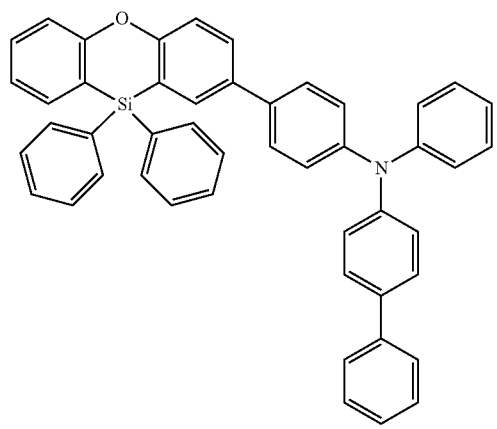

[C-227]
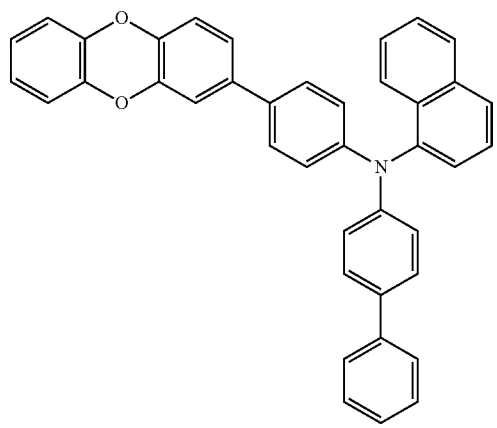
[C-230]
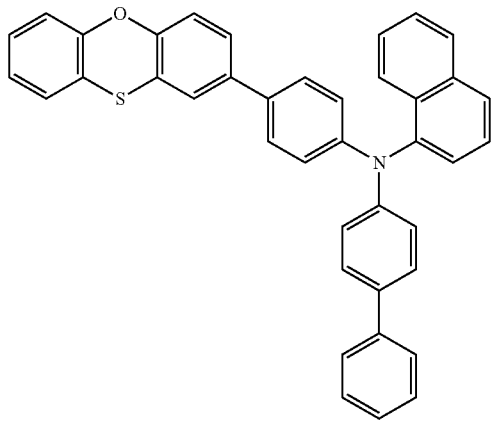
[C-228]
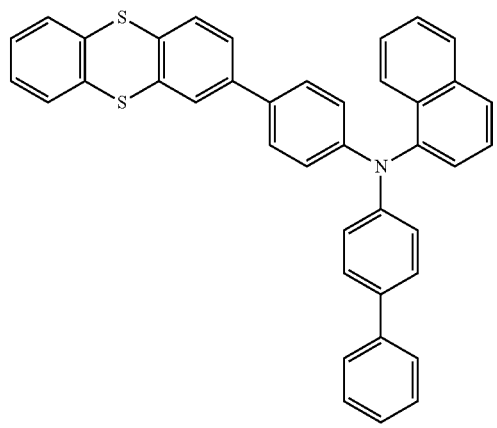
[C-231]
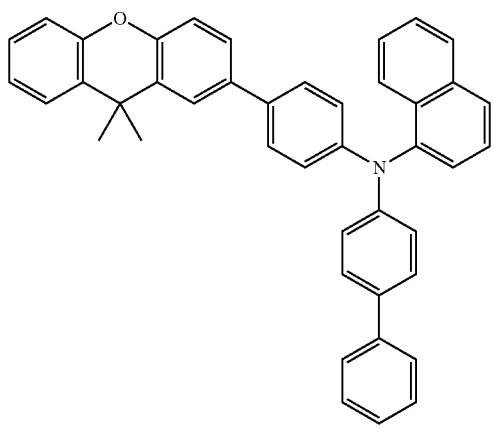
[C-229]
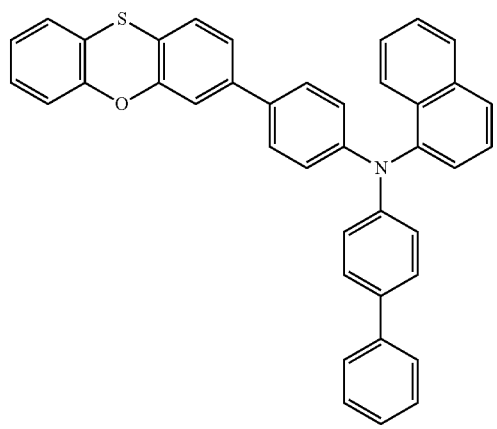
[C-232]
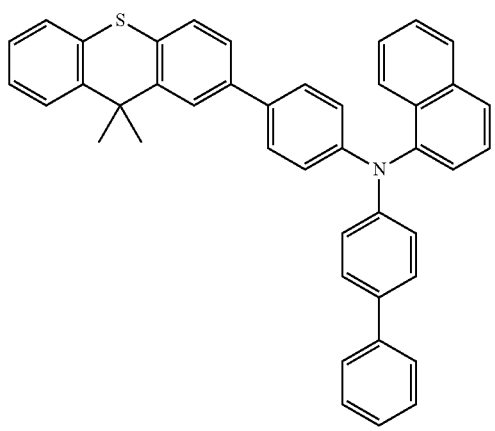

-continued
[C-233]
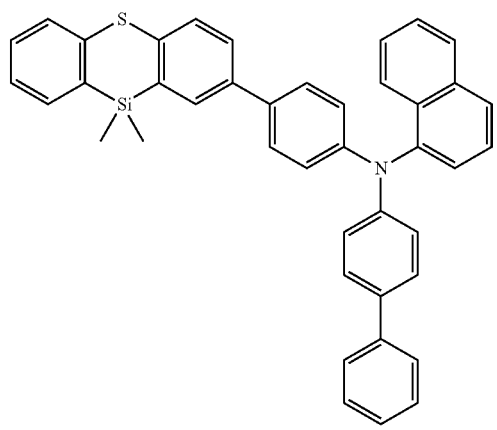
[C-234]
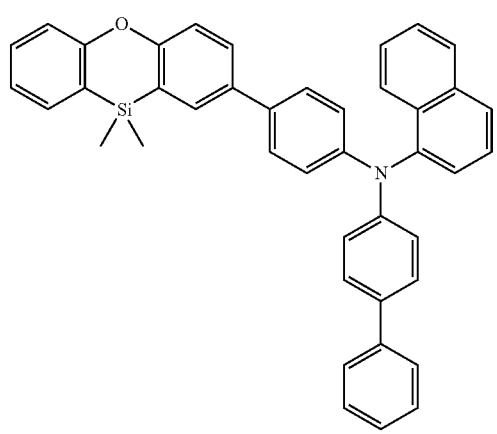
[C-235]
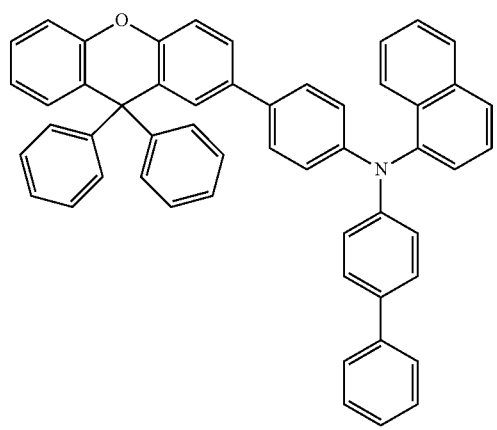
[C-236]
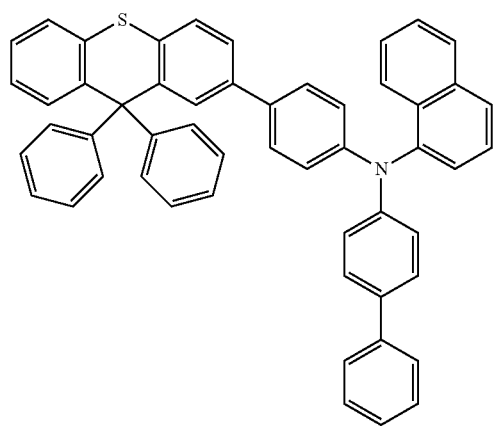
[C-237]
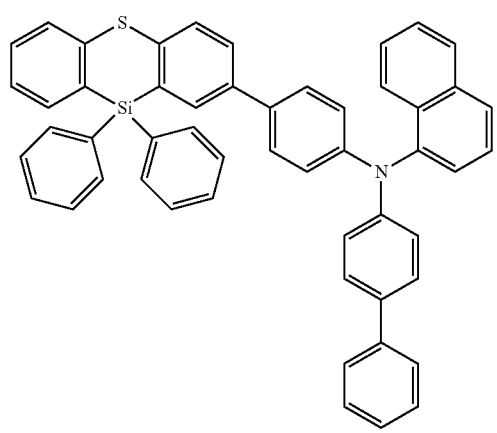
[C-238]
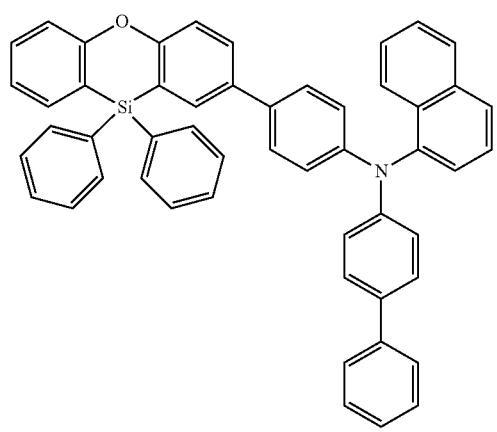

[C-239]
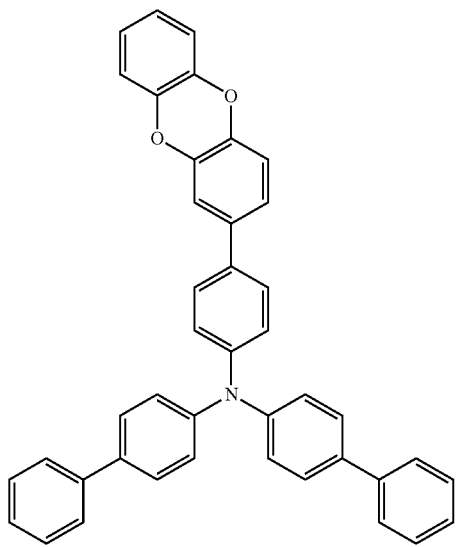
[C-240]
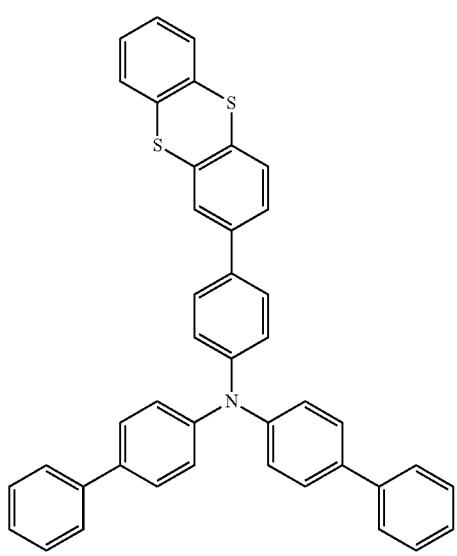
[C-241]
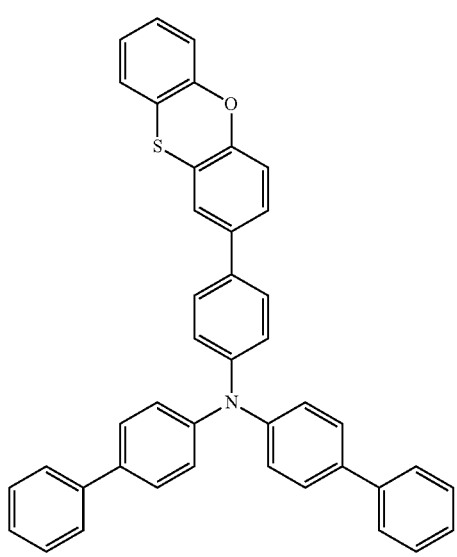
[C-242]
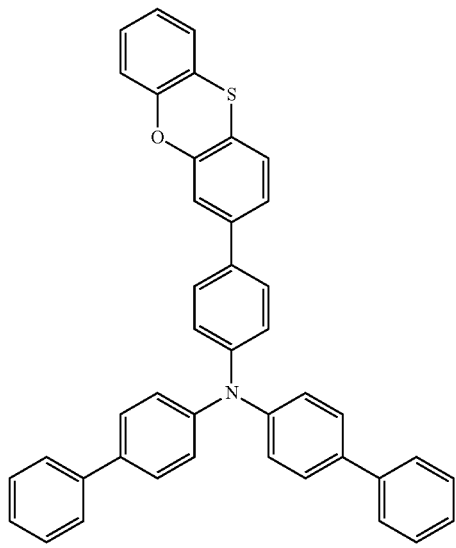
[C-243]
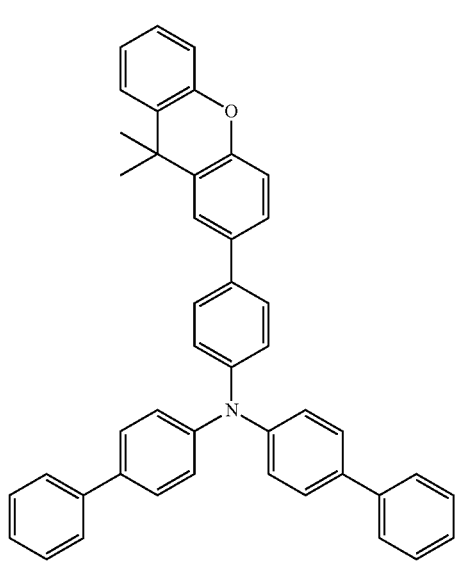
[C-244]
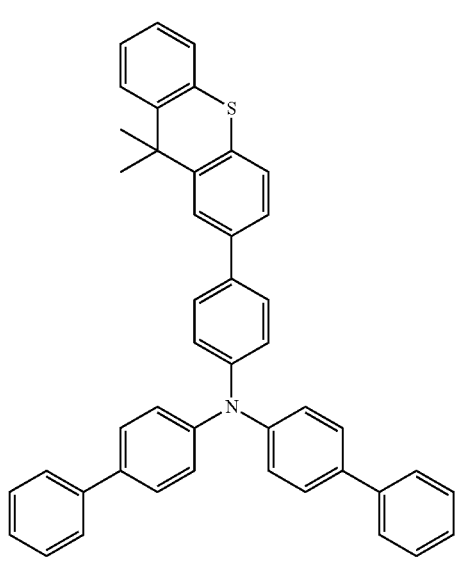

[C-245]
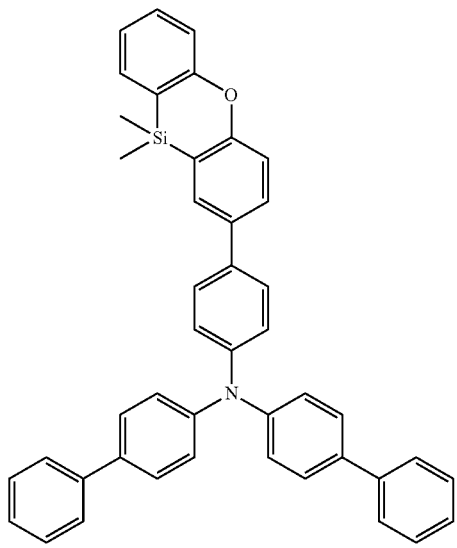
[C-248]
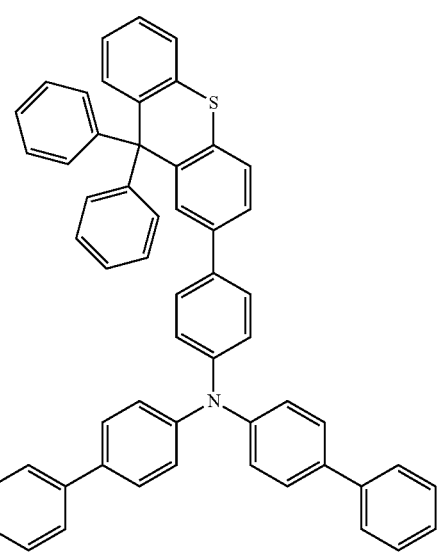
[C-246]
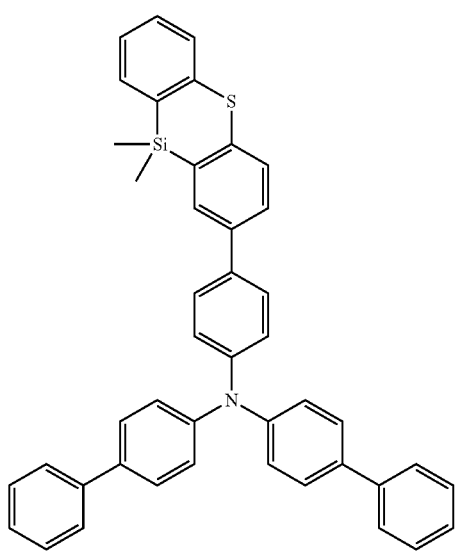
[C-249]
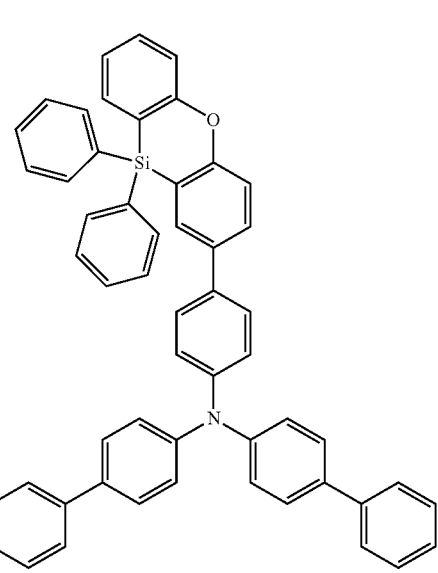
[C-247]
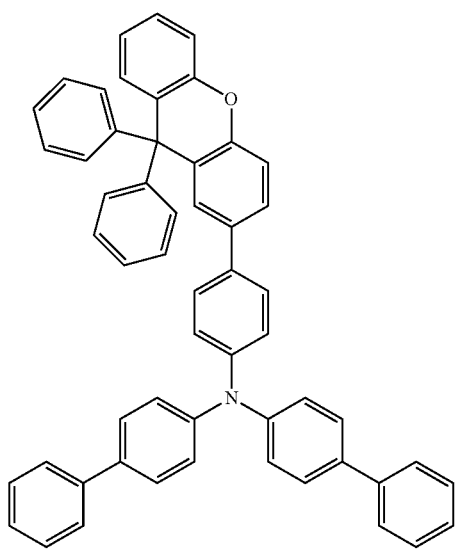
[C-250]
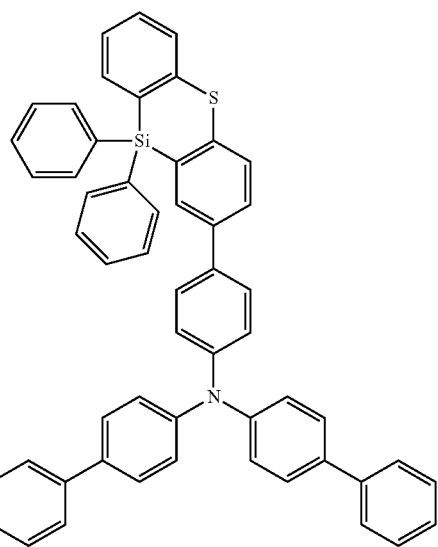

-continued
[C-251]
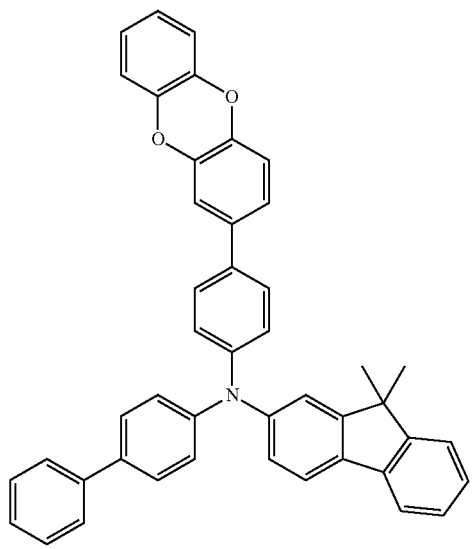
[C-254]
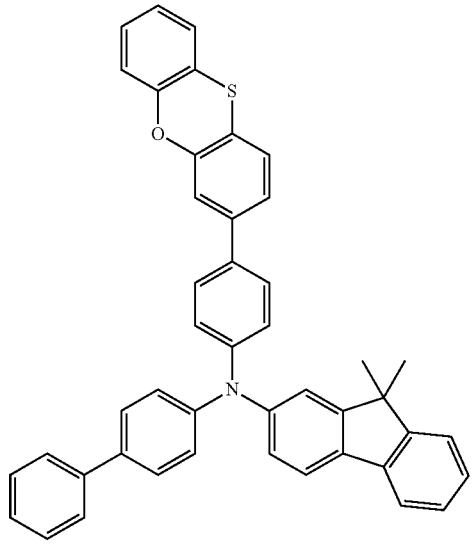
[C-252]
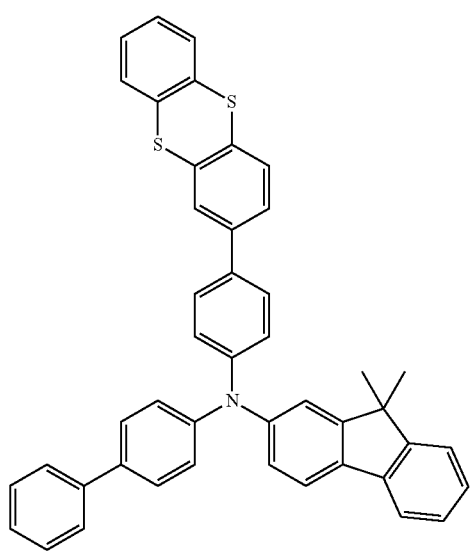
[C-255]
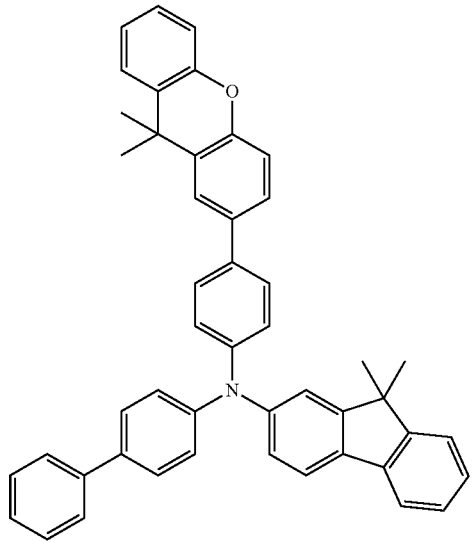
[C-253]
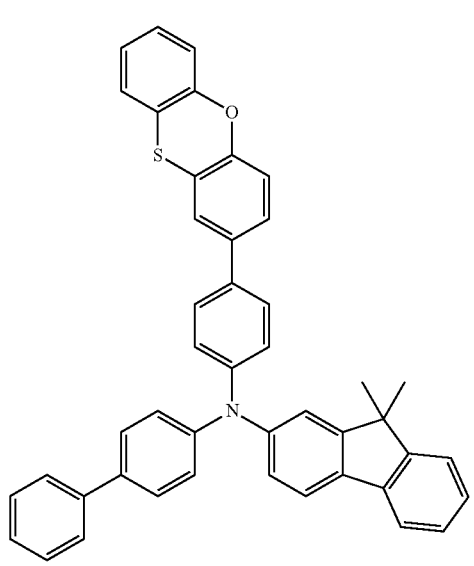
[C-256]
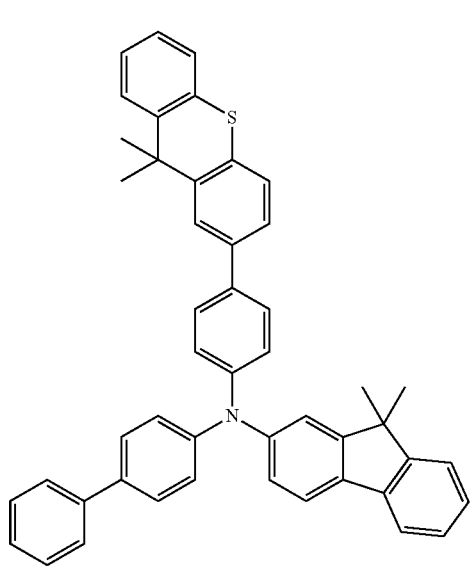

[C-257]
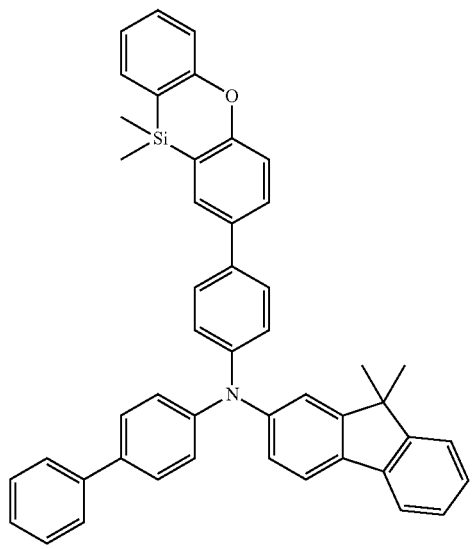
[C-258]
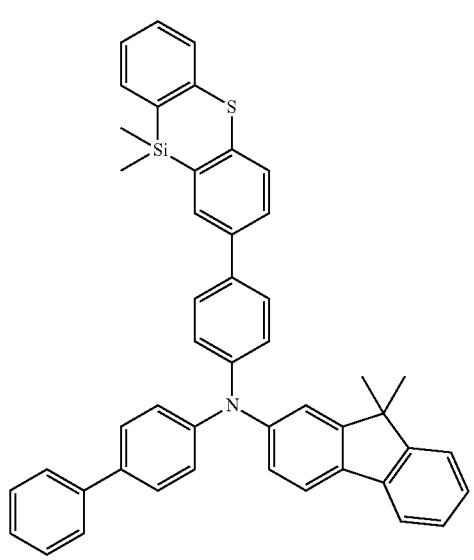
[C-259]
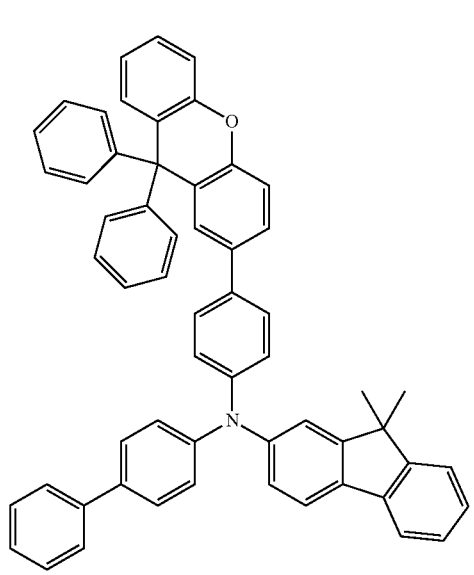
[C-260]
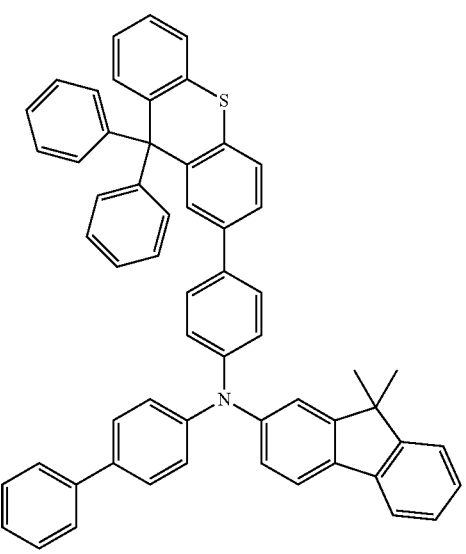
[C-261]
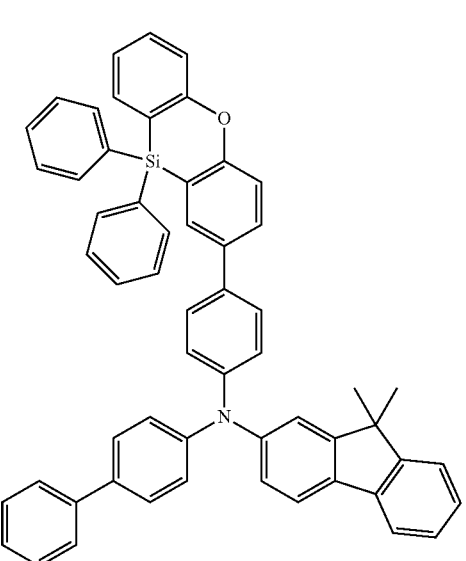
[C-262]
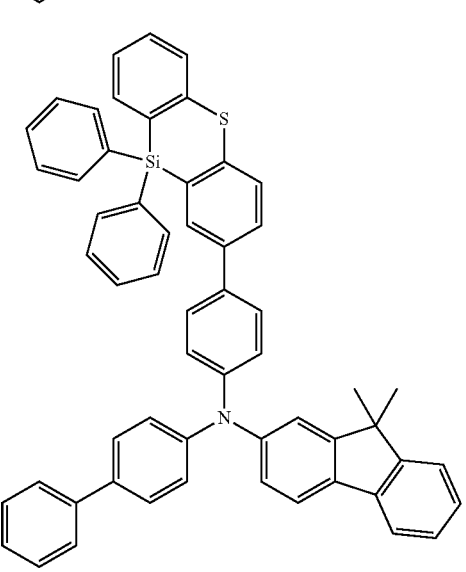

[C-263]
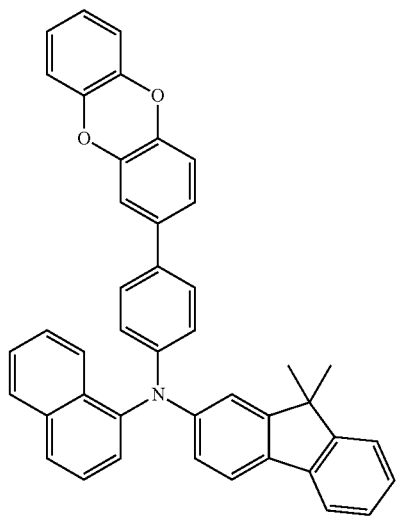
[C-266]
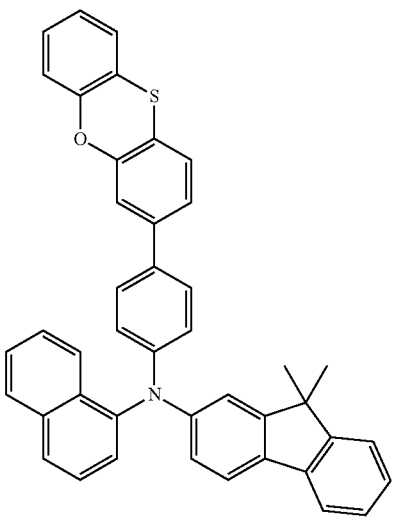
[C-264]
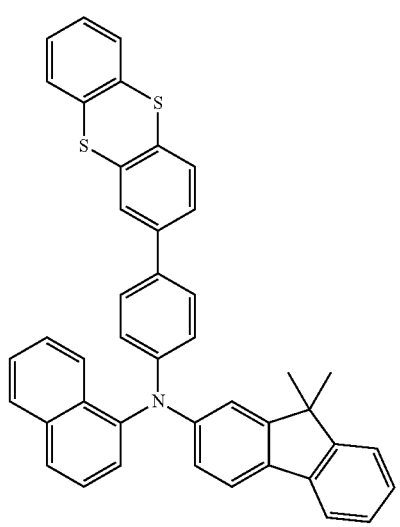
[C-267]
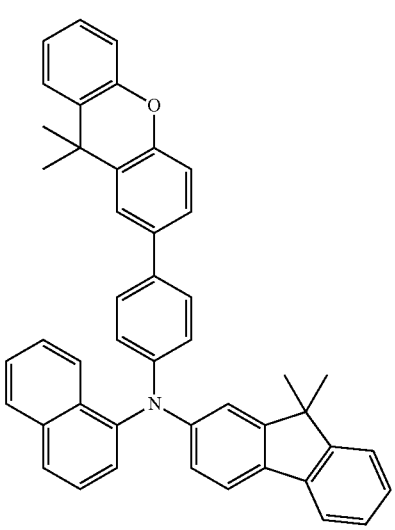
[C-265]
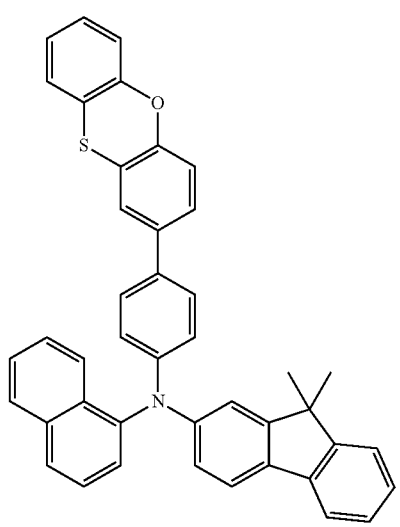
[C-268]
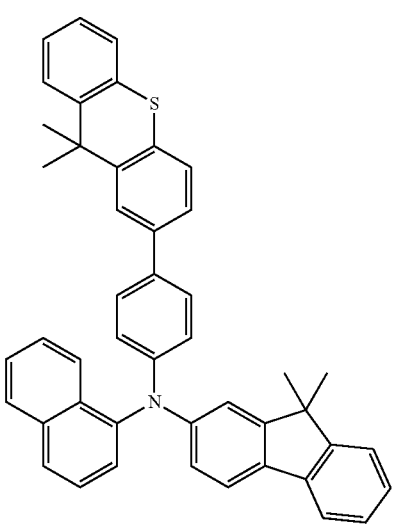

-continued
[C-269]
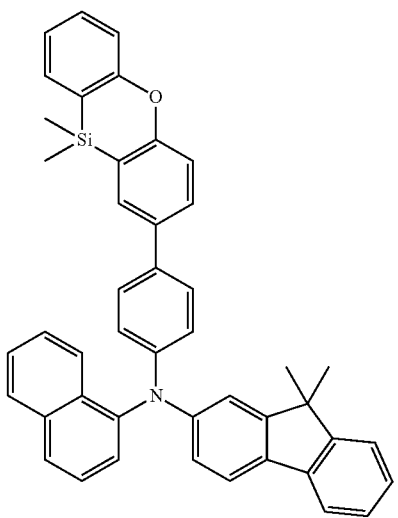
[C-270]
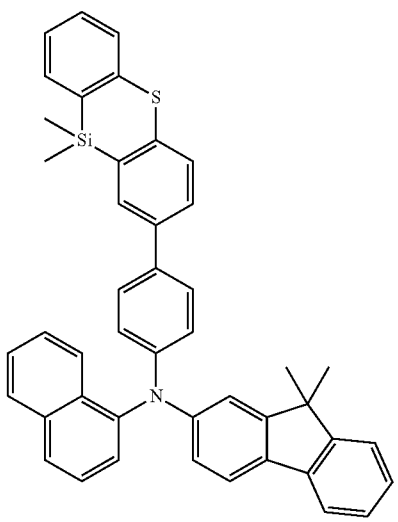
[C-271]
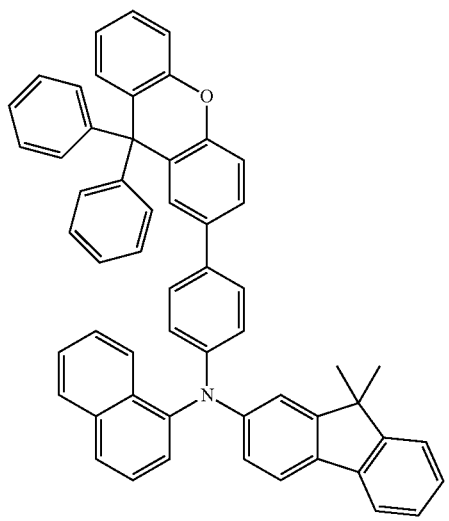
-continued
[C-272]
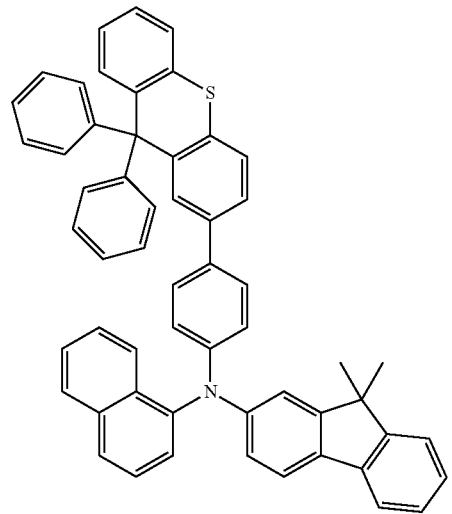
[C-273]
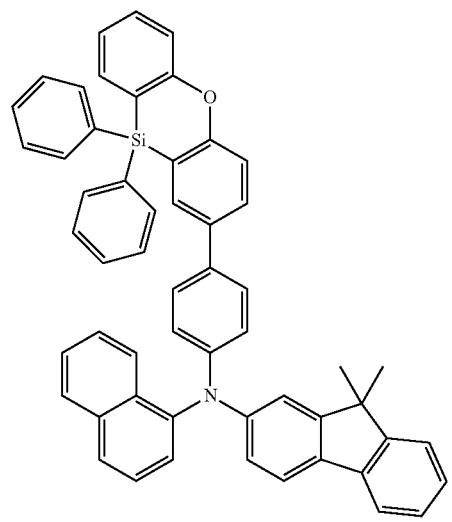
[C-274]
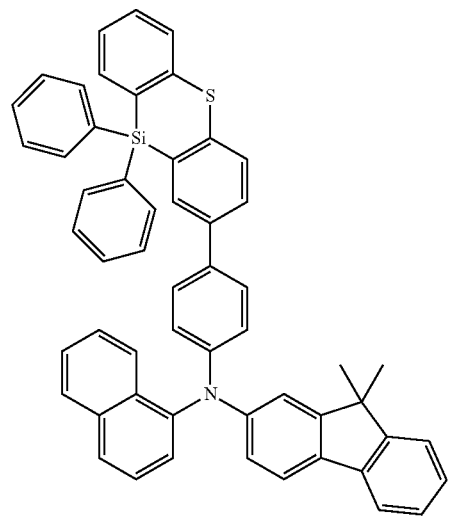

[C-275]
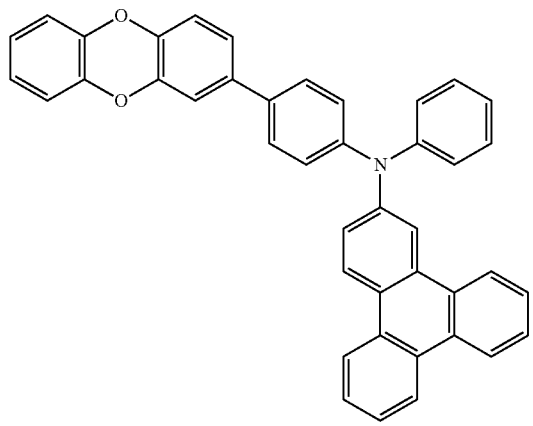
[C-276]
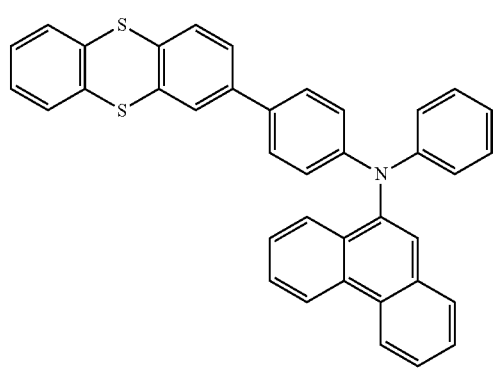
[C-277]
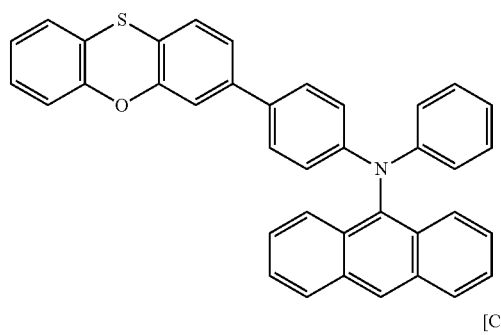
[C-278]
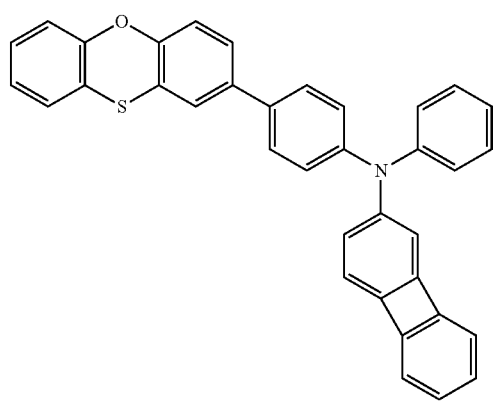
[C-279]
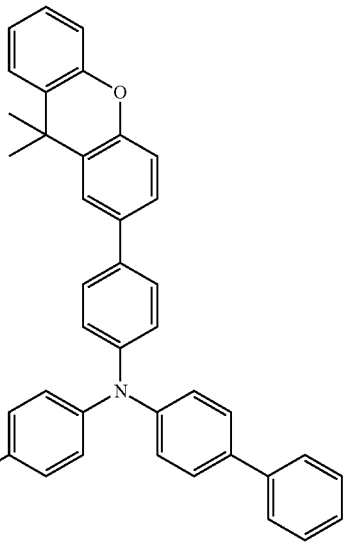
[C-280]
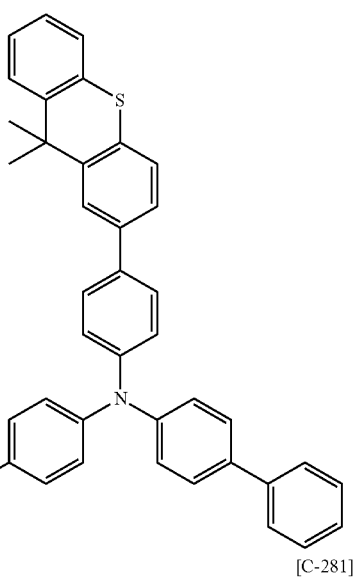
[C-281]
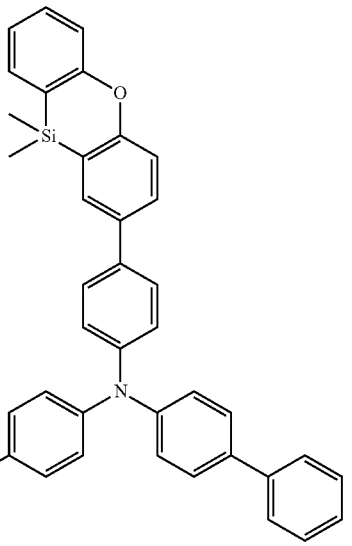

[C-282]

[C-283]

[C-284]

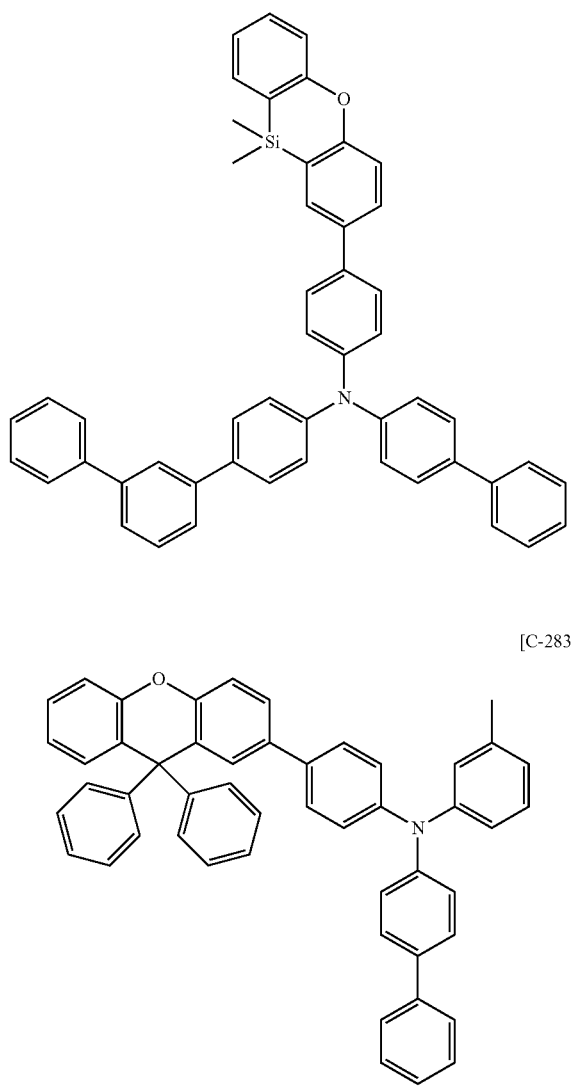

[C-285]

[C-286]

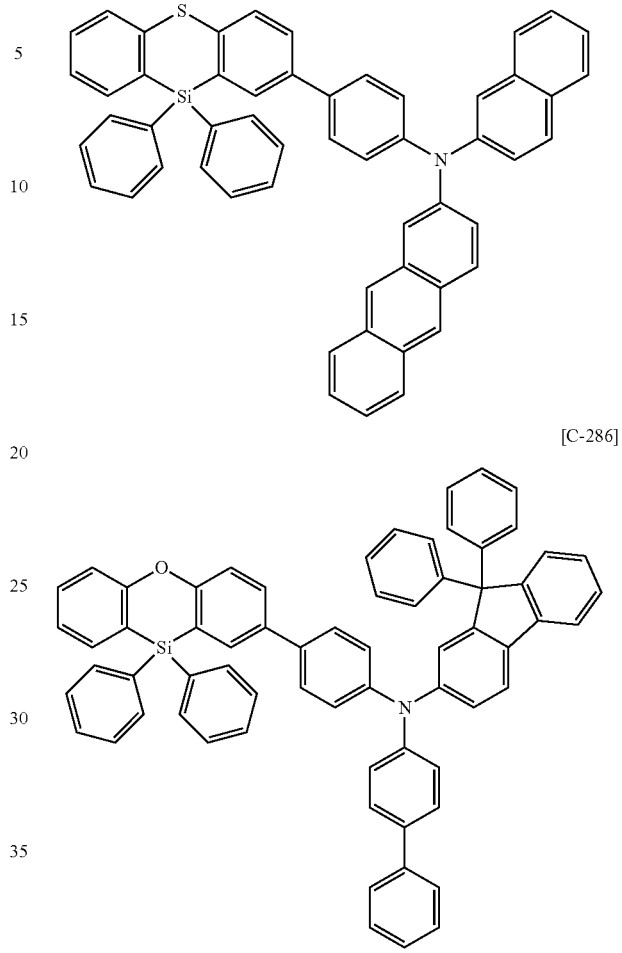

When a compound according to one embodiment of the present invention requires both electron characteristics and hole characteristics, the functional group having the electron characteristics may be preferably introduced in terms of improvement of life-span of an organic light emitting diode and decrease of a driving voltage.

The compound for an organic optoelectronic device according to one embodiment of the present invention has a maximum light emitting wavelength of about 320 to about 500 nm, and triplet exciton energy (T1) of greater than or equal to 2.0 eV, and more specifically 2.0 to 4.0 eV, and charges of a host having high triplet exciton energy is transported to a dopant easily, improving luminous efficiency of a dopant, and a driving voltage may be lowered by controlling HOMO and LUMO energy levels of a material, and thus it may be used as a host material or a charge transport material.

In addition, the compound for an organic optoelectronic device has optical and electrical activity and thus, may be used as a non-linear optical material, an electrode material, an electrochromic material, an optical switch, a sensor, a module, a wave guide, an organic transistor, a laser, an optical absorbing material, a dielectric material, and a material for a separation membrane and the like.

The compound for an organic optoelectronic device including the above compounds has a glass transition temperature of greater than or equal to about 90° C. and a

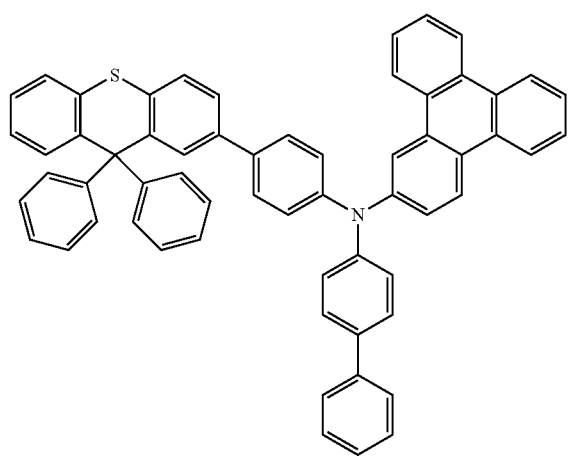

thermal decomposition temperature of greater than or equal to about 400° C., indicating improved thermal stability. Thereby, it is possible to produce an organic optoelectronic device having a high efficiency.

The compound for an organic optoelectronic device including the above compounds may play a role for emitting light or injecting and/or transporting electrons, and also act as a light emitting host with an appropriate dopant. In other words, the compound for an organic optoelectronic device may be used as a phosphorescent or fluorescent host material, a blue light emitting dopant material, or an electron transport material.

The compound for an organic optoelectronic device according to one embodiment of the present invention is used for an organic thin layer, and it may improve the life-span characteristics, efficiency characteristics, electrochemical stability, and thermal stability of an organic optoelectronic device and decrease the driving voltage.

Therefore, according to another embodiment, an organic optoelectronic device that includes the compound for an organic optoelectronic device is provided. The organic optoelectronic device may include an organic photoelectric device, an organic light emitting diode, an organic solar cell, an organic transistor, an organic photo-conductor drum, an organic memory device, and the like. For example, the compound for an organic optoelectronic device according to one embodiment may be included in an electrode or an electrode buffer layer in the organic solar cell to improve the quantum efficiency, and it may be used as an electrode material for a gate, a source-drain electrode, or the like in the organic transistor.

Hereinafter, an organic light emitting diode is specifically described.

An organic light emitting diode according to another embodiment of the present invention includes an anode, a cathode, and at least one or more organic thin layer between the anode and the cathode, and at least one of the organic thin layers may include the compound for an organic optoelectronic device according to one embodiment of the present invention.

The organic thin layer including the compound for an organic optoelectronic device may include a layer selected from an emission layer, a hole transport layer, a hole injection layer, an electron transport layer, an electron injection layer, a hole blocking layer, and a combination thereof. The at least one layer includes the compound for an organic optoelectronic device according to one embodiment. Particularly, the compound for an organic optoelectronic device according to one embodiment may be included in an electron transport layer or electron injection layer. In addition, when the compound for an organic optoelectronic device is included in the emission layer, the compound for an organic optoelectronic device may be included as a phosphorescent or fluorescent host, and particularly, as a fluorescent blue dopant material.

FIGS. 1 to 5 are cross-sectional views showing organic light emitting diodes including the compound for an organic optoelectronic device according to one embodiment of the present invention.

Referring to FIGS. 1 to 5, organic light emitting diodes 100, 200, 300, 400, and 500 according to one embodiment include at least one organic thin layer 105 interposed between an anode 120 and a cathode 110.

The anode 120 includes an anode material, which is preferably a material having a large work function to help hole injection into an organic thin layer. Specific examples of the anode material include: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as $ZnO:Al$ or $SnO_2:Sb$; or a conductive polymer such as poly(3-methylthiophene), poly[3,4-(ethylene-1,2-dioxy)thiophene] (PEDT), polypyrrole, and polyaniline, but is not limited thereto. It is preferable to include a transparent electrode including indium tin oxide (ITO) as an anode.

The cathode 110 includes a cathode material, which is a material having a small work function to help electron injection into an organic thin layer. Specific examples of the cathode material include: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Ak LiF/Ca, LiF/Al, and $BaF_2$/Ca, but is not limited thereto. It is preferable to include a metal electrode including aluminum as a cathode.

First, referring to FIG. 1, the organic light emitting diode 100 includes the only emission layer 130 as an organic thin layer 105, and the organic thin layer 105 may be present as the only emission layer 130.

Figure 2:
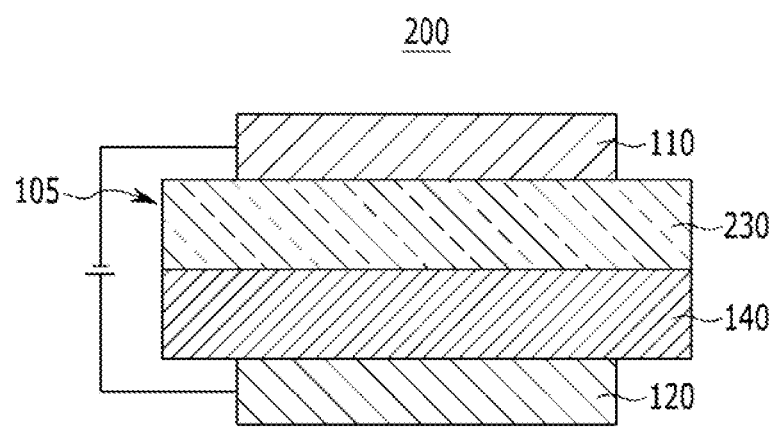

Referring to FIG. 2, a double-layered organic light emitting diode 200 includes an organic thin layer 105 including an emission layer 230 including an electron transport layer (ETL), and a hole transport layer (HTL) 140 and as shown in FIG. 2, the organic thin layer 105 includes a double layer of the emission layer 230 and hole transport layer (HTL) 140. The emission layer 230 also functions as an electron transport layer (ETL), and the hole transport layer (HTL) 140 layer has an excellent binding property with a transparent electrode such as ITO or an excellent hole transport capability.

Figure 3:
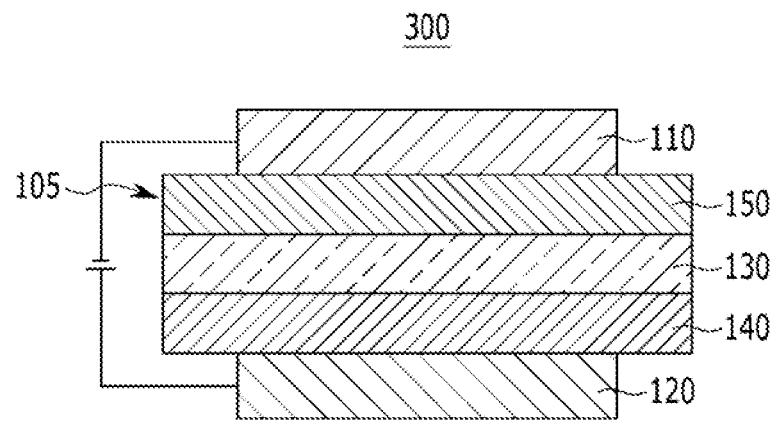

Referring to FIG. 3, a three-layered organic light emitting diode 300 includes an organic thin layer 105 including an electron transport layer (ETL) 150, an emission layer 130, and a hole transport layer (HTL) 140. The emission layer 130 is independently installed, and layers having an excellent electron transport capability or an excellent hole transport capability are separately stacked.

Figure 4:
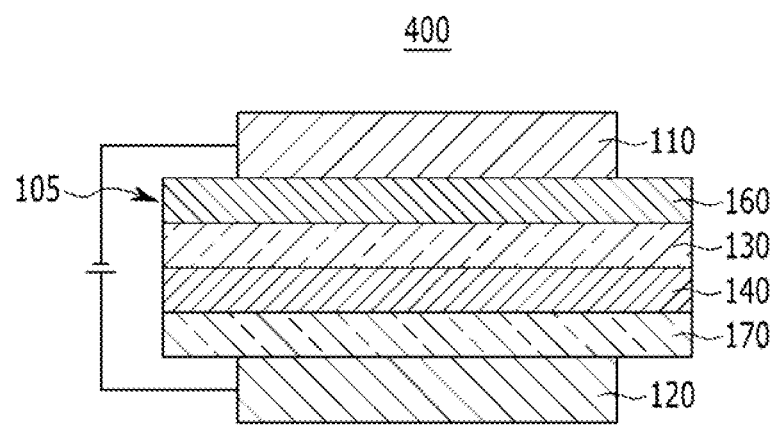

Referring to FIG. 4, a four-layered organic light emitting diode 400 includes an organic thin layer 105 including an electron injection layer (EIL) 160, an emission layer 130, a hole transport layer (HTL) 140, and a hole injection layer (HIL) 170 for adherence with the cathode of ITO.

Figure 5:
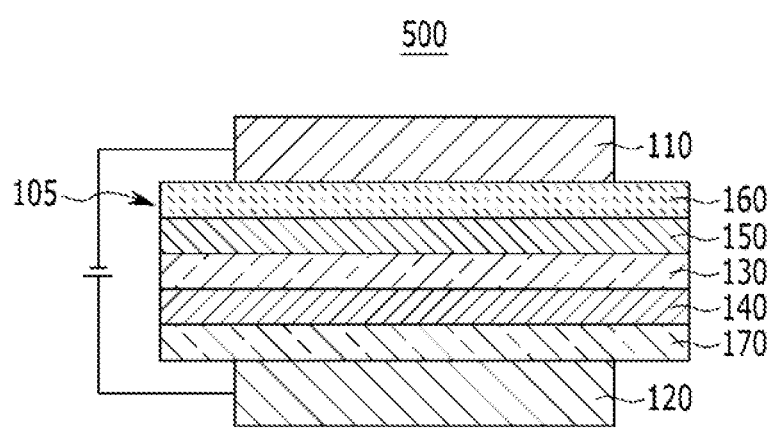

Referring to FIG. 5, a five-layered organic light emitting diode 500 includes an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

In FIGS. 1 to 5, the organic thin layer 105 including at least one selected from the group consisting of an electron transport layer (ETL) 150, an electron injection layer (EIL) 160, emission layers 130 and 230, a hole transport layer (HTL) 140, a hole injection layer (HIL) 170, and combinations thereof includes the compound for an organic optoelectronic device. Herein, the compound for an organic optoelectronic device may be used for an electron transport layer (ETL) 150 including the electron transport layer (ETL) 150 or electron injection layer (EIL) 160, and when it is used for the electron transport layer (ETL), it is possible to provide an organic light emitting diode having a more simple structure because it does not require an additional hole blocking layer (not shown).

Furthermore, when the compound for an organic optoelectronic device is included in the emission layers 130 and 230, the compound for an organic optoelectronic device may be included as a phosphorescent or fluorescent host or a fluorescent blue dopant.

The organic light emitting diode may be manufactured by: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

According to another embodiment of the present invention, a display device including the organic light emitting diode is provided.

Hereinafter, the embodiments are illustrated in more detail with reference to examples.

According to another embodiment of the present invention, a display device including the organic light emitting diode is provided.

(Preparation of Compound for Organic Optoelectronic Device)

Synthesis of Intermediate

Synthesis of Intermediate M-1

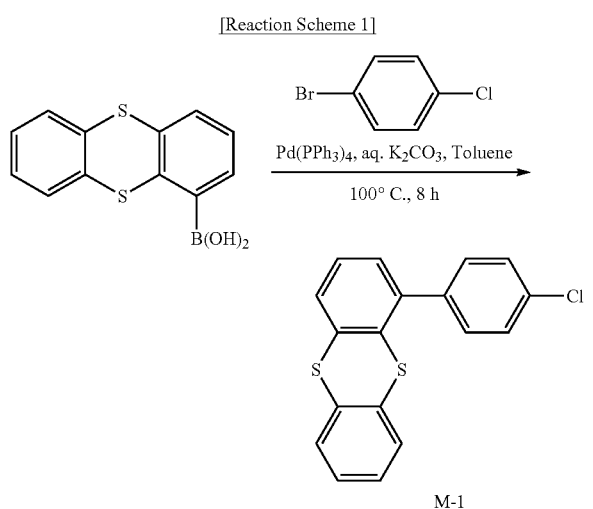

20 g (76.88 mmol) of tianthrene-1-boronic acid, 14.7 g (76.88 mmol) of 1-bromo-4-chlorobenzene, and 0.89 g (0.769 mmol) of tetrakistriphenylphosphine palladium are put in a flask, and dissolved in 257 mL of toluene under a nitrogen atmosphere, 17 g (115.4 mmol) of potassium carbonate dissolved in 128 mL of an aqueous solution was added, and the resultant was agitated for 8 hours at 100° C. while refluxing. When the reaction was terminated, the resultant was extracted with ethylacetate, the obtained extracted solution was dried with magnesium sulfate, and filtered, and then the filtrated solution was concentrated under a reduced pressure. The product was purified with n-hexane/dichloromethane (9:1 volume ratio) using silica gel column chromatography, obtaining 22.1 g (yield 88%) of a target compound, an intermediate M-1.

LC-Mass (theoretical value: 326.00 g/mol, measurement value: M+1=327.34 g/mol)

Synthesis of Intermediate M-2

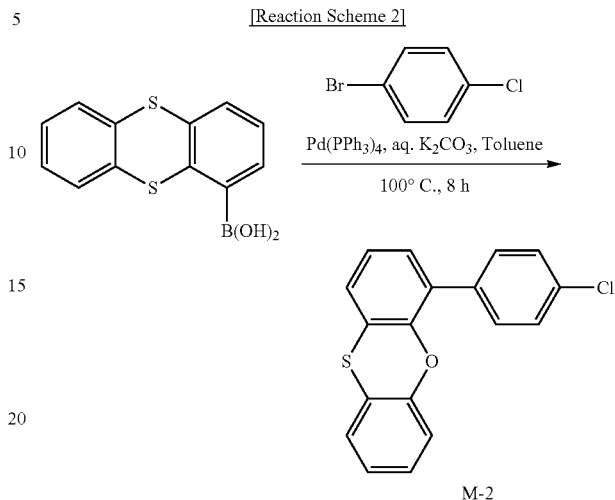

18.8 g (76.88 mmol) of 4-phenoxathiinylboronic acid, 14.7 g (76.88 mmol) of 1-bromo-4-chlorobenzene and 0.89 g (0.769 mmol) of tetrakistriphenylphosphine palladium were put in a flask, and dissolved in 257 mL of toluene under a nitrogen atmosphere, 17 g (115.4 mmol) of potassium carbonate dissolved in 128 mL of an aqueous solution was added, and the resultant was agitated for 8 hours at 100° C. while refluxing. When the reaction was terminated, the resultant was extracted with ethylacetate, the obtained extracted solution was dried with magnesium sulfate, and filtered, and then the filtrated solution was concentrated under a reduced pressure. The product was purified with n-hexane/dichloromethane (9:1 volume ratio) using silica gel column chromatography, obtaining 20.3 g (yield 85%) of a target compound, an intermediate M-2.

LC-Mass (theoretical value: 310.02 g/mol, measurement value: M+1=311.37 g/mol)

Synthesis of Intermediate M-3

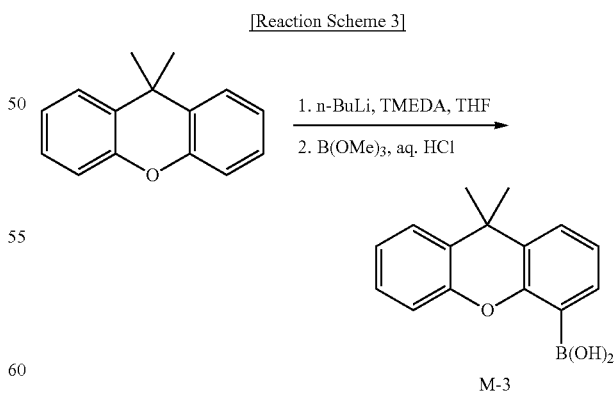

30 g (142.7 mmol) of 9,9-dimethyl xanthene was put in a 2-neck round-bottomed flask dried and heated under vacuum, under a nitrogen atmosphere 476 mL of anhydrous tetrahydrofuran was dissolved, then cooled and agitated at −40° C.

57 mL (in hexane, 142.7 mmol) of 2.5M n-butyllithium was slowly added thereto, and 16.5 g (142.7 mmol) of N,N,N',N'-tetramethylethylenediamine was added. The reaction solution was increased to room temperature and agitated under a nitrogen atmosphere for 8 hours. After cooling the reaction solution to −78° C., 10.9 g (157 mmol) of trimethylborate dissolved in 10 mL of anhydrous tetrahydrofuran was slowly added and agitated at room temperature for 8 hours. After cooling the reaction solution to 0° C., 234 mL of 2N HCl aqueous solution was added and agitated at room temperature for 1 hour. When the reaction was terminated, the solution was extracted with distilled water and diethylether, the organic layer solution was dried with magnesium sulfate and filtered, and then the filtrated solution was concentrated under a reduced pressure. The reaction solution was dissolved in acetone and recrystallized with n-hexane, obtaining 23.6 g (yield 65%) of a target compound, an intermediate M-3, a white solid.

GC-Mass (theoretical value: 254.11 g/mol, measurement value: M+1=255.42 g/mol)

Synthesis of Intermediate M-4

[Reaction Scheme 4]

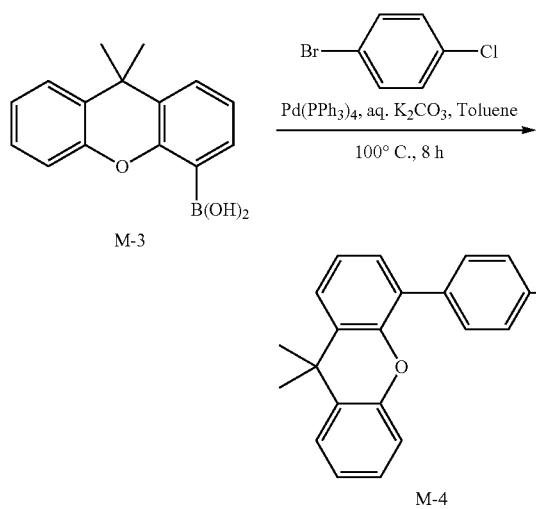

M-3

19.5 g (76.88 mmol) of the intermediate M-3, 14.7 g (76.88 mmol) of 1-bromo-4-chlorobenzene, and 0.89 g (0.769 mmol) of tetrakistriphenylphosphine palladium were put in a flask, and dissolved in 257 mL of toluene under a nitrogen atmosphere, 17 g (115.4 mmol) of potassium carbonate dissolved in 128 mL of an aqueous solution was added, and the resultant was agitated for 8 hours at 100° C. while refluxing. When the reaction was terminated, the resultant was extracted with ethylacetate, the obtained extracted solution was dried with magnesium sulfate, and filtered, and then the filtrated solution was concentrated under a reduced pressure. The product was purified with n-hexane/dichloromethane (9:1 volume ratio) using silica gel column chromatography, obtaining 21 g (yield 85%) of a target compound, an intermediate M-4.

LC-Mass (theoretical value: 320.10 g/mol, measurement value: M+1=321.24 g/mol)

Synthesis of Intermediate M-5

[Reaction Scheme 5]

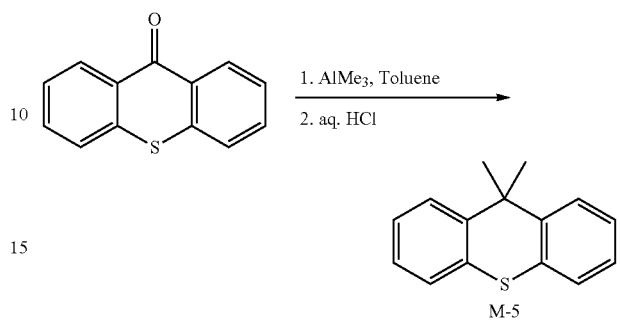

M-5

40 g (188.4 mmol) of thioxanthone was put in a 2-neck round-bottomed flask dried and heated under vacuum, under a nitrogen atmosphere, 377 mL of anhydrous toluene was dissolved, cooled to 0° C. and agitated.

188 mL (in toluene, 377 mmol) of 2.0M trimethylaluminum was slowly added thereto, the reaction solution was increased to room temperature and agitated under a nitrogen atmosphere for 12 hours.

The reaction solution was slowly added to slurry including 188 mL of 6N HCl aqueous solution and 181 g of ice and agitated at room temperature for 30 minutes. When the reaction was terminated, the solution was extracted with distilled water and toluene, the organic layer solution was dried with magnesium sulfate and filtered, and then the filtrated solution was concentrated under a reduced pressure. The product was purified with n-hexane using silica gel column chromatography, obtaining 34.1 g (yield 80%) of a target compound, an intermediate M-5.

LC-Mass (theoretical value: 226.08 g/mol, measurement value: M+1=227.35 g/mol)

Synthesis of Intermediate M-6

[Reaction Scheme 6]

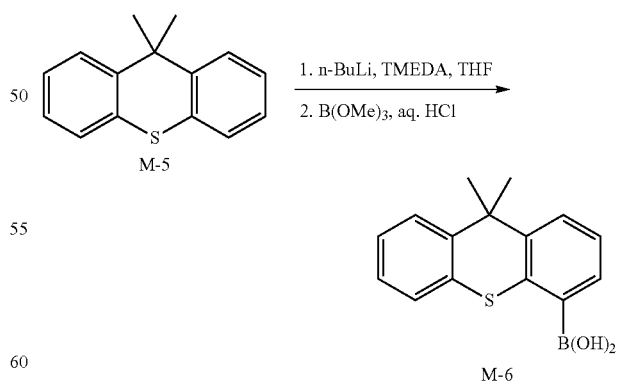

The intermediate M-5 32.3 g (142.7 mmol) was put to 2-neck round-bottomed flask dried and heated under vacuum, under a nitrogen atmosphere, dissolved by adding 476 mL of anhydrous tetrahydrofuran, cooled to −40° C. and agitated.

57 mL (in hexane, 142.7 mmol) of 2.5M n-butyllithium was slowly added thereto, and 16.5 g (142.7 mmol) of N,N,N',N'-tetramethylethylenediamine was added. The reaction solution was increased to room temperature and agitated under a nitrogen atmosphere for 8 hours. After cooling the reaction solution to −78° C., 10.9 g (157 mmol) of trimethylborate dissolved in 10 mL of anhydrous tetrahydrofuran was slowly added and agitated at room temperature for 8 hours. After cooling the reaction solution to 0° C., 234 mL of 2N HCl aqueous solution was added and agitated at room temperature for 1 hour. When the reaction was terminated, the solution was extracted with distilled water and diethylether, the organic layer solution was dried with magnesium sulfate and filtered, and then the filtrated solution was concentrated under a reduced pressure. The reaction solution was dissolved in acetone and recrystallized with n-hexane, obtaining 23.5 g (yield 61%) of a target compound, an intermediate M-6, a white solid.

GC-Mass (theoretical value: 270.09 g/mol, measurement value: M+1=271.27 g/mol)

Synthesis of Intermediate M-7

[Reaction Scheme 7]

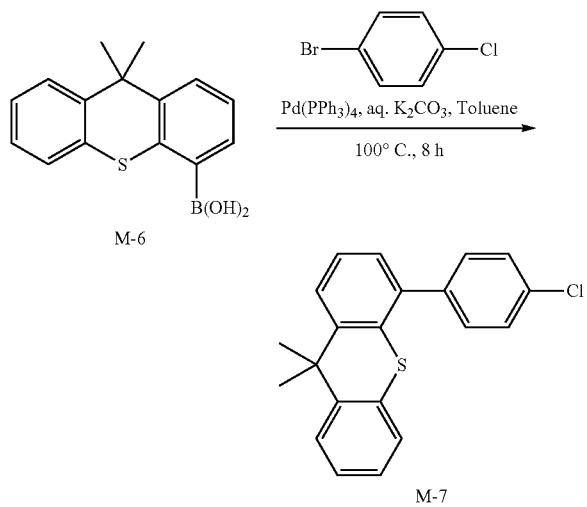

M-6

M-7

20.8 g (76.88 mmol) of the intermediate M-6, 1-bromo-4-chlorobenzene 14.7 g (76.88 mmol) and 0.89 g (0.769 mmol) of tetrakistriphenylphosphine palladium were put in a flask, and dissolved in 257 mL of toluene under a nitrogen atmosphere, 17 g (115.4 mmol) of potassium carbonate dissolved in 128 mL of an aqueous solution was added, and the resultant was agitated for 8 hours at 100° C. while refluxing. When the reaction was terminated, the resultant was extracted with ethylacetate, the obtained extracted solution was dried with magnesium sulfate, and filtered, and then the filtrated solution was concentrated under a reduced pressure. The product was purified with n-hexane/dichloromethane (9:1 volume ratio) using silica gel column chromatography, obtaining 21.7 g (yield 88%) of a target compound intermediate M-7.

LC-Mass (theoretical value: 336.07 g/mol, measurement value: M+1=337.31 g/mol)

Synthesis of Intermediate M-8

[Reaction Scheme 8]

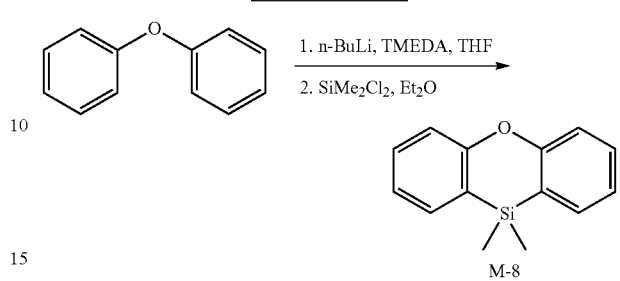

M-8

60 g (352.6 mmol) of diphenylether was put in 2-neck round-bottomed flask dried and heated under vacuum, under a nitrogen atmosphere, dissolved by adding 352 mL of anhydrous tetrahydrofuran, cooled to 0° C. and agitated.

310 mL (in hexane, 776 mmol) of 2.5M n-butyllithium was slowly added thereto, and 90.2 g (776 mmol) of N,N,N',N'-tetramethylethylenediamine was added. A reaction solution was increased to room temperature and agitated under a nitrogen atmosphere for 16 hours. After cooling the reaction solution to 0° C., 45.6 g (352.6 mmol) of dimethyldichlorosilane dissolved in 60 mL of anhydrous diethylether was slowly added and agitated at room temperature for 16 hours. After cooling the reaction solution to 0° C., 240 mL of distilled water was added and agitated at room temperature for 30 minutes. When the reaction was terminated, the solution was extracted with distilled water and diethylether the organic layer solution was dried with magnesium sulfate and filtered, and then the filtrated solution was concentrated under a reduced pressure. The product was recrystallized with methanol, obtaining 35.2 g (yield 44%) of a target compound, an intermediate M-8 a white solid.

GC-Mass (theoretical value: 226.08 g/mol, measurement value: M+1=227.27 g/mol)

Synthesis of Intermediate M-9

[Reaction Scheme 9]

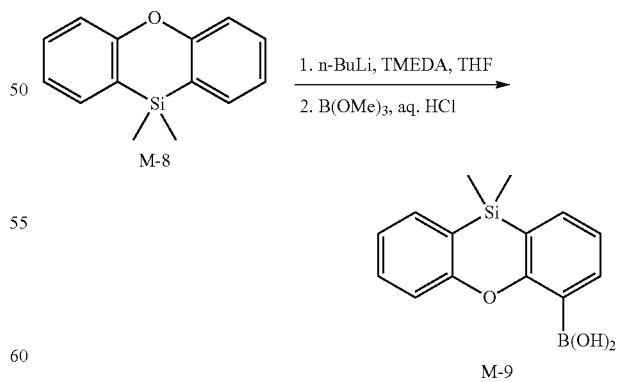

M-8

M-9

32.3 g (142.7 mmol) of the intermediate M-8 was put in 2-neck round-bottomed flask dried and heated under vacuum, under a nitrogen atmosphere, dissolved by adding 352 mL of anhydrous tetrahydrofuran, cooled to −40° C. and agitated.

57 mL (in hexane, 142.7 mmol) of 2.5M n-butyllithium was slowly added thereto, and 16.5 g (142.7 mmol) of N,N,N',N'-tetramethylethylenediamine was added. The reaction solution was increased to room temperature and agitated under a nitrogen atmosphere for 8 hours. After cooling the reaction solution to −78° C., 10.9 g (157 mmol) of trimethylborate dissolved in 10 mL of anhydrous tetrahydrofuran was slowly added and agitated at room temperature for 8 hours. After cooling the reaction solution to 0 oC, 234 mL of 2N HCl aqueous solution was added and agitated at room temperature for 1 hour. When the reaction was terminated, the solution was extracted with distilled water and diethylether the organic layer solution was dried with magnesium sulfate and filtered, and then the filtrated solution was concentrated under a reduced pressure. The reaction solution was dissolved in acetone and recrystallized with n-hexane, obtaining 22.7 g (yield 59%) of a target compound, an intermediate M-9, a white solid.

GC-Mass (theoretical value: 270.09 g/mol, measurement value: M+1=271.35 g/mol)

Synthesis of Intermediate M-10

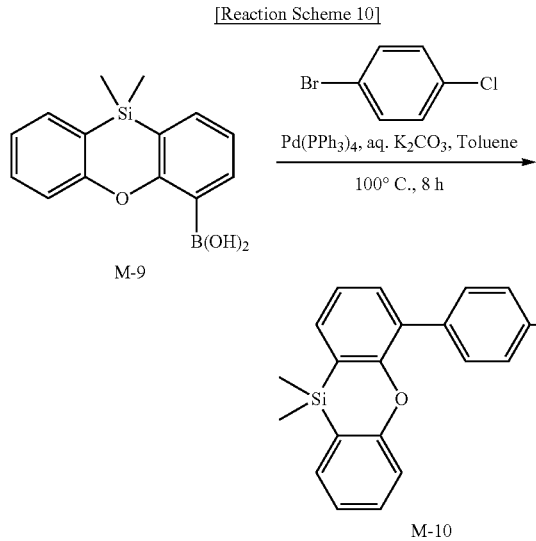

M-9

M-10

20.8 g (76.88 mmol) of the intermediate M-9, 14.7 g (76.88 mmol) of 1-bromo-4-chlorobenzene and 0.89 g (0.769 mmol) of tetrakistriphenylphosphine palladium were put in a flask, and dissolved in 257 mL of toluene under a nitrogen atmosphere, 17 g (115.4 mmol) of potassium carbonate dissolved in 128 mL of an aqueous solution was added, and the resultant was agitated for 8 hours at 100° C. while refluxing. When the reaction was terminated, the resultant was extracted with ethylacetate, the obtained extracted solution was dried with magnesium sulfate, and filtered, and then the filtrated solution was concentrated under a reduced pressure. The product was purified with n-hexane/dichloromethane (9:1 volume ratio) using silica gel column chromatography, obtaining 21.8 g (yield 84%) of a target compound intermediate M-10.

LC-Mass (theoretical value: 336.07 g/mol, measurement value: M+1=337.28 g/mol)

Synthesis of Intermediate M-11

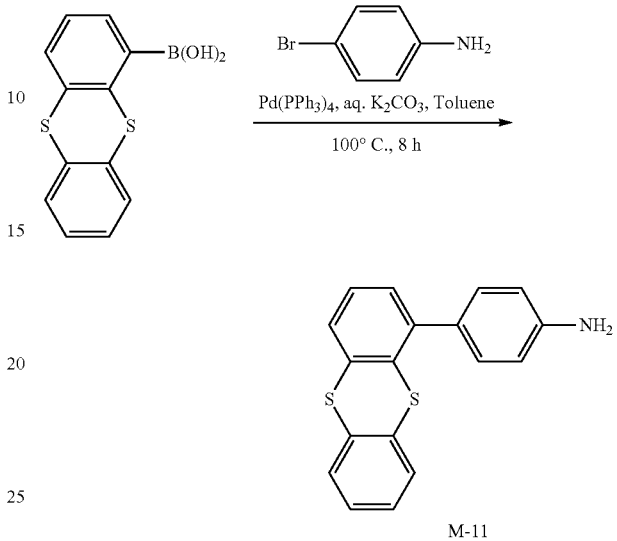

M-11

20 g (76.88 mmol) of tianthrene-1-boronic acid, 13.2 g (76.88 mmol) of 4-bromoaniline, and 0.89 g (0.769 mmol) of tetrakistriphenylphosphine palladium were put in a flask, and dissolved in 257 mL of toluene under a nitrogen atmosphere, 17 g (115.4 mmol) of potassium carbonate dissolved in 128 mL of an aqueous solution was added, and the resultant was agitated for 8 hours at 100° C. while refluxing. When the reaction was terminated, the resultant was extracted with ethylacetate, the obtained extracted solution was dried with magnesium sulfate, and filtered, and then the filtrated solution was concentrated under a reduced pressure. The product was purified with n-hexane/dichloromethane (9:1 volume ratio) using silica gel column chromatography, obtaining 19.1 g (yield 81%) of a target compound, an intermediate M-11.

LC-Mass (theoretical value: 307.05 g/mol, measurement value: M+1=308.29 g/mol)

Synthesis of Intermediate M-12

[Reaction Scheme 12]

M-11

+

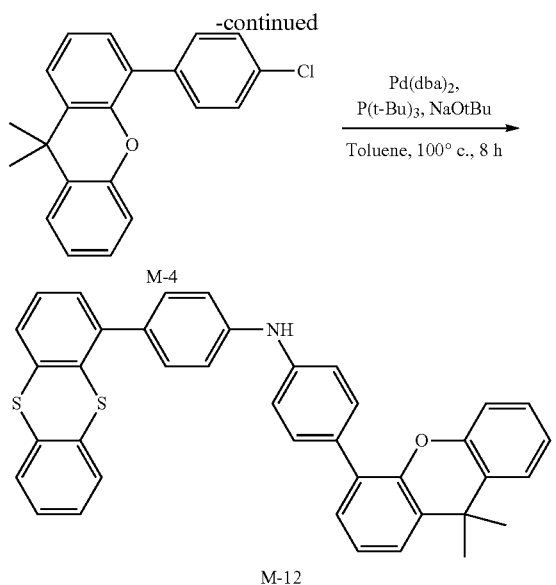

M-4

M-12

10.9 g (34.0 mmol) of the intermediate M-4, 11 g (35.7 mmol) of the intermediate M-11, 4.9 g (51 mmol) of sodium t-butoxide and 0.20 g (1.02 mmol) of tri-tertiary-butylphosphine were dissolved in 340 ml of toluene, 0.20 g (0.34 mmol) of Pd(dba)$_2$ was added, and the and the resultant was agitated for 8 hours at 100° C. under a nitrogen atmosphere while refluxing. When the reaction was terminated, the resultant was extracted with toluene and distilled water, the organic layer was dried with magnesium sulfate, and filtered, and then the filtrated solution was concentrated under a reduced pressure. The product was purified with n-hexane/dichloromethane (9:1 volume ratio) using silica gel column chromatography, obtaining 15.1 g (yield 75%) of a target compound, an intermediate M-12, a white solid.

LC-Mass (theoretical value: 591.17 g/mol, measurement value: M+1=592.39 g/mol)

Synthesis of Intermediate M-13

[Reaction Scheme 13]

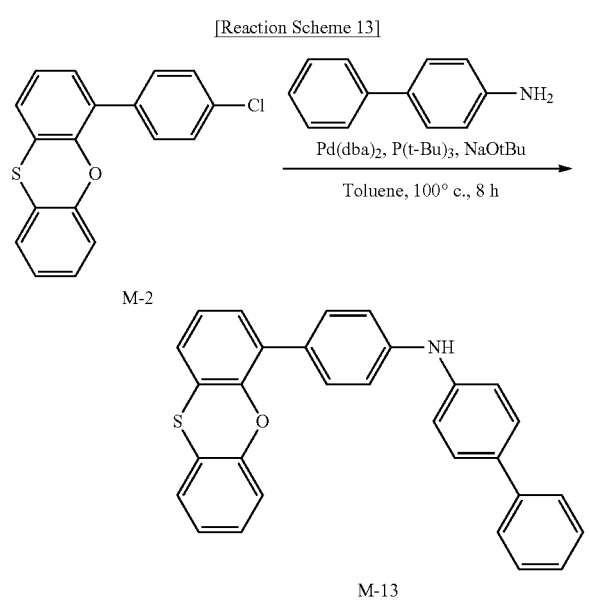

M-2

M-13

10.6 g (34.0 mmol) of the intermediate M-2, 6.9 g (40.8 mmol) of 4-aminobiphenyl, 4.9 g (51 mmol) of sodium t-butoxide and 0.20 g (1.02 mmol) of tri-tertiary-butylphosphine were dissolved in 340 ml of toluene, 0.20 g (0.34 mmol) of Pd(dba)$_2$ was added, and the resultant was agitated for 12 hours while refluxing. When the reaction was terminated, the resultant was extracted with toluene and distilled water, the organic layer was dried with magnesium sulfate, and filtered, and then the filtrated solution was concentrated under a reduced pressure. The product was purified with n-hexane/dichloromethane (7:3 volume ratio) using silica gel column chromatography, obtaining 11.6 g (yield 77%) of a target compound, an intermediate M-13, a white solid.

LC-Mass (theoretical value: 443.13 g/mol, measurement value: M+1=444.29 g/mol)

Synthesis of Intermediate M-14

[Reaction Scheme 14]

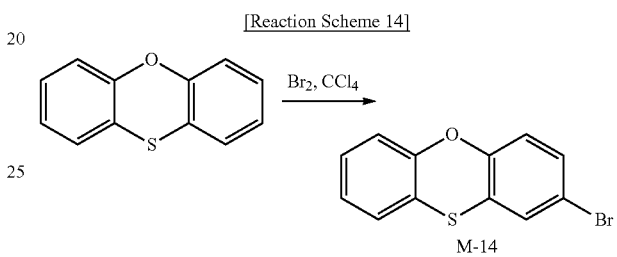

M-14

30 g (149.8 mmol) of phenoxathin was put in a round-bottomed flask, and dissolved in 150 mL of carbon tetrachloride, and 23.9 g (149.8 mmol) of bromine was slowly added at room temperature for 10 minutes. The reaction solution was additionally agitated at 30° C. for 6 hours, and then cooled, and sodium thiosulfite aqueous solution was added and extracted. The organic layer was dried with magnesium sulfite, and filtered, and the filtrated solution was concentrated under reduced pressure. The product was recrystallized with methanol, obtaining 33.9 g (yield 81%) of a target compound, an intermediate M-14, a white solid.

LC-Mass (theoretical value: 277.94 g/mol, measurement value: 279.12 g/mol)

Synthesis of Intermediate M-15

[Reaction Scheme 15]

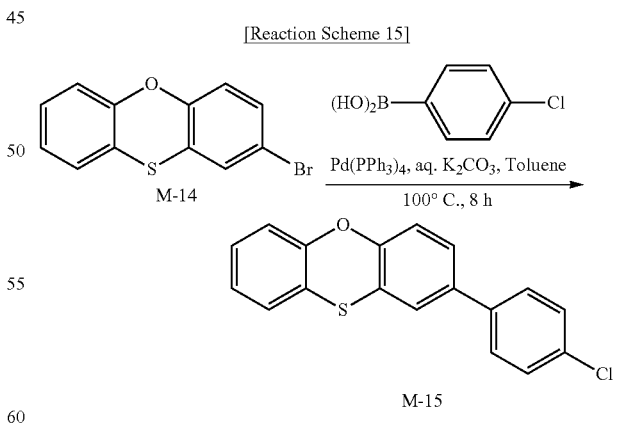

M-14

M-15

21.5 g (76.88 mmol) of intermediate M-14, 12 g (76.88 mmol) of 4-chlorophenyl boronic acid, and 0.89 g (0.769 mmol) of tetrakistriphenylphosphine palladium were put in a flask, and dissolved in 257 mL of toluene under a nitrogen atmosphere, 17 g (115.4 mmol) of potassium carbonate dissolved in 128 mL of an aqueous solution was added, and the resultant was agitated for 8 hours at 100° C. while refluxing. When the reaction was terminated, the resultant was extracted with ethylacetate, the obtained extracted solution was dried with magnesium sulfate, and filtered, and then the filtrated solution was concentrated under a reduced pressure. The product was purified with n-hexane/dichloromethane (9:1 volume ratio) using silica gel column chromatography, obtaining 20.5 g (yield 86%) of a target compound, an intermediate M-15.

LC-Mass (theoretical value: 310.02 g/mol, measurement value: M+1=311.19 g/mol)

Synthesis of Intermediate M-16

[Reaction Scheme 16]

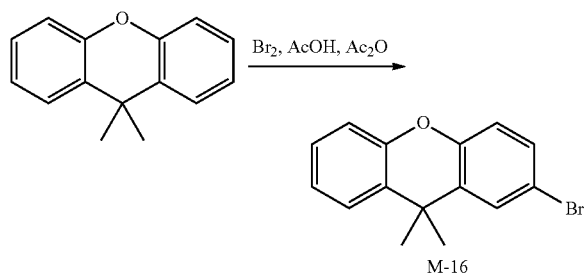

31.5 g (149.8 mmol) of 9,9-dimethyl xanthene was put in a round-bottomed flask, dissolved in 350 mL of acetic anhydride, then cooled to 0° C., and agitated. A solution including 23.9 g (149.8 mmol) of bromine dissolved acetic acid 15 mL was slowly added for 10 minutes. The reaction solution was further agitated at room temperature for 2 hours, was slowly added to ice water, and a precipitate was filtered. The precipitated solid was extracted with dichloromethane/sodium thiosulfite aqueous solution. The organic layer was dried with magnesium sulfate, and filtered, and the filtrated solution was concentrated under reduced pressure. The product was purified with n-hexane using silica gel column chromatography, obtaining 27.7 g (yield 64%) of a target compound, an intermediate M-16.

LC-Mass (theoretical value: 288.01 g/mol, measurement value: 289.35 g/mol)

Synthesis of Intermediate M-17

[Reaction Scheme 17]

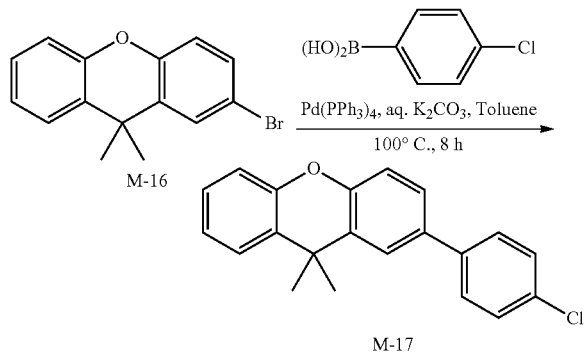

22.2 g (76.88 mmol) of the intermediate M-16, 12 g (76.88 mmol) of 4-chlorophenyl boronic acid and 0.89 g (0.769 mmol) of tetrakistriphenylphosphine palladium were put in a flask, and dissolved in 257 mL of toluene under a nitrogen atmosphere, 17 g (115.4 mmol) of potassium carbonate dissolved in 128 mL of an aqueous solution was added, and the resultant was agitated for 8 hours at 100° C.

while refluxing. When the reaction was terminated, the resultant was extracted with ethylacetate, the obtained extracted solution was dried with magnesium sulfate, and filtered, and then the filtrated solution was concentrated under a reduced pressure. The product was purified with n-hexane/dichloromethane (9:1 volume ratio) using silica gel column chromatography, obtaining 22 g (yield 89%) of a target compound, an intermediate M-17.

LC-Mass (theoretical value: 320.10 g/mol, measurement value: M+1=321.36 g/mol)

Synthesis of Intermediate M-18

[Reaction Scheme 18]

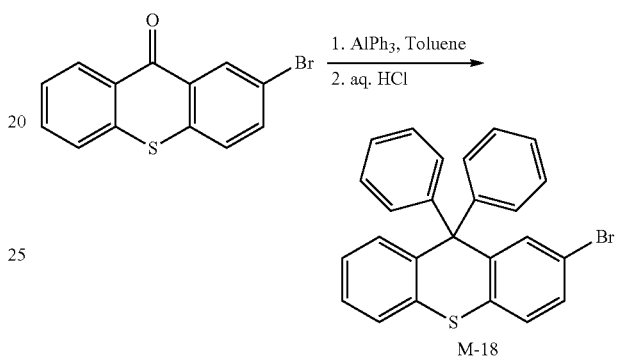

27.5 g (94.2 mmol) of bromotieoxanthene-9-one was put in a 2-neck round-bottomed flask dried and heated under vacuum, under a nitrogen atmosphere, dissolved by adding 250 mL of anhydrous toluene, cooled to 0° C. and agitated.

189 mL (in dibutylether, 189 mmol) of 1.0M triphenylaluminum was slowly added thereto, the reaction solution was increased to room temperature and agitated under a nitrogen atmosphere for 12 hours.

The reaction solution was slowly added to slurry including 94 mL of 6N HCl aqueous solution and 91 g of ice and agitated at room temperature for 30 minutes. When the reaction was terminated, the solution was extracted with distilled water and toluene, the organic layer solution was dried with magnesium sulfate and filtered, and then the filtrated solution was concentrated under a reduced pressure. The product was purified with n-hexane/dichloromethane (9:1 volume ratio) using silica gel column chromatography, obtaining 24.7 g (yield 61%) of a target compound, an intermediate M-18.

LC-Mass (theoretical value: 428.02 g/mol, measurement value: M+1=429.41 g/mol)

Synthesis of Intermediate M-19

[Reaction Scheme 19]

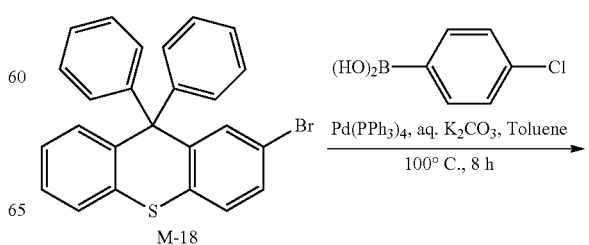

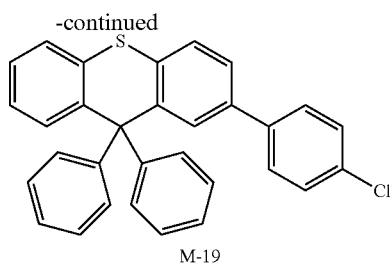

M-19

22 g (47.72 mmol) of the intermediate M-18, 7.5 g (47.72 mmol) of 4-chlorophenyl boronic acid, and 0.55 g (0.477 mmol) of tetrakistriphenylphosphinepalladium were put in a round-bottomed flask and dissolved in 200 mL of toluene under a nitrogen atmosphere, 10.5 g (71.6 mmol) of potassium carbonate dissolved in 100 ml of an aqueous solution was added, and the resultant was agitated for 8 hours at 100° C. while refluxing. When the reaction was terminated, the resultant was extracted with ethylacetate, the obtained extracted solution was dried with magnesium sulfate, and filtered, and then the filtrated solution was concentrated under a reduced pressure. The product was purified with n-hexane/dichloromethane (9:1 volume ratio) using silica gel column chromatography, obtaining 18.5 g (yield 84%) of a target compound, an intermediate M-19.

LC-Mass (theoretical value: 460.11 g/mol, measurement value: M+1=461.33 g/mol)

EXAMPLE 1

Preparation of Compound Represented by Chemical Formula C-143

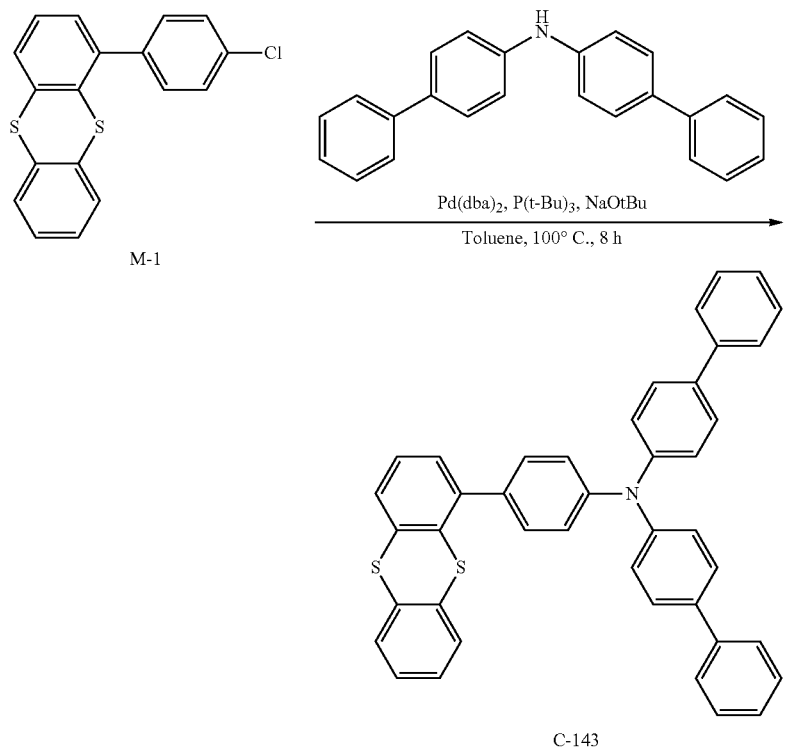

10 g (30.59 mmol) of the intermediate M-1, 9.8 g (30.59 mmol) of bis-biphenyl-4-yl-amine, and 3.8 g (39.8 mmol) of sodium t-butoxide were put in a round-bottomed flask, 200 mL of toluene was added, 0.19 g (0.92 mmol) of tri-tert-butylphosphine and 0.18 g (0.31 mmol) of Pd(dba)$_2$ were added, and the resultant was agitated under a nitrogen atmosphere for 12 hours at 100° C. When the reaction was terminated, the resultant was extracted with toluene and distilled water, the organic layer was dried with magnesium sulfate, and filtered, and then the filtrated solution was concentrated under a reduced pressure. The product was purified with n-hexane/dichloromethane (7:3 volume ratio) using silica gel column chromatography, obtaining 17.2 g (yield 92%) of a target compound C-143.

LC-Mass (theoretical value: 611.17 g/mol, measurement value: M+1=612.34 g/mol)

EXAMPLE 2

Preparation of Compound Represented by Chemical Formula C-144

[Reaction Scheme 21]

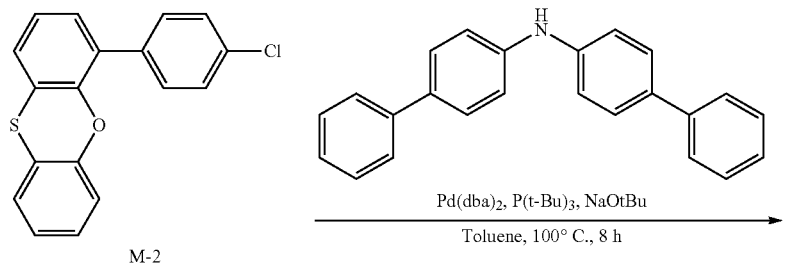

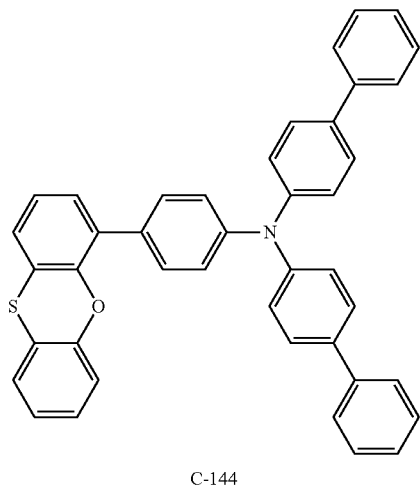

C-144

9.5 g (30.59 mmol) of the intermediate M-2, 9.8 g (30.59 mmol) of bis-biphenyl-4-yl-amine, and 3.8 g (39.8 mmol) of sodium t-butoxide were put in a round-bottomed flask, 200 mL of toluene was added, 0.19 g (0.92 mmol) of tri-tert-butylphosphine and 0.18 g (0.31 mmol) of Pd(dba)$_2$ were added, and the resultant was agitated under a nitrogen atmosphere for 12 hours at 100° C. When the reaction was terminated, the resultant was extracted with toluene and distilled water, the organic layer was dried with magnesium sulfate, and filtered, and then the filtrated solution was concentrated under a reduced pressure. The product was purified with n-hexane/dichloromethane (7:3 volume ratio) using silica gel column chromatography, obtaining 16.6 g (yield 91%) of a target compound C-144.

LC-Mass (theoretical value: 595.20 g/mol, measurement value: M+1=596.42 g/mol)

EXAMPLE 3

Preparation of Compound Represented by Chemical Formula C-113

[Reaction Scheme 22]

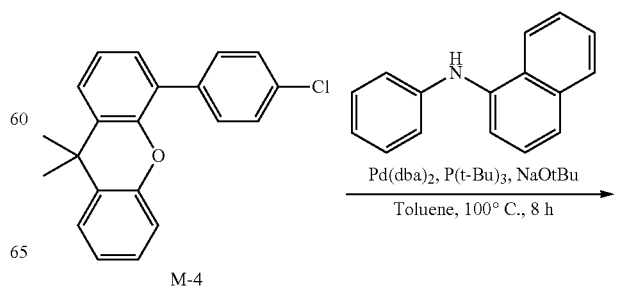

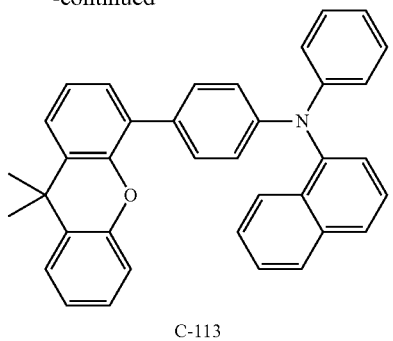

C-113

9.8 g (30.59 mmol) of the intermediate M-4, 6.7 g (30.59 mmol) of naphthalen-1-yl-phenyl-amine, 3.8 g (39.8 mmol) of sodium t-butoxide were put in a round-bottomed flask, 200 mL of toluene was added, 0.19 g (0.92 mmol) of tri-tert-butylphosphine and 0.18 g (0.31 mmol) of Pd(dba)$_2$ were added, and the resultant was agitated under a nitrogen atmosphere for 12 hours at 100° C. When the reaction was terminated, the resultant was extracted with toluene and distilled water, the organic layer was dried with magnesium sulfate, and filtered, and then the filtrated solution was concentrated under a reduced pressure. The product was purified with n-hexane/dichloromethane (7:3 volume ratio) using silica gel column chromatography, obtaining 14.5 g (yield 94%) of a target compound C-113.

LC-Mass (theoretical value: 503.22 g/mol, measurement value: M+1=504.36 g/mol)

EXAMPLE 4

Preparation of Compound Represented by Chemical Formula C-160

[Reaction Scheme 23]

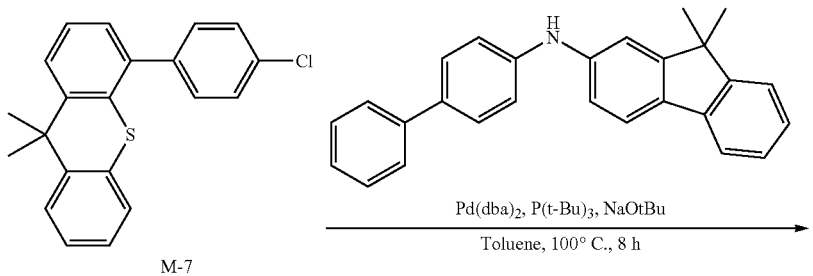

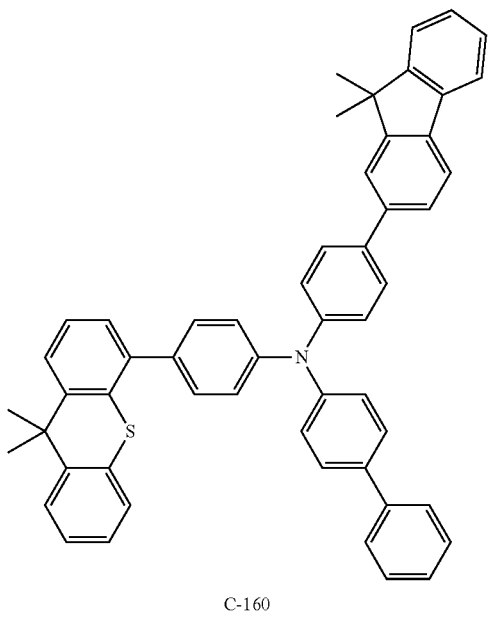

C-160

10.3 g (30.59 mmol) of intermediate M-7, 11.1 g (30.59 mmol) of biphenyl-4-yl-(9,9-dimethyl-9H-fluoren-2-yl)-amine, and 3.8 g (39.8 mmol) of sodium t-butoxide were put in a round-bottomed flask, 200 mL of toluene was added, 0.19 g (0.92 mmol) of tri-tert-butylphosphine and 0.18 g (0.31 mmol) of Pd(dba)$_2$ were added, and the resultant was agitated under a nitrogen atmosphere for 12 hours at 100° C. When the reaction was terminated, the resultant was extracted with toluene and distilled water, the organic layer was dried with magnesium sulfate, and filtered, and then the filtrated solution was concentrated under a reduced pressure. The product was purified with n-hexane/dichloromethane (7:3 volume ratio) using silica gel column chromatography, obtaining 18.4 g (yield 91%) of a target compound C-160.

LC-Mass (theoretical value: 661.28 g/mol, measurement value: M+1=662.35 g/mol)

EXAMPLE 5

Preparation of Compound Represented by Chemical Formula C-127

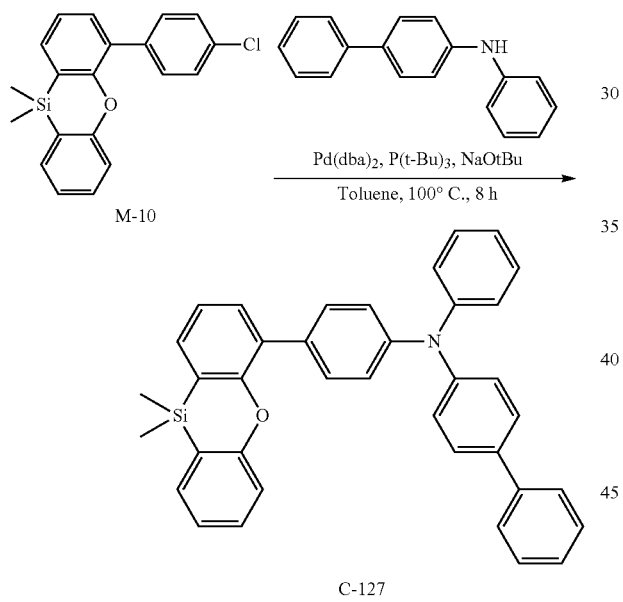

10.3 g (30.59 mmol) of intermediate M-10, 7.5 g (30.59 mmol) of biphenyl-4-yl-phenyl-amine, and 3.8 g (39.8 mmol) of sodium t-butoxide were put in a round-bottomed flask, 200 mL of toluene was added, 0.19 g (0.92 mmol) of tri-tert-butylphosphine and 0.18 g (0.31 mmol) of Pd(dba)$_2$ were added, and the resultant was agitated under a nitrogen atmosphere for 12 hours at 100° C. When the reaction was terminated, the resultant was extracted with toluene and distilled water, the organic layer was dried with magnesium sulfate, and filtered, and then the filtrated solution was concentrated under a reduced pressure. The product was purified with n-hexane/dichloromethane (7:3 volume ratio) using silica gel column chromatography, obtaining 15.5 g (yield 93%) of a target compound C-127.

LC-Mass (theoretical value: 545.22 g/mol, measurement value: M+1=546.23 g/mol)

EXAMPLE 6

Preparation of Compound Represented by Chemical Formula A-132

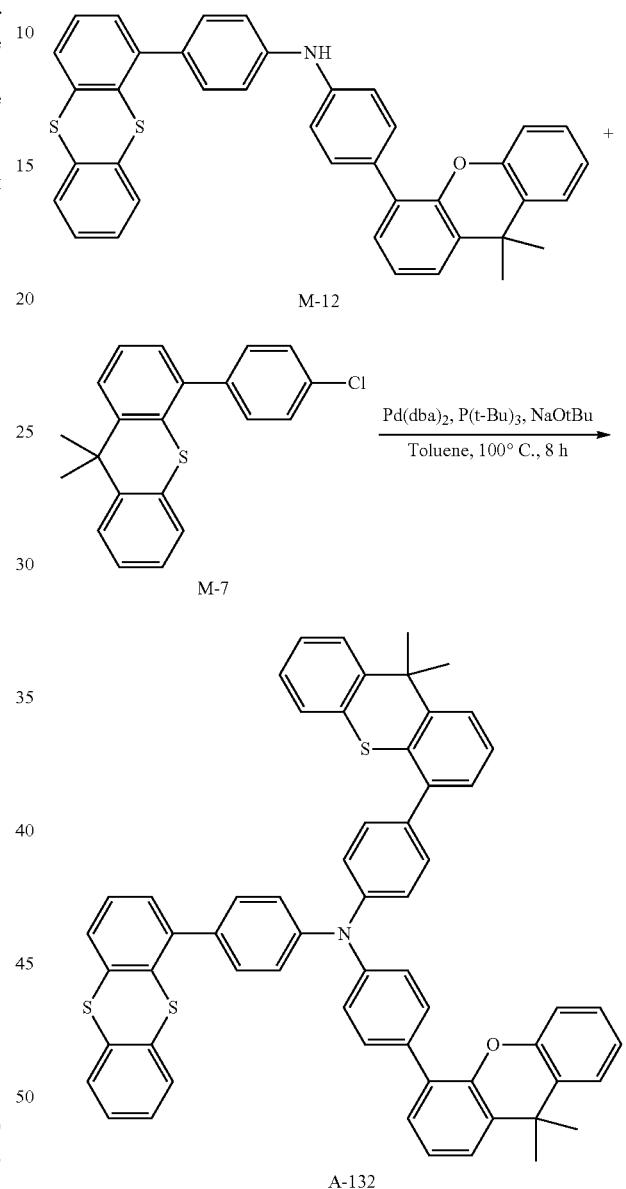

18.1 g (30.59 mmol) of the intermediate M-12, 10.3 g (30.59 mmol) of the intermediate M-7, and 3.8 g (39.8 mmol) of sodium t-butoxide were put in a round-bottomed flask, 200 mL of toluene was added, 0.19 g (0.92 mmol) of tri-tert-butylphosphine and 0.18 g (0.31 mmol) of Pd(dba)$_2$ were added, and the resultant was agitated under a nitrogen atmosphere for 12 hours at 100° C. When the reaction was terminated, the resultant was extracted with toluene and distilled water, the organic layer was dried with magnesium sulfate, and filtered, and then the filtrated solution was concentrated under a reduced pressure.

The product was purified with n-hexane/dichloromethane (7:3 volume ratio) using silica gel column chromatography, obtaining 24.3 g (yield 89%) of a target compound A-132.

LC-Mass (theoretical value: 891.27 g/mol, measurement value: M+1=892.43 g/mol)

EXAMPLE 7

Preparation of Compound Represented by Chemical Formula C-206

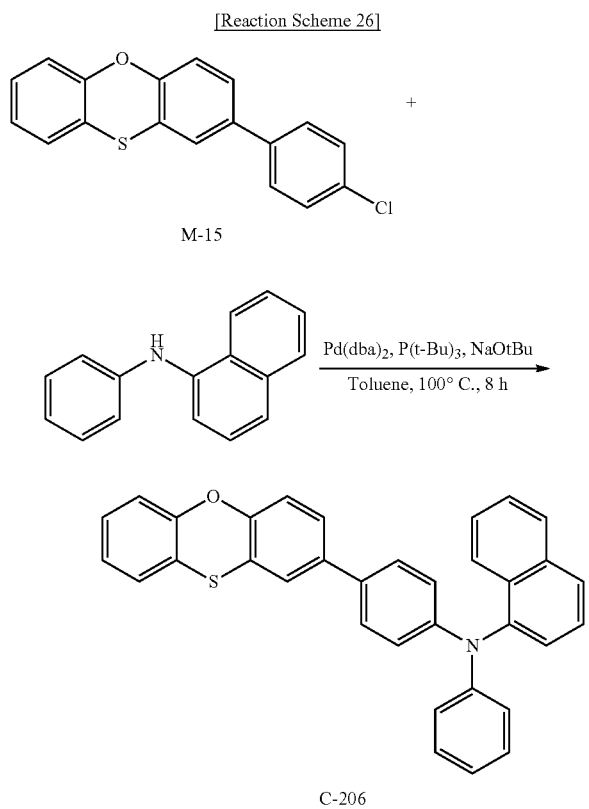

EXAMPLE 8

Preparation of Compound Represented by Chemical Formula B-56

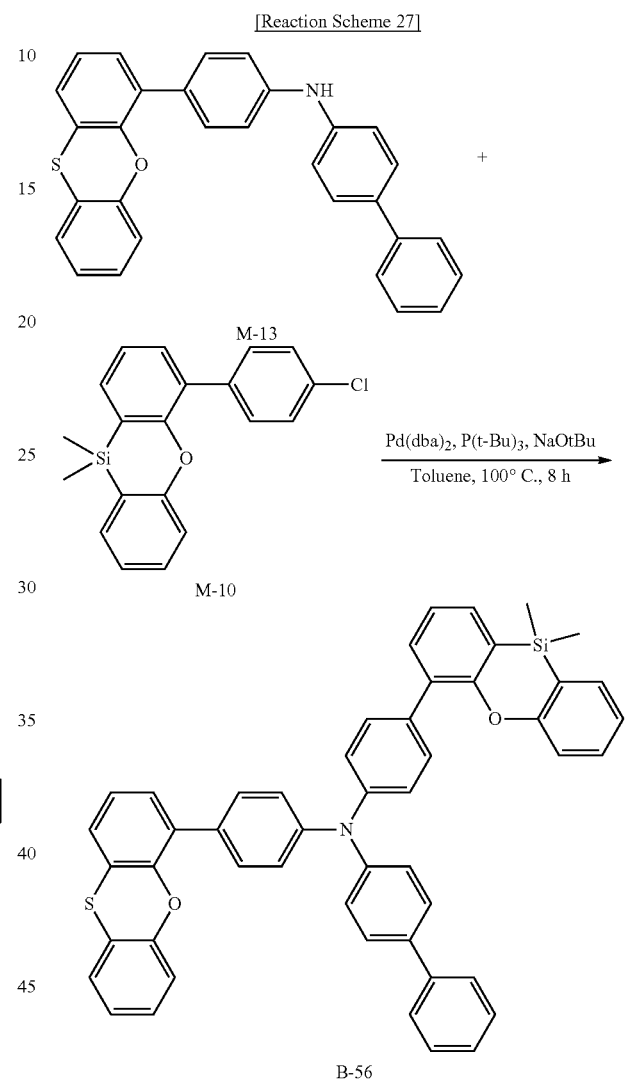

9.5 g (30.59 mmol) of the intermediate M-15, 6.7 g (30.59 mmol) of naphthalen-1-yl-phenyl-amine, and 3.8 g (39.8 mmol) of sodium t-butoxide were put in a round-bottomed flask, 200 mL of toluene was added, 0.19 g (0.92 mmol) of tri-tert-butylphosphine and 0.18 g (0.31 mmol) of Pd(dba)$_2$ were added, and the resultant was agitated under a nitrogen atmosphere for 12 hours at 100° C. When the reaction was terminated, the resultant was extracted with toluene and distilled water, the organic layer was dried with magnesium sulfate, and filtered, and then the filtrated solution was concentrated under a reduced pressure. The product was purified with n-hexane/dichloromethane (7:3 volume ratio) using silica gel column chromatography, obtaining 14.1 g (yield 93%) of a target compound C-206.

LC-Mass (theoretical value: 493.15 g/mol, measurement value: M+1=494.21 g/mol)

13.6 g (30.59 mmol) of the intermediate M-13, 10.3 g (30.59 mmol) of the intermediate M-10, and 3.8 g (39.8 mmol) of sodium t-butoxide were put in a round-bottomed flask, 200 mL of toluene was added, 0.19 g (0.92 mmol) of tri-tert-butylphosphine and 0.18 g (0.31 mmol) of Pd(dba)$_2$ were added, and the resultant was agitated under a nitrogen atmosphere for 12 hours at 100° C. When the reaction was terminated, the resultant was extracted with toluene and distilled water, the organic layer was dried with magnesium sulfate, and filtered, and then the filtrated solution was concentrated under a reduced pressure. The product was purified with n-hexane/dichloromethane (7:3 volume ratio) using silica gel column chromatography, obtaining 20.5 g (yield 90%) of a target compound B-56.

LC-Mass (theoretical value: 743.23 g/mol, measurement value: M+1=744.33 g/mol)

EXAMPLE 9

Preparation of Compound Represented by Chemical Formula C-243

[Reaction Scheme 28]

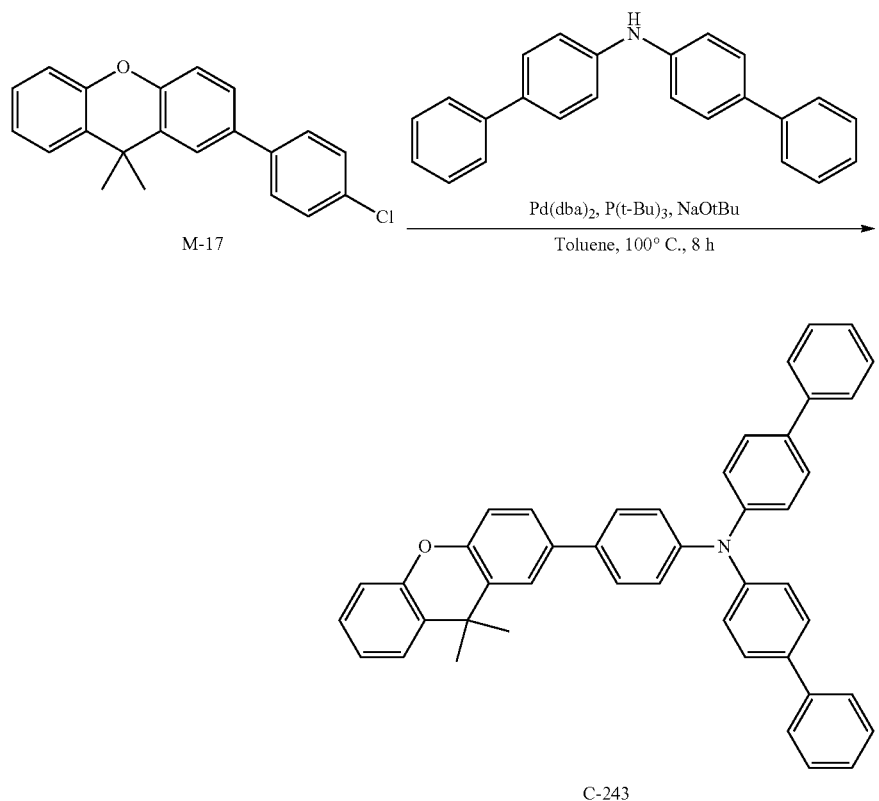

9.8 g (30.59 mmol) of the intermediate M-17, 9.8 g (30.59 mmol) of bis-biphenyl-4-yl-amine, and 3.8 g (39.8 mmol) of sodium t-butoxide were put in a round-bottomed flask, 200 mL of toluene was added, 0.19 g (0.92 mmol) of tri-tert-butylphosphine and 0.18 g (0.31 mmol) of Pd(dba)$_2$ were added, and the resultant was agitated under a nitrogen atmosphere for 12 hours at 100° C. When the reaction was terminated, the resultant was extracted with toluene and distilled water, the organic layer was dried with magnesium sulfate, and filtered, and then the filtrated solution was concentrated under a reduced pressure. The product was purified with n-hexane/dichloromethane (7:3 volume ratio) using silica gel column chromatography, obtaining 16.7 g (yield 90%) of a target compound C-243.

LC-Mass (theoretical value: 605.27 g/mol, measurement value: M+1=606.13 g/mol)

EXAMPLE 10

Preparation of Compound Represented by Chemical Formula C-236

[Reaction Scheme 29]

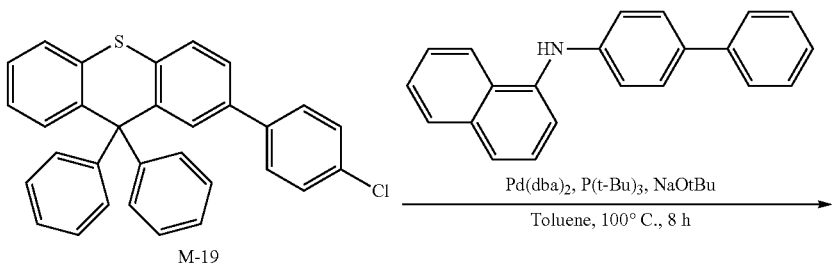

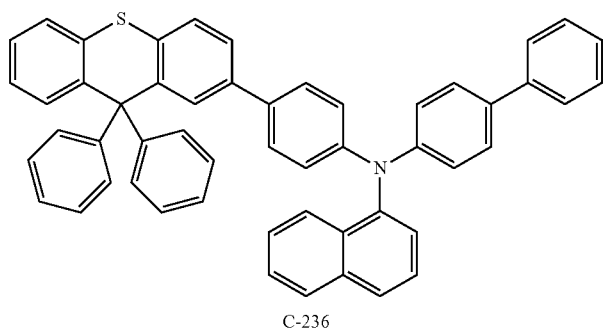

C-236

14.1 g (30.59 mmol) of the intermediate M-19, 9.0 g (30.59 mmol) of biphenyl-4-yl-naphthalen-1-yl-amine, and 3.8 g (39.8 mmol) of sodium t-butoxide were put in a round-bottomed flask, 200 mL of toluene was added, 0.19 g (0.92 mmol) of tri-tert-butylphosphine and 0.18 g (0.31 mmol) of Pd(dba)$_2$ were added, and the resultant was agitated under a nitrogen atmosphere for 12 hours at 100° C. When the reaction was terminated, the resultant was extracted with toluene and distilled water, the organic layer was dried with magnesium sulfate, and filtered, and then the filtrated solution was concentrated under a reduced pressure. The product was purified with n-hexane/dichloromethane (7:3 volume ratio) using silica gel column chromatography, obtaining f20.0 g (yield 91%) of a target compound C-236.

LC-Mass (theoretical value: 719.26 g/mol, measurement value: M+1=720.24 g/mol)

(Manufacture of Organic Light Emitting Diode)

EXAMPLE 11

A glass substrate coated with ITO (indium tin oxide) to be 1500 Å thick was ultrasonic wave-washed with a distilled water. Subsequently, the glass substrate was ultrasonic wave-washed with a solvent such as isopropyl alcohol, acetone, methanol, and the like, moved to a plasma cleaner, cleaned by using oxygen plasma for 10 minutes, and then, moved to a vacuum depositor. This obtained ITO transparent electrode was used as a anode, and 4,4'-bis[N-[4-{N,N-bis(3-methylphenyl)amino}-phenyl]-N-phenylamino]biphenyl [DNTPD] was vacuum-deposited on the ITO substrate to form 600 Å-thick hole injection layer. Then, the compound Example 1 was vacuum-deposited thereon to form a 300 Å-thick auxiliary hole transport layer. On the auxiliary hole transport layer, a 250 Å-thick emission layer was formed by vacuum-depositing 9,10-di-(2-naphthyl)anthracene(ADN) as a host doped with 3 wt % of 2,5,8,11-tetra(tert-butyl) perylene (TBPe) as a dopant.

Subsequently, Alq3 was vacuum-deposited on the emission layer to form a 250 Å-thick electron transport layer. LiF 10 Å and Al 1000 Å were sequentially vacuum-deposited on the electron transport layer to form a cathode, manufacturing an organic light emitting diode.

The organic light emitting diode had a five-layered organic thin film structure and specifically, a structure of Al 1000 Å/LiF 10 Å/Alq3 250 Å/EML [ADN:TBPe=97:3] 250 Å/HTL 300 Å/DNTPD 600 Å/ITO 1500 Å.

EXAMPLE 12

An organic light emitting diode was manufactured according to the same method as Example 11 except for using Example 2 instead of Example 1.

EXAMPLE 13

An organic light emitting diode was manufactured according to the same method as Example 11 except for using Example 4 instead of Example 1.

EXAMPLE 14

An organic light emitting diode was manufactured according to the same method as Example 11 except for using Example 6 instead of Example 1.

EXAMPLE 15

An organic light emitting diode was manufactured according to the same method as Example 11 except for using Example 7 instead of Example 1.

EXAMPLE 16

An organic light emitting diode was manufactured according to the same method as Example 11 except for using Example 8 instead of Example 1.

COMPARATIVE EXAMPLE 1

An organic light emitting diode was manufactured according to the same method as Example 11 except for using NPB instead of Example 1. The NPB has the following structure.

The structures of the DNTPD, ADN, TBPe, NPB, and Alq3 used for manufacturing the organic light emitting diode were as follows.

[DNTPD]
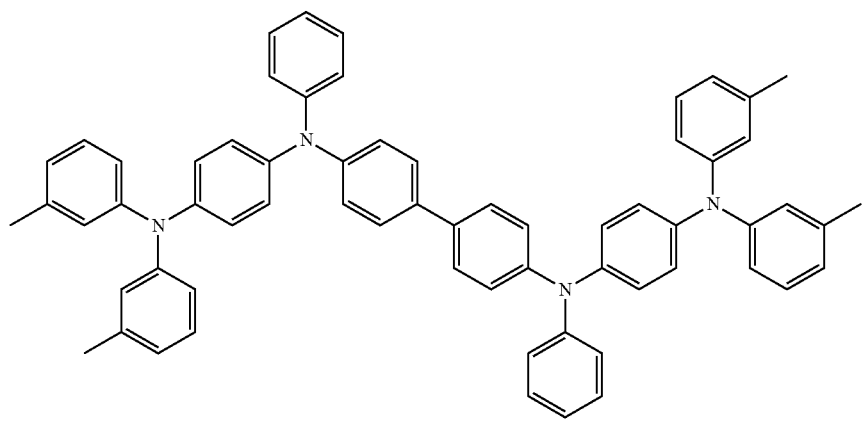
[ADN]
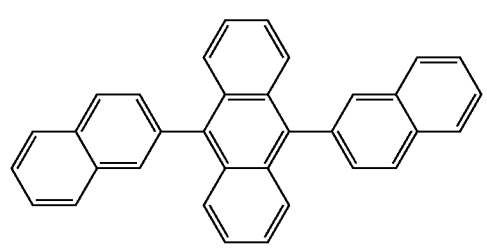
[TBPe]
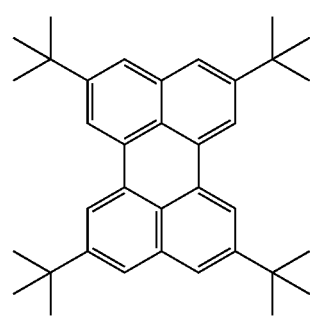
[NPB]
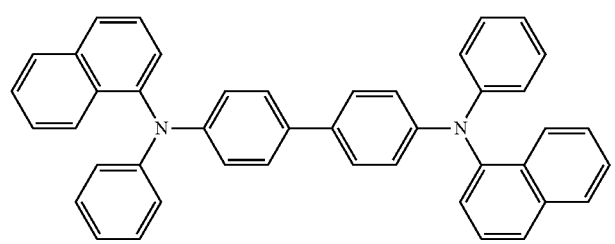
[Alq3]
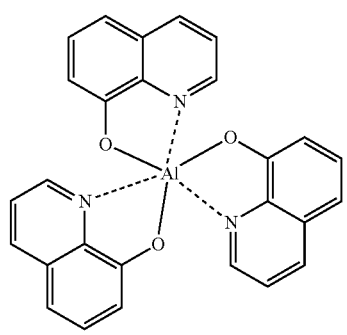

(Performance Measurement of Organic Light Emitting Diode)

Current density and luminance changes depending on a voltage and luminous efficiency of each organic light emitting diode according to Examples 11 to 16 and Comparative Example 1 were measured. The measurements were specifically performed in the following method, and the results were provided in the following Table 2.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

TABLE 2

| Device | Compound used in hole transport layer (HTL) | Voltage (V) | Color (EL color) | Efficiency (cd/A) | Half-life life-span (h) at 1000 cd/m$^2$ |
|---|---|---|---|---|---|
| Example 11 | C-143 | 6.6 | Blue | 6.1 | 1,610 |
| Example 12 | C-144 | 6.6 | Blue | 6.3 | 1,710 |
| Example 13 | C-160 | 6.7 | Blue | 6.3 | 1,470 |
| Example 14 | A-132 | 6.5 | Blue | 6.0 | 1,590 |
| Example 15 | C-206 | 6.3 | Blue | 6.0 | 1,610 |
| Example 16 | B-56 | 6.5 | Blue | 6.2 | 1,680 |
| Comparative Example 1 | NPB | 7.1 | Blue | 4.9 | 1,250 |

Current density: 10 mA/cm$^2$

Referring to the Table 2, when hole transport layers for an organic light emitting diode according to the Example 11 to 16 were used, a driving voltage organic of a light emitting diode may be lowered, and luminance and efficiency may be improved.

In addition, half-life life-span of the Example 11 to Example 16 are remarkably improved compared with the Comparative Example 1, and particularly the half-life life-span of the Example 12 is 1,690 hours (h) which is 35% or more improved compared with Comparative Example 1. The device results of Examples are considered to be sufficient for device commercialization because a life-span of a device is a requirement for actual device commercialization.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic device, the compound being represented by the following Chemical Formula 1:

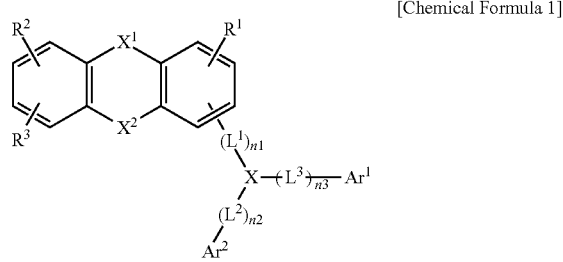

[Chemical Formula 1]

wherein, in Chemical Formula 1,

X is nitrogen (N),

X$^1$ is —O—, —S—, —CR'R"—, or —SiR'R"—, wherein R' and R" are each independently hydrogen, deuterium, a substituted or unsubstituted C1 to C10 alkyl group, or a substituted or unsubstituted C6 to C18 aryl group, X$^2$ is —O— or —S—, L$^1$, L$^2$, and L$^3$ are each an unsubstituted phenyl group, Ar$^1$ and Ar$^2$ are each independently substituted or unsubstituted C6 to C30 aryl group, R$^1$ is hydrogen, deuterium, a substituted or unsubstituted C1 to C10 alkyl group, a substituted or unsubstituted C6 to C30 aryl group, or a substituted or unsubstituted C2 to C30 heteroaryl group, R$^2$ and R$^3$ are each independently hydrogen, deuterium, a substituted or unsubstituted C1 to C10 alkyl group, a substituted or unsubstituted C6 to C30 aryl group, or a substituted or unsubstituted C2 to C18 heteroaryl group, n1 is 1, and n2 and n3 are each independently 0 or 1.

2. The compound for an organic optoelectronic device as claimed in claim 1, wherein Ar$^1$ and Ar$^2$ are each independently a substituted or unsubstituted phenyl group, a substituted or unsubstituted biphenyl group, a substituted or unsubstituted triphenyl group, a substituted or unsubstituted phenanthryl group, a substituted or unsubstituted naphthyl group, a substituted or unsubstituted anthracenyl group, or a substituted or unsubstituted fluorenyl group.

3. The compound for an organic optoelectronic device as claimed in claim 1, wherein the compound represented by Chemical Formula 1 is represented by one of the following Chemical Formulae A-132, B-56, C-113, C-127, C-143, C-144, C-160, C-206, C-236, or C-243:

[A-132]
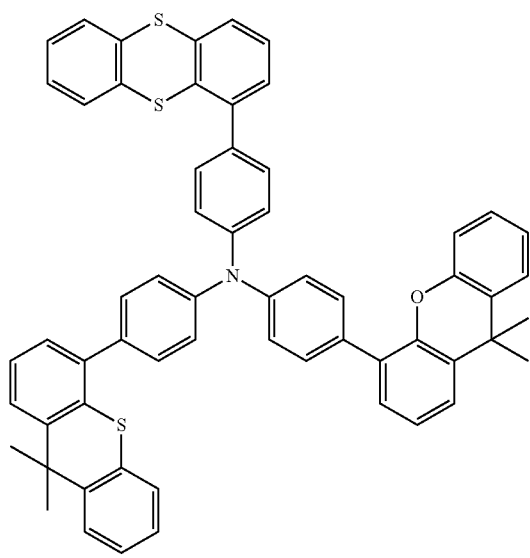
[B-56]
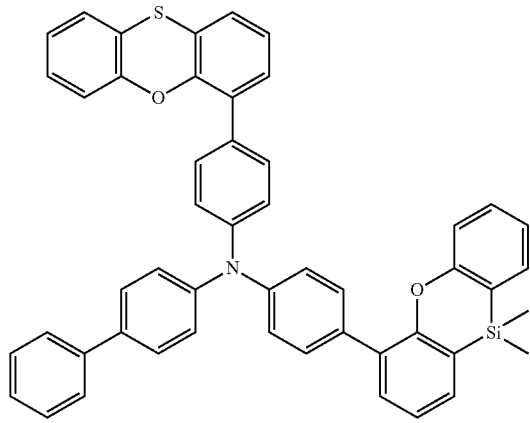
[C-113]
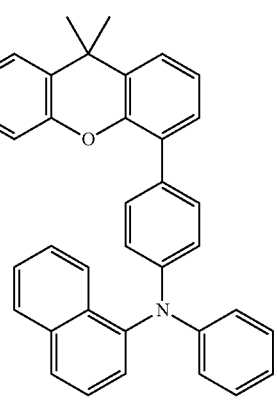
[C-127]
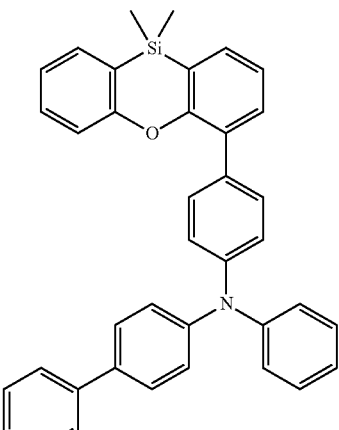
[C-143]
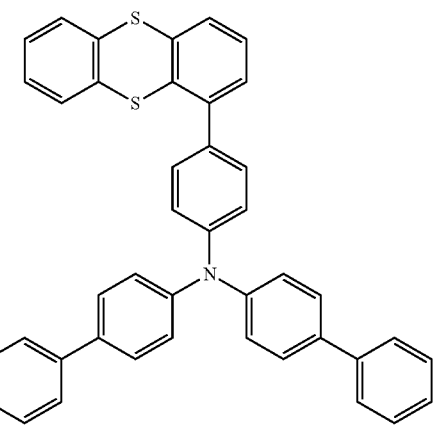
[C-144]
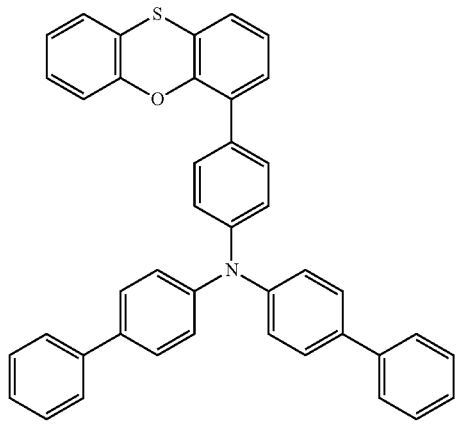

255
-continued

[C-160]

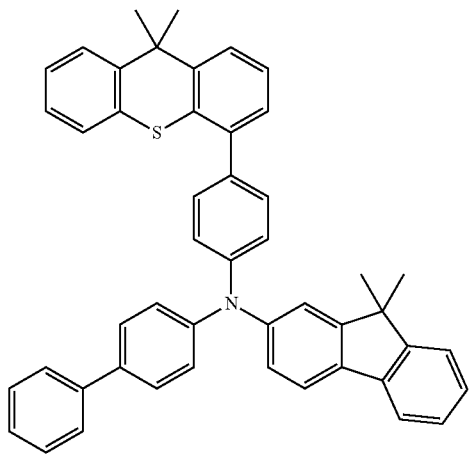

[C-206]

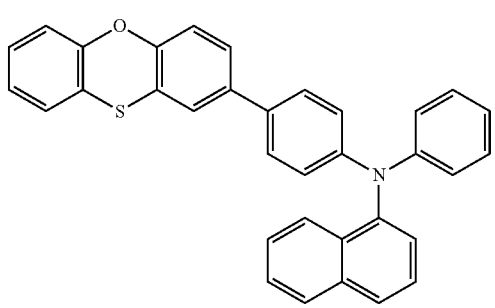

[C-236]

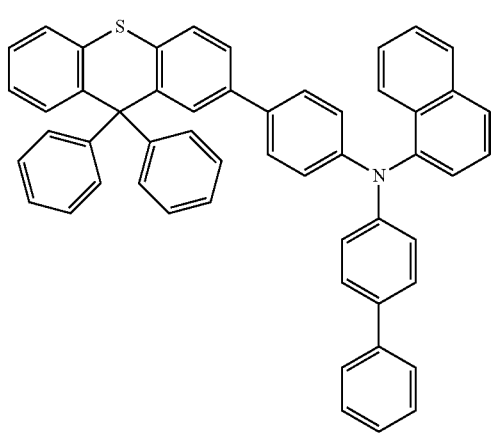

256
-continued

[C-243]

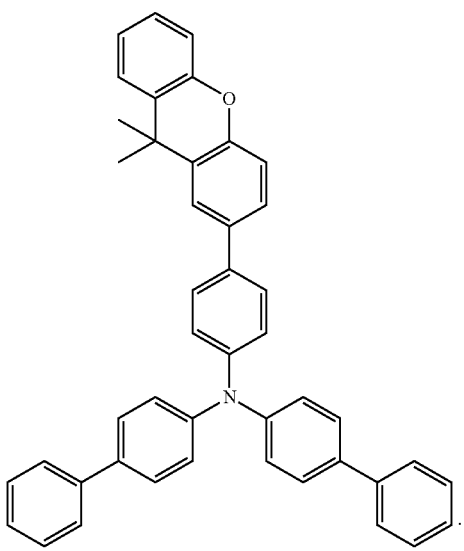

4. The compound for an organic optoelectronic device as claimed in claim 1, wherein the organic optoelectronic device is an organic photoelectric device, an organic light emitting diode, an organic solar cell, an organic transistor, an organic photo-conductor drum, or an organic memory device.

5. An organic light emitting diode, comprising:
   an anode, a cathode, and at least one organic thin layer interposed between the anode and cathode,
   wherein the at least one organic thin layer includes the compound for an organic optoelectronic device as claimed in claim 1.

6. The organic light emitting diode as claimed in claim 5, wherein the at least one organic thin layer includes an emission layer, a hole transport layer, a hole injection layer, an electron transport layer, an electron injection layer, a hole blocking layer, or a combination thereof.

7. The organic light emitting diode as claimed in claim 5, wherein the compound for an organic optoelectronic device is included in a hole transport layer, a hole injection layer, or an emission layer.

8. The organic light emitting diode as claimed in claim 7, wherein:
   the at least one organic thin layer includes the emission layer, and
   the compound for an organic optoelectronic device is a phosphorescent host material or fluorescent host material in the emission layer.

9. A compound for an organic optoelectronic device, the compound being represented by the following Chemical Formula 2:

[Chemical Formula 2]

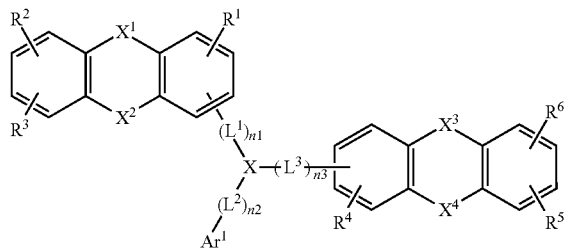

wherein, in Chemical Formula 2,

X is boron (B), nitrogen (N), or phosphorus (P), $X^1$ to $X^4$ are each independently —O—, —S—, —S(O$_2$)—, —CR'R"—, —SiR'R"—, or —GeR'R"—, wherein R' and R" are each independently hydrogen, deuterium, a substituted or unsubstituted C1 to C10 alkyl group, a substituted or unsubstituted C6 to C30 aryl group or a substituted or unsubstituted C2 to C30 heteroaryl group, and at least one of $X^1$ or $X^3$ is —CR'R"—, —SiR'R"—, or —GeR'R"—, $L^1$ to $L^3$ are each independently a substituted or unsubstituted C2 to C10 alkenylene group, a substituted or unsubstituted C2 to C10 alkynylene group, a substituted or unsubstituted C6 to C30 arylene group, or a substituted or unsubstituted C2 to C30 heteroarylene group, $Ar^1$ is a substituted or unsubstituted C6 to C30 aryl group or a substituted or unsubstituted C2 to C30 heteroaryl group, $R^1$ and $R^4$ to $R^6$ are each independently hydrogen, deuterium, a substituted or unsubstituted C1 to C10 alkyl group, a substituted or unsubstituted C6 to C30 aryl group, or a substituted or unsubstituted C2 to C30 heteroaryl group, $R^2$ and $R^3$ are each independently hydrogen, deuterium, a substituted or unsubstituted C1 to C10 alkyl group, a substituted or unsubstituted C6 to C30 aryl group, or a substituted or unsubstituted C2 to C18 heteroaryl group, and n1 to n3 are each independently an integer of 0 to 3.

10. The compound for an organic optoelectronic device as claimed in claim 9, wherein $Ar^1$ is a substituted or unsubstituted C6 to C30 aryl group.

11. The compound for an organic optoelectronic device as claimed in claim 9, wherein $Ar^1$ is a substituted or unsubstituted C2 to C30 heteroaryl group.

12. A compound for an organic optoelectronic device, the compound being represented by the following Chemical Formula 3:

[Chemical Formula 3]

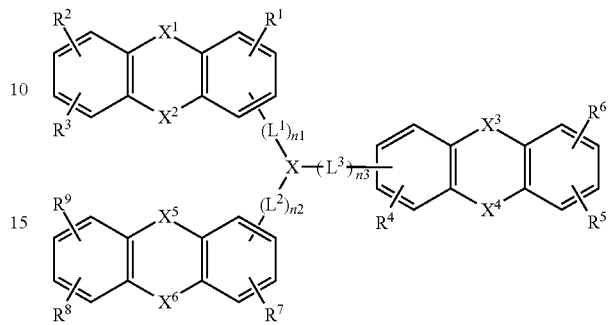

wherein, in Chemical Formula 3,

X is boron (B), nitrogen (N), or phosphorus (P), $X^1$ to $X^5$ are each independently —O—, —S—, —S(O$_2$)—, —CR'R"—, —SiR'R"—, or —GeR'R"—, $X^6$ is a single bond, —O—, —S—, —S(O$_2$)—, —CR'R"—, —SiR'R"—, or —GeR'R"—, wherein R' and R" are each independently hydrogen, deuterium, a substituted or unsubstituted C1 to C10 alkyl group, a substituted or unsubstituted C6 to C30 aryl group or a substituted or unsubstituted C2 to C30 heteroaryl group, and at least one of $X^1$, $X^3$, and $X^5$ is —CR'R"—, —SiR'R"—, or —GeR'R"—, $L^1$ to $L^3$ are each independently a substituted or unsubstituted C2 to C10 alkynylene group, a substituted or unsubstituted C2 to C10 alkynylene group, a substituted or unsubstituted C6 to C30 arylene group, or a substituted or unsubstituted C2 to C30 heteroarylene group, $R^1$ and $R^4$ to $R^9$ are each independently hydrogen, deuterium, a substituted or unsubstituted C1 to C10 alkyl group, a substituted or unsubstituted C6 to C30 aryl group, or a substituted or unsubstituted C2 to C30 heteroaryl group, $R^2$ and $R^3$ are each independently hydrogen, deuterium, a substituted or unsubstituted C1 to C10 alkyl group, a substituted or unsubstituted C6 to C30 aryl group, or a substituted or unsubstituted C2 to C18 heteroaryl group, and n1 to n3 are each independently an integer of 0 to 3.

* * * * *